United States Patent
Hao

(10) Patent No.: US 11,673,889 B2
(45) Date of Patent: *Jun. 13, 2023

(54) SUBSTITUTED IMIDAZO[4,5-C][1,8]NAPHTHYRIDINES AS PHOSPHODIESTERASE INHIBITORS

(71) Applicant: Nanjing Zhengxiang Pharmaceuticals Co., Ltd., Nanjing (CN)

(72) Inventor: Xiaolin Hao, Foster City, CA (US)

(73) Assignee: NANJING ZHENGXIANG PHARMACEUTICALS CO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/702,704

(22) Filed: Mar. 23, 2022

(65) Prior Publication Data

US 2022/0220114 A1    Jul. 14, 2022

Related U.S. Application Data

(63) Continuation of application No. 17/641,633, filed as application No. PCT/US2020/052260 on Sep. 23, 2020.

(60) Provisional application No. 62/968,755, filed on Jan. 31, 2020, provisional application No. 62/904,501, filed on Sep. 23, 2019.

(51) Int. Cl.
| | |
|---|---|
| *A61K 31/437* | (2006.01) |
| *C07D 471/12* | (2006.01) |
| *C07D 471/04* | (2006.01) |
| *C07D 487/04* | (2006.01) |
| *C07D 471/14* | (2006.01) |
| *C07D 498/04* | (2006.01) |

(52) U.S. Cl.
CPC ......... *C07D 471/04* (2013.01); *C07D 471/14* (2013.01); *C07D 487/04* (2013.01); *C07D 498/04* (2013.01)

(58) Field of Classification Search
CPC ............. A61K 31/437; C07D 471/12
USPC ............................. 514/293; 546/84
See application file for complete search history.

(56) References Cited

U.S. PATENT DOCUMENTS

| | | | |
|---|---|---|---|
| 8,026,366 B2 | 9/2011 | Prince et al. | |
| 9,458,184 B2 * | 10/2016 | Vernejoul | A61K 47/543 |
| 2010/0311714 A1 | 12/2010 | Furet et al. | |
| 2011/0251202 A1 | 10/2011 | Garcia-echeverria et al. | |
| 2015/0291607 A1 | 10/2015 | Bakonyi et al. | |
| 2018/0222906 A1 | 8/2018 | Stoermer et al. | |

FOREIGN PATENT DOCUMENTS

| | | | |
|---|---|---|---|
| JP | 11080156 | * | 3/1999 |
| WO | 2009024585 A2 | | 2/2009 |
| WO | 2009024585 A3 | | 8/2009 |
| WO | 2010002998 A1 | | 1/2010 |
| WO | 2011054846 A1 | | 5/2011 |
| WO | 2012028233 A1 | | 3/2012 |
| WO | 2014152029 A2 | | 9/2014 |
| WO | 2014152029 A3 | | 12/2014 |
| WO | 2018030550 A1 | | 2/2018 |
| WO | 2019046778 A1 | | 3/2019 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Abate, N. et al. (Dec. 2006). "Mechanisms of Disease: Ectonucleotide Pyrophosphatase Phosphodiesterase 1 as a 'Gatekeeper' of Insulin Receptors," Nature Clin. Pract. Endocrinol. Metab. 2(12):694-701.
Feng, H. et al. (2016). "Copper-Catalyzed [3+2] Cycloaddition Reactions: Synthesis of Substituted Pyrazolo[1,5-c] Quinazolines With N-Iminoquinazolinium Ylides and Olefins as Starting Materials," RSC Adv. 6:95774-95779.
Ferretti, E. et al. (2018). "Canonical and Non-Canonical Adenosinergic Pathways," Immunol. Lett. 3:307, 6 pages.
Gopalsamy, A. et al. (Nov. 15, 2007, e-pub. Oct. 17, 2007). "Discovery of Dibenzo[c,f][2,7]naphthyridines as Potent and Selective 3-Phosphoinositide-Dependent Kinase-1 Inhibitors," Journal of Medicinal Chemistry 50:5547-5549.
International Search Report and Written Opinion, dated Feb. 17, 2021, for PCT Application No. PCT/US2020/052260, filed Sep. 23, 2020, 12 pages.
Lu, X. et el. (Apr. 9, 2018). "Acid-Promoted Cascade Reaction of N-(4-Chloroquinolin-3-yl)carbamates with Amines One-Pot Assembly of Imidazo[4,5-c]quinolin-2-one," Eur. J. Org. Chem. 2018(13):1572-1580, 25 pages.

(Continued)

*Primary Examiner* — Douglas M Willis
(74) *Attorney, Agent, or Firm* — Morrison & Foerster LLP

(57) ABSTRACT

The invention provides compounds of Formula (A) that may inhibit ENPP1, and that are accordingly useful for treatment of disorders related to ENPP1. The invention further provides pharmaceutical compositions containing these compounds and methods of using these compounds to treat or prevent disorders related to ENPP1.

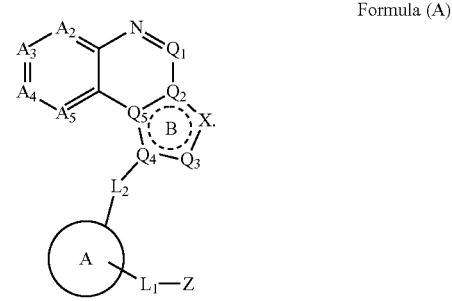

Formula (A)

17 Claims, 5 Drawing Sheets

(56) References Cited

OTHER PUBLICATIONS

Morgentin, R. et al. (Mar. 17, 2008, e-pub. Jan. 16, 2008). "Strategic Studies In The Syntheses of Novel 6,7-Substituted Quinolones and 7- or 6-Substituted 1,6- and 1,7-Naphthyridones," Tetrahedron 64(12):2772-2782.

Patel, S.D. et al. (2009, e-pub. Apr. 9, 2009). "Quinazolin-4-piperidin-4-methyl Sulfamide PC-1 Inhibitors: Alleviating hERG Interactions Through Structure Based Design," Bioorganic & Medicinal Chemistry Letters 19:3339-3343.

Pubchem (Aug. 8, 2012). CID: 57515496 "1-[[4-Amino-2-(ethozymethyl)imidazo[4,5-c][1,5]naphthyridin-1-yl]methyl]cyclopropane-101," 8 pages.

Remington's Pharmaceutical Sciences, Mack Publishing Company, Philadelphia, PA, 21th ed. (2000) TOC, 4 Pages.

Sharma, M. et al. (Sep. 10, 2018). "Development of Enpp1 Inhibitors as a Strategy to Activate Stimulator of Interferon Genes (STING) in Cancers and Other Diseases," Int. J. Cell Sci. & Mol. Biol. 5:555655, 24 pages.

Terkeltaub, R. et al. (2006, e-pub. Jun. 1, 2006). "Physiologic and Pathologic Functions of The NPP Nucleotide Pyrophosphatase/Phosphodiesterase Family Focusing on NPP1 In Calcification," Purinergic Signaling 2:371-377.

Vaingankar, S.M. et al. (2004, e-pub. Dec. 24, 2003.). "Subcellular Targeting and Function of Osteoblast Nucleotide Pyrophosphatase Phosphodiesterase 1," Cell Physiol. 286:C1177-C1187.

International Preliminary Report on Patentability, dated Mar. 15, 2022, for PCT Application No. PCT/US2020/052260, filed Sep. 23, 2020, 8 pages.

\* cited by examiner

SUBSTITUTED IMIDAZO[4,5-C][1,8]NAPHTHYRIDINES AS PHOSPHODIESTERASE INHIBITORS

CROSS REFERENCE TO RELATED APPLICATIONS

This application is a continuation of U.S. patent application Ser. No. 17/641,633, which is a national stage application under 35 U.S.C. § 371 of International Application No. PCT/US2020/052260, filed Sep. 23, 2020, which claims prior benefit of U.S. Provisional Patent Application No. 62/904,501, filed Sep. 23, 2019, and U.S. Provisional Patent Application No. 62/968,755, filed Jan. 31, 2020, the disclosures of each of which are hereby incorporated herein by reference in their entirety.

FIELD OF THE INVENTION

This disclosure relates generally to compounds and compositions that may be useful as phosphodiesterase inhibitors.

BACKGROUND

The Ectonucleotide Pyrophophatase/Phosphodiesterase (ENPP) family consists of seven members, ENNP1-7, which are either membrane-bound glycoproteins or ectoenzymes with an active site or as soluble proteins in body fluids. Among them, ENPP1 (Plasma cell membrane glycoprotein, also known as PC-1), is involved in a number of physiological processes, such as development, formation and trafficking, as well as in pathophysiological conditions. ENPP1 may use nucleotides and nucleotide derivatives as substrates and hydrolyze them with the formation of nucleoside-5' monophosphates. ATP is an identified substrate of ENPP1, which is hydrolyzed to AMP and PPi. Another known subtract 2'3'-cyclic guanosine monophosphate-adenosine monophosphate (2'3'-cGAMP) is an intracellular secondary messenger produced in response to cytosolic dsDNA. Moreover, artificial phosphoric acid esters p-nitrophenyl 5'-thymidine monophosphate (TMP-pNP) and p-nitrophenyl 5'-adenosine monophosphate (AMP-pNP) are also taken by ENPP1 as substrates.

ENPP1 is type II transmembrane glycoprotein originally identified as a negative regulator of bone mineralization, it expressed on the extracellular membrane of osteoblasts and chondrocytes and hydrolyzes extracellular ATP to produce AMP and diphosphate, an inhibitor of bone mineralization (Terkeltaub, R et, al. Purinergic Signaling 2006, 2, 371-377; Vaingankar, S. M. et, al. Cell Physiol. 2004, 286, C1177-C1187). ENPP1 is involved in many different biological processes. In lymphoid organs, ENPP1 hydrolysis produces AMP, which subsequently is metabolized by ecto-5-nucleotidase CD73 into the immunosuppressive adenosine(Ferretti, E., Immunol. Lett. 2018, 3, 307). In animal model, ENPP1 inhibits insulin receptor tyrosine kinase activity in peripheral tissues, which are major targets of insulin action (Abate, N. et, al. Nature Clin. Pract. Endocrinol. Metab. 2006, 2, 694-701). Aberrant ENPP1 expression has also been reported in breast cancers, Hodgkin's lymphoma, hepatocellular carcinoma follicular lymphoma, glioblastoma and in other malignant tumor tissues.

In recent years, ENPP1 was found to play an important role in cancer immunity. Li et al reported ENPP1 is the dominant 2'3'-cGAMP hydrolase, breaking it down to 5'-AMP and 5'-GMP. 2'3'-cGAMP is the most potent natural agonist to the Stimulator of Interferon Genes (STING) pathway, a central pathway in anti-viral and anti-cancer innate immunity. 2'3'-cyclic guanosine monophosphate-adenosine monophosphate (2'3'-cGAMP) functions as an endogenous second messenger in response of cytosolic double-strand DNA. It binds and activates STING to stimulate production of type I interferon (IFN) and other cytokines that subsequently trigger the anti-viral and anti-tumor immune response (Manas Sharma, et, al. Int J cell Sci & Mol Biol., 2018,5,555655). Therefore, ENPP1 inhibitors block 2'3'-cGAMP hydrolysis, subsequently enhance the cGAMP-induced STING pathway activation and stimulate anti-tumor immune response.

Therefore, there is a need to develop ENPP inhibitors for therapeutics.

SUMMARY OF THE DISCLOSURE

Figure 1A:
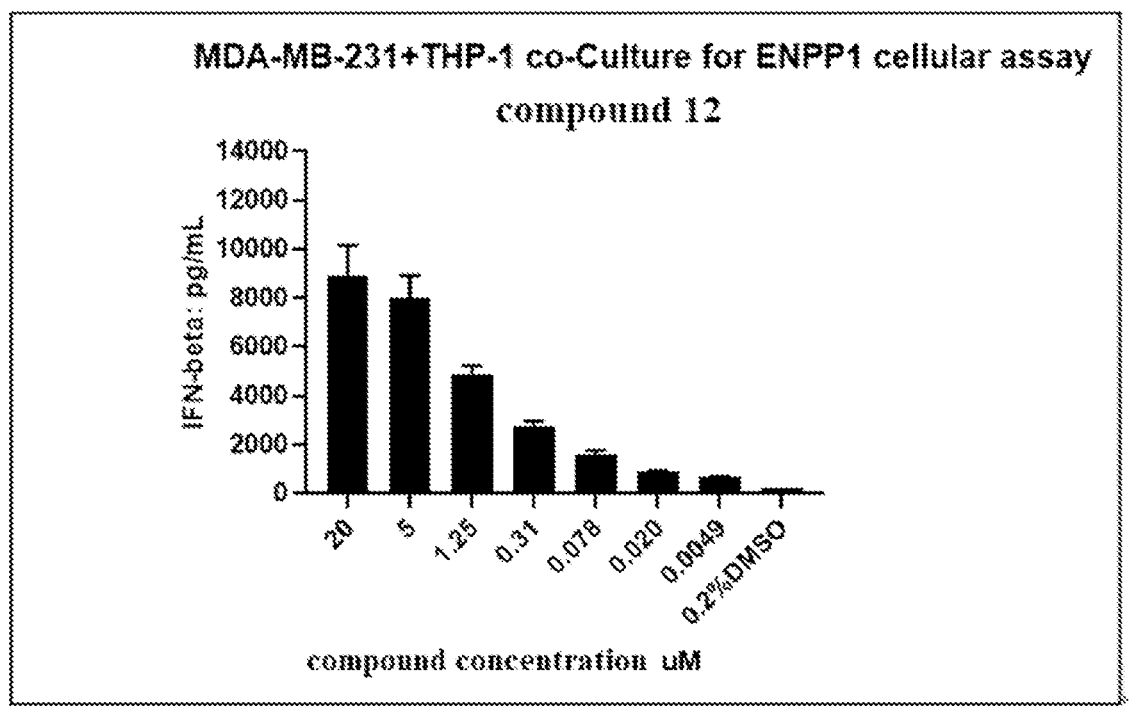
FIG. 1A, FIG. 1B, FIG. 1C, FIG. 1D and FIG. 1E show the % increase measured for IFN-β in cells treated with representative compounds of 12, 48, 89, 103 and 121 relative to that of untreated cells.

In one aspect, provided is a compound of Formula (A):

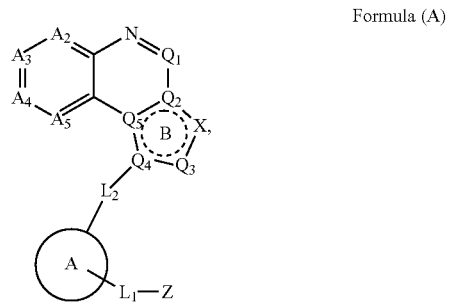

Formula (A)

or a pharmaceutically acceptable salt, stereoisomer, solvate, or prodrug thereof, wherein each variable is as detailed herein.

Also disclosed herein is a compound of Formula (I)-(VI):

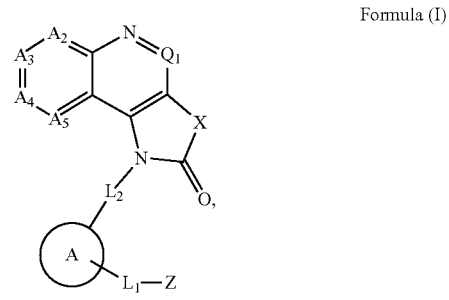

Formula (I)

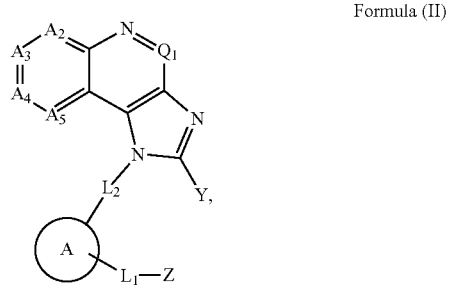

Formula (II)

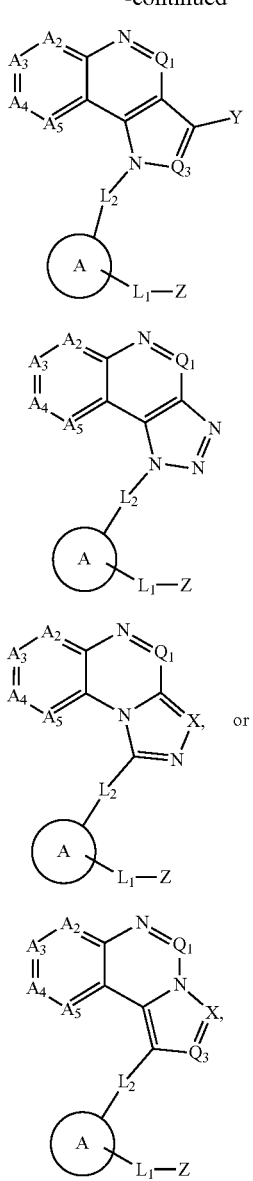

Formula (III)

Formula (IV)

Formula (V)

Formula (VI)

or a pharmaceutically acceptable salt, stereoisomer, solvate, or prodrug thereof, wherein each variable is as detailed herein.

In some embodiments, a compound of formula (A), or a pharmaceutically acceptable salt, stereoisomer, solvate, or prodrug thereof, is of formulae (I)-(VI) as detailed herein.

In another aspect, provided is a method of treating or preventing a disorder of uncontrolled cellular proliferation related to ENPP1, skeletal and soft tissue mineralization related disorders, disorders related to ENPP1 genetic changes, viral infections, and/or cancers.

In some embodiments, provided is a method of treating a disorder or disease, comprising administering to a subject in need thereof a therapeutically effective amount of a compound of formula (A), including a compound of formulae (I)-(VI), or pharmaceutically acceptable salt, stereoisomer or solvate thereof thereof.

Also provided are pharmaceutical compositions comprising: (A) a compound detailed herein, such as a compound of formula (A), including a compound of formulae (I)-(VI), or a pharmaceutically acceptable salt, stereoisomer, solvate, or prodrug thereof; and (B) a pharmaceutically acceptable carrier or excipient. Kits comprising a compound detailed herein or a pharmaceutically acceptable salt, stereoisomer, solvate, or prodrug thereof and optionally instructions for use are also provided.

Compounds as detailed herein or a pharmaceutically acceptable salt, stereoisomer, solvate, or prodrug thereof are provided for use as a medicament. Compounds as detailed herein or a pharmaceutically acceptable salt, stereoisomer, solvate, or prodrug thereof are also provided for the manufacture of a medicament for the treatment or prevention of a disorder of uncontrolled cellular proliferation related to ENPP1, for example, a cancer.

DETAILED DESCRIPTION

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$).

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases which can be used to prepared salts include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of an individual. In some embodiments, "treatment" of a disorder does not include prevention of the disorder, and "prevention" is understood to refer to the prophylactic administration of a drug to substantially diminish the likelihood or severity of a disorder or biological manifestation thereof, or to delay the onset of such disorder or biological manifestation thereof.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount is an amount sufficient to delay development. In some embodiments, an effective amount is an amount sufficient to prevent or delay recurrence. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "subject" is a mammal, including humans. A subject includes, but is not limited to, human, bovine, horse, feline, canine, rodent, or primate. In some embodiments, the subject is human (including adults and children).

Unless otherwise stated, "substantially pure" intends a composition that contains no more than 10% impurity, such as a composition comprising less than about 9%, 7%, 5%, 3%, 1%, 0.5% impurity.

It is understood that aspects and variations described herein also include "consisting" and/or "consisting essentially of" aspects and variations.

All references throughout, such as publications, patents, patent applications and published patent applications, are incorporated herein by reference in their entireties.

Compounds

In one aspect, the invention provides a compound of Formula (A):

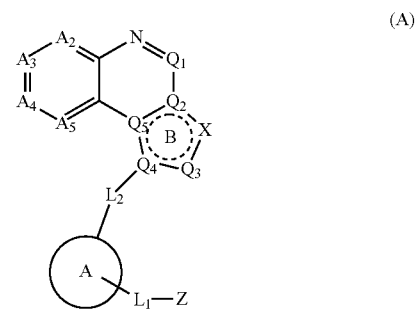

(A)

or a pharmaceutically acceptable salt, stereoisomer, solvate, or prodrug thereof, wherein:

$L_1$ is a bond, O, $CR_1R_2$, $NR_3$, or $*CR_1R_2NR_3$, wherein * denotes the point of attachment to ring A;

$L_2$ is a bond, $CR_1R_2$, or $C(=O)$;

$Q_1$, $Q_2$, $Q_3$, $Q_4$, and $Q_5$ are independently N, C or C-E, $A_2$, $A_3$, $A_4$ and $A_5$ are independently N or $CR_4$;

X is S, O, $CR_1R_2$, C-E, N or $NR_3$;

Z is $SO_2NHR_5$, $SO_2R_5$, C(O)OH, C(O)$NHR_5$, C(O)$NHOR_5$, P(O)(O$R_5$)$_2$, or B(OH)$_2$;

E is, independently at each occurrence, selected from the group consisting of hydrogen, deuterium, halogen, oxo, —CN, —O$R_3$, —NO$_2$, —N$R_3R_3'$, —C(O)$R_3$, —C(O)O$R_3$, —C(O)N$R_3R_3'$, —SO$_2R_3$, —SO$_2$N$R_3R_3'$, $C_1$-$C_6$ alkyl, $C_2$-$C_6$ alkenyl, $C_2$-$C_6$ alkynyl, $C_1$-$C_4$ alkoxy, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, NH$_2$, N($C_1$-$C_6$ alkyl)$_2$, $C_1$-$C_3$ alkyl, phenyl, $C_1$-$C_4$ alkoxy, $C_1$-$C_3$ haloalkyl, $C_1$-$C_3$ haloalkoxy, 3-8 membered heterocyclyl, —C(O)—$C_1$-$C_4$ alkoxy, —C(O)—NH$_2$, and —S(O)$_2$-$C_1$-$C_6$ alkyl;

$R_1$ and $R_2$ are independently selected from the group consisting of hydrogen, deuterium, halogen, $C_1$-$C_6$ alkyl, and $C_3$-$C_8$ cycloalkyl, wherein the $C_1$-$C_6$ alkyl, and $C_3$-$C_8$ cycloalkyl are optionally substituted with one or more substituents selected from the group consisting of halogen, CN, OH, NH$_2$, $C_1$-$C_3$ alkyl, phenyl, $C_1$-$C_4$ alkoxy, $C_1$-$C_3$ haloalkyl, and $C_1$-$C_3$ haloalkoxy, or $R_1$ and $R_2$ together form a $C_3$-$C_6$ cycloalkyl;

$R_3$ and $R_3'$ are independently selected from the group consisting of hydrogen, $C_1$-$C_6$ alkyl, 3-6 membered cycloalkyl, and 3-8 membered heterocyclyl, wherein the $C_1$-$C_6$ alkyl, and $C_3$-$C_6$ cycloalkyl are optionally substituted with one or more substituents selected from the group consisting of halogen, CN, OH, NH$_2$, $C_1$-$C_3$ alkyl, phenyl, $C_1$-$C_4$ alkoxy, $C_1$-$C_3$ haloalkyl, and $C_1$-$C_3$ haloalkoxy;

$R_4$ is selected from the group consisting of hydrogen, deuterium, halogen, —CN, —O$R_3$, —NO$_2$, —N$R_3R_3'$, —C(O)$R_3$, —C(O)O$R_3$, —C(O)N$R_3R_3'$, —SO$_2R_3$, —SO$_2$N$R_3R_3'$, $C_1$-$C_6$ alkyl, $C_2$-$C_6$ alkenyl, $C_2$-$C_6$ alkynyl, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, NH$_2$, $C_1$-$C_3$ alkyl, phenyl, $C_1$-$C_4$ alkoxy, $C_1$-$C_3$ haloalkyl, and $C_1$-$C_3$ haloalkoxy;

$R_5$ is, independently at each occurrence, selected from the group consisting of hydrogen, $C_1$-$C_6$ alkyl, $C_3$-$C_8$ cycloalkyl, 3-8 membered heterocyclyl, and —C(=O)—$C_1$-$C_6$ alkyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are independently optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy; and ring A is $C_3$-$C_8$ cycloalkyl, 3- to 12-membered heterocyclyl, $C_6$-$C_{14}$ aryl, or 5- to 10-membered heteroaryl, wherein the $C_3$-$C_8$ cycloalkyl, 3- to 12-membered heterocyclyl, $C_6$-$C_{14}$ aryl, and 5- to 10-membered heteroaryl of ring A are optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen; and

 indicates that ring B is fully unsaturated, or partially unsaturated.

In some embodiments, provided herein is a compound of Formula (A), wherein $Q_2$ is C, $Q_3$ is C-E, wherein E is oxo, $Q_4$ is N, and $Q_5$ is C, such that the compound of Formula (A) is a compound of Formula (I):

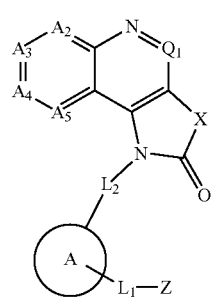

(I)

or a pharmaceutically acceptable salt, stereoisomer, solvate, or prodrug thereof, wherein:

$L_1$ is a bond, O, $CR_1R_2$, $NR_3$, or *$CR_1R_2NR_3$, wherein * denotes the point of attachment to ring A;

$L_2$ is a bond, $CR_1R_2$, or C(=O);

$Q_1$ is N or C-E;

$A_2$, $A_3$, $A_4$ and $A_5$ are independently N or $CR_4$;

X is S, O, $CR_1R_2$ or $NR_3$;

Z is $SO_2NHR_5$, $SO_2R_5$, C(O)OH, C(O)$NHR_5$, C(O)$NHOR_5$, P(O)(OR$_5$)$_2$, or B(OH)$_2$;

E is selected from the group consisting of hydrogen, deuterium, halogen, oxo, —CN, —$OR_3$, —$NO_2$, —$NR_3R_3$', —C(O)$R_3$, —C(O)$OR_3$, —C(O)$NR_3R_3$', —$SO_2R_3$, —$SO_2NR_3R_3$', $C_1$-$C_6$ alkyl, $C_2$-$C_6$ alkenyl, $C_2$-$C_6$ alkynyl, $C_1$-$C_4$ alkoxy, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, N($C_1$-$C_6$ alkyl)$_2$, $C_1$-$C_3$ alkyl, phenyl, $C_1$-$C_4$ alkoxy, $C_1$-$C_3$ haloalkyl, $C_1$-$C_3$ haloalkoxy, 3-8 membered heterocyclyl, —C(O)—$C_1$-$C_4$ alkoxy, —C(O)—$NH_2$, and —S(O)$_2$-$C_1$-$C_6$ alkyl;

$R_1$ and $R_2$ are independently selected from the group consisting of hydrogen, deuterium, halogen, $C_1$-$C_6$ alkyl, and $C_3$-$C_8$ cycloalkyl, wherein the $C_1$-$C_6$ alkyl, and $C_3$-$C_8$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy, or $R_1$ and $R_2$ together form a $C_3$-$C_6$ cycloalkyl;

$R_3$ and $R_3$' are independently selected from the group consisting of hydrogen, $C_1$-$C_6$ alkyl, 3-6 membered cycloalkyl, and 3-8 membered heterocyclyl, wherein the $C_1$-$C_6$ alkyl, and $C_3$-$C_6$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_4$ is selected from the group consisting of hydrogen, deuterium, halogen, —CN, —$OR_3$, —$NO_2$, —$NR_3R_3$', —C(O)$R_3$, —C(O)$OR_3$, —C(O)$NR_3R_3$', —$SO_2R_3$, —$SO_2NR_3R_3$', $C_1$-$C_6$ alkyl, $C_2$-$C_6$ alkenyl, $C_2$-$C_6$ alkynyl, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_5$ is, independently at each occurrence, selected from the group consisting of hydrogen, $C_1$-$C_6$ alkyl, $C_3$-$C_8$ cycloalkyl, 3-8 membered heterocyclyl, and —C(=O)—$C_1$-$C_6$ alkyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are independently optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy; and ring A is $C_3$-$C_8$ cycloalkyl, 3- to 12-membered heterocyclyl, $C_6$-$C_{14}$ aryl, or 5- to 10-membered heteroaryl, wherein the $C_3$-$C_8$ cycloalkyl, 3- to 12-membered heterocyclyl, $C_6$-$C_{14}$ aryl, and 5- to 10-membered heteroaryl of ring A are optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen.

In some embodiments, provided herein is a compound of Formula (A), wherein $Q_2$ is C, $Q_3$ is C-E, $Q_4$ is N, $Q_5$ is C, and X is N, such that the compound of Formula (A) is a compound of Formula (II):

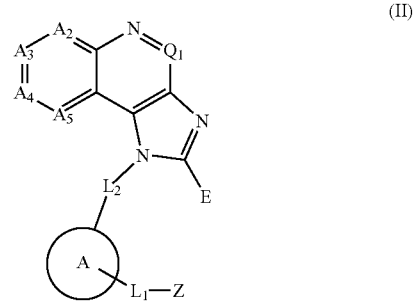

(II)

or a pharmaceutically acceptable salt, stereoisomer, solvate, or prodrug thereof, wherein:

$L_1$ is a bond, O, $CR_1R_2$, $NR_3$, or *$CR_1R_2NR_3$, wherein * denotes the point of attachment to ring A;

$L_2$ is a bond, $CR_1R_2$, or C(=O);

$Q_1$ is N or C-E;

$A_2$, $A_3$, $A_4$ and $A_5$ are independently N or $CR_4$;

Z is $SO_2NHR_5$, $SO_2R_5$, $C(O)OH$, $C(O)NHR_5$, $C(O)NHOR_5$, $P(O)(OR_5)_2$, or $B(OH)_2$;

E is, independently at each occurrence, selected from the group consisting of hydrogen, deuterium, halogen, oxo, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_1$-$C_4$ alkoxy, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $N(C_1$-$C_6$ alkyl$)_2$, $C_1$-$C_3$ alkyl, phenyl, $C_1$-$C_4$ alkoxy, $C_1$-$C_3$ haloalkyl, $C_1$-$C_3$ haloalkoxy, 3-8 membered heterocyclyl, —$C(O)$—$C_1$-$C_4$ alkoxy, —$C(O)$—$NH_2$, and —$S(O)_2$-$C_1$-$C_6$ alkyl;

$R_1$ and $R_2$ are independently selected from the group consisting of hydrogen, deuterium, halogen, $C_1$-$C_6$ alkyl, and $C_3$-$C_8$ cycloalkyl, wherein the $C_1$-$C_6$ alkyl, and $C_3$-$C_8$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy, or $R_1$ and $R_2$ together form a $C_3$-$C_6$ cycloalkyl;

$R_3$ and $R_3'$ are independently selected from the group consisting of hydrogen, $C_1$-$C_6$ alkyl, 3-6 membered cycloalkyl, and 3-8 membered heterocyclyl, wherein the $C_1$-$C_6$ alkyl, and $C_3$-$C_6$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_4$ is selected from the group consisting of hydrogen, deuterium, halogen, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_5$ is, independently at each occurrence, selected from the group consisting of hydrogen, $C_1$-$C_6$ alkyl, $C_3$-$C_8$ cycloalkyl, 3-8 membered heterocyclyl, and —$C(=O)$—$C_1$-$C_6$ alkyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are independently optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy; and ring A is $C_3$-$C_8$ cycloalkyl, 3- to 12-membered heterocyclyl, $C_6$-$C_{14}$ aryl, or 5- to 10-membered heteroaryl, wherein the $C_3$-$C_8$ cycloalkyl, 3- to 12-membered heterocyclyl, $C_6$-$C_{14}$ aryl, and 5- to 10-membered heteroaryl of ring A are optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen.

In some embodiments, provided is a compound of Formula (A), wherein $Q_2$ is C, $Q_4$ is N, $Q_5$ is C, and X is C-E, such that the compound of Formula (A) is a compound of Formula (III):

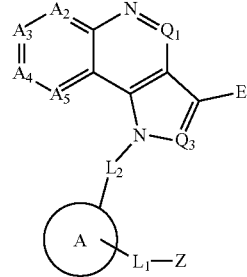

(III)

or a pharmaceutically acceptable salt, stereoisomer, solvate, or prodrug thereof, wherein:

$L_1$ is a bond, O, $CR_1R_2$, $NR_3$, or *$CR_1R_2NR_3$, wherein * denotes the point of attachment to ring A;

$L_2$ is a bond, $CR_1R_2$, or $C(=O)$;

$Q_1$ is N or C-E;

$Q_3$ is N or C-E;

$A_2$, $A_3$, $A_4$ and $A_5$ are independently N or $CR_4$;

Z is $SO_2NHR_5$, $SO_2R_5$, $C(O)OH$, $C(O)NHR_5$, $C(O)NHOR_5$, $P(O)(OR_5)_2$, or $B(OH)_2$;

E is, independently at each occurrence, selected from the group consisting of hydrogen, deuterium, halogen, oxo, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_1$-$C_4$ alkoxy, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $N(C_1$-$C_6$ alkyl$)_2$, $C_1$-$C_3$ alkyl, phenyl, $C_1$-$C_4$ alkoxy, $C_1$-$C_3$ haloalkyl, $C_1$-$C_3$ haloalkoxy, 3-8 membered heterocyclyl, —$C(O)$—$C_1$-$C_4$ alkoxy, —$C(O)$—$NH_2$, and —$S(O)_2$-$C_1$-$C_6$ alkyl;

$R_1$ and $R_2$ are independently selected from the group consisting of hydrogen, deuterium, halogen, $C_1$-$C_6$ alkyl, and $C_3$-$C_8$ cycloalkyl, wherein the $C_1$-$C_6$ alkyl, and $C_3$-$C_8$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy, or $R_1$ and $R_2$ together form a $C_3$-$C_6$ cycloalkyl;

$R_3$ and $R_3'$ are independently selected from the group consisting of hydrogen, $C_1$-$C_6$ alkyl, 3-6 membered cycloalkyl, and 3-8 membered heterocyclyl, wherein the $C_1$-$C_6$ alkyl, and $C_3$-$C_6$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_4$ is selected from the group consisting of hydrogen, deuterium, halogen, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_5$ is, independently at each occurrence, selected from the group consisting of hydrogen, $C_1$-$C_6$ alkyl, $C_3$-$C_8$ cycloalkyl, 3-8 membered heterocyclyl, and —$C(=O)$—$C_1$-$C_6$ alkyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are independently optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy; and ring A is $C_3$-$C_8$ cycloalkyl, 3- to 12-membered heterocyclyl, $C_6$-$C_{14}$ aryl, or 5- to 10-membered heteroaryl, wherein the $C_3$-$C_8$ cycloalkyl, 3- to 12-membered heterocyclyl, $C_6$-$C_{14}$ aryl, and 5- to 10-membered heteroaryl of ring A are optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen.

In some embodiments, provided is a compound of Formula (A), wherein $Q_2$ is C, $Q_3$ is N, $Q_4$ is N, $Q_5$ is C, and X is N, such that the compound of Formula (A) is a compound of Formula (IV):

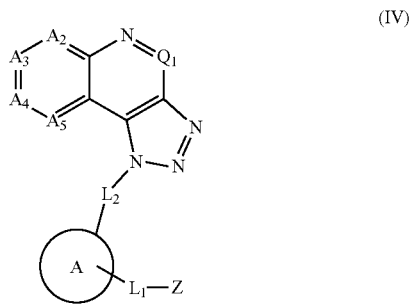

(IV)

or a pharmaceutically acceptable salt, stereoisomer, solvate, or prodrug thereof, wherein:

$L_1$ is a bond, O, $CR_1R_2$, $NR_3$, or *$CR_1R_2NR_3$, wherein * denotes the point of attachment to ring A;

$L_2$ is a bond, $CR_1R_2$, or C(=O);

$Q_1$ is N or C-E;

$A_2$, $A_3$, $A_4$ and $A_5$ are independently N or $CR_4$;

Z is $SO_2NHR_5$, $SO_2R_5$, C(O)OH, C(O)$NHR_5$, C(O)$NHOR_5$, P(O)($OR_5$)$_2$, or B(OH)$_2$;

E is selected from the group consisting of hydrogen, deuterium, halogen, oxo, —CN, —$OR_3$, —$NO_2$, —$NR_3R_3'$, —C(O)$R_3$, —C(O)$OR_3$, —C(O)$NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_1$-$C_4$ alkoxy, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, N($C_1$-$C_6$ alkyl)$_2$, $C_1$-$C_3$ alkyl, phenyl, $C_1$-$C_4$ alkoxy, $C_1$-$C_3$ haloalkyl, $C_1$-$C_3$ haloalkoxy, 3-8 membered heterocyclyl, —C(O)—$C_1$-$C_4$ alkoxy, —C(O)—$NH_2$, and —S(O)$_2$-$C_1$-$C_6$ alkyl;

$R_1$ and $R_2$ are independently selected from the group consisting of hydrogen, deuterium, halogen, $C_1$-$C_6$ alkyl, and $C_3$-$C_8$ cycloalkyl, wherein the $C_1$-$C_6$ alkyl, and $C_3$-$C_8$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy, or $R_1$ and $R_2$ together form a $C_3$-$C_6$ cycloalkyl;

$R_3$ and $R_3'$ are independently selected from the group consisting of hydrogen, $C_1$-$C_6$ alkyl, 3-6 membered cycloalkyl, and 3-8 membered heterocyclyl, wherein the $C_1$-$C_6$ alkyl, and $C_3$-$C_6$ cycloalkyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_4$ is selected from the group consisting of hydrogen, deuterium, halogen, —CN, —$OR_3$, —$NO_2$, —$NR_3R_3'$, —C(O)$R_3$, —C(O)$OR_3$, —C(O)$NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy;

$R_5$ is, independently at each occurrence, selected from the group consisting of hydrogen, $C_1$-$C_6$ alkyl, $C_3$-$C_8$ cycloalkyl, 3-8 membered heterocyclyl, and —C(=O)—$C_1$-$C_6$ alkyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are independently optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy; and ring A is $C_3$-$C_8$ cycloalkyl, 3- to 12-membered heterocyclyl, $C_6$-$C_{14}$ aryl, or 5- to 10-membered heteroaryl, wherein the $C_3$-$C_8$ cycloalkyl, 3- to 12-membered heterocyclyl, $C_6$-$C_{14}$ aryl, and 5- to 10-membered heteroaryl of ring A are optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen.

In some embodiments, provided is a compound of Formula (A), wherein $Q_2$ is C, $Q_3$ is N, $Q_4$ is C, and $Q_5$ is N, such that the compound of Formula (A) is a compound of Formula (V):

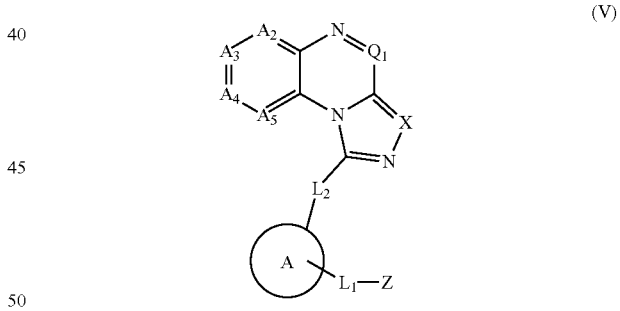

(V)

or a pharmaceutically acceptable salt, stereoisomer, solvate, or prodrug thereof, wherein:

$L_1$ is a bond, O, $CR_1R_2$, $NR_3$, or *$CR_1R_2NR_3$, wherein * denotes the point of attachment to ring A;

$L_2$ is a bond, $CR_1R_2$, or C(=O);

$Q_1$ and X are independently N or C-E;

$A_2$, $A_3$, $A_4$ and $A_5$ are independently N or $CR_4$;

Z is $SO_2NHR_5$, $SO_2R_5$, C(O)OH, C(O)$NHR_5$, C(O)$NHOR_5$, P(O)($OR_5$)$_2$, or B(OH)$_2$;

E is selected from the group consisting of hydrogen, deuterium, halogen, oxo, —CN, —$OR_3$, —$NO_2$, —$NR_3R_3'$, —C(O)$R_3$, —C(O)$OR_3$, —C(O)$NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_1$-$C_4$ alkoxy, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $N(C_1-C_6\ alkyl)_2$, $C_1-C_3$ alkyl, phenyl, $C_1-C_4$ alkoxy, $C_1-C_3$ haloalkyl, $C_1-C_3$ haloalkoxy, 3-8 membered heterocyclyl, —C(O)—$C_1-C_4$ alkoxy, —C(O)—$NH_2$, and —$S(O)_2$-$C_1-C_6$ alkyl;

$R_1$ and $R_2$ are independently selected from the group consisting of hydrogen, deuterium, halogen, $C_1-C_6$ alkyl, and $C_3-C_8$ cycloalkyl, wherein the $C_1-C_6$ alkyl, and $C_3-C_8$ cycloalkyl are optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy, or $R_1$ and $R_2$ together form a $C_3-C_6$ cycloalkyl;

$R_3$ and $R_3'$ are independently selected from the group consisting of hydrogen, $C_1-C_6$ alkyl, 3-6 membered cycloalkyl, and 3-8 membered heterocyclyl, wherein the $C_1-C_6$ alkyl, and $C_3-C_6$ cycloalkyl are optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy;

$R_4$ is selected from the group consisting of hydrogen, deuterium, halogen, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1-C_6$ alkyl, $C_2-C_6$ alkenyl, $C_2-C_6$ alkynyl, $C_3-C_8$ cycloalkyl, and 3-8 membered heterocyclyl, wherein the $C_1-C_6$ alkyl, $C_2-C_6$ alkenyl, $C_2-C_6$ alkynyl, $C_3-C_8$ cycloalkyl, and 3-8 membered heterocyclyl are optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy;

$R_5$ is, independently at each occurrence, selected from the group consisting of hydrogen, $C_1-C_6$ alkyl, $C_3-C_8$ cycloalkyl, 3-8 membered heterocyclyl, and —C(=O)—$C_1-C_6$ alkyl, wherein the $C_1-C_6$ alkyl, $C_2-C_6$ alkenyl, $C_2-C_6$ alkynyl, $C_3-C_8$ cycloalkyl, and 3-8 membered heterocyclyl are independently optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy; and ring A is $C_3-C_8$ cycloalkyl, 3- to 12-membered heterocyclyl, $C_6-C_{14}$ aryl, or 5- to 10-membered heteroaryl, wherein the $C_3-C_8$ cycloalkyl, 3- to 12-membered heterocyclyl, $C_6-C_{14}$ aryl, and 5- to 10-membered heteroaryl of ring A are optionally substituted with one or more substituents selected from the group consisting of halogen, CN, OH, $NH_2$, $C_1-C_3$ alkyl, and $C_1-C_4$ alkoxy, wherein the $C_1-C_3$ alkyl and $C_1-C_4$ alkoxy are independently optionally substituted with one or more halogen.

In some embodiments, provided is a compound of Formula (A), wherein $Q_2$ is N, $Q_4$ is C, and $Q_5$ is C, such that the compound of Formula (A) is a compound of Formula (VI):

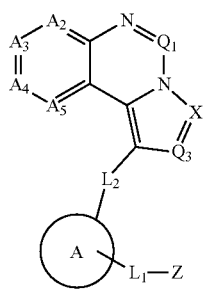

(VI)

or a pharmaceutically acceptable salt, stereoisomer, solvate, or prodrug thereof, wherein:

$L_1$ is a bond, O, $CR_1R_2$, $NR_3$, or *$CR_1R_2NR_3$, wherein * denotes the point of attachment to ring A;

$L_2$ is a bond, $CR_1R_2$, or C(=O);

$Q_1$, $Q_3$ and X are independently N or C-E;

$A_2$, $A_3$, $A_4$ and $A_5$ are independently N or $CR_4$;

Z is $SO_2NHR_5$, $SO_2R_5$, C(O)OH, $C(O)NHR_5$, $C(O)NHOR_5$, $P(O)(OR_5)_2$, or $B(OH)_2$;

E is, independently at each occurrence, selected from the group consisting of hydrogen, deuterium, halogen, oxo, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1-C_6$ alkyl, $C_2-C_6$ alkenyl, $C_2-C_6$ alkynyl, $C_1-C_4$ alkoxy, $C_3-C_8$ cycloalkyl, and 3-8 membered heterocyclyl, wherein the $C_1-C_6$ alkyl, $C_2-C_6$ alkenyl, $C_2-C_6$ alkynyl, $C_3-C_8$ cycloalkyl, and 3-8 membered heterocyclyl are optionally substituted with one or more substituents selected from the group consisting of halogen, CN, OH, $NH_2$, $N(C_1-C_6\ alkyl)_2$, $C_1-C_3$ alkyl, phenyl, $C_1-C_4$ alkoxy, $C_1-C_3$ haloalkyl, $C_1-C_3$ haloalkoxy, 3-8 membered heterocyclyl, —C(O)—$C_1-C_4$ alkoxy, —C(O)—$NH_2$, and —$S(O)_2$-$C_1-C_6$ alkyl;

$R_1$ and $R_2$ are independently selected from the group consisting of hydrogen, deuterium, halogen, $C_1-C_6$ alkyl, and $C_3-C_8$ cycloalkyl, wherein the $C_1-C_6$ alkyl, and $C_3-C_8$ cycloalkyl are optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy, or $R_1$ and $R_2$ together form a $C_3-C_6$ cycloalkyl;

$R_3$ and $R_3'$ are independently selected from the group consisting of hydrogen, $C_1-C_6$ alkyl, 3-6 membered cycloalkyl, and 3-8 membered heterocyclyl, wherein the $C_1-C_6$ alkyl, and $C_3-C_6$ cycloalkyl are optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy;

$R_4$ is selected from the group consisting of hydrogen, deuterium, halogen, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1-C_6$ alkyl, $C_2-C_6$ alkenyl, $C_2-C_6$ alkynyl, $C_3-C_8$ cycloalkyl, and 3-8 membered heterocyclyl, wherein the $C_1-C_6$ alkyl, $C_2-C_6$ alkenyl, $C_2-C_6$ alkynyl, $C_3-C_8$ cycloalkyl, and 3-8 membered heterocyclyl are optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy;

$R_5$ is, independently at each occurrence, selected from the group consisting of hydrogen, $C_1-C_6$ alkyl, $C_3-C_8$ cycloalkyl, 3-8 membered heterocyclyl, and —C(=O)—$C_1-C_6$ alkyl, wherein the $C_1-C_6$ alkyl, $C_2-C_6$ alkenyl, $C_2-C_6$ alkynyl, $C_3-C_8$ cycloalkyl, and 3-8 membered heterocyclyl are independently optionally substituted with one or more substituents selected from the group consisting of halogen, CN, OH, $NH_2$, $C_1-C_3$ alkyl, phenyl, $C_1-C_4$ alkoxy, $C_1-C_3$ haloalkyl, and $C_1-C_3$ haloalkoxy; and ring A is $C_3-C_8$ cycloalkyl, 3- to 12-membered heterocyclyl, $C_6-C_{14}$ aryl, or 5- to 10-membered heteroaryl, wherein the $C_3-C_8$ cycloalkyl, 3- to 12-membered heterocyclyl, $C_6-C_{14}$ aryl, and 5- to 10-membered heteroaryl of ring A are optionally substituted with one or more substituents selected from the group consisting of halogen, CN, OH, $NH_2$, $C_1-C_3$ alkyl, and $C_1-C_4$ alkoxy, wherein the $C_1-C_3$ alkyl and $C_1-C_4$ alkoxy are independently optionally substituted with one or more halogen.

In some embodiments, provided herein is a compound of formula (A), such as a compound of formula (I)-(VI), or a pharmaceutically acceptable salt, stereoisomer, solvate, or prodrug thereof, wherein ring B is fully unsaturated. In other embodiments, ring B is partially unsaturated. In some embodiments, ring B is a 5-membered aryl or 5-membered heteroaryl. In other embodiments, ring B is a 5-membered heterocyclyl or 5-membered cycloalkyl.

In some embodiments, provided herein is a compound of formula (A), such as a compound of formula (I)-(VI), or a pharmaceutically acceptable salt, stereoisomer, solvate, or prodrug thereof, wherein $A_2$, $A_3$, $A_4$ and $A_5$ are each independently N or $CR_4$, wherein $R_4$ is, independently at each occurrence, selected from the group consisting of hydrogen, deuterium, halogen, —CN, —$OR_3$, —$NO_2$, —$NR_3R_3'$, —$C(O)R_3$, —$C(O)OR_3$, —$C(O)NR_3R_3'$, —$SO_2R_3$, —$SO_2NR_3R_3'$, $C_1$-$C_6$ alkyl, $C_2$-$C_6$ alkenyl, $C_2$-$C_6$ alkynyl, $C_3$-$C_8$ cycloalkyl, and 3-8 membered heterocyclyl, wherein the $C_1$-$C_6$ alkyl, $C_2$-$C_6$ alkenyl, $C_2$-$C_6$ alkynyl, $C_3$-$C_8$ cycloalkyl, and 3-8 membered heterocyclyl are optionally substituted with one or more substituents selected from the group consisting of halogen, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy. In some embodiments, $A_2$, $A_3$, $A_4$ and $A_5$ are each independently $CR_4$, wherein $R_4$ is, independently of each other and independently at each occurrence, H, $C_1$-$C_4$ alkoxy, or CN. In some embodiments, $A_2$ is CH, $A_3$ is C—$C_1$-$C_4$ alkoxy, $A_4$ is C—$C_1$-$C_4$ alkoxy, and $A_5$ is CH. In some embodiments, $A_2$ is CH, $A_3$ is C—OMe, $A_4$ is C—OMe, and $A_5$ is CH. In some embodiments, $A_2$ is CH, $A_3$ is C—$C_1$-$C_4$ alkoxy, $A_4$ is CH, and $A_5$ is CH. In some embodiments, $A_2$ is CH, $A_3$ is C—OMe, $A_4$ is CH, and $A_5$ is CH. In some embodiments, $A_2$ is CH, $A_3$ is CH, $A_4$ is C—$C_1$-$C_4$ alkoxy, and $A_5$ is CH. In some embodiments, $A_2$ is CH, $A_3$ is CH, $A_4$ is C—OMe, and $A_5$ is CH. In some embodiments, $A_2$ is CH, $A_3$ is C—$C_1$-$C_4$ alkoxy, $A_4$ is CN, and $A_5$ is CH. In some embodiments, $A_2$ is CH, $A_3$ is C—OMe, $A_4$ is CN, and $A_5$ is CH. In some embodiments, $A_2$ is CH, $A_3$ is C—$C_1$-$C_4$ alkoxy, $A_4$ is N, and $A_5$ is CH. In some embodiments, $A_2$ is CH, $A_3$ is C—OMe, $A_4$ is N, and $A_5$ is CH. In some embodiments, $A_2$ is N, $A_3$ is C—$C_1$-$C_4$ alkoxy, $A_4$ is CH, and $A_5$ is CH. In some embodiments, $A_2$ is N, $A_3$ is C—OMe, $A_4$ is CH, and $A_5$ is CH. In some embodiments, $A_2$ is CH, $A_3$ is C—$C_1$-$C_4$ alkoxy, $A_4$ is CH, and $A_5$ is N. In some embodiments, $A_2$ is CH, $A_3$ is C—OMe, $A_4$ is CH, and $A_5$ is N. In some embodiments, $A_2$ is CH, $A_3$ is C—$C_1$-$C_4$ alkoxy, $A_4$ is N, and $A_5$ is CH. In some embodiments, $A_2$ is CH, $A_3$ is C—OMe, $A_4$ is N, and $A_5$ is CH. In some embodiments, $A_2$ is N, $A_3$ is C—$C_1$-$C_4$ alkoxy, $A_4$ is C-halogen, and $A_5$ is CH. In some embodiments, $A_2$ is N, $A_3$ is C—OMe, $A_4$ is C—$C_1$, and $A_5$ is CH.

In some embodiments, provided herein is a compound of formula (I), or a pharmaceutically acceptable salt, stereoisomer, solvate, or prodrug thereof, wherein $A_2$ is CH, $A_3$ is C—$C_1$-$C_4$ alkoxy, $A_4$ is C—$C_1$-$C_4$ alkoxy, and $A_5$ is CH. In some embodiments, provided herein is a compound of formula (I), or a pharmaceutically acceptable salt, stereoisomer, solvate, or prodrug thereof, wherein $A_2$ is CH, $A_3$ is C—OMe, $A_4$ is C—OMe, and $A_5$ is CH. In some embodiments, provided herein is a compound of formula (II), or a pharmaceutically acceptable salt, stereoisomer, solvate, or prodrug thereof, wherein $A_2$ is CH, $A_3$ is C—$C_1$-$C_4$ alkoxy, $A_4$ is C—$C_1$-$C_4$ alkoxy, and $A_5$ is CH. In some embodiments, provided herein is a compound of formula (II), or a pharmaceutically acceptable salt, stereoisomer, solvate, or prodrug thereof, wherein $A_2$ is, $A_3$ is C—OMe, $A_4$ is C—OMe, and $A_5$ is CH. In some embodiments, provided herein is a compound of formula (II), or a pharmaceutically acceptable salt, stereoisomer, solvate, or prodrug thereof, wherein $A_2$ is N, $A_3$ is C—$C_1$-$C_4$ alkoxy, $A_4$ is CH, and $A_5$ is CH. In some embodiments, provided herein is a compound of formula (II), or a pharmaceutically acceptable salt, stereoisomer, solvate, or prodrug thereof, wherein $A_2$ is N, $A_3$ is C—OMe, $A_4$ is CH, and $A_5$ is CH.

In some embodiments, provided herein is a compound of formula (A), such as a compound of formula (I)-(VI), or a pharmaceutically acceptable salt, stereoisomer, solvate, or prodrug thereof, wherein ring A is $C_3$-$C_8$ cycloalkyl, 3- to 12-membered heterocyclyl, $C_6$-$C_{14}$ aryl, or 5- to 10-membered heteroaryl, wherein the $C_3$-$C_8$ cycloalkyl, 3- to 12-membered heterocyclyl, $C_6$-$C_{14}$ aryl, and 5- to 10-membered heteroaryl of ring A are optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen.

In some embodiments, provided herein is a compound of formula (A), such as a compound of formula (I)-(VI), or a pharmaceutically acceptable salt, stereoisomer, solvate, or prodrug thereof, wherein ring A is $C_3$-$C_8$ cycloalkyl, wherein the $C_3$-$C_8$ cycloalkyl of ring A is optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen. In some embodiments, ring A is cyclobutyl.

In some embodiments, provided herein is a compound of formula (A), such as a compound of formula (I)-(VI), or a pharmaceutically acceptable salt, stereoisomer, solvate, or prodrug thereof, wherein ring A is 3- to 12-membered heterocyclyl, wherein the 3- to 12-membered heterocyclyl of ring A is optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen. In some embodiments, ring A is a 4- to 8-membered heterocyclyl. In some embodiments, ring A is a 5- or 6-membered heterocyclyl. In some embodiments, ring A is piperazinyl. In some embodiments, ring A is azetidinyl. In certain embodiments, ring A is piperidinyl. In other embodiments, ring A is pyrrolidinyl.

In some embodiments, provided herein is a compound of formula (A), such as a compound of formula (I)-(VI), or a pharmaceutically acceptable salt, stereoisomer, solvate, or prodrug thereof, wherein ring A is $C_6$-$C_{14}$ aryl, wherein the $C_6$-$C_{14}$ aryl of ring A is optionally substituted with one or more substituents selected from the group consisting of halogen, CN, OH, $NH_2$, $C_1$-$C_3$ alkyl, and $C_1$-$C_4$ alkoxy, wherein the $C_1$-$C_3$ alkyl and $C_1$-$C_4$ alkoxy are independently optionally substituted with one or more halogen. In some embodiments, ring A is $C_6$-$C_{10}$ aryl. In some embodiments, ring A is phenyl. In some embodiments, ring A is phenyl, wherein the phenyl of ring A is optionally substituted with one or more halogen, CN, $C_1$-$C_3$ alkyl, or $C_1$-$C_4$ alkoxy, wherein the $C_1$-$C_3$ alkyl and $C_1$-$C_4$ alkoxy are independently optionally substituted with one or more halogen. In some embodiments, the halogen is F.

In some embodiments, provided herein is a compound of formula (A), such as a compound of formula (I)-(VI), or a pharmaceutically acceptable salt, stereoisomer, solvate, or prodrug thereof, wherein ring A is 5- to 10-membered heteroaryl, wherein the 5- to 10-membered heteroaryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In some embodiments, ring A is 5- or 6-membered heteroaryl. In some embodiments, ring A is 6-membered heteroaryl. In some embodiments, ring A is pyridinyl. In other embodiments, ring A is pyrimidinyl. In some embodiments, ring A is pyridinyl or pyrimidinyl, wherein the pyridinyl or pyrimidinyl of ring A is optionally substituted with one or more halogen, CN, C$_1$-C$_3$ alkyl, or C$_1$-C$_4$ alkoxy, wherein the C$_1$-C$_3$ alkyl and C$_1$-C$_4$ alkoxy are independently optionally substituted with one or more halogen. In some embodiments, the halogen is F. In some embodiments, ring A is dihydroisoquinolinyl.

In some embodiments, provided herein is a compound of formula (A), such as a compound of formula (I)-(VI), or a pharmaceutically acceptable salt, stereoisomer, solvate, or prodrug thereof, wherein L$_1$ is a bond, O, CR$_1$R$_2$, NR$_3$, or *CR$_1$R$_2$NR$_3$, wherein * denotes the point of attachment to ring A. In some embodiments, L$_1$ is a bond. In other embodiments, L$_1$ is O, CR$_1$R$_2$, NR$_3$, or *CR$_1$R$_2$NR$_3$, wherein * denotes the point of attachment to ring A. In some embodiments, L$_1$ is O. In certain embodiments, L$_1$ is CR$_1$R$_2$. In some embodiments, L$_1$ is CR$_1$R$_2$, wherein R$_1$ and R$_2$ are independently selected from H and C$_1$-C$_6$ alkyl. In some embodiments, L$_1$ is CR$_1$R$_2$, wherein R$_1$ and R$_2$ are independently selected from H and methyl. In some embodiments, L$_1$ is CR$_1$R$_2$, wherein R$_1$ and R$_2$ are both H. In some embodiments, L$_1$ is CR$_1$R$_2$, wherein one of R$_1$ and R$_2$ is H and the other of R$_1$ and R$_2$ is C$_1$-C$_6$ alkyl. In some embodiments, L$_1$ is CR$_1$R$_2$, wherein one of R$_1$ and R$_2$ is H and the other of R$_1$ and R$_2$ is methyl. In other embodiments, L$_1$ is NR$_3$. In some embodiments, L$_1$ is NR$_3$, wherein R$_3$ is H or C$_1$-C$_6$ alkyl. In some embodiments, L$_1$ is NR$_3$, wherein R$_3$ is H. In other embodiments, L$_1$ is NR$_3$, wherein R$_3$ is methyl. In some embodiments, L$_1$ is *CR$_1$R$_2$NR$_3$, wherein * denotes the point of attachment to ring A. In certain embodiments, L$_1$ is *CR$_1$R$_2$NR$_3$, wherein * denotes the point of attachment to ring A, wherein R$_1$ and R$_2$ are both H.

In some embodiments, provided herein is a compound of formula (A), such as a compound of formula (I)-(VI), or a pharmaceutically acceptable salt, stereoisomer, solvate, or prodrug thereof, wherein L$_1$ is a bond, O, CR$_1$R$_2$, NR$_3$, or *CR$_1$R$_2$NR$_3$, wherein * denotes the point of attachment to ring A, and ring A is C$_6$-C$_{14}$ aryl, wherein the C$_6$-C$_{14}$ aryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen.

In some embodiments, L$_1$ is a bond and ring A is C$_6$-C$_{14}$ aryl, wherein the C$_6$-C$_{14}$ aryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In some embodiments, L$_1$ is a bond and ring A is phenyl, wherein the phenyl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen.

In some embodiments, L$_1$ is CR$_1$R$_2$, wherein R$_1$ and R$_2$ are independently selected from H and C$_1$-C$_6$ alkyl, and ring A is C$_6$-C$_{14}$ aryl, wherein the C$_6$-C$_{14}$ aryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In some embodiments, L$_1$ is CR$_1$R$_2$, wherein R$_1$ and R$_2$ are independently selected from H and C$_1$-C$_6$ alkyl, and ring A is phenyl, wherein the phenyl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In certain embodiments, L$_1$ is *CR$_1$R$_2$NR$_3$, wherein * denotes the point of attachment to ring A, wherein R$_1$, R$_2$ and R$_3$ are each H, and ring A is phenyl, wherein the phenyl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen.

In some embodiments, L$_1$ is a bond and ring A is 5- to 10-membered heteroaryl, wherein the 5- to 10-membered heteroaryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In some embodiments, L$_1$ is a bond and ring A is 6-membered heteroaryl, wherein the 6-membered heteroaryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In some embodiments, L$_1$ is a bond and ring A is pyridinyl or pyrimidinyl, wherein the pyridinyl or pyrimidinyl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen.

In some embodiments, L$_1$ is CR$_1$R$_2$, wherein R$_1$ and R$_2$ are independently selected from H and C$_1$-C$_6$ alkyl, and ring A is 5- to 10-membered heteroaryl, wherein the 5- to 10-membered heteroaryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. L$_1$ is CR$_1$R$_2$, wherein R$_1$ and R$_2$ are independently selected from H and C$_1$-C$_6$ alkyl, and ring A is 6-membered heteroaryl, wherein the 6-membered heteroaryl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In some embodiments, L$_1$ is CR$_1$R$_2$, wherein R$_1$ and R$_2$ are independently selected from H and C$_1$-C$_6$ alkyl, and ring A is pyridinyl or pyrimidinyl, wherein the pyridinyl or pyrimidinyl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In certain embodiments, L$_1$ is *CR$_1$R$_2$NR$_3$, wherein * denotes the point of attachment to ring A, wherein R$_1$, R$_2$ and R$_3$ are each H, and ring A is pyridinyl or pyrimidinyl, wherein the pyridinyl or pyrimidinyl of ring A is optionally substituted with one or more substituents selected from the group consisting of halogen, CN, OH, NH$_2$, C$_1$-C$_3$ alkyl, and C$_1$-C$_4$ alkoxy, wherein the C$_1$-C$_3$ alkyl and C$_1$-C$_4$ alkoxy are independently optionally substituted with one or more halogen. In some embodiments, provided herein is a compound of formula (A), such as a compound of formula (I)-(VI), or a pharmaceutically acceptable salt, stereoisomer, solvate, or prodrug thereof, wherein $L_2$ is a bond, $CR_1R_2$, or $C(=O)$. In some embodiments, $L_2$ is a bond. In some embodiments, $L_2$ is O. In certain embodiments, $L_2$ is $CR_1R_2$. In some embodiments, $L_2$ is $CR_1R_2$, wherein $R_1$ and $R_2$ are independently selected from H and $C_1$-$C_6$ alkyl. In some embodiments, $L_2$ is $CR_1R_2$, wherein $R_1$ and $R_2$ are independently selected from H and methyl. In some embodiments, $L_2$ is $CR_1R_2$, wherein $R_1$ and $R_2$ are both H. In some embodiments, $L_2$ is $CR_1R_2$, wherein one of $R_1$ and $R_2$ is H and the other of $R_1$ and $R_2$ is $C_1$-$C_6$ alkyl. In some embodiments, $L_2$ is $CR_1R_2$, wherein one of $R_1$ and $R_2$ is H and the other of $R_1$ and $R_2$ is methyl. In some embodiments, $L_2$ is $C(=O)$.

In some embodiments, provided herein is a compound of formula (A), such as a compound of formula (I)-(VI), as applicable, or a pharmaceutically acceptable salt, stereoisomer, solvate, or prodrug thereof, wherein X is S, O, $CR_1R_2$, C-E, N or $NR_3$. In some embodiments, X is O, $CR_1R_2$, C-E, N or $NR_3$. In some embodiments, X is O. In certain embodiments, X is N. In some embodiments, X is $NR_3$. In other embodiments, X is $NR_3$, wherein $R_3$ is H or $C_1$-$C_6$ alkyl. In some embodiments, X is C-E. In some embodiments, X is C-E, wherein E is H or $C_1$-$C_6$ alkyl, wherein the $C_1$-$C_6$ alkyl of E is optionally substituted with one or more OH, halogen, $C_1$-$C_4$ alkoxy, or 3-8 membered heterocyclyl. In some embodiments, X is N or C-E.

In some embodiments, provided herein is a compound of formula (A), such as a compound of formula (I)-(VI), or a pharmaceutically acceptable salt, stereoisomer, solvate, or prodrug thereof, wherein Z is $SO_2NHR_5$, $SO_2R_5$, C(O)OH, C(O)$NHR_5$, C(O)$NHOR_5$, P(O)(OR$_5$)$_2$, or B(OH)$_2$. In some embodiments, Z is $SO_2NHR_5$, wherein $R_5$ is H, $C_1$-$C_6$ alkyl, or —C(O)—$C_1$-$C_6$ alkyl. In some embodiments, Z is $SO_2NHR_5$, wherein $R_5$ is H. In some embodiments, Z is $SO_2R_5$. In certain embodiments, Z is C(O)OH, C(O)$NHR_5$, or C(O)$NHOR_5$. In certain embodiments, Z is C(O)OH. In some embodiments, Z is C(O)$NHOR_5$, wherein $R_5$ is H. In some embodiments, Z is C(O)$NHR_5$, wherein $R_5$ is H. In some embodiments, Z is B(OH)$_2$. In some embodiments, Z is P(O)(OR$_5$)$_2$, wherein each $R_5$ is independently H or $C_1$-$C_6$ alkyl. In some embodiments, Z is P(O)(OR$_5$)$_2$, wherein each $R_5$ is independently H.

Representative compounds are listed in Table 1. In some embodiments, provided herein is a compound of formula (A), such as a compound of formula (I)-(VI), or a pharmaceutically acceptable salt, stereoisomer, solvate, or prodrug thereof, wherein $L_1$ is a bond and Z is $SO_2NHR_5$, wherein $R_5$ is H, $C_1$-$C_6$ alkyl, or —C(O)—$C_1$-$C_6$ alkyl. In some embodiments, $L_1$ is a bond and Z is $SO_2NHR_5$, wherein $R_5$ is H. In other embodiments, $L_1$ is a bond and Z is $SO_2NHR_5$, wherein $R_5$ is $C_1$-$C_6$ alkyl. $L_1$ is $NR_3$, wherein $R_3$ is H, and Z is $SO_2NHR_5$, wherein $R_5$ is H, $C_1$-$C_6$ alkyl, or —C(O)—$C_1$-$C_6$ alkyl. In some embodiments, $L_1$ is $NR_3$, wherein $R_3$ is H, and Z is $SO_2NHR_5$, wherein $R_5$ is H. In some embodiments, $L_1$ is $CR_1R_2$, wherein $R_1$ and $R_2$ are independently selected from H and $C_1$-$C_6$ alkyl, and Z is $SO_2NHR_5$, wherein $R_5$ is H, $C_1$-$C_6$ alkyl, or —C(O)—$C_1$-$C_6$ alkyl. In some embodiments, $L_1$ is $CR_1R_2$, wherein $R_1$ and $R_2$ are independently selected from H and $C_1$-$C_6$ alkyl, and Z is $SO_2NHR_5$, wherein $R_5$ is H. In some embodiments, $L_1$ is a bond and Z is P(O)(OR$_5$)$_2$, wherein each $R_5$ is independently H or $C_1$-$C_6$ alkyl. In some embodiments, $L_1$ is a bond and Z is B(OH)$_2$. In some embodiments, $L_1$ is a bond and Z is C(O)OH, C(O)$NHR_5$, or C(O)$NHOR_5$. In some embodiments, $L_1$ is a bond and Z is C(O)OH, C(O)$NHR_5$, or C(O)$NHOR_5$, wherein each $R_5$ is independently H.

Representative compounds are listed in Table 1.

TABLE 1

| # | Structure | Name |
|---|-----------|------|
| 1 | ![structure] | 4-((7,8-dimethoxy-2-oxo-2,3-dihydro-1H-imidazo[4,5-c]quinolin-1-yl)methyl)benzenesulfonamide |
| 2 | ![structure] | 4-((7,8-dimethoxy-3-methyl-2-oxo-2,3-dihydro-1H-imidazo[4,5-c]quinolin-1-yl)methyl)benzenesulfonamide |

TABLE 1-continued

| # | Structure | Name |
|---|---|---|
| 3a | 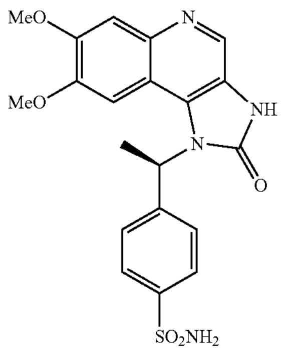 [SMILES: COc1cc2ncc3[nH]c(=O)n([C@H](C)c4ccc(S(N)(=O)=O)cc4)c3c2cc1OC] | (R)-4-(1-(7,8-dimethoxy-2-oxo-2,3-dihydro-1H-imidazo[4,5-c]quinolin-1-yl)ethyl)benzenesulfonamide |
| 3b | 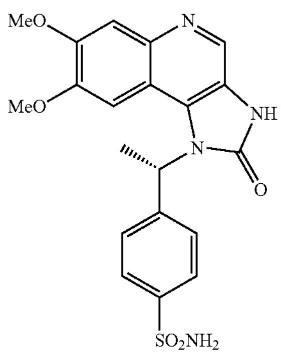 [SMILES: COc1cc2ncc3[nH]c(=O)n([C@@H](C)c4ccc(S(N)(=O)=O)cc4)c3c2cc1OC] | (S)-4-(1-(7,8-dimethoxy-2-oxo-2,3-dihydro-1H-imidazo[4,5-c]quinolin-1-yl)ethyl)benzenesulfonamide |
| 4 | 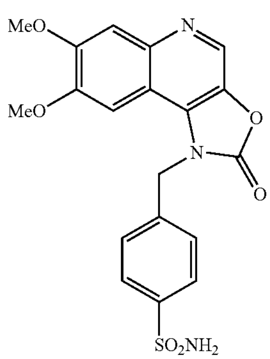 [SMILES: COc1cc2ncc3oc(=O)n(Cc4ccc(S(N)(=O)=O)cc4)c3c2cc1OC] | 4-((7,8-dimethoxy-2-oxooxazolo[5,4-c]quinolin-1(2H)-yl)methyl)benzenesulfonamide |
| 5 | 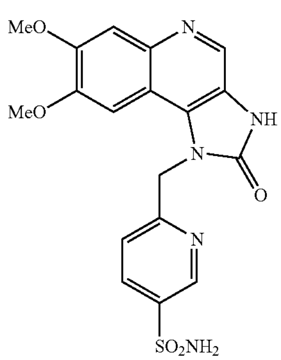 [SMILES: COc1cc2ncc3[nH]c(=O)n(Cc4ccc(S(N)(=O)=O)cn4)c3c2cc1OC] | 6-((7,8-dimethoxy-2-oxo-2,3-dihydro-1H-imidazo[4,5-c]quinolin-1-yl)methyl)pyridine-3-sulfonamide |

TABLE 1-continued

| # | Structure | Name |
|---|---|---|
| 6 | 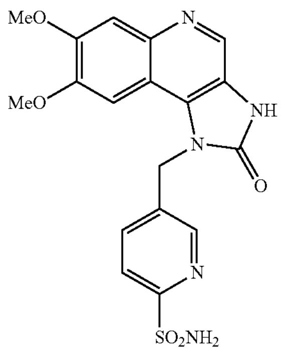 [SMILES: COc1cc2ncc3[nH]c(=O)n(Cc4ccc(S(N)(=O)=O)nc4)c3c2cc1OC] | 5-((6,7-dimethoxyquinazolin-4-yl)ethynyl)pyridine-3-sulfonamide |
| 7 | 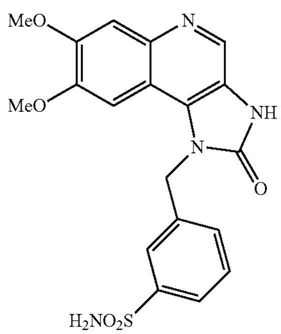 [SMILES: COc1cc2ncc3[nH]c(=O)n(Cc4cccc(S(N)(=O)=O)c4)c3c2cc1OC] | 3-((7,8-dimethoxy-2-oxo-2,3-dihydro-1H-imidazo[4,5-c]quinolin-1-yl)methyl)benzenesulfonamide |
| 8 | 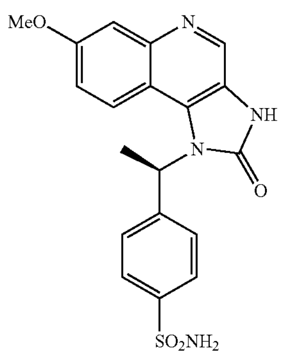 [SMILES: COc1ccc2c(c1)ncc1[nH]c(=O)n([C@H](C)c3ccc(S(N)(=O)=O)cc3)c12] | (R)-4-(1-(7-methoxy-2-oxo-2,3-dihydro-1H-imidazo[4,5-c]quinolin-1-yl)ethyl)benzenesulfonamide |
| 9 | 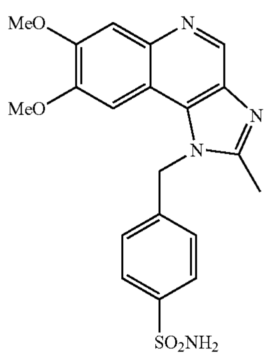 [SMILES: COc1cc2ncc3nc(C)n(Cc4ccc(S(N)(=O)=O)cc4)c3c2cc1OC] | 4-((7,8-dimethoxy-2-methyl-1H-imidazo[4,5-c]quinolin-1-yl)methyl)benzenesulfonamide |

TABLE 1-continued

| # | Structure | Name |
|---|---|---|
| 10 | 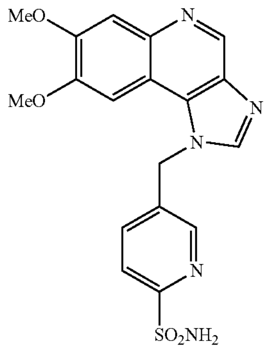 [SMILES: COc1cc2ncc3ncn(Cc4ccc(S(N)(=O)=O)nc4)c3c2cc1OC] | 5-((7,8-dimethoxy-1H-imidazo[4,5-c]quinolin-1-yl)methyl)pyridine-2-sulfonamide |
| 11a | 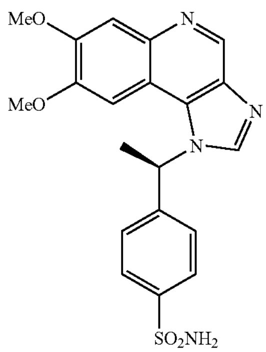 [SMILES: COc1cc2ncc3ncn([C@H](C)c4ccc(S(N)(=O)=O)cc4)c3c2cc1OC] | (R)-4-(1-(7,8-dimethoxy-1H-imidazo[4,5-c]quinolin-1-yl)ethyl)benzenesulfonamide |
| 11b | 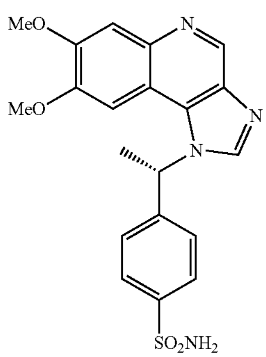 [SMILES: COc1cc2ncc3ncn([C@@H](C)c4ccc(S(N)(=O)=O)cc4)c3c2cc1OC] | (S)-4-(1-(7,8-dimethoxy-1H-imidazo[4,5-c]quinolin-1-yl)ethyl)benzenesulfonamide |
| 12 | 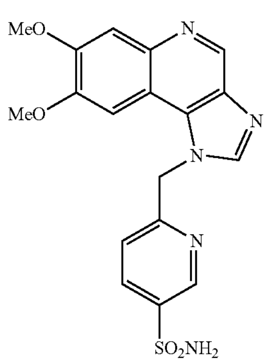 | 6-((7,8-dimethoxy-1H-imidazo[4,5-c]quinolin-1-yl)methyl)pyridine-3-sulfonamide |

TABLE 1-continued

| # | Structure | Name |
|---|---|---|
| 13 | 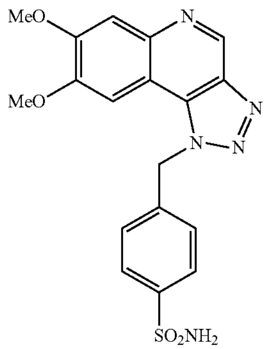 [SMILES: COc1cc2ncc3nnn(Cc4ccc(S(N)(=O)=O)cc4)c3c2cc1OC] | 4-((7,8-dimethoxy-1H-[1,2,3]triazolo[4,5-c]quinolin-1-yl)methyl)benzenesulfonamide |
| 14a | 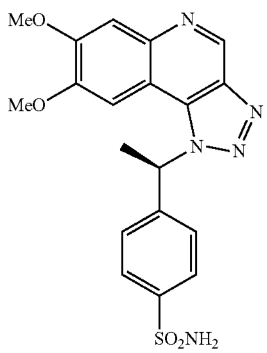 [SMILES: COc1cc2ncc3nnn([C@H](C)c4ccc(S(N)(=O)=O)cc4)c3c2cc1OC] | (R)-4-(1-(7,8-dimethoxy-1H-[1,2,3]triazolo[4,5-c]quinolin-1-yl)ethyl)benzenesulfonamide |
| 14b | 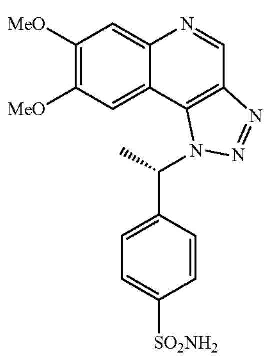 [SMILES: COc1cc2ncc3nnn([C@@H](C)c4ccc(S(N)(=O)=O)cc4)c3c2cc1OC] | (S)-4-(1-(7,8-dimethoxy-1H-[1,2,3]triazolo[4,5-c]quinolin-1-yl)ethyl)benzenesulfonamide |
| 15 | 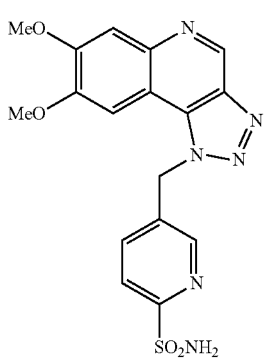 [SMILES: COc1cc2ncc3nnn(Cc4ccc(S(N)(=O)=O)nc4)c3c2cc1OC] | 5-((7,8-dimethoxy-1H-[1,2,3]triazolo[4,5-c]quinolin-1-yl)methyl)pyridine-2-sulfonamide |

TABLE 1-continued

| # | Structure | Name |
|---|---|---|
| 16 | 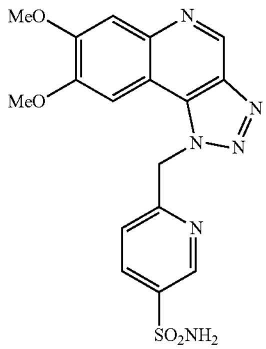 [SMILES: COc1cc2ncc3nnn(Cc4ccc(S(N)(=O)=O)cn4)c3c2cc1OC] | 6-((7,8-dimethoxy-1H-[1,2,3]triazolo[4,5-c]quinolin-1-yl)methyl)pyridine-3-sulfonamide |
| 17 | 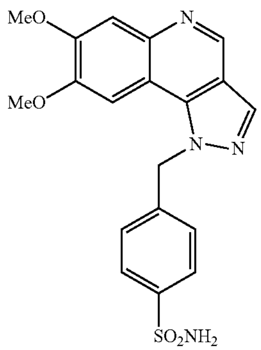 [SMILES: COc1cc2ncc3cnn(Cc4ccc(S(N)(=O)=O)cc4)c3c2cc1OC] | 4-((7,8-dimethoxy-1H-pyrazolo[4,3-c]quinolin-1-yl)methyl)benzenesulfonamide |
| 18 | 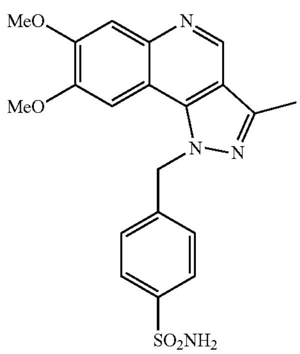 [SMILES: COc1cc2ncc3c(C)nn(Cc4ccc(S(N)(=O)=O)cc4)c3c2cc1OC] | 4-((7,8-dimethoxy-3-methyl-1H-pyrazolo[4,3-c]quinolin-1-yl)methyl)benzenesulfonamide |
| 19a | 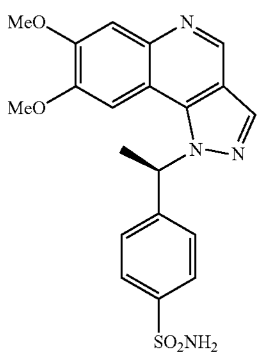 [SMILES: COc1cc2ncc3cnn([C@H](C)c4ccc(S(N)(=O)=O)cc4)c3c2cc1OC] | (R)-4-(1-(7,8-dimethoxy-1H-pyrazolo[4,3-c]quinolin-1-yl)ethyl)benzenesulfonamide |

TABLE 1-continued
| # | Structure | Name |
|---|---|---|
| 19b | 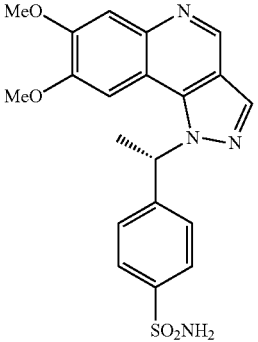 [SMILES: COc1cc2ncc3cnn([C@@H](C)c4ccc(S(N)(=O)=O)cc4)c3c2cc1OC] | (S)-4-(1-(7,8-dimethoxy-1H-pyrazolo[4,3-c]quinolin-1-yl)ethyl)benzenesulfonamide |
| 20 | 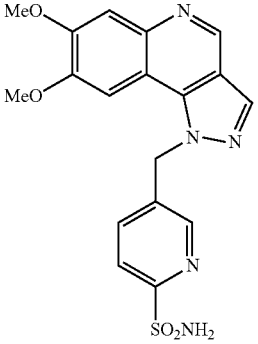 [SMILES: COc1cc2ncc3cnn(Cc4ccc(S(N)(=O)=O)nc4)c3c2cc1OC] | 5-((7,8-dimethoxy-1H-pyrazolo[4,3-c]quinolin-1-yl)methyl)pyridine-2-sulfonamide |
| 21 | 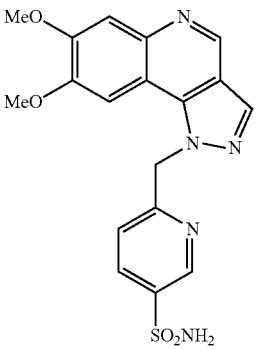 [SMILES: COc1cc2ncc3cnn(Cc4ccc(S(N)(=O)=O)cn4)c3c2cc1OC] | 6-((7,8-dimethoxy-1H-pyrazolo[4,3-c]quinolin-1-yl)methyl)pyridine-3-sulfonamide |
| 22 | 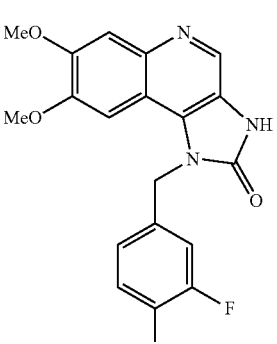 | 4-((7,8-dimethoxy-2-oxo-2,3-dihydro-1H-imidazo[4,5-c]quinolin-1-yl)methyl)-2-fluorobenzenesulfonamide |

TABLE 1-continued

| # | Structure | Name |
|---|---|---|
| 23 | 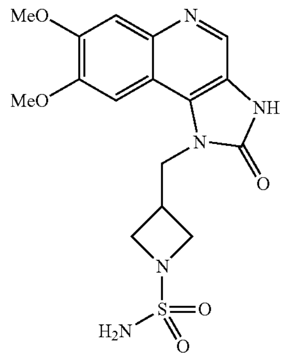 [SMILES: COc1cc2ncc3[nH]c(=O)n(CC4CN(S(N)(=O)=O)C4)c3c2cc1OC] | 2-(4-(6,7-dimethoxyquinazolin-4-yl)phenyl)pyrrolidine-1-sulfonamide |
| 24 | 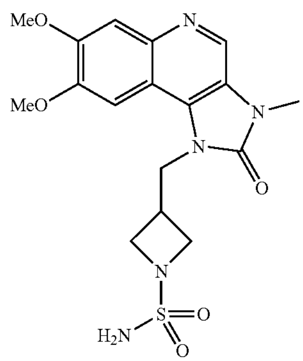 [SMILES: COc1cc2ncc3c(c2cc1OC)n(CC1CN(S(N)(=O)=O)C1)c(=O)n3C] | 3-((7,8-dimethoxy-3-methyl-2-oxo-2,3-dihydro-1H-imidazo[4,5-c]quinolin-1-yl)methyl)azetidine-1-sulfonamide |
| 25 | 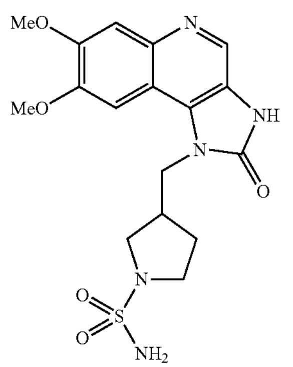 [SMILES: COc1cc2ncc3[nH]c(=O)n(CC4CCN(S(N)(=O)=O)C4)c3c2cc1OC] | 3-((7,8-dimethoxy-2-oxo-2,3-dihydro-1H-imidazo[4,5-c]quinolin-1-yl)methyl)pyrrolidine-1-sulfonamide |
| 26 | 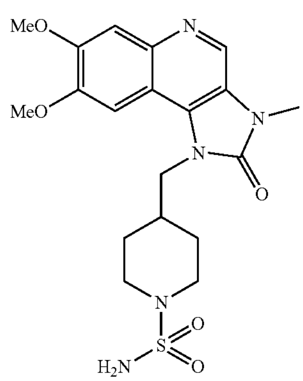 [SMILES: COc1cc2ncc3c(c2cc1OC)n(CC1CCN(S(N)(=O)=O)CC1)c(=O)n3C] | 4-((7,8-dimethoxy-3-methyl-2-oxo-2,3-dihydro-1H-imidazo[4,5-c]quinolin-1-yl)methyl)piperidine-1-sulfonamide |

TABLE 1-continued

| # | Structure | Name |
|---|---|---|
| 27 | 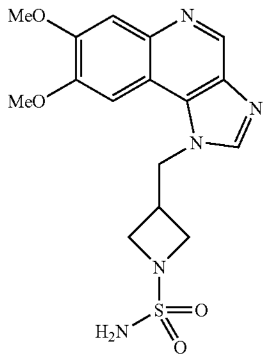 [SMILES: COc1cc2ncc3ncn(CC4CN(S(N)(=O)=O)C4)c3c2cc1OC] | 3-((7,8-dimethoxy-1H-imidazo[4,5-c]quinolin-1-yl)methyl)azetidine-1-sulfonamide |
| 28 | 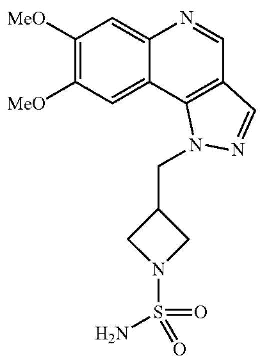 [SMILES: COc1cc2ncc3cnn(CC4CN(S(N)(=O)=O)C4)c3c2cc1OC] | 3-((7,8-dimethoxy-1H-pyrazolo[4,3-c]quinolin-1-yl)methyl)azetidine-1-sulfonamide |
| 29 | 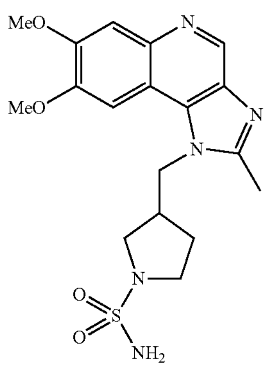 [SMILES: COc1cc2ncc3nc(C)n(CC4CCN(S(N)(=O)=O)C4)c3c2cc1OC] | 3-((7,8-dimethoxy-2-methyl-1H-imidazo[4,5-c]quinolin-1-yl)methyl)pyrrolidine-1-sulfonamide |
| 30 | 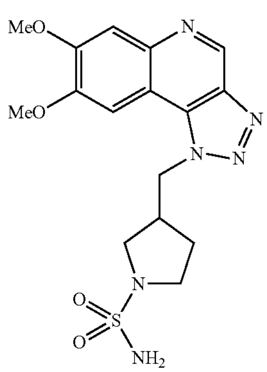 [SMILES: COc1cc2ncc3nnn(CC4CCN(S(N)(=O)=O)C4)c3c2cc1OC] | 3-((7,8-dimethoxy-1H-[1,2,3]triazolo[4,5-c]quinolin-1-yl)methyl)pyrrolidine-1-sulfonamide |

TABLE 1-continued

| # | Structure | Name |
|---|---|---|
| 31 | 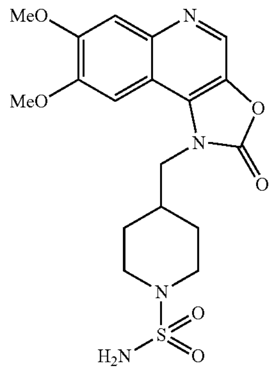 [SMILES: COc1cc2ncc3oc(=O)n(CC4CCN(S(N)(=O)=O)CC4)c3c2cc1OC] | 4-((7,8-dimethoxy-2-oxooxazolo[5,4-c]quinolin-1(2H)-yl)methyl)piperidine-1-sulfonamide |
| 32 | 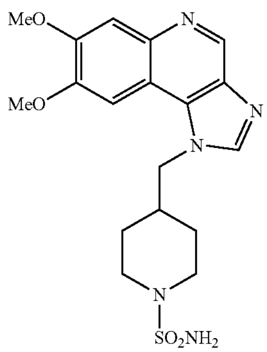 [SMILES: COc1cc2ncc3ncn(CC4CCN(S(N)(=O)=O)CC4)c3c2cc1OC] | 4-((7,8-dimethoxy-1H-imidazo[4,5-c]quinolin-1-yl)methyl)piperidine-1-sulfonamide |
| 33 | 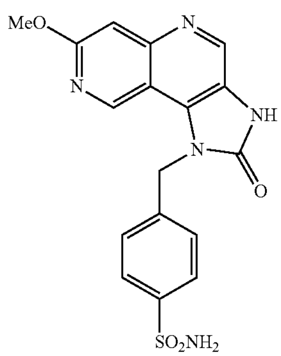 | 4-((7-methoxy-2-oxo-2,3-dihydro-1H-imidazo[4,5-c][1,6]naphthyridin-1-yl)methyl)benzenesulfonamide |
| 34 | 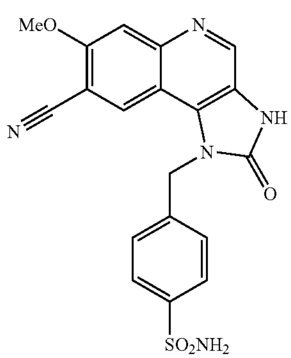 [SMILES: COc1cc2ncc3[nH]c(=O)n(Cc4ccc(S(N)(=O)=O)cc4)c3c2cc1C#N] | 4-((8-cyano-7-methoxy-2-oxo-2,3-dihydro-1H-imidazo[4,5-c]quinolin-1-yl)methyl)benzenesulfonamide |

TABLE 1-continued

| # | Structure | Name |
|---|---|---|
| 35 | 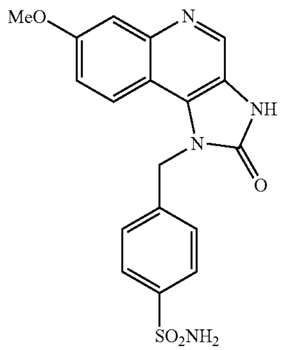 [SMILES: COc1ccc2c(c1)ncc1[nH]c(=O)n(Cc3ccc(S(N)(=O)=O)cc3)c12] | 4-((7-methoxy-2-oxo-2,3-dihydro-1H-imidazo[4,5-c]quinolin-1-yl)methyl)benzenesulfonamide |
| 36 | 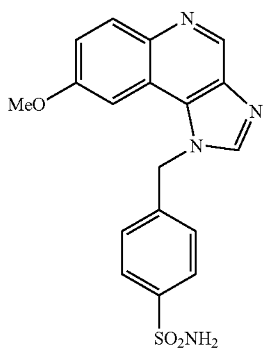 [SMILES: COc1ccc2ncc3ncn(Cc4ccc(S(N)(=O)=O)cc4)c3c2c1] | 4-((8-methoxy-1H-imidazo[4,5-c]quinolin-1-yl)methyl)benzenesulfonamide |
| 37 | 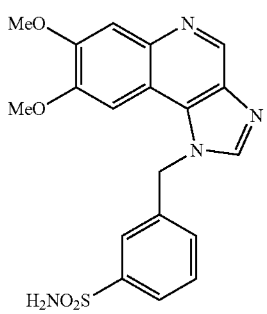 [SMILES: COc1cc2ncc3ncn(Cc4cccc(S(N)(=O)=O)c4)c3c2cc1OC] | 3-((7,8-dimethoxy-1H-imidazo[4,5-c]quinolin-1-yl)methyl)benzenesulfonamide |
| 38 | 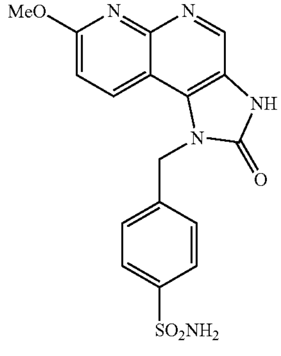 | 4-((7-methoxy-2-oxo-2,3-dihydro-1H-imidazo[4,5-c][1,8]naphthyridin-1-yl)methyl)benzenesulfonamide |

TABLE 1-continued

| # | Structure | Name |
|---|-----------|------|
| 39 | 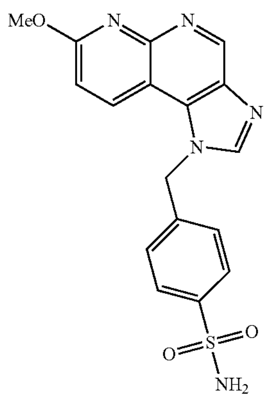 | 4-((7-methoxy-1H-imidazo[4,5-c][1,8]naphthyridin-1-yl)methyl)benzenesulfonamide |
| 40 | 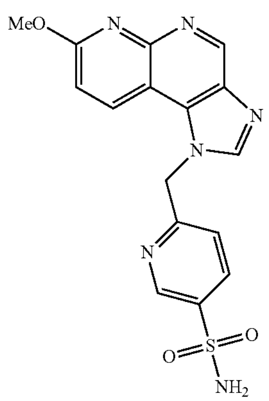 [SMILES: COc1ccc2c(ncc3ncn(Cc4ccc(S(N)(=O)=O)cn4)c32)n1] | 6-((7-methoxy-1H-imidazo[4,5-c][1,8]naphthyridin-1-yl)methyl)pyridine-3-sulfonamide |
| 41 | 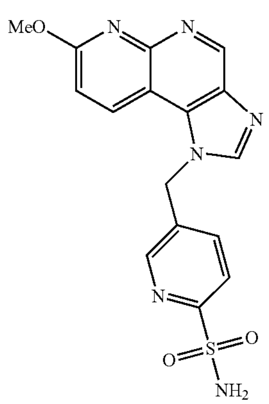 [SMILES: COc1ccc2c(ncc3ncn(Cc4ccc(S(N)(=O)=O)nc4)c32)n1] | 5-((7-methoxy-1H-imidazo[4,5-c][1,8]naphthyridin-1-yl)methyl)pyridine-2-sulfonamide |
| 42 | 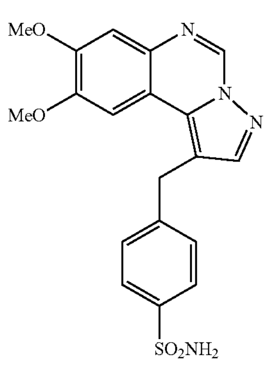 [SMILES: COc1cc2ncn3ncc(Cc4ccc(S(N)(=O)=O)cc4)c3c2cc1OC] | 4-((8,9-dimethoxypyrazolo[1,5-c]quinazolin-1-yl)methyl)benzenesulfonamide |

TABLE 1-continued

| # | Structure | Name |
|---|---|---|
| 43 | 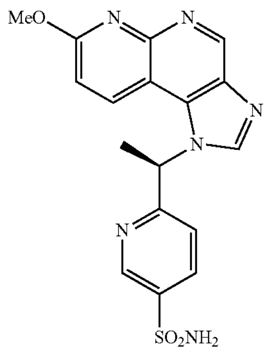 [SMILES: COc1ccc2c(ncc3ncn([C@H](C)c4ccc(S(N)(=O)=O)cn4)c32)n1] | (R)-6-(1-(7-methoxy-1H-imidazo[4,5-c][1,8]naphthyridin-1-yl)ethyl)pyridine-3-sulfonamide |
| 44 | 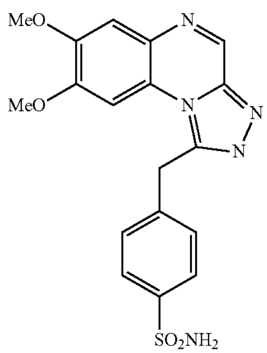 | 4-((7,8-dimethoxy-2λ$^2$,10λ$^4$-[1,2,4]triazolo[4,3-a]quinoxalin-1-yl)methyl)benzenesulfonamide |
| 45 | 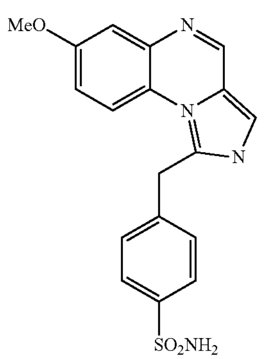 | 4-((7-methoxy-2λ$^2$,10λ$^4$-imidazo[3,4-a]quinoxalin-1-yl)methyl)benzenesulfonamide |
| 46 | 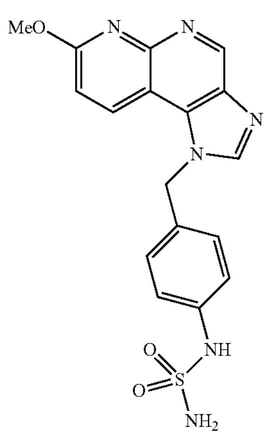 [SMILES: COc1ccc2c(ncc3ncn(Cc4ccc(NS(N)(=O)=O)cc4)c32)n1] | 4-((7-methoxy-1H-imidazo[4,5-c][1,8]naphthyridin-1-yl)methyl)phenyl sulfamide |

TABLE 1-continued

| # | Structure | Name |
|---|-----------|------|
| 47 | 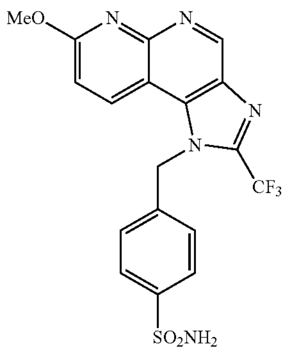 [SMILES: COc1ccc2c(ncc3nc(C(F)(F)F)n(Cc4ccc(S(N)(=O)=O)cc4)c32)n1] | 4-((7-methoxy-2-(trifluoromethyl)-1H-imidazo[4,5-c][1,8]naphthyridin-1-yl)methyl)benzenesulfonamide |
| 48 | 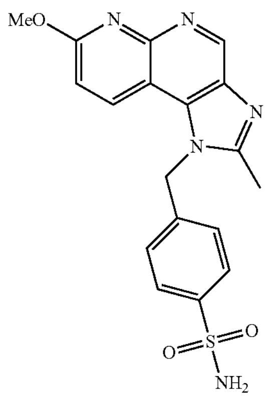 [SMILES: COc1ccc2c(ncc3nc(C)n(Cc4ccc(S(N)(=O)=O)cc4)c32)n1] | 4-((7-methoxy-2-methyl-1H-imidazo[4,5-c][1,8]naphthyridin-1-yl)methyl)benzenesulfonamide |
| 49 | 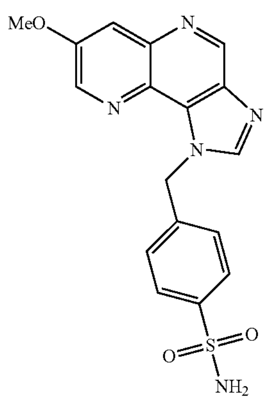 [SMILES: COc1cnc2c(c1)ncc1ncn(Cc3ccc(S(N)(=O)=O)cc3)c12] | 4-((7-methoxy-1H-imidazo[4,5-c][1,5]naphthyridin-1-yl)methyl)benzenesulfonamide |
| 50 | 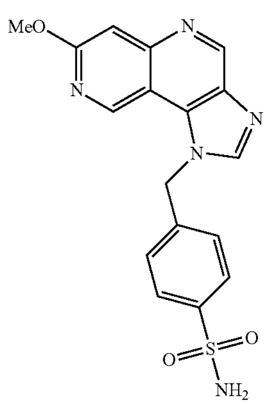 [SMILES: COc1cc2ncc3ncn(Cc4ccc(S(N)(=O)=O)cc4)c3c2cn1] | 4-((7-methoxy-1H-imidazo[4,5-c][1,6]naphthyridin-1-yl)methyl)benzenesulfonamide |

TABLE 1-continued

| # | Structure | Name |
|---|---|---|
| 51 | 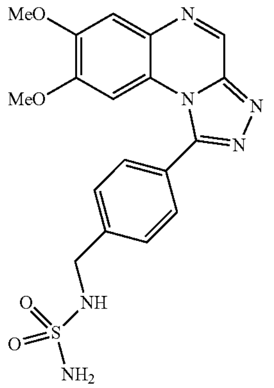 [SMILES: COc1cc2ncc3nnc(-c4ccc(CNS(N)(=O)=O)cc4)n3c2cc1OC] | 4-(7,8-dimethoxy-[1,2,4]triazolo[4,3-a]quinoxalin-1-yl)benzyl sulfamide |
| 52 | 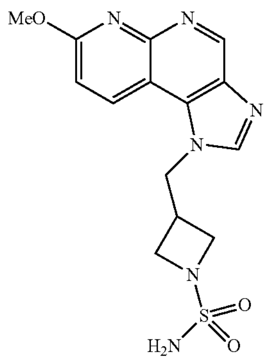 [SMILES: COc1ccc2c(ncc3ncn(CC4CN(S(N)(=O)=O)C4)c32)n1] | 3-((7-methoxy-1H-imidazo[4,5-c][1,8]naphthyridin-1-yl)methyl)azetidine-1-sulfonamide |
| 53 | 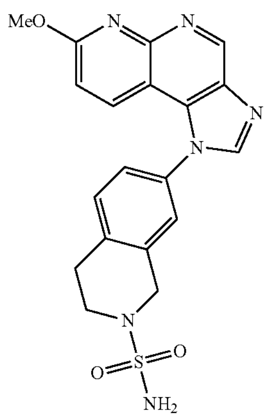 [SMILES: COc1ccc2c(ncc3ncn(-c4ccc5c(c4)CN(S(N)(=O)=O)CC5)c32)n1] | 7-(7-methoxy-1H-imidazo[4,5-c][1,8]naphthyridin-1-yl)-3,4-dihydroisoquinoline-2(1H)-sulfonamide |
| 54 | 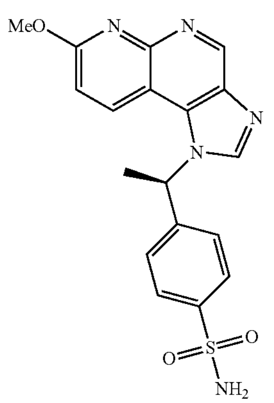 [SMILES: COc1ccc2c(ncc3ncn([C@H](C)c4ccc(S(N)(=O)=O)cc4)c32)n1] | (R)-4-(1-(7-methoxy-1H-imidazo[4,5-c][1,8]naphthyridin-1-yl)ethyl)benzenesulfonamide |

TABLE 1-continued

| # | Structure | Name |
|---|---|---|
| 55 | 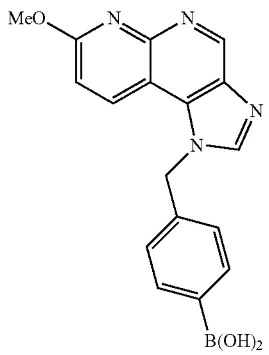 [SMILES: COc1ccc2c(ncc3ncn(Cc4ccc(B(O)O)cc4)c32)n1] | (4-((7-methoxy-1H-imidazo[4,5-c][1,8]naphthyridin-1-yl)methyl)phenyl)boronic acid |
| 56 | 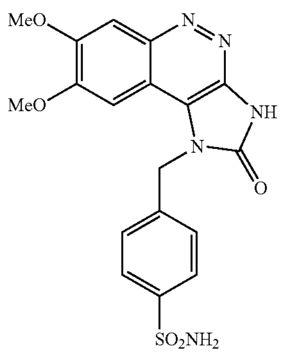 [SMILES: COc1cc2nnc3[nH]c(=O)n(Cc4ccc(S(N)(=O)=O)cc4)c3c2cc1OC] | 4-((7,8-dimethoxy-2-oxo-2,3-dihydro-1H-imidazo[4,5-c]cinnolin-1-yl)methyl)benzenesulfonamide |
| 57 | 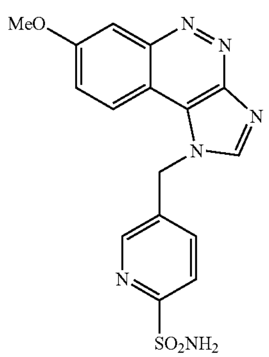 [SMILES: COc1ccc2c(c1)nnc1ncn(Cc3ccc(S(N)(=O)=O)nc3)c12] | 5-((7-methoxy-1H-imidazo[4,5-c]cinnolin-1-yl)methyl)pyridine-2-sulfonamide |
| 58 | 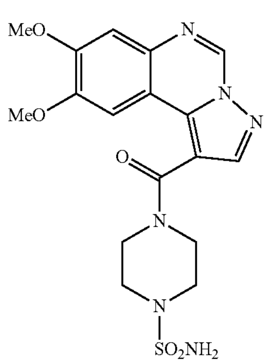 [SMILES: COc1cc2ncn3ncc(C(=O)N4CCN(S(N)(=O)=O)CC4)c3c2cc1OC] | 4-(8,9-dimethoxypyrazolo[1,5-c]quinazoline-1-carbonyl)piperazine-1-sulfonamide |

TABLE 1-continued

| # | Structure | Name |
|---|---|---|
| 59 | 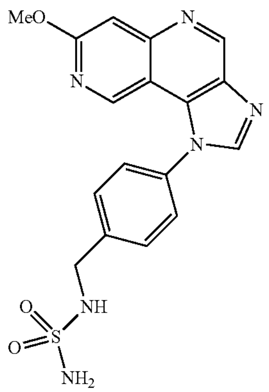 [SMILES: COc1cc2ncc3ncn(-c4ccc(CNS(N)(=O)=O)cc4)c3c2cn1] | 4-(7-methoxy-1H-imidazo[4,5-c][1,6]naphthyridin-1-yl)benzyl sulfamide |
| 60 | 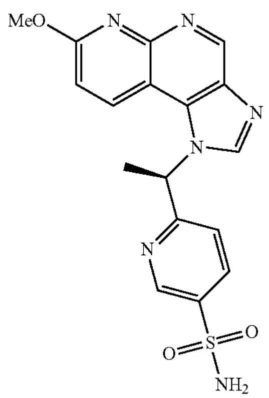 [SMILES: COc1ccc2c(ncc3ncn([C@H](C)c4ccc(S(N)(=O)=O)cn4)c32)n1] | (R)-6-(1-(7-methoxy-1H-imidazo[4,5-c][1,8]naphthyridin-1-yl)ethyl)pyridine-3-sulfonamide |
| 61 | 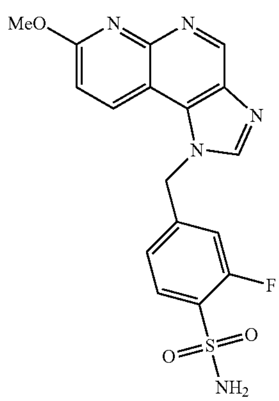 [SMILES: COc1ccc2c(ncc3ncn(Cc4ccc(S(N)(=O)=O)c(F)c4)c32)n1] | 2-fluoro-4-((7-methoxy-1H-imidazo[4,5-c][1,8]naphthyridin-1-yl)methyl)benzenesulfonamide |
| 62 | 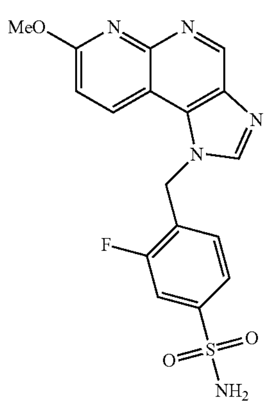 [SMILES: COc1ccc2c(ncc3ncn(Cc4ccc(S(N)(=O)=O)cc4F)c32)n1] | 3-fluoro-4-((7-methoxy-1H-imidazo[4,5-c][1,8]naphthyridin-1-yl)methyl)benzenesulfonamide |

TABLE 1-continued

| # | Structure | Name |
|---|---|---|
| 63 | 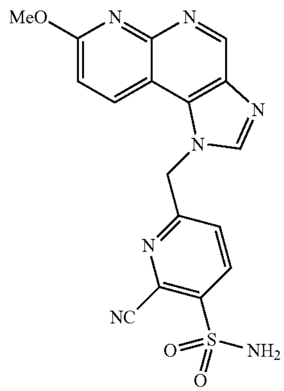 [SMILES: COc1ccc2c(ncc3ncn(Cc4ccc(S(N)(=O)=O)c(C#N)n4)c32)n1] | 2-cyano-6-((7-methoxy-1H-imidazo[4,5-c][1,8]naphthyridin-1-yl)methyl)pyridine-3-sulfonamide |
| 64 | 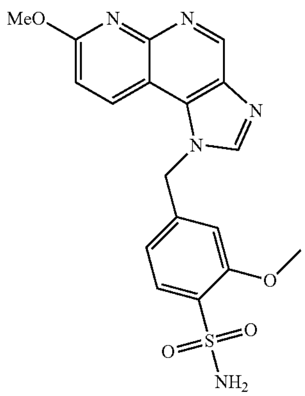 [SMILES: COc1ccc2c(ncc3ncn(Cc4ccc(S(N)(=O)=O)c(OC)c4)c32)n1] | 2-methoxy-4-((7-methoxy-1H-imidazo[4,5-c][1,8]naphthyridin-1-yl)methyl)benzenesulfonamide |
| 65 | 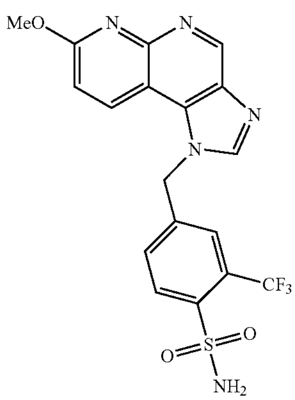 [SMILES: COc1ccc2c(ncc3ncn(Cc4ccc(S(N)(=O)=O)c(C(F)(F)F)c4)c32)n1] | 4-((7-methoxy-1H-imidazo[4,5-c][1,8]naphthyridin-1-yl)methyl)-2-(trifluoromethyl)benzenesulfonamide |
| 66 | 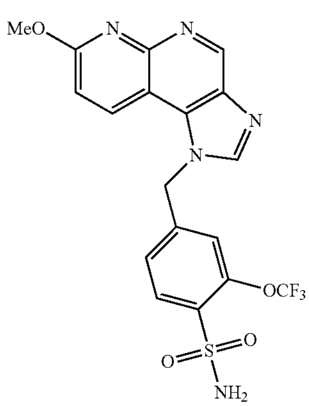 [SMILES: COc1ccc2c(ncc3ncn(Cc4ccc(S(N)(=O)=O)c(OC(F)(F)F)c4)c32)n1] | 4-((7-methoxy-1H-imidazo[4,5-c][1,8]naphthyridin-1-yl)methyl)-2-(trifluoromethoxy)benzenesulfonamide |

TABLE 1-continued

| # | Structure | Name |
|---|---|---|
| 67 | 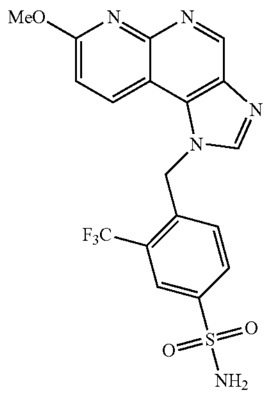 [SMILES: COc1ccc2c(ncc3ncn(Cc4ccc(S(N)(=O)=O)cc4C(F)(F)F)c32)n1] | 4-((7-methoxy-1H-imidazo[4,5-c][1,8]naphthyridin-1-yl)methyl)-3-(trifluoromethyl)benzenesulfonamide |
| 68 | 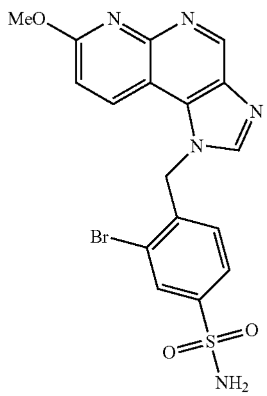 [SMILES: COc1ccc2c(ncc3ncn(Cc4ccc(S(N)(=O)=O)cc4Br)c32)n1] | 3-bromo-4-((7-methoxy-1H-imidazo[4,5-c][1,8]naphthyridin-1-yl)methyl)benzenesulfonamide |
| 69 | 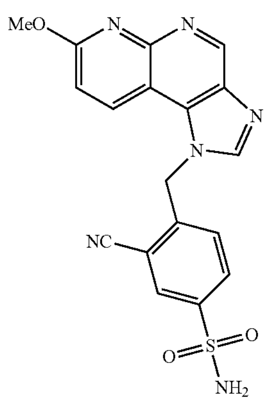 [SMILES: COc1ccc2c(ncc3ncn(Cc4ccc(S(N)(=O)=O)cc4C#N)c32)n1] | 3-cyano-4-((7-methoxy-1H-imidazo[4,5-c][1,8]naphthyridin-1-yl)methyl)benzenesulfonamide |
| 70 | 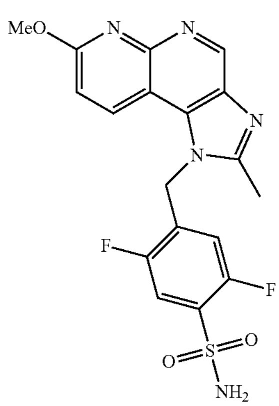 [SMILES: COc1ccc2c(ncc3nc(C)n(Cc4cc(F)c(S(N)(=O)=O)cc4F)c32)n1] | 2,5-difluoro-4-((7-methoxy-2-methyl-1H-imidazo[4,5-c][1,8]naphthyridin-1-yl)methyl)benzenesulfonamide |

TABLE 1-continued
| # | Structure | Name |
|---|---|---|
| 71 | 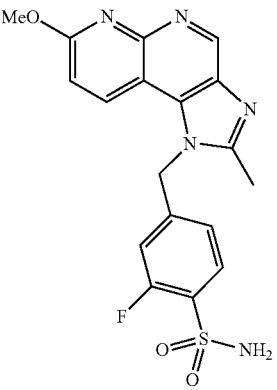 [SMILES: COc1ccc2c(ncc3nc(C)n(Cc4ccc(S(N)(=O)=O)c(F)c4)c32)n1] | 2-fluoro-4-((7-methoxy-2-methyl-1H-imidazo[4,5-c][1,8]naphthyridin-1-yl)methyl)benzenesulfonamide |
| 72 | 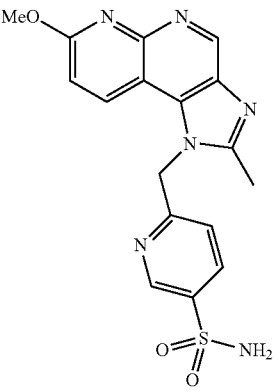 [SMILES: COc1ccc2c(ncc3nc(C)n(Cc4ccc(S(N)(=O)=O)cn4)c32)n1] | 6-((7-methoxy-2-methyl-1H-imidazo[4,5-c][1,8]naphthyridin-1-yl)methyl)pyridine-3-sulfonamide |
| 73 | 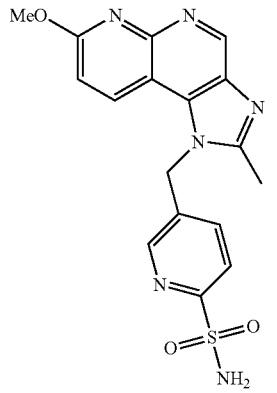 [SMILES: COc1ccc2c(ncc3nc(C)n(Cc4ccc(S(N)(=O)=O)nc4)c32)n1] | 5-((7-methoxy-2-methyl-1H-imidazo[4,5-c][1,8]naphthyridin-1-yl)methyl)pyridine-2-sulfonamide |
| 74 | 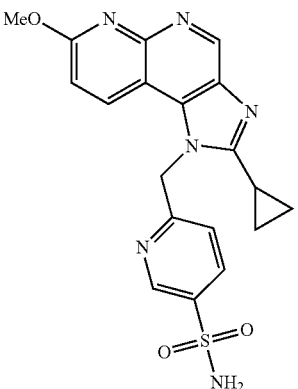 | 6-((2-cyclopropyl-7-methoxy-1H-imidazo[4,5-c][1,8]naphthyridin-1-yl)methyl)pyridine-3-sulfonamide |

TABLE 1-continued

| # | Structure | Name |
|---|---|---|
| 75 | 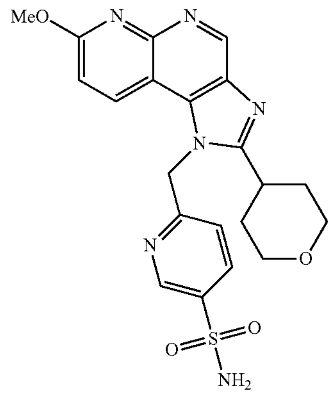 [SMILES: COc1ccc2c(ncc3nc(C4CCOCC4)n(Cc4ccc(S(N)(=O)=O)cn4)c32)n1] | 6-((7-methoxy-2-(tetrahydro-2H-pyran-4-yl)-1H-imidazo[4,5-c][1,8]naphthyridin-1-yl)methyl)pyridine-3-sulfonamide |
| 76 | 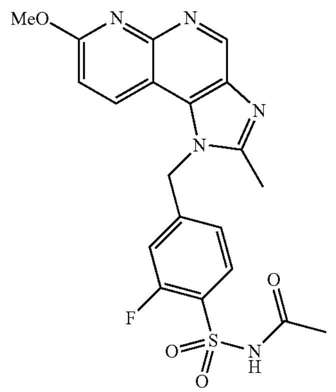 [SMILES: COc1ccc2c(ncc3nc(C)n(Cc4ccc(S(=O)(=O)NC(C)=O)c(F)c4)c32)n1] | N-((2-fluoro-4-((7-methoxy-2-methyl-1H-imidazo[4,5-c][1,8]naphthyridin-1-yl)methyl)phenyl)sulfonyl)acetamide |
| 77 | 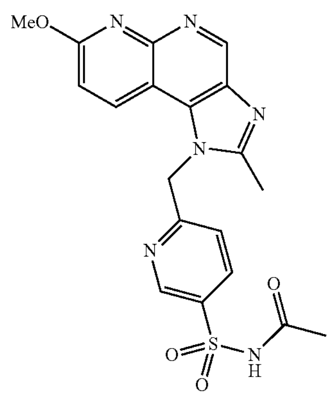 [SMILES: COc1ccc2c(ncc3nc(C)n(Cc4ccc(S(=O)(=O)NC(C)=O)cn4)c32)n1] | N-((6-((7-methoxy-2-methyl-1H-imidazo[4,5-c][1,8]naphthyridin-1-yl)methyl)pyridin-3-yl)sulfonyl)acetamide |
| 78 | 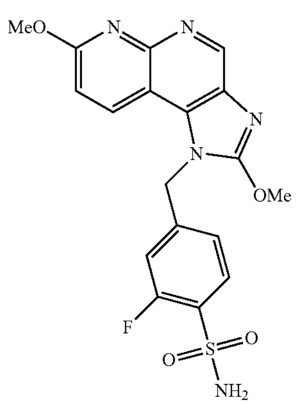 [SMILES: COc1ccc2c(ncc3nc(OC)n(Cc4ccc(S(N)(=O)=O)c(F)c4)c32)n1] | 4-((2,7-dimethoxy-1H-imidazo[4,5-c][1,8]naphthyridin-1-yl)methyl)-2-fluorobenzenesulfonamide |

TABLE 1-continued

| # | Structure | Name |
|---|---|---|
| 79 | 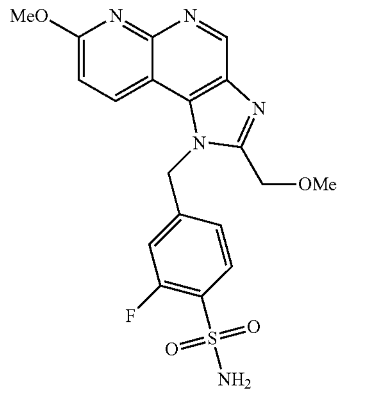 [SMILES: COCc1nc2cnc3nc(OC)ccc3c2n1Cc1ccc(S(N)(=O)=O)c(F)c1] | 2-fluoro-4-((7-methoxy-2-(methoxymethyl)-1H-imidazo[4,5-c][1,8]naphthyridin-1-yl)methyl)benzenesulfonamide |
| 80 | 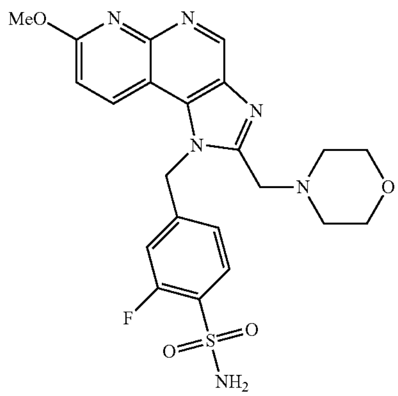 [SMILES: COc1ccc2c(ncc3nc(CN4CCOCC4)n(Cc4ccc(S(N)(=O)=O)c(F)c4)c32)n1] | 2-fluoro-4-((7-methoxy-2-(morpholinomethyl)-1H-imidazo[4,5-c][1,8]naphthyridin-1-yl)methyl)benzenesulfonamide |
| 81 | 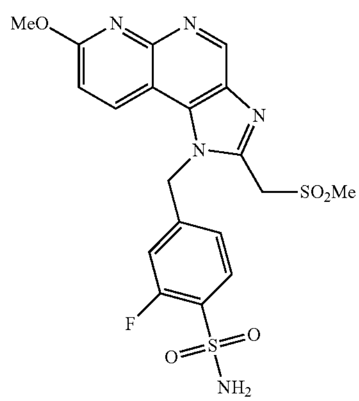 | 2-fluoro-4-((7-methoxy-2-((methylsulfonyl)methyl)-1H-imidazo[4,5-c][1,8]naphthyridin-1-yl)methyl)benzenesulfonamide |
| 82 | 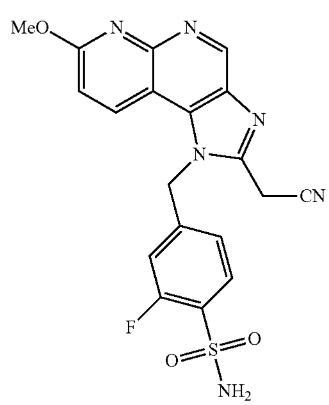 [SMILES: COc1ccc2c(ncc3nc(CC#N)n(Cc4ccc(S(N)(=O)=O)c(F)c4)c32)n1] | 4-((2-(cyanomethyl)-7-methoxy-1H-imidazo[4,5-c][1,8]naphthyridin-1-yl)methyl)-2-fluorobenzenesulfonamide |

TABLE 1-continued

| # | Structure | Name |
|---|-----------|------|
| 83 | 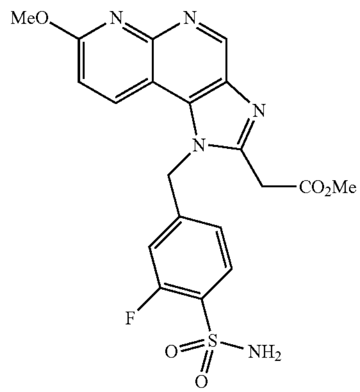 [SMILES: COC(=O)Cc1nc2cnc3nc(OC)ccc3c2n1Cc1ccc(S(N)(=O)=O)c(F)c1] | methyl 2-(1-(3-fluoro-4-sulfamoylbenzyl)-7-methoxy-1H-imidazo[4,5-c][1,8]naphthyridin-2-yl)acetate |
| 84 | 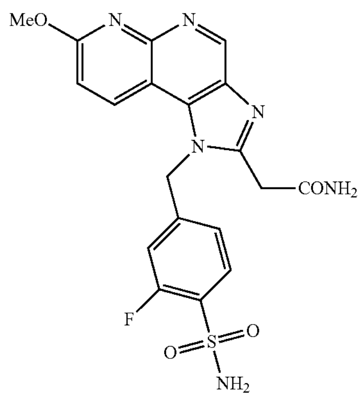 [SMILES: COc1ccc2c(ncc3nc(CC(N)=O)n(Cc4ccc(S(N)(=O)=O)c(F)c4)c32)n1] | 2-(1-(3-fluoro-4-sulfamoylbenzyl)-7-methoxy-1H-imidazo[4,5-c][1,8]naphthyridin-2-yl)acetamide |
| 85 | 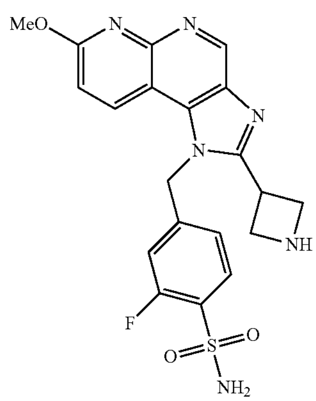 [SMILES: COc1ccc2c(ncc3nc(C4CNC4)n(Cc4ccc(S(N)(=O)=O)c(F)c4)c32)n1] | 4-((2-(azetidin-3-yl)-7-methoxy-1H-imidazo[4,5-c][1,8]naphthyridin-1-yl)methyl)-2-fluorobenzenesulfonamide |
| 86 | 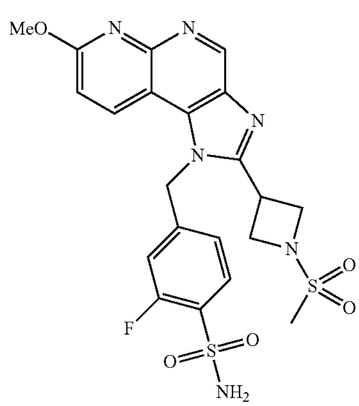 [SMILES: COc1ccc2c(ncc3nc(C4CN(S(C)(=O)=O)C4)n(Cc4ccc(S(N)(=O)=O)c(F)c4)c32)n1] | 2-fluoro-4-((7-methoxy-2-(1-(methylsulfonyl)azetidin-3-yl)-1H-imidazo[4,5-c][1,8]naphthyridin-1-yl)methyl)benzenesulfonamide |

TABLE 1-continued

| # | Structure | Name |
|---|---|---|
| 87 | 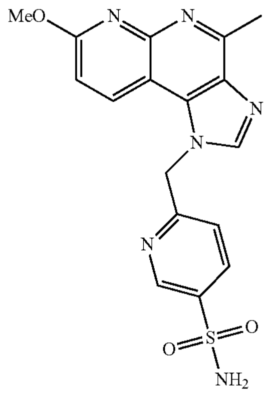 [SMILES: COc1ccc2c(n1)nc(C)c1ncn(Cc3ccc(S(N)(=O)=O)cn3)c12] | 6-((7-methoxy-4-methyl-1H-imidazo[4,5-c][1,8]naphthyridin-1-yl)methyl)pyridine-3-sulfonamide |
| 88 | 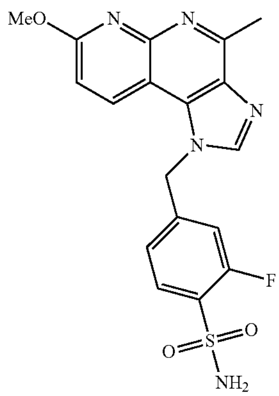 [SMILES: COc1ccc2c(n1)nc(C)c1ncn(Cc3ccc(S(N)(=O)=O)c(F)c3)c12] | 2-fluoro-4-((7-methoxy-4-methyl-1H-imidazo[4,5-c][1,8]naphthyridin-1-yl)methyl)benzenesulfonamide |
| 89 | 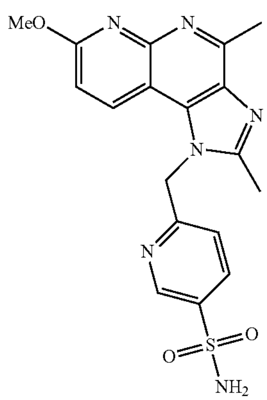 [SMILES: COc1ccc2c(n1)nc(C)c1nc(C)n(Cc3ccc(S(N)(=O)=O)cn3)c12] | 6-((7-methoxy-2,4-dimethyl-1H-imidazo[4,5-c][1,8]naphthyridin-1-yl)methyl)pyridine-3-sulfonamide |
| 90 | 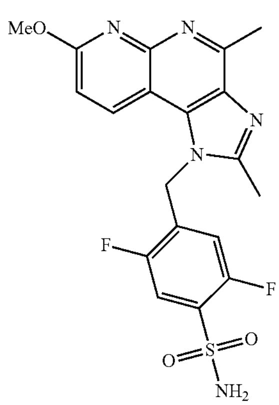 [SMILES: COc1ccc2c(n1)nc(C)c1nc(C)n(Cc3cc(F)c(S(N)(=O)=O)cc3F)c12] | 2,5-difluoro-4-((7-methoxy-2,4-dimethyl-1H-imidazo[4,5-c][1,8]naphthyridin-1-yl)methyl)benzenesulfonamide |

TABLE 1-continued

| # | Structure | Name |
|---|---|---|
| 91a | 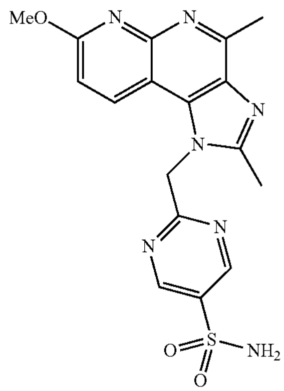 [SMILES: COc1ccc2c(n1)nc(C)c1nc(C)n(Cc3ncc(S(N)(=O)=O)cn3)c12] | 2-((7-methoxy-2,4-dimethyl-1H-imidazo[4,5-c][1,8]naphthyridin-1-yl)methyl)pyrimidine-5-sulfonamide |
| 91b | 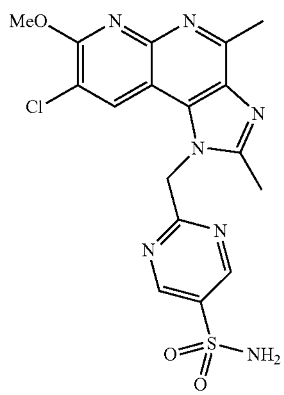 [SMILES: COc1nc2nc(C)c3nc(C)n(Cc4ncc(S(N)(=O)=O)cn4)c3c2cc1Cl] | 2-((6-chloro-7-methoxy-2,4-dimethyl-1H-imidazo[4,5-c][1,8]naphthyridin-1-yl)methyl)pyrimidine-5-sulfonamide |
| 92 | 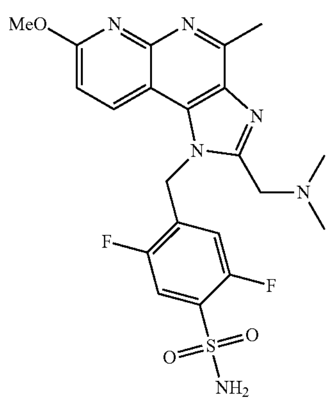 [SMILES: COc1ccc2c(n1)nc(C)c1nc(CN(C)C)n(Cc3cc(F)c(S(N)(=O)=O)cc3F)c12] | 4-((2-((dimethylamino)methyl)-7-methoxy-4-methyl-1H-imidazo[4,5-c][1,8]naphthyridin-1-yl)methyl)-2,5-difluorobenzenesulfonamide |
| 93 | 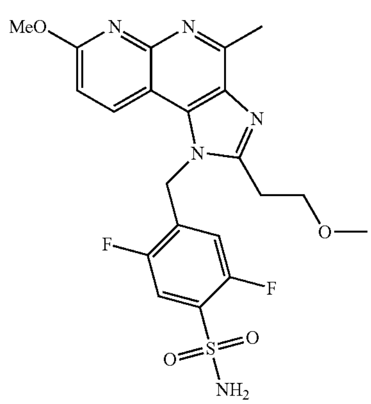 [SMILES: COCCc1nc2c(C)nc3nc(OC)ccc3c2n1Cc1cc(F)c(S(N)(=O)=O)cc1F] | 2,5-difluoro-4-((7-methoxy-2-(2-methoxyethyl)-4-methyl-1H-imidazo[4,5-c][1,8]naphthyridin-1-yl)methyl)benzenesulfonamide |

TABLE 1-continued

| # | Structure | Name |
|---|---|---|
| 94 | 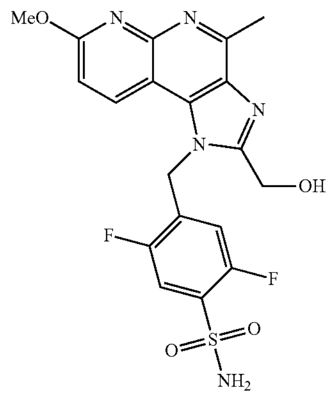 | 2,5-difluoro-4-((2-(hydroxymethyl)-7-methoxy-4-methyl-1H-imidazo[4,5-c][1,8]naphthyridin-1-yl)methyl)benzenesulfonamide |
| 95 | 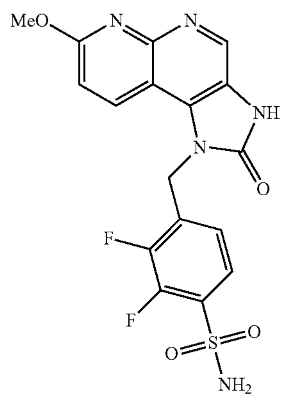 [SMILES: COc1ccc2c(ncc3[nH]c(=O)n(Cc4ccc(S(N)(=O)=O)c(F)c4F)c32)n1] | 2,3-difluoro-4-((7-methoxy-2-oxo-2,3-dihydro-1H-imidazo[4,5-c][1,8]naphthyridin-1-yl)methyl)benzenesulfonamide |
| 96 | 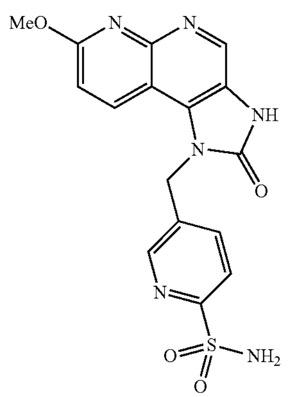 [SMILES: COc1ccc2c(ncc3[nH]c(=O)n(Cc4ccc(S(N)(=O)=O)nc4)c32)n1] | 5-((7-methoxy-2-oxo-2,3-dihydro-1H-imidazo[4,5-c][1,8]naphthyridin-1-yl)methyl)pyridine-2-sulfonamide |
| 97 | 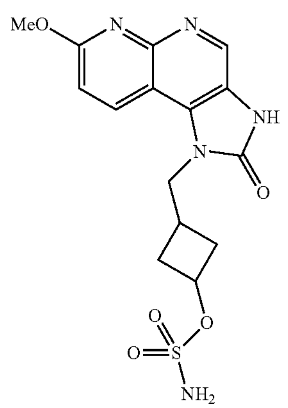 [SMILES: COc1ccc2c(ncc3[nH]c(=O)n(CC4CC(OS(N)(=O)=O)C4)c32)n1] | 3-((7-methoxy-2-oxo-2,3-dihydro-1H-imidazo[4,5-c][1,8]naphthyridin-1-yl)methyl)cyclobutyl sulfamate |

TABLE 1-continued

| # | Structure | Name |
|---|---|---|
| 98 | 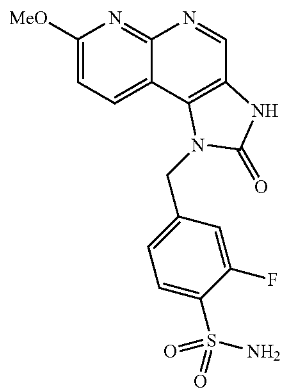 [SMILES: COc1ccc2c(ncc3[nH]c(=O)n(Cc4ccc(S(N)(=O)=O)c(F)c4)c32)n1] | 2-fluoro-4-((7-methoxy-2-oxo-2,3-dihydro-1H-imidazo[4,5-c][1,8]naphthyridin-1-yl)methyl)benzenesulfonamide |
| 99 | 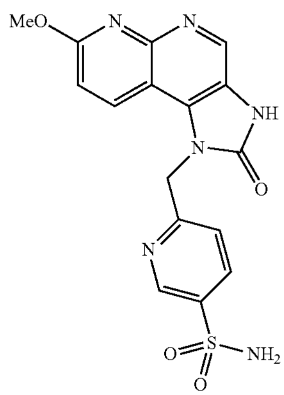 [SMILES: COc1ccc2c(ncc3[nH]c(=O)n(Cc4ccc(S(N)(=O)=O)cn4)c32)n1] | 6-((7-methoxy-2-oxo-2,3-dihydro-1H-imidazo[4,5-c][1,8]naphthyridin-1-yl)methyl)pyridine-3-sulfonamide |
| 100 | 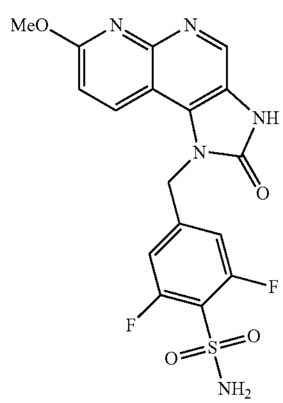 [SMILES: COc1ccc2c(ncc3[nH]c(=O)n(Cc4cc(F)c(S(N)(=O)=O)c(F)c4)c32)n1] | 2,6-difluoro-4-((7-methoxy-2-oxo-2,3-dihydro-1H-imidazo[4,5-c][1,8]naphthyridin-1-yl)methyl)benzenesulfonamide |
| 101 | 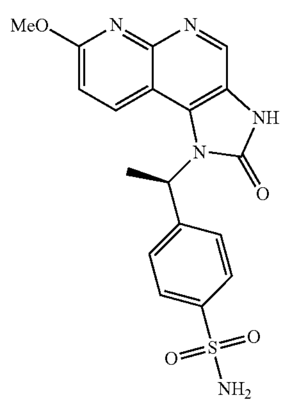 [SMILES: COc1ccc2c(ncc3[nH]c(=O)n([C@H](C)c4ccc(S(N)(=O)=O)cc4)c32)n1] | (R)-4-(1-(7-methoxy-2-oxo-2,3-dihydro-1H-imidazo[4,5-c][1,8]naphthyridin-1-yl)ethyl)benzenesulfonamide |

TABLE 1-continued
| # | Structure | Name |
|---|---|---|
| 102 | 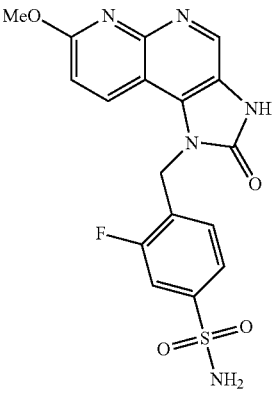 [SMILES: COc1ccc2c(ncc3[nH]c(=O)n(Cc4ccc(S(N)(=O)=O)cc4F)c32)n1] | 3-fluoro-4-((7-methoxy-2-oxo-2,3-dihydro-1H-imidazo[4,5-c][1,8]naphthyridin-1-yl)methyl)benzenesulfonamide |
| 103 | 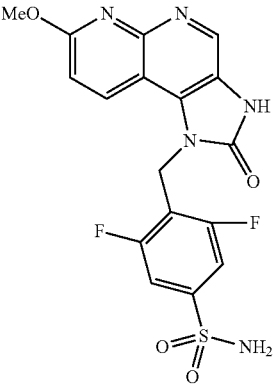 [SMILES: COc1ccc2c(ncc3[nH]c(=O)n(Cc4c(F)cc(S(N)(=O)=O)cc4F)c32)n1] | 3,5-difluoro-4-((7-methoxy-2-oxo-2,3-dihydro-1H-imidazo[4,5-c][1,8]naphthyridin-1-yl)methyl)benzenesulfonamide |
| 104 | 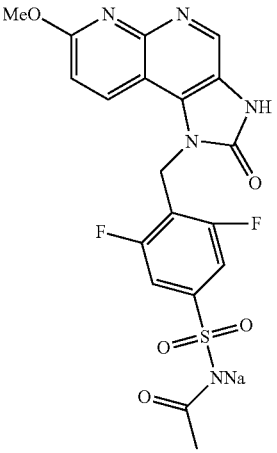 | sodium acetyl((3,5-difluoro-4-((7-methoxy-2-oxo-2,3-dihydro-1H-imidazo[4,5-c][1,8]naphthyridin-1-yl)methyl)phenyl)sulfonyl)amide |

TABLE 1-continued

| # | Structure | Name |
|---|---|---|
| 105 | 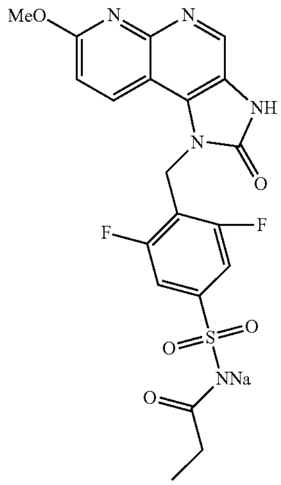 | sodium ((3,5-difluoro-4-((7-methoxy-2-oxo-2,3-dihydro-1H-imidazo[4,5-c][1,8]naphthyridin-1-yl)methyl)phenyl)sulfonyl)(propionyl)amide |
| 106 | 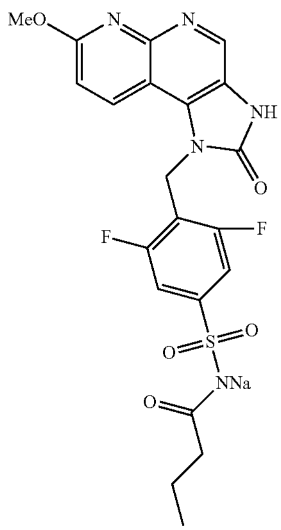 | sodium butyryl((3,5-difluoro-4-((7-methoxy-2-oxo-2,3-dihydro-1H-imidazo[4,5-c][1,8]naphthyridin-1-yl)methyl)phenyl)sulfonyl)amide |
| 107 | 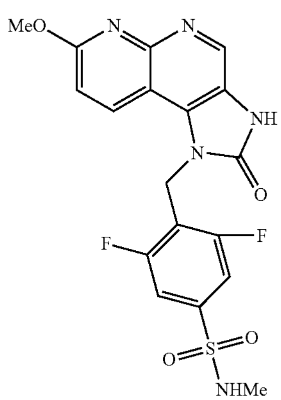 [SMILES: CNS(=O)(=O)c1cc(F)c(Cn2c(=O)[nH]c3cnc4nc(OC)ccc4c32)c(F)c1] | 3,5-difluoro-4-((7-methoxy-2-oxo-2,3-dihydro-1H-imidazo[4,5-c][1,8]naphthyridin-1-yl)methyl)-N-methylbenzenesulfonamide |

TABLE 1-continued

| # | Structure | Name |
|---|-----------|------|
| 108 | 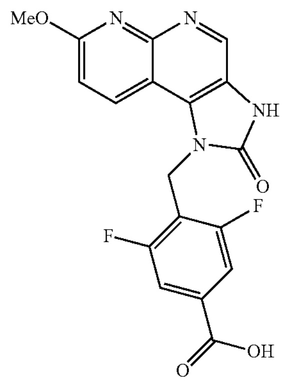 [SMILES: COc1ccc2c(ncc3[nH]c(=O)n(Cc4c(F)cc(C(=O)O)cc4F)c32)n1] | 3,5-difluoro-4-((7-methoxy-2-oxo-2,3-dihydro-1H-imidazo[4,5-c][1,8]naphthyridin-1-yl)methyl)benzoic acid |
| 109 | 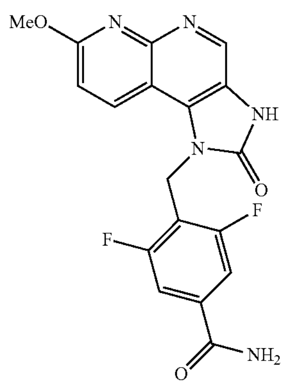 [SMILES: COc1ccc2c(ncc3[nH]c(=O)n(Cc4c(F)cc(C(N)=O)cc4F)c32)n1] | 3,5-difluoro-4-((7-methoxy-2-oxo-2,3-dihydro-1H-imidazo[4,5-c][1,8]naphthyridin-1-yl)methyl)benzamide |
| 110 | 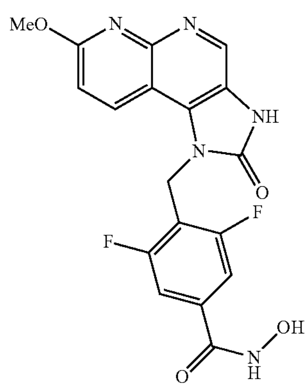 [SMILES: COc1ccc2c(ncc3[nH]c(=O)n(Cc4c(F)cc(C(=O)NO)cc4F)c32)n1] | 3,5-difluoro-N-hydroxy-4-((7-methoxy-2-oxo-2,3-dihydro-1H-imidazo[4,5-c][1,8]naphthyridin-1-yl)methyl)benzamide |
| 111 | 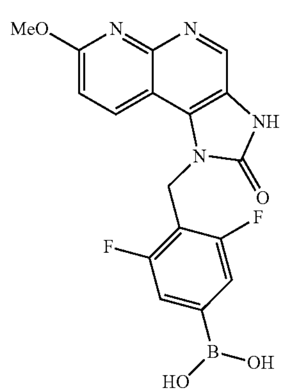 [SMILES: COc1ccc2c(ncc3[nH]c(=O)n(Cc4c(F)cc(B(O)O)cc4F)c32)n1] | (3,5-difluoro-4-((7-methoxy-2-oxo-2,3-dihydro-1H-imidazo[4,5-c][1,8]naphthyridin-1-yl)methyl)phenyl)boronic acid |

TABLE 1-continued

| # | Structure | Name |
|---|---|---|
| 112 | 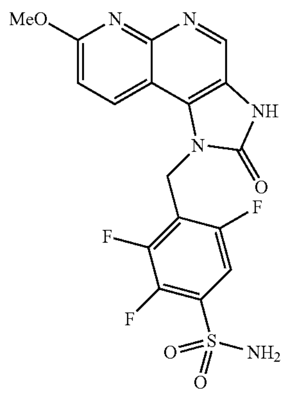 [SMILES: COc1ccc2c(ncc3[nH]c(=O)n(Cc4c(F)cc(S(N)(=O)=O)c(F)c4F)c32)n1] | 2,3,5-trifluoro-4-((7-methoxy-2-oxo-2,3-dihydro-1H-imidazo[4,5-c][1,8]naphthyridin-1-yl)methyl)benzenesulfonamide |
| 113 | 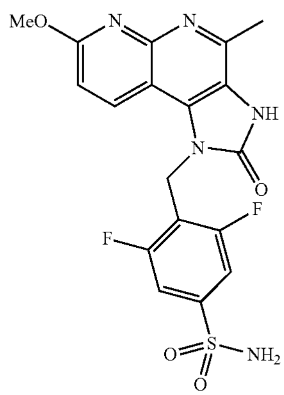 [SMILES: COc1ccc2c(n1)nc(C)c1[nH]c(=O)n(Cc3c(F)cc(S(N)(=O)=O)cc3F)c12] | 3,5-difluoro-4-((7-methoxy-4-methyl-2-oxo-2,3-dihydro-1H-imidazo[4,5-c][1,8]naphthyridin-1-yl)methyl)benzenesulfonamide |
| 114 | 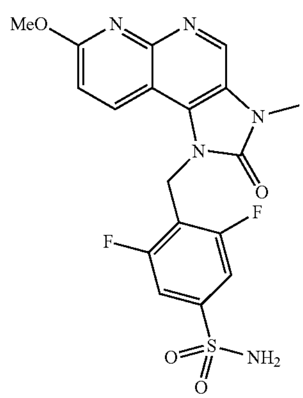 [SMILES: COc1ccc2c(ncc3c2n(Cc2c(F)cc(S(N)(=O)=O)cc2F)c(=O)n3C)n1] | 3,5-difluoro-4-((7-methoxy-3-methyl-2-oxo-2,3-dihydro-1H-imidazo[4,5-c][1,8]naphthyridin-1-yl)methyl)benzenesulfonamide |
| 115 | 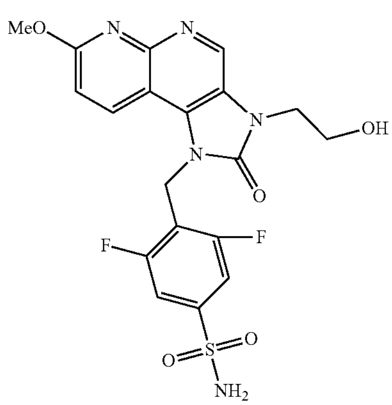 [SMILES: COc1ccc2c(ncc3c2n(Cc2c(F)cc(S(N)(=O)=O)cc2F)c(=O)n3CCO)n1] | 3,5-difluoro-4-((3-(2-hydroxyethyl)-7-methoxy-2-oxo-2,3-dihydro-1H-imidazo[4,5-c][1,8]naphthyridin-1-yl)methyl)benzenesulfonamide |

TABLE 1-continued

| # | Structure | Name |
|---|---|---|
| 116 | 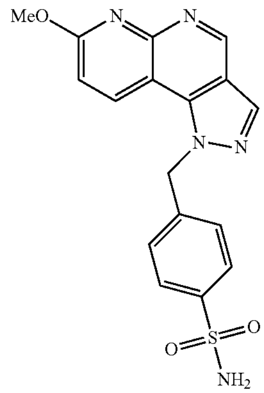 [SMILES: COc1ccc2c(ncc3cnn(Cc4ccc(S(N)(=O)=O)cc4)c32)n1] | 4-((7-methoxy-1H-pyrazolo[4,3-c][1,8]naphthyridin-1-yl)methyl)benzenesulfonamide |
| 117 | 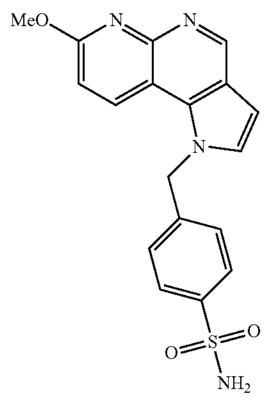 [SMILES: COc1ccc2c(ncc3ccn(Cc4ccc(S(N)(=O)=O)cc4)c32)n1] | 4-((7-methoxy-1H-pyrrolo[3,2-c][1,8]naphthyridin-1-yl)methyl)benzenesulfonamide |
| 118 | 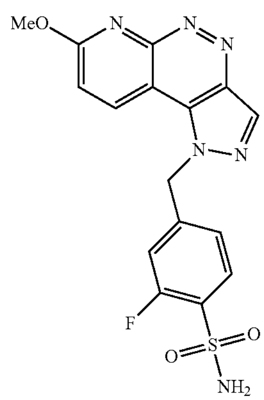 [SMILES: COc1ccc2c(nnc3cnn(Cc4ccc(S(N)(=O)=O)c(F)c4)c32)n1] | 2-fluoro-4-((7-methoxy-1H-pyrazolo[4,3-c]cinnolin-1-yl)methyl)benzenesulfonamide |
| 119 | 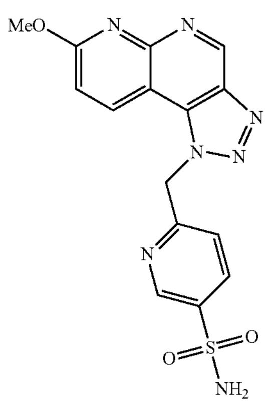 [SMILES: COc1ccc2c(ncc3nnn(Cc4ccc(S(N)(=O)=O)cn4)c32)n1] | 6-((7-methoxy-1H-[1,2,3]triazolo[4,5-c][1,8]naphthyridin-1-yl)methyl)pyridine-3-sulfonamide |

TABLE 1-continued

| # | Structure | Name |
|---|---|---|
| 120 | 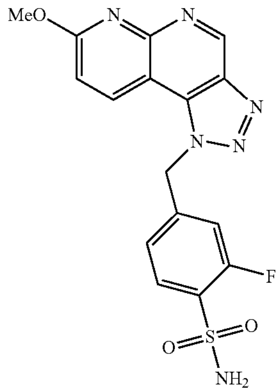 [SMILES: COc1ccc2c(ncc3nnn(Cc4ccc(S(N)(=O)=O)c(F)c4)c32)n1] | 2-fluoro-4-((7-methoxy-1H-[1,2,3]triazolo[4,5-c][1,8]naphthyridin-1-yl)methyl)benzenesulfonamide |
| 121 | 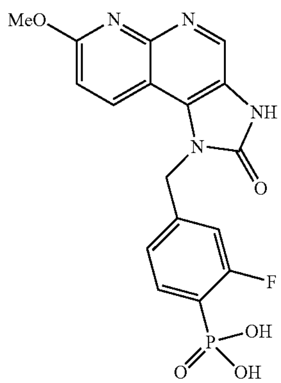 [SMILES: COc1ccc2c(ncc3[nH]c(=O)n(Cc4ccc(P(=O)(O)O)c(F)c4)c32)n1] | (2-fluoro-4-((7-methoxy-2-oxo-2,3-dihydro-1H-imidazo[4,5-c][1,8]naphthyridin-1-yl)methyl)phenyl)phosphonic acid |
| 122a | 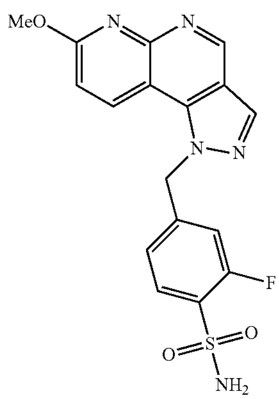 [SMILES: COc1ccc2c(ncc3cnn(Cc4ccc(S(N)(=O)=O)c(F)c4)c32)n1] | 2-fluoro-4-((7-methoxy-1H-pyrazolo[4,3-c][1,8]naphthyridin-1-yl)methyl)benzenesulfonamide |
| 122b | 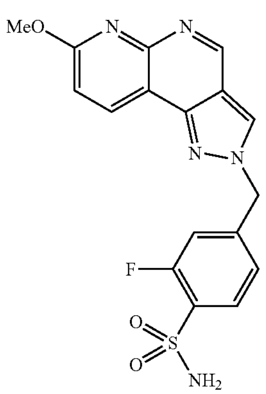 [SMILES: COc1ccc2c(ncc3cn(Cc4ccc(S(N)(=O)=O)c(F)c4)nc32)n1] | 2-fluoro-4-((7-methoxy-2H-pyrazolo[4,3-c][1,8]naphthyridin-2-yl)methyl)benzenesulfonamide |

TABLE 1-continued

| # | Structure | Name |
|---|---|---|
| 123 | 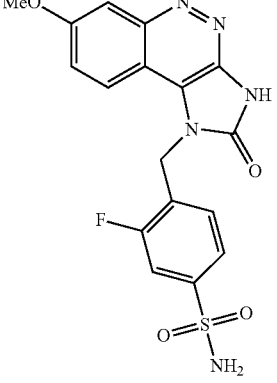 | 3-fluoro-4-((7-methoxy-2-oxo-2,3-dihydro-1H-imidazo[4,5-c]cinnolin-1-yl)methyl)benzenesulfonamide |
| 124 | 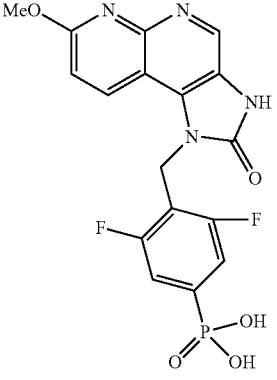 [SMILES: COc1ccc2c(ncc3[nH]c(=O)n(Cc4c(F)cc(P(=O)(O)O)cc4F)c32)n1] | (3,5-difluoro-4-((7-methoxy-2-oxo-2,3-dihydro-1H-imidazo[4,5-c][1,8]naphthyridin-1-yl)methyl)phenyl)phosphonic acid |
| 125 | 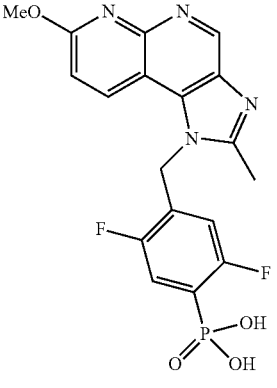 [SMILES: COc1ccc2c(ncc3nc(C)n(Cc4cc(F)c(P(=O)(O)O)cc4F)c32)n1] | (2,5-difluoro-4-((7-methoxy-2-methyl-1H-imidazo[4,5-c][1,8]naphthyridin-1-yl)methyl)phenyl)phosphonic acid |
| 126 | 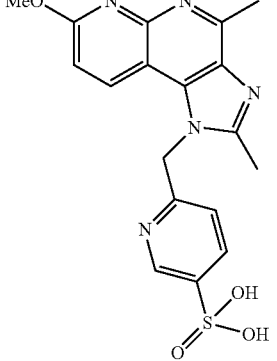 | (6-((7-methoxy-2,4-dimethyl-1H-imidazo[4,5-c][1,8]naphthyridin-1-yl)methyl)pyridin-3-yl)phosphonic acid |

TABLE 1-continued

| # | Structure | Name |
|---|---|---|
| 127 | 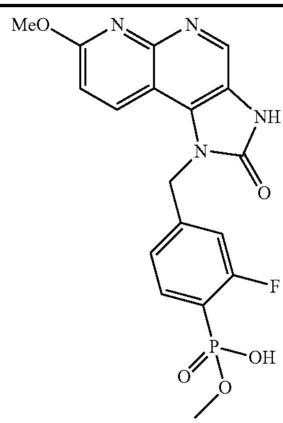 | methyl hydrogen (2-fluoro-4-((7-methoxy-2-oxo-2,3-dihydro-1H-imidazo[4,5-c][1,8]naphthyridin-1-yl)methyl)phenyl)phosphonate |
| 128 | 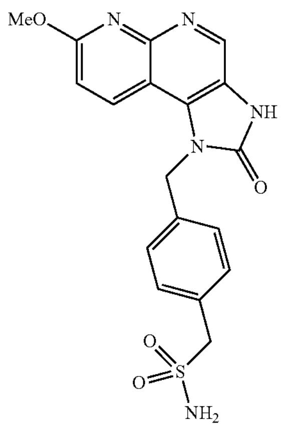 [SMILES: COc1ccc2c(ncc3[nH]c(=O)n(Cc4ccc(CS(N)(=O)=O)cc4)c32)n1] | (4-((7-Methoxy-2-oxo-2,3-dihydro-1H-imidazo[4,5-c][1,8]naphthyridin-1-yl)methyl)phenyl)-methanesulfonamide |
| 129 | 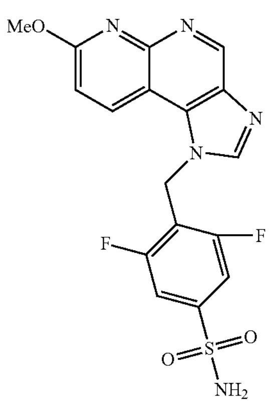 [SMILES: COc1ccc2c(ncc3ncn(Cc4c(F)cc(S(N)(=O)=O)cc4F)c32)n1] | 3,5-difluoro-4-((7-methoxy-1H-imidazo[4,5-c][1,8]naphthyridin-1-yl)methyl)benzenesulfonamide |
| 130 | 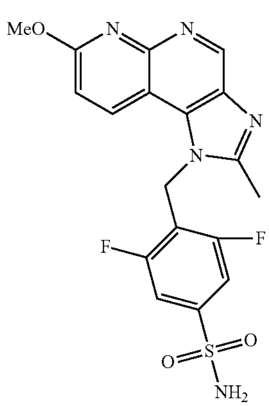 [SMILES: COc1ccc2c(ncc3nc(C)n(Cc4c(F)cc(S(N)(=O)=O)cc4F)c32)n1] | 3,5-difluoro-4-((7-methoxy-2-methyl-1H-imidazo[4,5-c][1,8]naphthyridin-1-yl)methyl)benzenesulfonamide |

TABLE 1-continued

| # | Structure | Name |
|---|-----------|------|
| 131 | 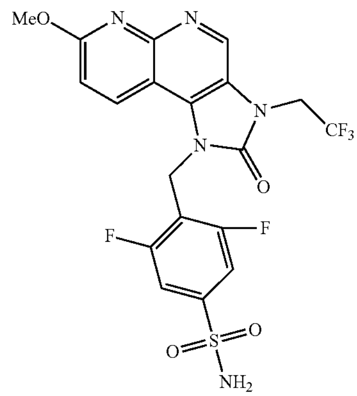 [SMILES: COc1ccc2c(ncc3c2n(Cc2c(F)cc(S(N)(=O)=O)cc2F)c(=O)n3CC(F)(F)F)n1] | 3,5-difluoro-4-((7-methoxy-2-oxo-3-(2,2,2-trifluoroethyl)-2,3-dihydro-1H-imidazo[4,5-c][1,8]naphthyridin-1-yl)methyl)benzenesulfonamide |
| 132 | 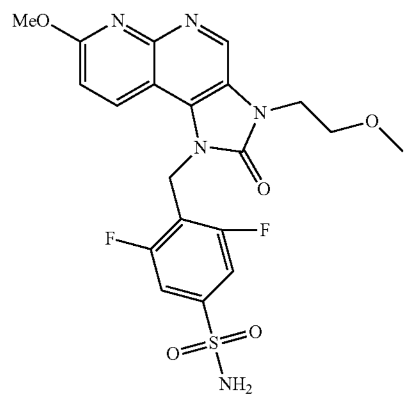 [SMILES: COCCn1c(=O)n(Cc2c(F)cc(S(N)(=O)=O)cc2F)c2c3ccc(OC)nc3ncc21] | 3,5-difluoro-4-((7-methoxy-3-(2-methoxyethyl)-2-oxo-2,3-dihydro-1H-imidazo[4,5-c][1,8]naphthyridin-1-yl)methyl)benzenesulfonamide |
| 133 | 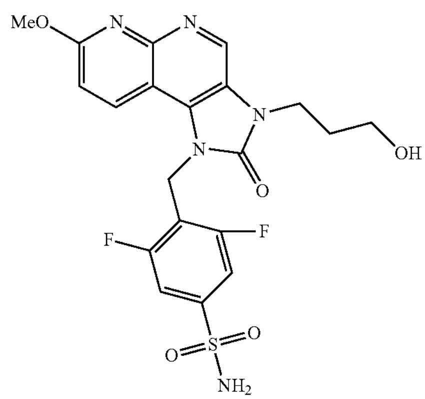 [SMILES: COc1ccc2c(ncc3c2n(Cc2c(F)cc(S(N)(=O)=O)cc2F)c(=O)n3CCCO)n1] | 3,5-difluoro-4-((3-(3-hydroxypropyl)-7-methoxy-2-oxo-2,3-dihydro-1H-imidazo[4,5-c][1,8]naphthyridin-1-yl)methyl)benzenesulfonamide |
| 134 | 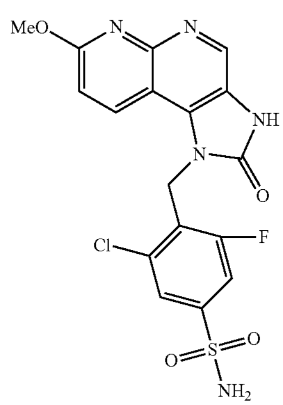 [SMILES: COc1ccc2c(ncc3[nH]c(=O)n(Cc4c(F)cc(S(N)(=O)=O)cc4Cl)c32)n1] | 3-chloro-5-fluoro-4-((7-methoxy-2-oxo-2,3-dihydro-1H-imidazo[4,5-c][1,8]naphthyridin-1-yl)methyl)benzenesulfonamide |

TABLE 1-continued

| # | Structure | Name |
|---|---|---|
| 135a | 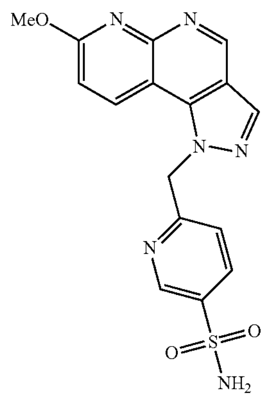 [SMILES: COc1ccc2c(ncc3cnn(Cc4ccc(S(N)(=O)=O)cn4)c32)n1] | 6-((7-methoxy-1H-pyrazolo[4,3-c][1,8]naphthyridin-1-yl)methyl)pyridine-3-sulfonamide |
| 135b | 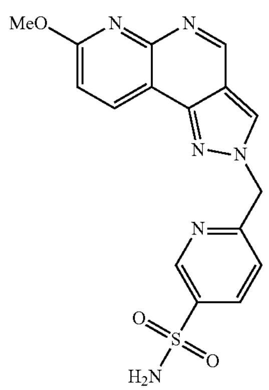 [SMILES: COc1ccc2c(ncc3cn(Cc4ccc(S(N)(=O)=O)cn4)nc32)n1] | 6-((7-methoxy-2H-pyrazolo[4,3-c][1,8]naphthyridin-2-yl)methyl)pyridine-3-sulfonamide |
| 136 | 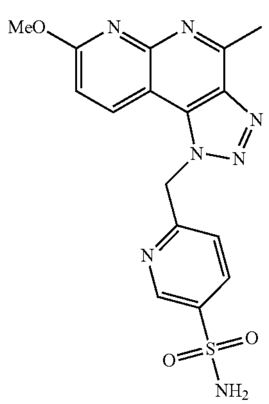 [SMILES: COc1ccc2c(n1)nc(C)c1nnn(Cc3ccc(S(N)(=O)=O)cn3)c12] | 6-((7-methoxy-4-methyl-1H-[1,2,3]triazolo[4,5-c][1,8]naphthyridin-1-yl)methyl)pyridine-3-sulfonamide |
| 137 | 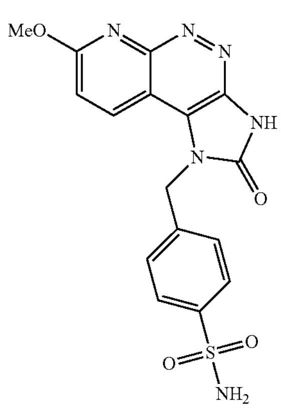 [SMILES: COc1ccc2c(nnc3[nH]c(=O)n(Cc4ccc(S(N)(=O)=O)cc4)c32)n1] | 4-((7-methoxy-2-oxo-2,3-dihydro-1H-imidazo[4,5-c]cinnolin-1-yl)methyl)benzenesulfonamide |

TABLE 1-continued
| # | Structure | Name |
|---|-----------|------|
| 138 | 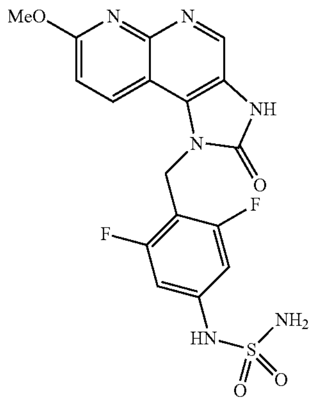 [SMILES: COc1ccc2c(ncc3[nH]c(=O)n(Cc4c(F)cc(NS(N)(=O)=O)cc4F)c32)n1] | 3,5-difluoro-4-(7-methoxy-2-oxo-2,3-dihydro-1H-imidazo[4,5-c][1,8]naphthyridin-1-yl)methyl)benzenesulfamide |
| 139 | 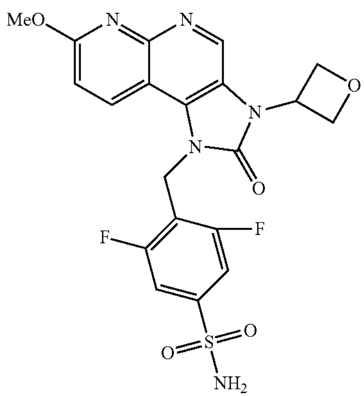 [SMILES: COc1ccc2c(ncc3c2n(Cc2c(F)cc(S(N)(=O)=O)cc2F)c(=O)n3C2COC2)n1] | 3,5-difluoro-4-((7-methoxy-3-(oxetan-3-yl)-2-oxo-2,3-dihydro-1H-imidazo[4,5-c][1,8]naphthyridin-1-yl)methyl)benzenesulfonamide |
In some embodiments, compounds of formula (A), or compounds of formula (I)-(VI) are not the following analogs:
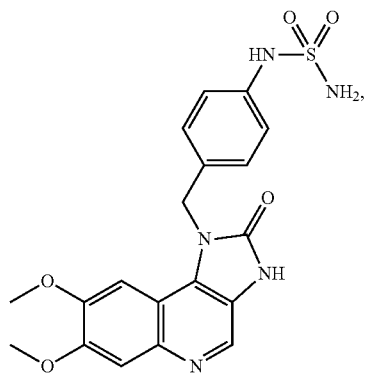
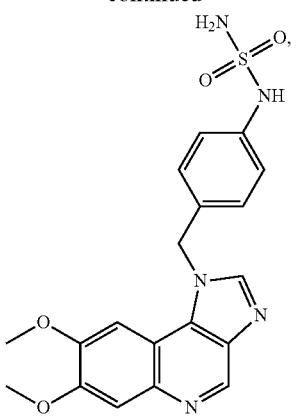

97
-continued
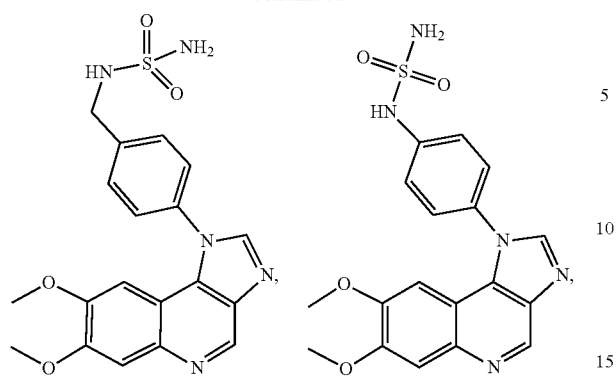
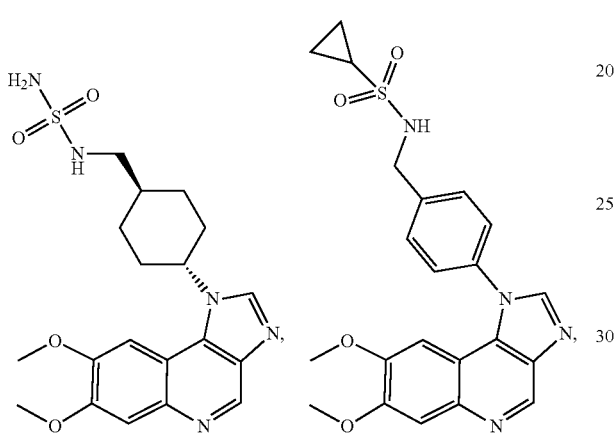
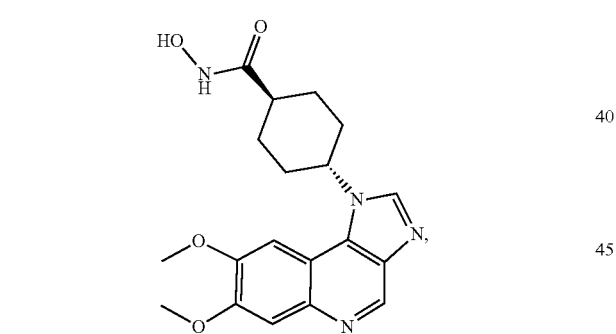
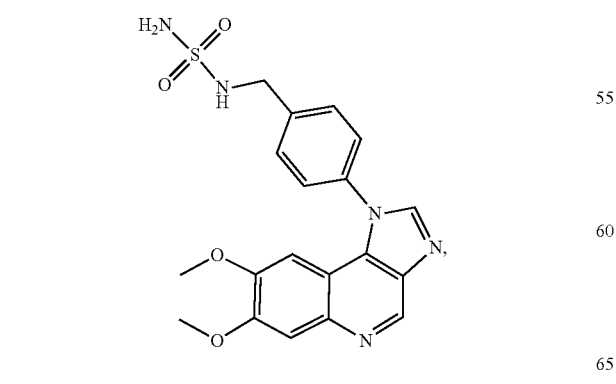
98
-continued
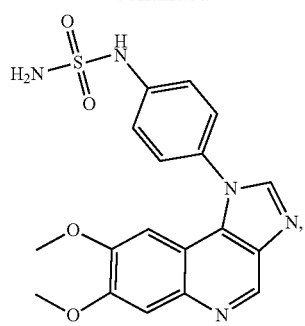
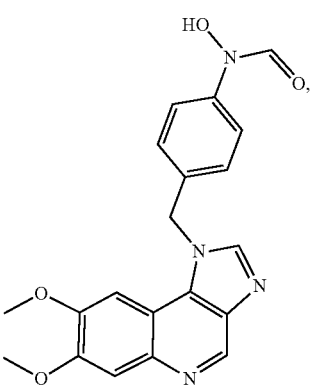
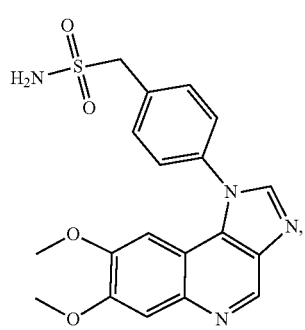
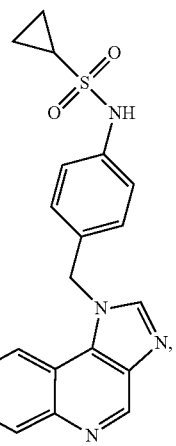

99
-continued
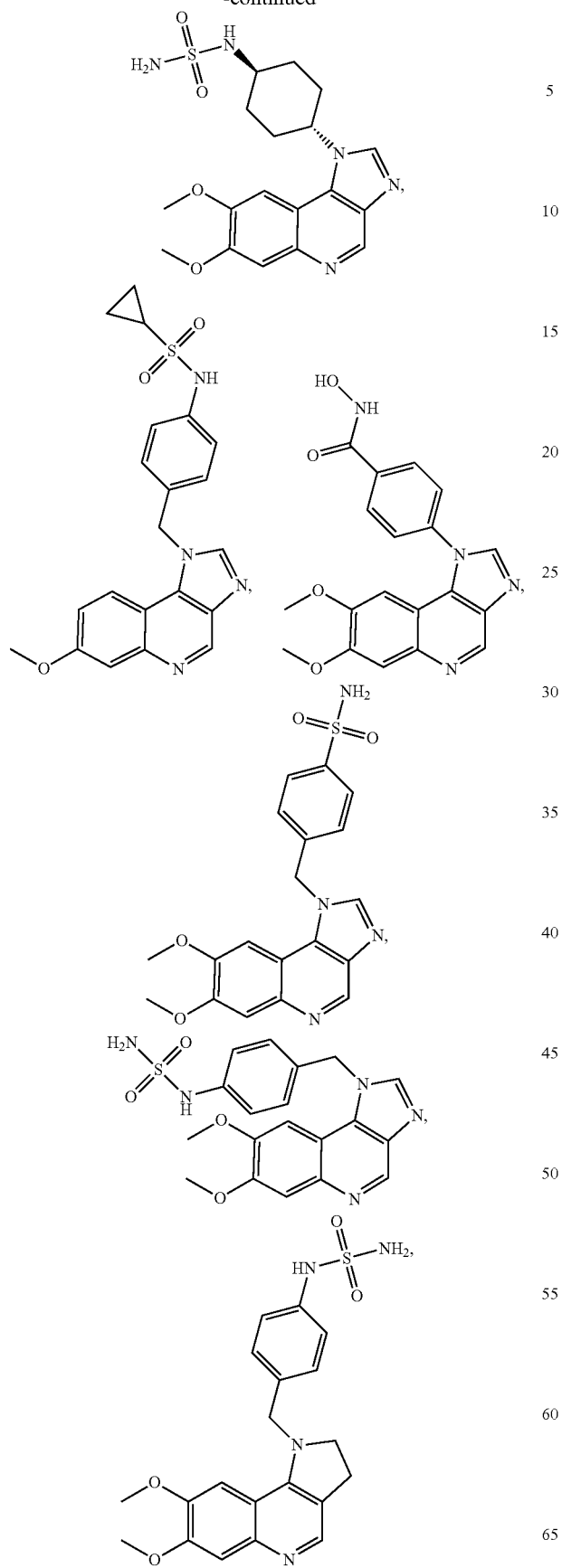
100
-continued
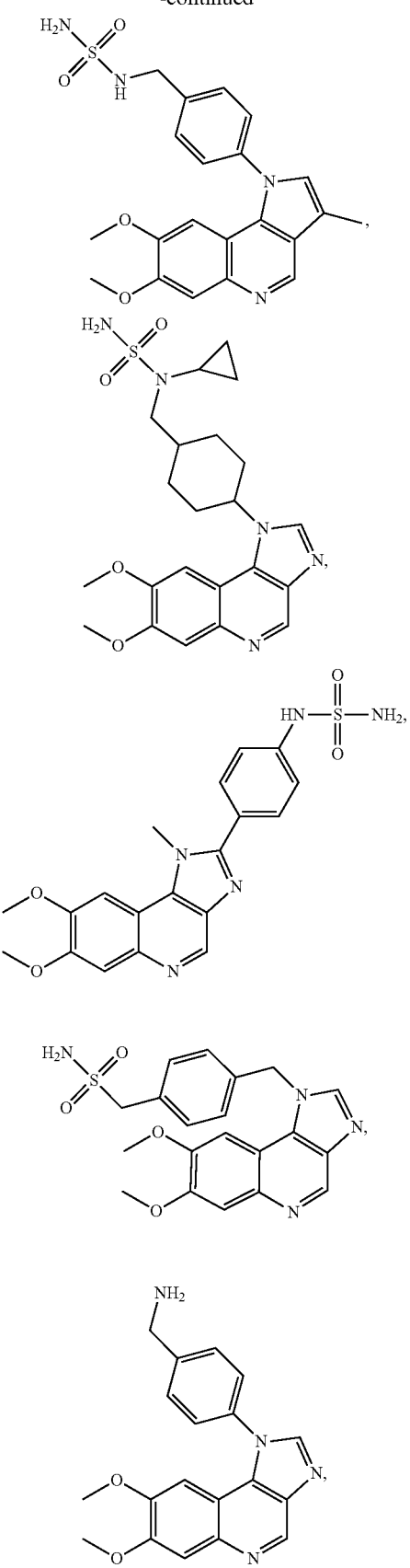

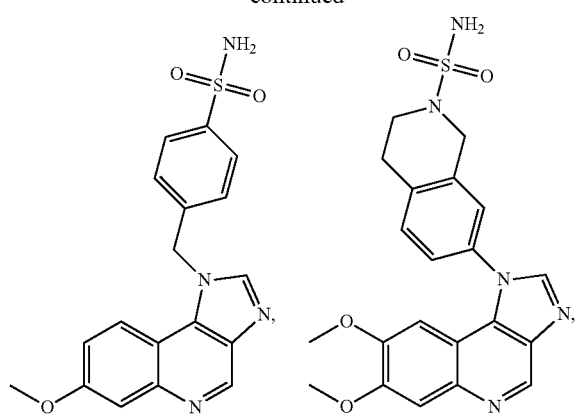
or a pharmaceutically acceptable salt, stereoisomer, or solvate thereof.
In some embodiments, compounds of formula (A), or compounds of formula (I)-(VI) are not the following analogs:
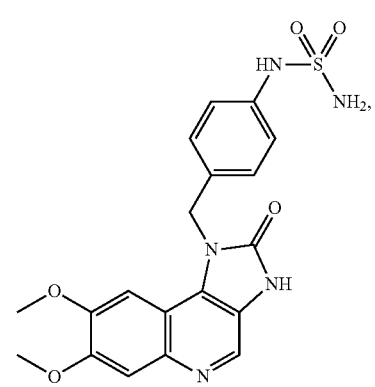
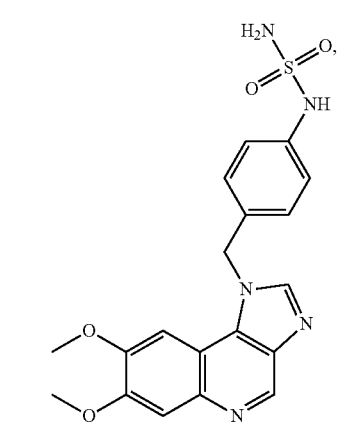
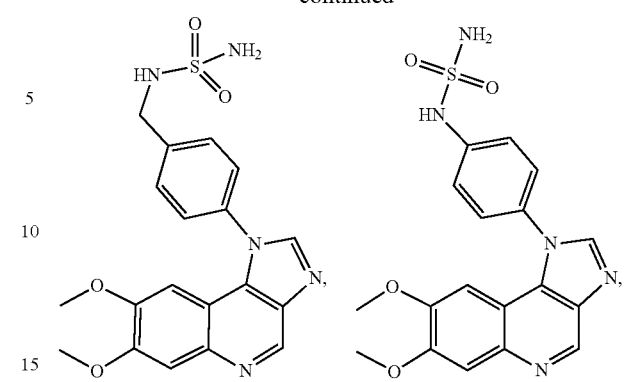
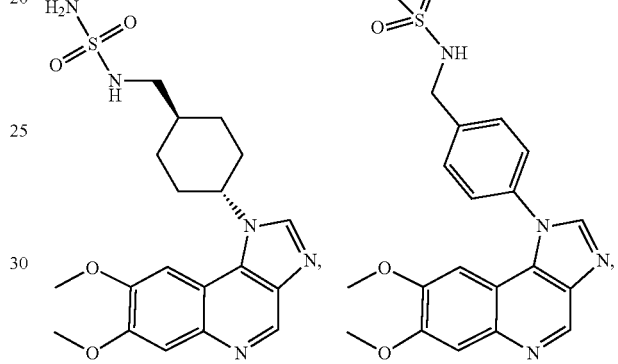

103
-continued
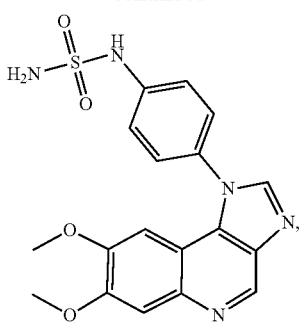
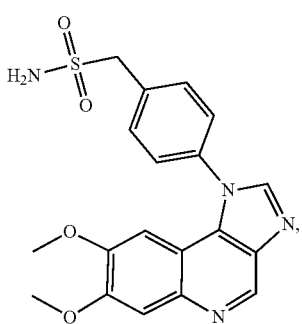
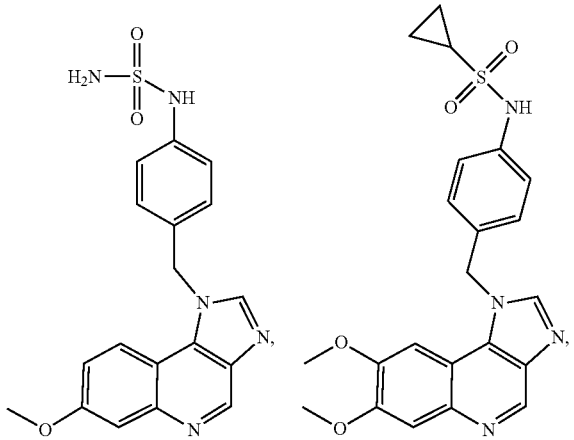
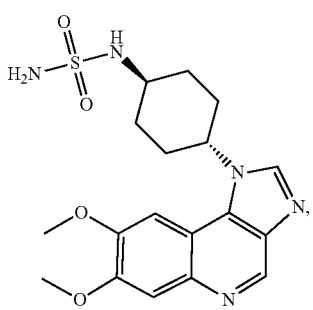
104
-continued
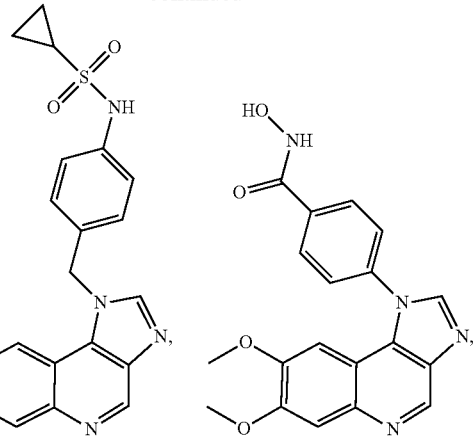
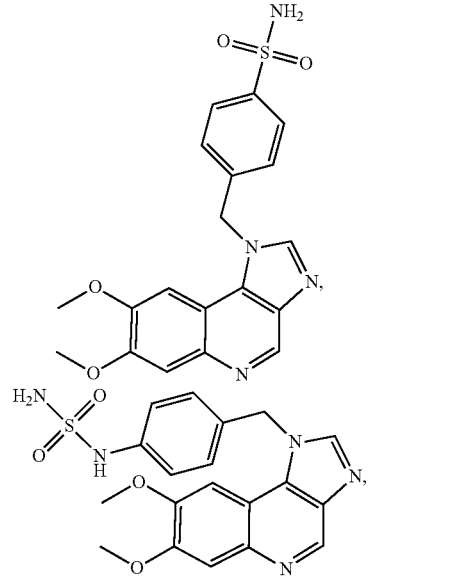
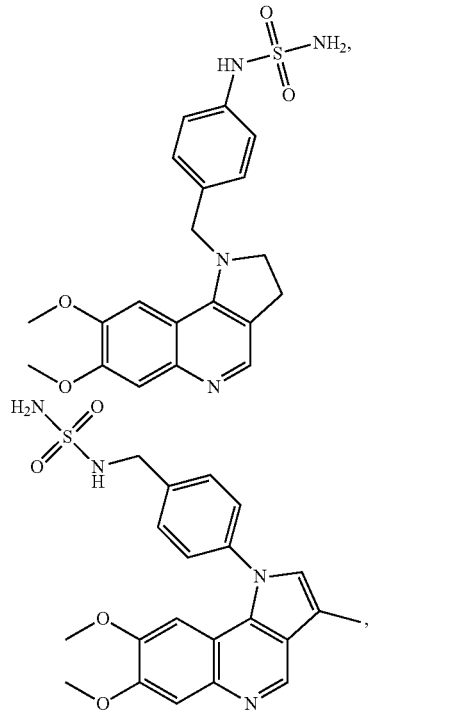

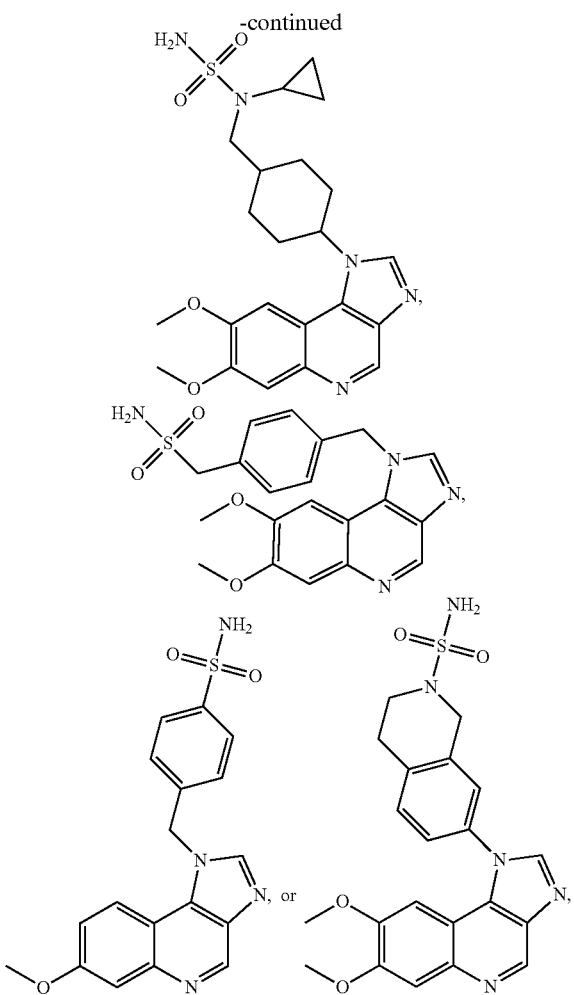

or a pharmaceutically acceptable salt, stereoisomer, or solvate thereof.

In some embodiments, provided herein is a compound described in Table 1 or a pharmaceutically acceptable salt, stereoisomer, solvate, or prodrug thereof.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzene sulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fiimarate, glucoheptanoate, glycerophosphate, glycolate, hemisulfate, heptanoate, hexanoate, hexyne-1,6-dioate, hydroxybenzoate, g-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalene sulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methane sulfonic acid, ethanesulfonic acid, 1,2-ethanedisulfonic acid, 2-hydroxyethane sulfonic acid, benzene sulfonic acid, 2-naphthalene sulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\ alkyl)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Also provided are prodrugs of the compounds described herein. In some embodiments, the prodrug can be converted to a compound of formula (A), or formulae (I)-(VI), when administered to a subject, e.g., upon metabolic processing of the prodrug.

The following prodrugs are examples using compound 40 for illustration purposes. In some embodiments, similar analogs can be made using sulfonamide as a handle.

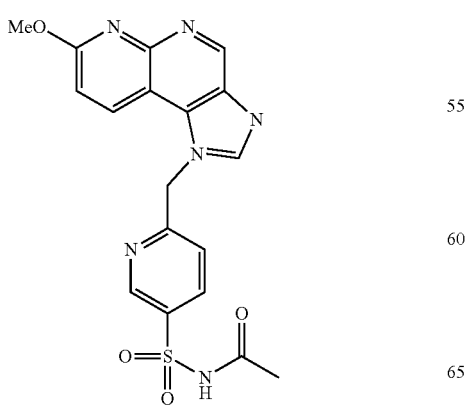

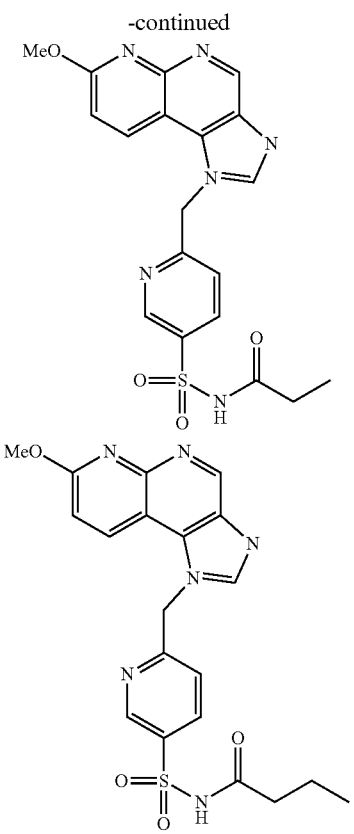

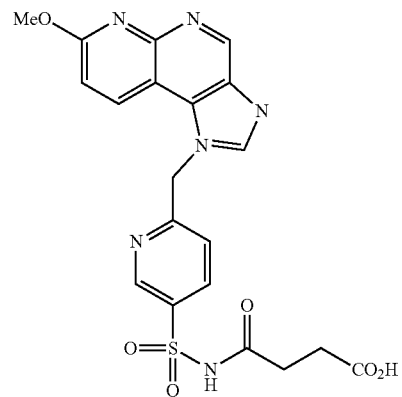

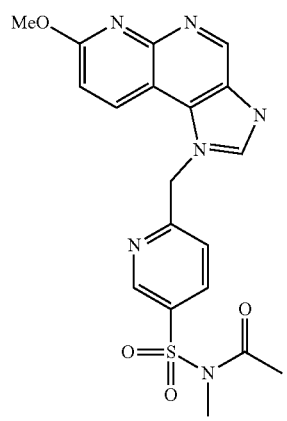

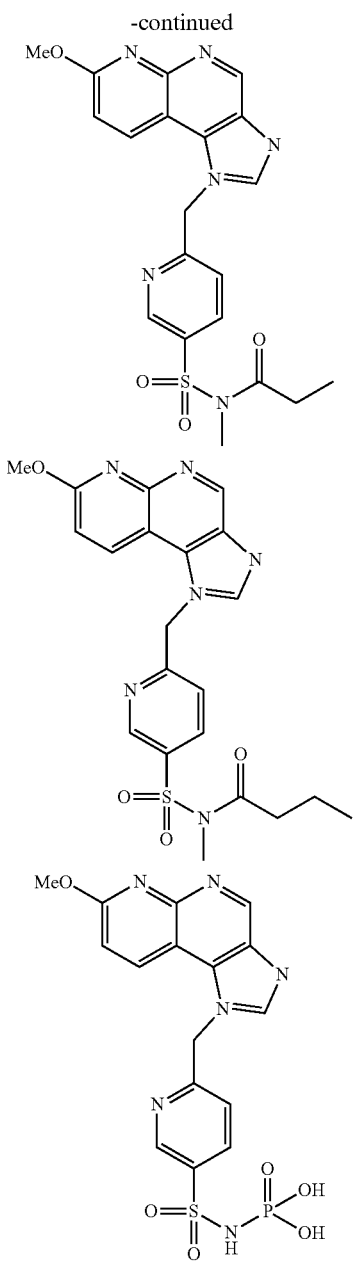

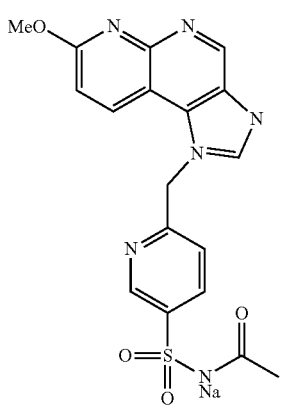

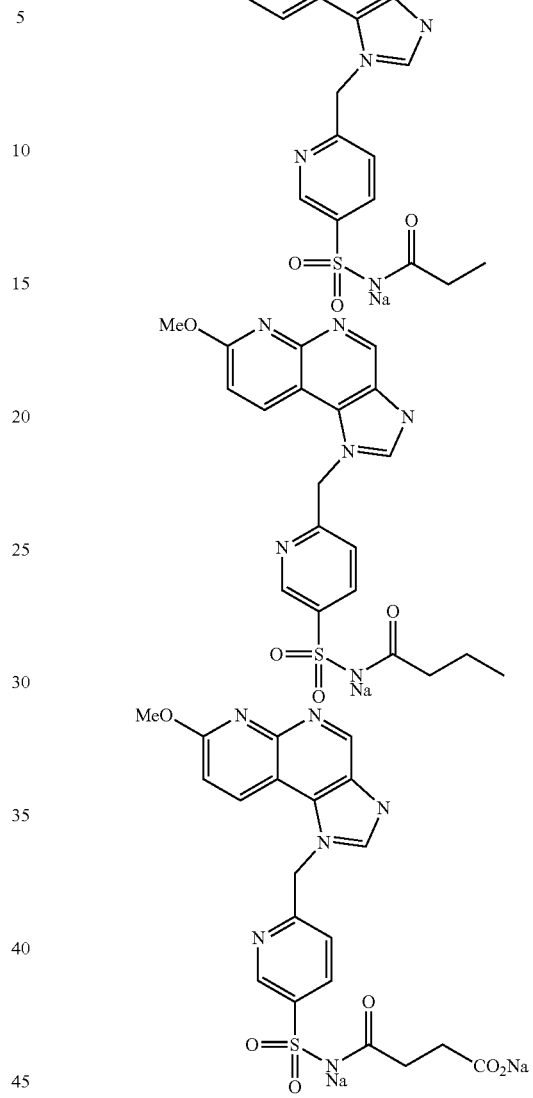

Pharmaceutical Compositions and Formulations

Pharmaceutical compositions of any of the compounds detailed herein or a pharmaceutically acceptable salt, stereoisomer, solvate, or prodrug thereof, are embraced by this disclosure. Thus, the present disclosure includes pharmaceutical compositions comprising a compound as detailed herein or a pharmaceutically acceptable salt, stereoisomer, solvate, or prodrug thereof, and a pharmaceutically acceptable carrier or excipient. In one aspect, the pharmaceutically acceptable salt is an acid addition salt, such as a salt formed with an inorganic or organic acid. Pharmaceutical composition can be formulated for particular routes of administration such as oral administration, parenteral administration, and topical administration, etc. In some embodiments, pharmaceutical compositions may take a form suitable for oral, buccal, parenteral, nasal, topical or rectal administration or a form suitable for administration by inhalation.

A compound as detailed herein or a pharmaceutically acceptable salt, stereoisomer, solvate, or prodrug thereof, may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein or a pharmaceutically acceptable salt, stereoisomer, solvate, or prodrug thereof, and a pharmaceutically acceptable carrier. In another variation, methods of administering a compound are provided. The purified forms, pharmaceutical compositions and methods of administering the compounds are suitable for any compound or form thereof detailed herein.

A compound detailed herein or a pharmaceutically acceptable salt, stereoisomer, solvate, or prodrug thereof, may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a pharmaceutically acceptable salt, stereoisomer, solvate, or prodrug thereof, can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compositions intended for oral use are prepared according to any method known in the art for the manufacture of pharmaceutical compositions and can be prepared in the form of tablets, pills, powders, suspensions, emulsions, solutions, syrups, and capsules. Oral composition may contain the active ingredient in admixture with nontoxic pharmaceutically acceptable excipients which are suitable for the manufacture of tablets. The tablets are uncoated or coated by known techniques to delay disintegration and absorption in the gastrointestinal tract and thereby provide a sustained action over a longer period. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or spray formulations, e.g., for delivery by aerosol or the like. Such topical delivery systems will in particular be appropriate for dermal application, e.g., for the treatment of skin cancer, e.g., for prophylactic use in sun creams, lotions, sprays and the like.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Methods and Therapeutic Uses

In addition to the compounds as disclosed herein, their pharmaceutically acceptable salts, stereoisomers, solvates, and compositions and combinations comprising these compounds, the invention includes methods of using the same as further described herein.

The compounds of formula (A), or formulae (I)-(VI), or pharmaceutically acceptable salt, prodrug, or solvate thereof may be used for treating STING pathway mediated diseases or disorders. Provided herein, in some embodiments, are methods for inhibiting ENPP1 activity using a compound of formula (A), or formulae (I)-(VI), or a pharmaceutically acceptable salt, stereoisomer, solvate, or prodrug thereof. In some embodiments, a compound of formula (A), or formulae (I)-(VI), or a pharmaceutically acceptable salt, stereoisomer, solvate, or prodrug thereof, have desired physicochemical properties, for example, solubility in water.

The Ectonucleotide Pyrophophatase/Phosphodiesterase (ENPP) family consists of seven members, ENNP1-7, which are membrane-bound glycoproteins or ectoenzymes with an active site or as soluble proteins in body fluids. ENPP1 has been involved in many different biological processes. In animal model, it was reported that overexpressed ENPP1 inhibits insulin receptor tyrosine kinase activity in peripheral tissues, which are major targets of insulin action. (Abate, N. et, al. *Nature Clin. Pract. Endocrinol. Metab.* 2006, 2, 694-701). ENPP1 is also expressed on the extracellular membrane of osteoblasts and chondrocytes, and it has a great effect on bone mineralization. (Terkeltaub, R et, al. *Purinergic Signalling* 2006, 2, 371-377; Vaingankar, S. M. et, al. *Cell Physiol*. 2004, 286, C1177-C1187).

Recently, ENPP1 was shown to play an important role in cancer immunotherapy and autoimmune diseases. ENPP1 hydrolyzes 2'3'-cyclic guanosine monophosphate-adenosine monophosphate (2'3'-cGAMP), breaking it down into 5'-AMP and 5'-GMP. cGAMP activates the Stimulator of Interferon Genes (STING) pathway, leading to production of type I interferon (IFN) and other cytokines that trigger the immune response. (Manas Sharma, et, al. *Int J cell Sci & Mol Biol.*, 2018,5,555655). Therefore, ENPP1 inhibitors which block the hydrolysis of cGAMP and induce sting activity can be potentially utilized to increase immune response. Similar to checkpoint inhibitors such as anti PD-1 or PD-$L_1$ which are promising immune-therapeutics for various cancers, activation of STING pathway by these inhibitors become more critical for tumor control in cancer immunotherapies.

Additionally, Lau WM and Kominsky SL [2013, PLoS ONE 8(7)] found that expression of "Enpp1 was elevated in human breast cancer cell lines known to produce bone metastasis in animal models compared to non-metastatic and normal mammary epithelial cell lines." They further demonstrated that levels of ENPP1 were significantly elevated in human primary breast tumors relative to normal mammary epithelium, in clinical specimens, with highest levels observed in breast-bone metastasis.

In one aspect, the invention provides a method of treating a disorder mediated by inappropriate ENPP1 activity comprising administering a safe and effective dose of a compound of formula (A), or formulae (I)-(VI), or a pharmaceutically acceptable salt, stereoisomer, solvate, or prodrug thereof.

In some embodiments, ENPP1 mediated diseases or disorders are selected from the group consisting of diseases related to skeletal and soft tissue mineralization, T2D, cardiovascular diseases, cancers, autoimmune diseases and osteoarthritis.

In some embodiments, ENPP1 mediated diseases or disorders are autoimmune diseases such as asthma, type I diabetes, rheumatoid arthritis, multiple sclerosis, chronic obstructive pulmonary disease (COPD), and lupus.

In some embodiments, the compounds described herein may be used to treat cancers that are mediated by inappropriate ENPP1 activity. In certain embodiments, the disease is a hematologic malignancy. In some embodiments, the disease is a solid tumor. In some embodiments, the indication is to treat solid tumor with abnormal ENPP1expression, such as astrocytic brain tumors, and glioblastoma stem-like cells and metastasis of breast cancer.

The potencies of compounds as inhibitors of an enzyme activity (or other biological activity) can be established by determining the concentrations at which each compound inhibits the activity to a predefined extent and then comparing the results. "IC50" or "IC90" of an inhibitor can be determined by the concentration that inhibits 50% or 90% of the activity in a biochemical assay, which can be accomplished using conventional techniques known in the art, including the techniques describes in the Examples below. As used herein, "inhibition of ENPP1 activity" or variants refer to a decrease in ENPP1 activity as a direct or indirect response to the presence of a compound of formula (A), or formulae (I)-(VI), or a pharmaceutically acceptable salt, stereoisomer, solvate, or prodrug thereof, relative to the activity of ENPP1 in the absence of the compound of formula (A), or formulae (I)-(VI), or a pharmaceutically acceptable salt, stereoisomer, solvate, or prodrug thereof.

In some embodiments, a compound of formula (A), or formulae (I)-(VI), or a pharmaceutically acceptable salt, stereoisomer, solvate, or prodrug thereof may be used in combination with one or more additional therapeutic agents to treat cancers or inflammatory disorders. The one or more additional therapeutic agents may be a chemotherapeutic agent, a radiotherapy, a targeted therapy, an immunotherapeutic agent or any current best of care treatment, either as a small molecule or a biologic nature.

Chemotherapeutic agents may be categorized by their mechanism of action into: alkylating agents, antimetabolites, anti-microtubule agents, topoisomerase inhibitors and cytotoxic agents. A compound of formula (A), or formulae (I)-(VI), or a pharmaceutically acceptable salt, stereoisomer, solvate, or prodrug thereof may be used in combination with chemotherapeutics to sensitize and improve the efficacy of certain chemotherapeutic agents to treat blood or solid tumors.

Immunotherapeutic agents that may be suitable to be used in combination with a compound of formula (A), or formulae (I)-(VI), or a pharmaceutically acceptable salt, stereoisomer, solvate, or prodrug thereof include but are not limited to therapeutic antibodies, small molecules and vaccines suitable for treating patients; such as IDO1 and TDO2 inhibitors, A2A receptor inhibitors, arginase inhibitors, toll-like receptor agonists, chemokine regulators (including CCR and CXCR families), STING agonists, check point blockage antibodies such as antibodies that regulate PD-1, PD-L1, CTLA-4, OX40-OX40 ligand, LAG3, TIM3, or any combination thereof.

Radiotherapy is part of cancer treatment to control or kill malignant cells and commonly applied to the cancerous tumor because of its ability to control cell growth. A compound of formula (A), or formulae (I)-(VI), or a pharmaceutically acceptable salt, stereoisomer, solvate, or prodrug thereof may be used in combination with radiotherapy, to improve the efficacy of radiotherapy to treat blood or solid tumors, or with surgery, chemotherapy, immunotherapy and combination of the four.

Targeted therapies that may be suitable to be used in combination therapies include but are not limit to an inhibitor to PI3Ks, cyclin-dependent kinase (CDK) such as CDK1, CDK2, CDK4/6, CDK7, and CDK9, Janus kinase (JAK) such as JAK1, JAK2 and/or JAK3, spleen tyrosine kinase (SYK), Bruton's tyrosine kinase (BTK), mitogen-activated protein kinase (MEK) such as MEK 1 and MEK2, bromodomain containing protein inhibitors (BRD) such as BRD4, isocitrate dehydrogenase (IDH) such as IDH1, histone deacetylase (HDAC), or any combination thereof.

In some embodiments, a compound of formula (A), or formulae (I)-(VI), or a pharmaceutically acceptable salt, stereoisomer, solvate, or prodrug thereof may be used in combination with one or more additional therapeutic agents to treat patients who are substantially refractory to at least one chemotherapy treatment, or in relapse after treatment with chemotherapy.

A dose of a pharmaceutical composition or combination is dependent on the body weight, age and individual condition, the disorder or disease or the severity thereof being treated. The effective dose is determined by a physician or clinician to prevent, treat or inhibit the progress of the disorder or disease. In some embodiments, a safe and effective dose is an amount sufficient to treat the patient's condition but low enough to avoid serious side effects. A safe and effective dose may vary with the particular compound chosen (e.g.

consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors.

In the practice of the method of the present invention, a therapeutically effective amount of any one of the compounds of this invention or a combination of any of the compounds of this invention or a pharmaceutically acceptable salt, stereoisomer, solvate, or prodrug thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The pharmaceutical compositions may be administered in either single or multiple doses. A compound of formula (A), or formulae (I)-(VI), or a pharmaceutically acceptable salt, stereoisomer, solvate, or prodrug thereof can be formulated so as to provide the desired release schedule of the active ingredient based on the therapeutic treatment purpose.

The pharmaceutical composition is preferably made in the form of a dosage unit containing a particular amount of the active ingredient in the form of tablets, pills, powders, suspensions, emulsions, solutions, syrups, and capsules. For example, these may contain an amount of active ingredient from about 0.1 to 1000 mg, preferably from about 0.1 to 500 mg. A suitable daily dose for a human or other mammal may vary widely depending on the condition of the patient and other factors, but, once again, can be determined using routine methods. The daily dose can be administered in one to four doses per day. For therapeutic purposes, the active compounds of this invention are ordinarily combined with one or more adjuvants appropriate to the indicated route of administration drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g. from 1% to 2% by weight of the formulation, preferably not more than 5% w/w, and more preferably from 0.1% to 1% of the formulation.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

In certain embodiment, the method comprises administering to the subject an initial daily dose of about 0.1 to 500 mg of a compound of formula (A), or formulae (I)-(VI) and increasing the dose by increments until clinical efficacy is achieved. Increments of about 5, 10, 25, 50, or 100 mg can be used to increase the dose. The dosage can be increased daily, every other day, twice per week, or once per week.

Articles of Manufacture and Kits

The present disclosure further provides articles of manufacture comprising a compound of the disclosure or a salt thereof, composition, and unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the disclosure, which comprises one or more compounds described herein or a composition comprising a compound described herein. The kits may employ any of the compounds disclosed herein. In one variation, the kit employs a compound described herein or a pharmaceutically acceptable salt, stereoisomer, solvate, or prodrug thereof. The kits may be used for any one or more of the uses described herein, and, accordingly, may contain instructions for the treatment of disease described herein.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

Reagents and solvents used below can be obtained from commercial sources. $^1$H-NMR spectra were recorded on a Bruker 400 and 600 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Mass spectrometry results are reported as the ratio of mass over charge, followed by the relative abundance of each ion (in parentheses). Electrospray ionization (ESI) mass spectrometry analysis was conducted on an Agilent 1100 LC/MSD electrospray mass spectrometer.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), ethyl acetate (EA or EtOAc), dichloromethane (DCM), diethyl ether, methanol, pyridine and the like. Unless specified to the contrary, the solvents used in the reactions of the present invention are inert organic solvents, and the reactions are carried out under an inert gas, preferably nitrogen and argon.

The compounds of formula (I)-(VI) may be prepared using the methods disclosed herein and routine modifications thereof, which will be apparent given the disclosure herein and methods are well known in the art. Conventional and well-known synthetic methods may be used in addition to the teachings herein. The synthesis of representative compounds described herein may be accomplished as described in the following examples. If available, reagents may be purchased commercially, e.g., from Sigma Aldrich or other chemical suppliers.

General Procedures

Example 1

4-((7,8-dimethoxy-2-oxo-2,3-dihydro-1H-imidazo[4,5-c]quinolin-1 yl)methyl)benzenesulfonamide (1)

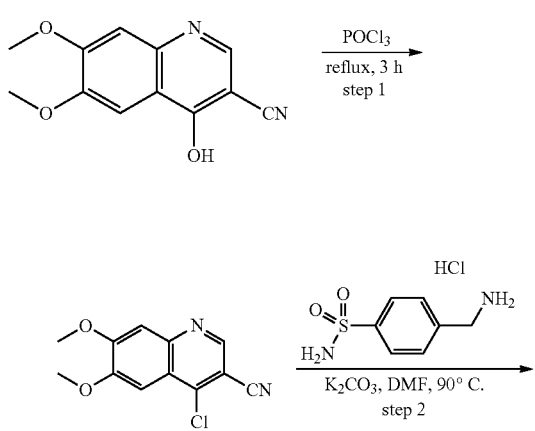

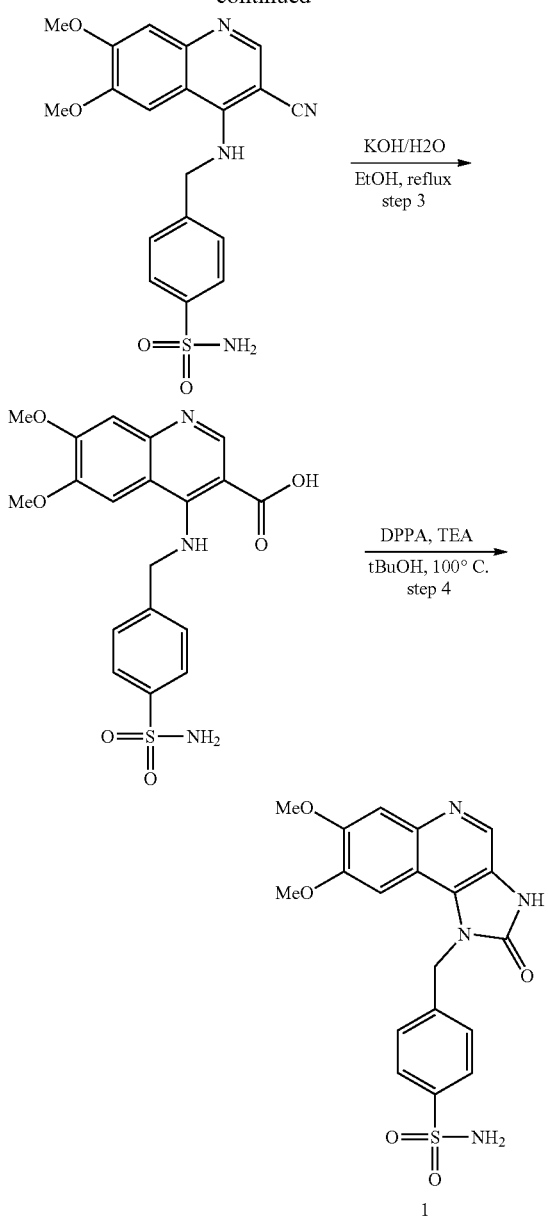

Step 1: Synthesis of 4-chloro-6,7-dimethoxyquinoline-3-carbonitrile

A stirred mixture of 4-hydroxy-6,7-dimethoxyquinoline-3-carbonitrile (550 mg, 2.39 mmol) and 10 mL of POCl$_3$ was heated at reflux for 3 h. Volatile materials were removed under vacuum at about 70° C. The residue was stirred at 0° C. with methylene chloride and H$_2$O, solid K$_2$CO$_3$ was carefully added until the pH was 8-9. After stirring for 30 min at 25° C. the organic layer was separated, washed with H$_2$O, dried, filtered through Celite, and concentrated to give crude product. The residue was purified by flash column chromatography (0-30% EA in PE) to give the product of 4-chloro-6,7-dimethoxyquinoline-3-carbonitrile 2 as a light yellow solid (600 mg, 95% yield). LCMS(ESI) [M+H]$^+$=249.

Step 2: Synthesis of 4-(((3-cyano-6,7-dimethoxy-quinolin-4-yl)amino]methyl)-benzenesulfonamide To a solution of 4-chloro-6,7-dimethoxyquinoline-3-carbonitrile (550 mg, 2.21 mmol), 4-(Aminomethyl)benzenesulfonamide hydrochloride (591 mg, 2.65 mmol) and potassium carbonate (1.528 g, 11.06 mmol) in DMF (15 ml). The reaction mixture was stirred at 70° C. for 16 h, monitored by LCMS. After filtrated, the organic layer was concentrated in vacuum, the residue was purified by recrystallization from DCM/MeOH (10:1) to give the product of 4-(((3-cyano-6,7-dimethoxyquinolin-4-yl)amino)methyl)benzenesulfonamide as a yellow solid (800 mg, 72.6% yield). LCMS(ESI) [M+H]$^+$=399.

Step 3: Synthesis of 6,7-dimethoxy-4-(((4-sulfamoylphenyl)methyl)amino)quinoline-3-carboxylic Acid To a solution of 4-(((3-cyano-6,7-dimethoxyquinolin-4-yl)amino)methyl)benzenesulfonamide (500 mg, 1.255 mmol) in EtOH (5 ml) was added KOH (1734 mg, 12.55 mmol, dissolved in 5 ml water). The reaction mixture was heated to reflux for 16 h. The solution was concentrated in vacuum, the crude product was purified by prep-HPLC to give the product of 6,7-dimethoxy-4-(((4-sulfamoylphenyl)methyl)amino)quinoline-3-carboxylic acid as a white solid (90 mg, 16% yield). LCMS (ESI) [M+H]$^+$=418.

Step 4: Synthesis of 4-((7,8-dimethoxy-2-oxo-2,3-dihydro-1H-imidazo[4,5-c]quinolin-1-yl)methyl) benzene-sulfonamide To a solution of 6,7-dimethoxy-4-(((4-sulfamoylphenyl) methyl)amino)quinoline-3-carboxylic acid (20 mg, 0.048 mmol) in t-BuOH (2 ml) was added triethylamine (5.8 mg, 0.057 mmol) and DPPA (15.8 mg, 0.057 mmol). The reaction mixture was stirred at 100° C. for 16 h under nitrogen. The solution was concentrated to dryness, purified by prep-HPLC to give the product of 4-((7,8-dimethoxy-2-oxo-2,3-dihydro-1H-imidazo[4,5-c]quinolin-1-yl)methyl)benzenesulfonamide (1) as a white solid (5 mg, 21% yield). LCMS (ESI) [M+H]$^+$=415; $^1$H NMR (400 MHz, DMSO) δ 11.58 (br, 1H), 8.51 (s, 1H), 8.17 (s, 1H), 7.79 (d, J=8.3 Hz, 2H), 7.45 (d, J=8.3 Hz, 2H), 7.31 (s, 2H), 6.95 (s, 1H), 5.63 (s, 2H), 3.84 (s, 3H), 3.59 (s, 3H).

Example 2

Preparation of 2,3-dihydro-1H-imidazo[4,5-c]quinolin-1-yl (General Procedure 1)

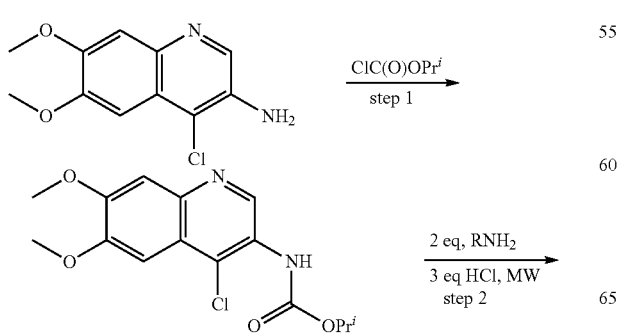

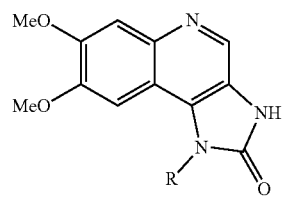

A similar synthetic method (W, Huang et el, Eur. J. Org. Chem. 2018, 1572-1580) was adapted to provide the titled analogs from a known starting material (4-chloro-6,7-dimethoxyquinolin-3-amine, made according to a literature procedure, Fuchss, Thomas et al, PCT Int. Appl., 2012028233).

Preparation of 1H-imidazo[4,5-c]quinoline (General Procedure 3)

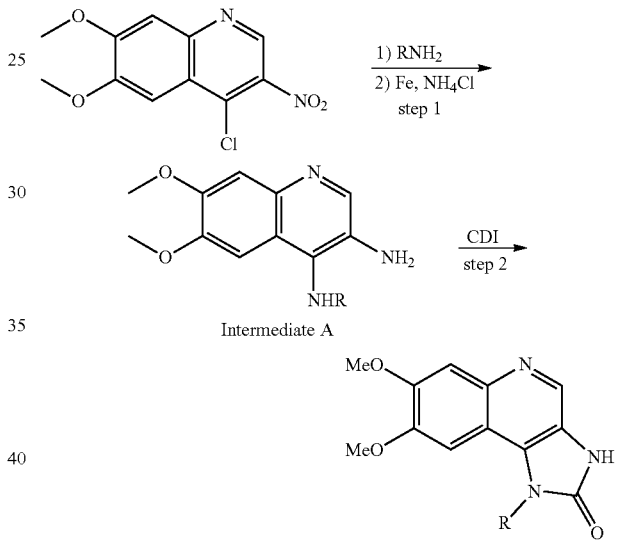

Preparation of 2,3-dihydro-1H-imidazo[4,5-c]quinolin-1-yl (General Procedure 2)

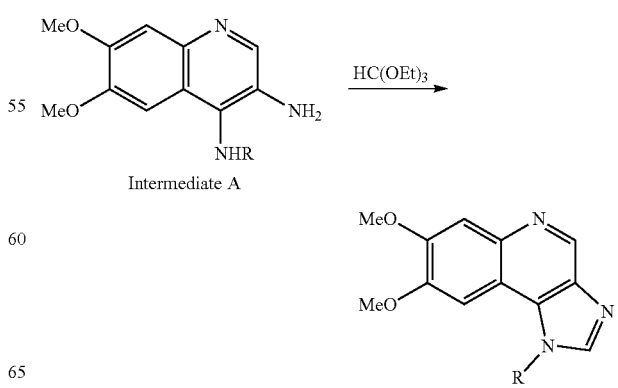

Preparation of 1H-[1,2,3]triazolo[4,5-c]quinoline (General Procedure 4)

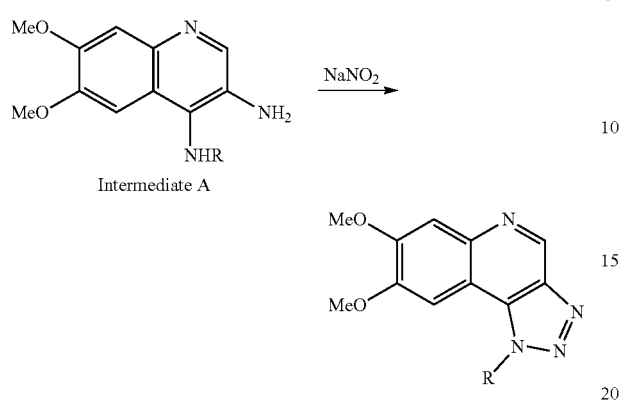

Similar synthetic methods (A. Boullilot, WO 2011/054846 A1) were adapted to provide the titled analogs (General procedures 2, 3, and 4) from a known starting material (4-chloro-3-nitro-6,7-dimethoxyquinoline, made according to a literature procedure, Fuchss, Thomas et al, PCT Int. Appl., 2012028233).

Preparation of 1H-[1,2,3]triazolo[4,5-c]quinoline (General Procedure 5)

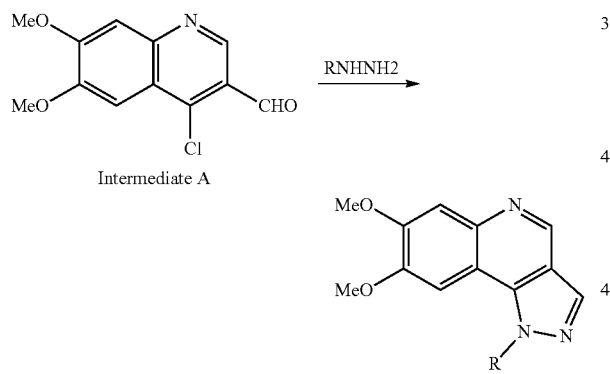

A similar synthetic method (A Gopalsamy et al, Journal of Medicinal Chemistry 2007, 50, 5547-5549) was adapted to provide the titled analogs from 4-chloro-6,7-dimethoxyquinoline-3-carbaldehyde.

Preparation of 1H-[1,2,3]triazolo[4,5-c]quinoline (General Procedure 6)

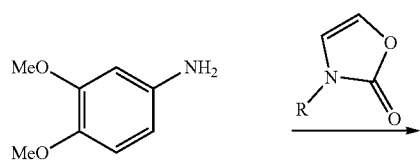

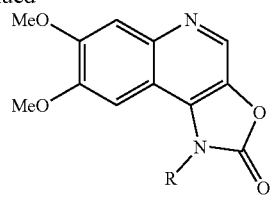

A similar synthetic method (By A. Jeffrey S. et al, PCT Int. Appl., 2014152029) was adapted to provide the titled analogs from 3,4-dimethoxyaniline.

Example 3

4-((7,8-dimethoxy-3-methyl-2-oxo-2,3-dihydro-1H-imidazo[4,5-c]quinolin-1-yl)methyl)benzenesulfonamide (2)

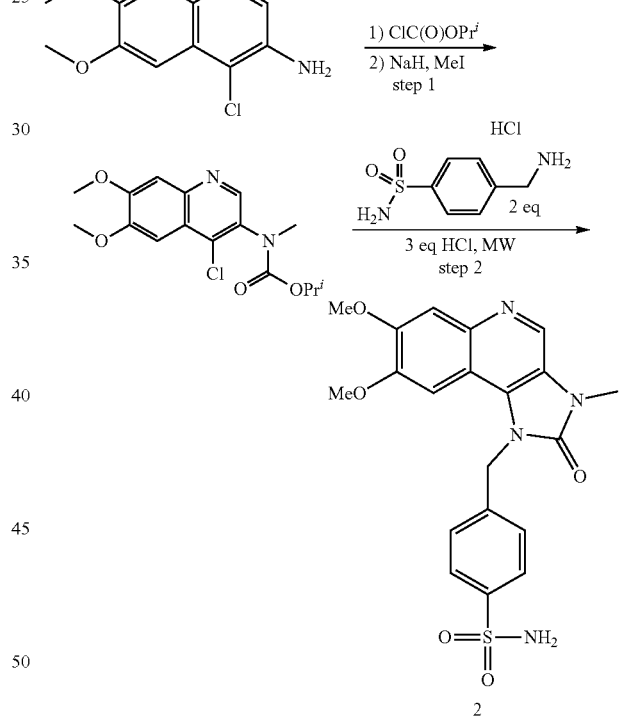

A similar synthetic method (W, Huang et el, Eur. J. Org. Chem. 2018, 1572-1580) was adapted to provide the titled analogs 2 from a known starting material (4-chloro-6,7-dimethoxyquinolin-3-amine, made according to a literature procedure, Fuchss, Thomas et al, PCT Int. Appl., 2012028233). LCMS (ESI) [M+H]+=428; $^1$H NMR (400 MHz, DMSO) S LCMS [M+H]+=429; $^1$H NMR (600 MHz, DMSO-d6) δ ppm 3.62 (d, J=4.03 Hz, 6H) 3.86-3.93 (m, 3H) 5.76 (s, 2H) 7.04 (s, 1H) 7.33 (s, 2H) 7.41 (s, 1H) 7.50 (d, J=8.44 Hz, 2H) 7.78-7.81 (m, 2H) 8.95 (br s, 1H).

Example 4

(R)-4-(1-(7,8-dimethoxy-2-oxo-2,3-dihydro-1H-imidazo[4,5-c]quinolin-1-yl)ethyl)benzenesulfonamide (3a) and (S)-4-(1-(7,8-dimethoxy-2-oxo-2,3-dihydro-1H-imidazo[4,5-c]quinolin-1-yl)ethyl)benzenesulfonamide (3b)

(R)-4-(1-(7,8-dimethoxy-2-oxo-2,3-dihydro-1H-imidazo[4,5-c]quinolin-1-yl)ethyl)benzenesulfonamide (3a) and (S)-4-(1-(7,8-dimethoxy-2-oxo-2,3-dihydro-1H-imidazo[4,5-c]quinolin-1-yl)ethyl)benzenesulfonamide (3b) are prepared according to General procedure 2 from known compound (R)-4-(1-aminoethyl)benzenesulfonamide and (S)-4-(1-aminoethyl)benzenesulfonamide (Canales et al, PCT Int. Appl., 2010002998).

Example 5

4-((7,8-dimethoxy-2-oxooxazolo[5,4-c]quinolin-1(2H)-yl)methyl)benzenesulfonamide (4)

4-((7,8-dimethoxy-2-oxooxazolo[5,4-c]quinolin-1(2H)-yl)methyl)benzenesulfonamide is prepared according to General procedure 6.

Example 6

6-((7,8-dimethoxy-2-oxo-2,3-dihydro-1H-imidazo[4,5-c]quinolin-1-yl)methyl)pyridine-3-sulfonamide (5)

6-((7,8-dimethoxy-2-oxo-2,3-dihydro-1H-imidazo[4,5-c]quinolin-1-yl)methyl)pyridine-3-sulfonamide is prepared according to General procedure 2 from a known compound 6-(aminomethyl)pyridine-3-sulfonamide (J. Bakonyi, et al, U.S. Pat. Appl. Publ., 20150291607).

Example 7

5-((7,8-dimethoxy-2-oxo-2,3-dihydro-1H-imidazo[4,5-c]quinolin-1-yl)methyl)pyridine-2-sulfonamide (6)

5-((7,8-dimethoxy-2-oxo-2,3-dihydro-1H-imidazo[4,5-c]quinolin-1-yl)methyl)pyridine-2-sulfonamide is prepared according to General procedure 2 from a known compound 5-(aminomethyl)pyridine-2-sulfonamide (A. Macleod, et al, PCT Int. Appl., 2009024585).

Example 8

3-((7,8-dimethoxy-2-oxo-2,3-dihydro-1H-imidazo[4,5-c]quinolin-1-yl)methyl)benzenesulfonamide (7)

3-((7,8-dimethoxy-2-oxo-2,3-dihydro-1H-imidazo[4,5-c]quinolin-1 yl)methyl)-benzenesulfonamide is prepared according to General procedure 2 from 3-(aminomethyl)benzenesulfonamide.

Example 9

(R)-4-(1-(7-methoxy-2-oxo-2,3-dihydro-1H-imidazo[4,5-c]quinolin-1-yl)ethyl)benzene-sulfonamide (8)

(R)-4-(1-(7-methoxy-2-oxo-2,3-dihydro-1H-imidazo[4,5-c]quinolin-1-yl)ethyl)benzene-sulfonamide is prepared in a similar manner as compound 1. LCMS (ESI) [M+H]$^+$=399; $^1$H NMR (600 MHz, DMSO-d6) δ ppm 1.98 (br d, J=6.97 Hz, 4H) 3.85 (s, 3H) 6.28 (q, J=7.21 Hz, 1H) 7.01 (br s, 1H) 7.33-7.39 (m, 3H) 7.54 (d, J=8.07 Hz, 2H) 7.78-7.83 (m, 2H) 8.66 (s, 1H) 11.62 (br s, 1H).

Example 10

4-((7,8-dimethoxy-2-methyl-1H-imidazo[4,5-c]quinolin-1-yl)methyl)benzenesulfonamide (9)

4-((7,8-dimethoxy-2-methyl-1H-imidazo[4,5-c]quinolin-1-yl)methyl)benzenesulfonamide is prepared according to General procedure 3 using triethyl orthoacetate.

Example 11

5-((7,8-dimethoxy-1H-imidazo[4,5-c]quinolin-1-yl)methyl)pyridine-2-sulfonamide (10)

5-((7,8-dimethoxy-1H-imidazo[4,5-c]quinolin-1-yl)methyl)pyridine-2-sulfonamide was prepared according to General procedure 3. LCMS (ESI) [M+H]$^+$=400; $^1$H NMR (600 MHz, DMSO-d6) δ ppm 3.70-3.76 (m, 4H) 3.94 (s, 3H) 6.31 (s, 2H) 7.25 (s, 1H) 7.47 (s, 2H) 7.61 (s, 1H) 7.72 (dd, J=8.44, 2.20 Hz, 1H) 7.87 (d, J=8.07 Hz, 1H) 8.71 (d, J=1.83 Hz, 1H) 8.84 (s, 1H) 9.53 (br s, 1H).

Example 12

(R)-4-(1-(7,8-dimethoxy-1H-imidazo[4,5-c]quinolin-1-yl)ethyl)benzenesulfonamide (11a) and (S)-4-(1-(7,8-dimethoxy-1H-imidazo[4,5-c]quinolin-1-yl)ethyl)benzenesulfonamide (11b)

(R)-4-(1-(7,8-dimethoxy-1H-imidazo[4,5-c]quinolin-1-yl)ethyl)benzenesulfonamide (11a) and (S)-4-(1-(7,8-dimethoxy-1H-imidazo[4,5-c]quinolin-1-yl)ethyl)benzenesulfonamide (11b) were prepared according to General procedure 3. 11a: LCMS (ESI) [M+H]$^+$=413; $^1$H NMR (600 MHz, DMSO-d6) δ ppm 2.15 (d, J=6.60 Hz, 3H) 3.77-3.84 (m, 4H) 3.90-3.97 (m, 4H) 6.73-6.81 (m, 1H) 7.34 (s, 2H) 7.40 (br d, J=8.44 Hz, 3H) 7.64 (br s, 1H) 7.79 (d, J=8.80 Hz, 2H) 9.16 (br s, 1H) 9.67 (br s, 1H). 11b: LCMS (ESI) [M+H]$^+$=413.

Example 13

6-((7,8-dimethoxy-1H-imidazo[4,5-c]quinolin-1-yl)methyl)pyridine-3-sulfonamide (12)

6-((7,8-dimethoxy-1H-imidazo[4,5-c]quinolin-1-yl)methyl)pyridine-3-sulfonamide (12) was prepared according to General procedure 3. LCMS [M+H]$^+$=400; $^1$H NMR (600 MHz, DMSO-d6) δ ppm 1.16 (s, 1H) 2.09 (s, 1H) 3.77 (s, 3H) 3.94 (s, 3H) 6.33 (s, 2H) 7.39 (s, 1H) 7.58 (s, 3H) 8.21 (dd, J=8.44, 2.20 Hz, 1H) 8.80 (br s, 1H) 8.84 (d, J=1.83 Hz, 1H).

Example 14

4-((7,8-dimethoxy-1H-[1,2,3]triazolo[4,5-c]quinolin-1-yl)methyl)benzenesulfonamide (13)

Compound 13 was prepared according to General procedure 4. LCMS [M+H]+=400; $^1$H NMR (600 MHz, DMSO-d6) δ ppm 3.78 (s, 3H) 3.93 (s, 3H) 6.56 (s, 2H) 7.33 (d, J=12.10 Hz, 3H) 7.37 (d, J=8.80 Hz, 2H) 7.64 (s, 1H) 7.80 (d, J=8.44 Hz, 2H) 9.43 (s, 1H) 11.69 (s, 1H).

Example 15

Compounds 14a, 14b, 15 and 16 are prepared according to General procedure 4.

Example 16

Compound 17, 18, 19a, 19b, 20 and 21 are prepared according to General procedure 5.

Example 17

4-((7,8-dimethoxy-2-oxo-2,3-dihydro-1H-imidazo[4,5-c]quinolin-1-yl)methyl)-2-fluorobenzenesulfonamide (22)

4-((7,8-dimethoxy-2-oxo-2,3-dihydro-1H-imidazo[4,5-c]quinolin-1-yl)methyl)-2-fluorobenzenesulfonamide (22) is prepared according to General procedure 2 from 4-(aminomethyl)-2-fluorobenzenesulfonamide (prepared according to S. Yamamoto et al, PCT Int. Appl., 2018030550).

Example 18

Preparation of 3-(aminomethyl)azetidine-1-sulfonamide, 3-(aminomethyl)pyrrolidine-1-sulfonamide, and 4-(aminomethyl)piperidine-1-sulfonamide

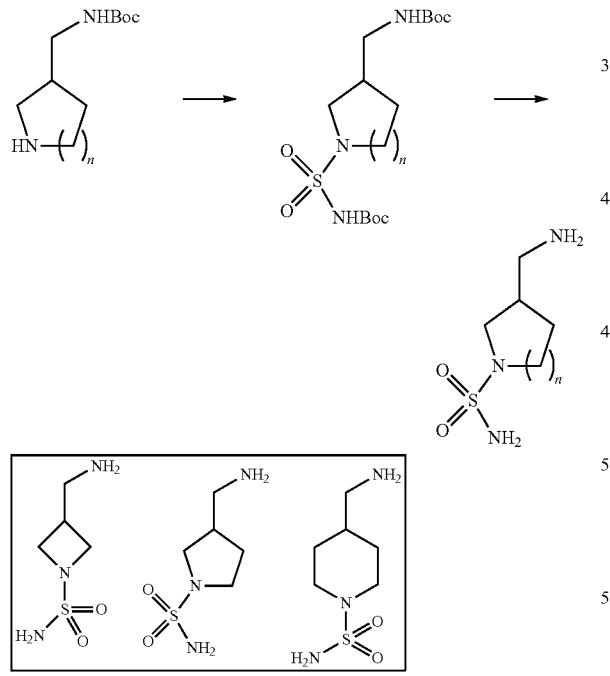

Step 1. Boc diamines (0.8 mmol, 1 eq) were dissolved in DCM (4.4 mL, 0.2 M) followed by the addition of (tert-butoxycarbonyl)((4-(dimethyliminio)pyridin-1(4H)-yl)sulfonyl)amide (262 mg, 1 eq). The mixture was stirred at room temperature for 18 hrs. Upon completion, the mixture was concentrated in vacuo. The crude was purified through FCC using Hex/THF (100%/0% to 60%/40%) yielding the product.

Step 2. The above product (1 eq) was dissolved in DCM (5 mL, 0.1 M) then cooled to 0° C. TFA (5 mL, 0.1 M) was added to the mixture then the cooling bath was removed. The mixture was stirred at room temperature for 2 hrs. Upon completion, the mixture was concentrated in vacuo and neutralized by NaHCO$_3$ and extracted with DCM. The crude was used in the next step without further purification.

Example 19

4-((7,8-dimethoxy-1H-imidazo[4,5-c]quinolin-1-yl)methyl)piperidine-1-sulfonamide (32)

4-((7,8-dimethoxy-1H-imidazo[4,5-c]quinolin-1-yl)methyl)piperidine-1-sulfonamide was prepared according to general procedure 3 from intermediate 4-(aminomethyl)piperidine-1-sulfonamide. LCMS (ESI) [M+H]$^+$=406; $^1$H NMR (600 MHz, DMSO-d6) δ ppm 1.22-1.28 (m, 2H) 1.41-1.50 (m, 2H) 1.65 (br d, J=11.37 Hz, 2H) 2.01-2.10 (m, 1H) 2.41-2.48 (m, 2H) 3.40-3.52 (m, 6H) 3.99 (s, 3H) 4.01-4.07 (m, 3H) 4.72 (br d, J=6.97 Hz, 2H) 6.63-6.69 (m, 2H) 7.60 (s, 1H) 7.66 (s, 1H) 8.53 (brs, 1H).

Example 20

Compounds 23-31 are prepared from the above intermediates according to General procedure 2-6.

Example 21

4-((7-methoxy-2-oxo-2,3-dihydro-1H-imidazo[4,5-c][1,6]naphthyridin-1-yl)methyl)benzenesulfonamide (33)

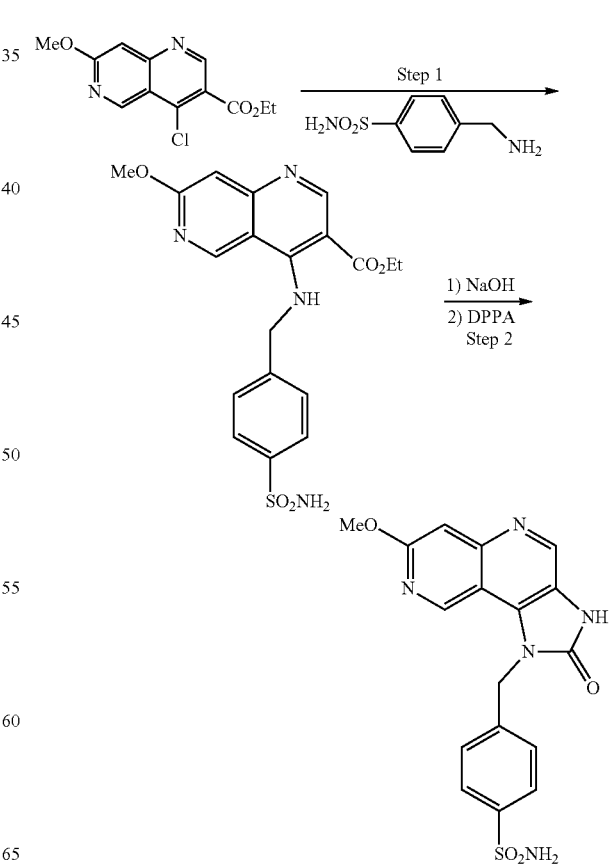

4-((7-methoxy-2-oxo-2,3-dihydro-1H-imidazo[4,5-c][1,6]naphthyridin-1-yl)methyl)benzenesulfonamide is prepared in a similar manner as the preparation of compound 1 from ethyl 4-chloro-7-methoxy-1,6-naphthyridine-3-carboxylate.

Example 22

4-((8-cyano-7-methoxy-2-oxo-2,3-dihydro-1H-imidazo[4,5-c]quinolin-1-yl)methyl)benzenesulfonamide (34)

4-((8-cyano-7-methoxy-2-oxo-2,3-dihydro-1H-imidazo[4,5-c]quinolin-1-yl)methyl)benzenesulfonamide is prepared in a similar manner as the preparation of compound 1 from ethyl 4-chloro-6-cyano-7-methoxyquinoline-3-carboxylate.

Example 23

4-((7-methoxy-2-oxo-2,3-dihydro-1H-imidazo[4,5-c]quinolin-1-yl)methyl)-benzenesulfonamide (35)

4-((7-methoxy-2-oxo-2,3-dihydro-1H-imidazo[4,5-c]quinolin-1-yl)methyl)-benzenesulfonamide was prepared according to General procedure 2. LCMS (ESI) [M+H]$^+$=385; $^1$H NMR (600 MHz, DMSO-d6) δ ppm 3.85 (s, 3H) 5.59 (s, 2H) 7.10 (dd, J=9.35, 2.75 Hz, 1H) 7.31 (s, 2H) 7.37 (d, J=2.57 Hz, 1H) 7.42 (d, J=8.80 Hz, 2H) 7.77 (d, J=7.91 Hz, 2H) 7.82 (d, J=9.54 Hz, 1H) 8.66 (s, 1H) 11.63 (s, 1H).

Example 24

4-((8-methoxy-1H-imidazo[4,5-c]quinolin-1-yl)methyl)benzenesulfonamide (36)

4-((8-methoxy-1H-imidazo[4,5-c]quinolin-1-yl)methyl)benzenesulfonamide was prepared according to General procedure 3. LCMS (ESI) [M+H]$^+$=369; $^1$H NMR (600 MHz, DMSO-d6) δ ppm 3.71 (s, 4H) 6.20 (s, 2H) 7.28 (d, J=2.57 Hz, 1H) 7.32-7.38 (m, 5H) 7.79 (d, J=7.76 Hz, 2H) 8.08 (d, J=9.17 Hz, 1H) 8.75 (s, 1H) 9.33 (br s, 1H).

Example 25

3-((7,8-dimethoxy-1H-imidazo[4,5-c]quinolin-1-yl)methyl)benzenesulfonamide (37)

3-((7,8-dimethoxy-1H-imidazo[4,5-c]quinolin-1-yl)methyl)benzenesulfonamide was prepared according to General procedure 3. LCMS (ESI) [M+H]$^+$=399; $^1$H NMR (600 MHz, DMSO-d6) δ ppm 0.83-0.90 (m, 3H) 0.99-1.09 (m, 2H) 1.15 (d, J=5.87 Hz, 3H) 1.18-1.23 (m, 5H) 1.23-1.36 (m, 4H) 1.39-1.50 (m, 2H) 1.79 (dd, J=13.94, 2.93 Hz, 1H) 3.38-3.44 (m, 19H) 3.44-3.56 (m, 7H) 3.69-3.74 (m, 3H) 3.89-3.94 (m, 3H) 6.20 (s, 2H) 7.28 (s, 1H) 7.35 (d, J=8.07 Hz, 1H) 7.38 (s, 2H) 7.54-7.59 (m, 2H) 7.74 (s, 1H) 7.77 (d, J=7.70 Hz, 1H).

Example 26

4-((7-methoxy-2-oxo-2,3-dihydro-1H-imidazo[4,5-c][1,8]naphthyridin-1-yl)methyl)benzene-sulfonamide (38)

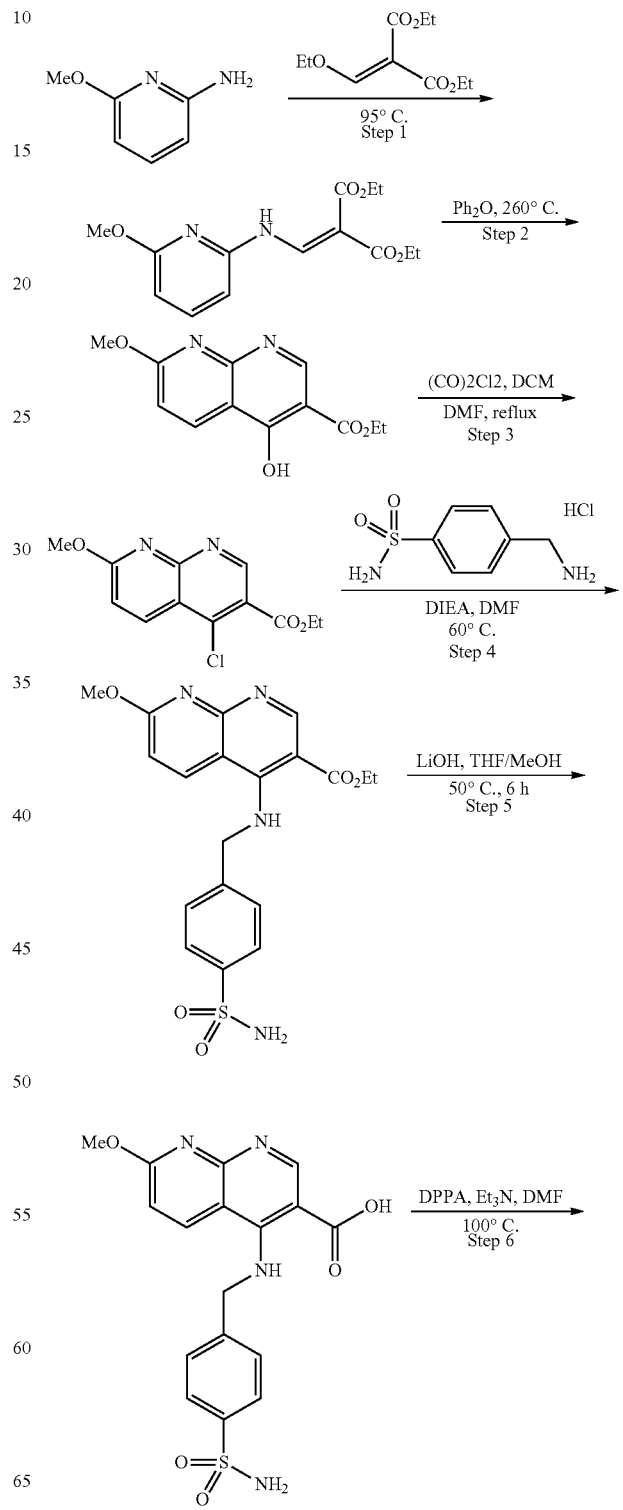

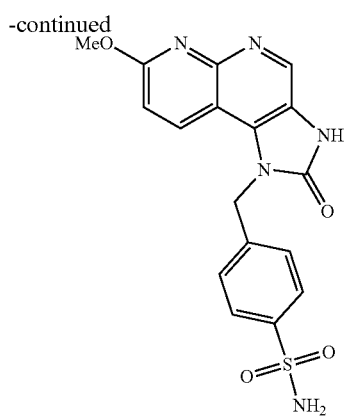

Step 1. 6-Methoxypyridin-2-amine (9.8 g, 78.9 mmol, 1.1 eq) was dissolved in ethyoxymethylene diethylmalonate (15.5 g, 71.8 mmol, 1 eq). The mixture was heated to 95° C. for 1 hr under vacuum. After completion, the mixture was cooled to 45° C. and hexanes was added. The mixture was further cooled by dry ice to induce precipitation. The resulting precipitate was filtered and dried (14.8 g, 70%). The crude product was used without further purification.

Step 2. Diethyl 2-(((6-methoxypyridin-2-yl)amino)methylene)malonate (14.8 g, 50.3 mmol) was added to a solution of diphenyl ether (125 mL, 0.4 M) at 260° C. After addition, the mixture was heated at reflux for another 45 mins. After completion, the mixture was cooled to 85° C. and hexanes was added. Once cooled to room temperature, the solid was filtered and purified through FCC yielding the product.

Step 3. Ethyl 4-hydroxy-7-methoxy-1,8-naphthyridine-3-carboxylate (130 mg, 0.52 mmol, 1 eq) was dissolved in DCM (2.6 mL, 0.2 M) followed by the addition of oxylyl chloride (53 µL, 0.63 mmol, 1.2 eq) and DMF (1 drop). The mixture was heated to reflux for 5 mins. Upon completion, the mixture was cooled to room temperature and concentrated in vacuo. The crude was used without further purification.

Step 4. Ethyl 4-chloro-7-methoxy-1,8-naphthyridine-3-carboxylate (0.26 mmol, 1 eq) and 4-(aminomethyl)benzenesulfonamide HCl (75 mg, 0.34 mmol, 1.3 eq) were dissolved in DMF (2.6 mL, 0.1 M) followed by the addition of DIEA (226 µL, 1.3 mmol, 5 eq). The mixture was heated to 60° C. Upon completion, the mixture was cooled to room temperature then added to water. The resulting precipitate was filtered and dried (21 mg, 19%).

Step 5. Ethyl 7-methoxy-4-((4-sulfamoylbenzyl)amino)-1,8-naphthyridine-3-carboxylate (21 mg, 0.05 mmol, 1 eq) was dissolved in THF/MeOH (1 mL/0.3 mL) then cooled to 0° C. Aqueous LiOH (1 M, 0.5 mmol, 10 eq) was added to the mixture. The resulting mixture was heated to 50° C. Upon completion, the mixture was cooled to room temperature and diluted with water. The aqueous layer was washed with EtOAc then the aqueous layer was acidified to pH 4 with 2 N HCl. The resulting precipitate was filtered and dried (14 mg, 74%).

Step 6. 7-Methoxy-4-((4-sulfamoylbenzyl)amino)-1,8-naphthyridine-3-carboxylic acid (14 mg, 0.04 mmol, 1 eq) was dissolved in DMF (2 mL) followed by the addition of DPPA (9.3 µL, 0.043 mmol, 1.2 eq). The resulting mixture was heated to 110° C. Upon completion, the mixture was cooled to room temperature and concentrated in vacuo. The crude was purified through FCC yielding the product (8.8 mg, 44%). LCMS [M+H]$^+$=386; $^1$H NMR (600 MHz, DMSO-d6) δ ppm 4.00 (s, 3H) 5.63 (s, 2H) 7.00-7.06 (m, 1H) 7.06-7.11 (m, 1H) 7.13-7.18 (m, 1H) 7.25-7.31 (m, 1H) 7.34 (s, 2H) 7.43 (d, J=8.44 Hz, 2H) 7.77 (d, J=8.44 Hz, 2H) 8.29 (br d, J=9.35 Hz, 1H) 8.74 (s, 1H).

Example 27

Synthesis of 5-chloro-2-methoxy-6-nitro-1,8-naphthyridine (Intermediate B)

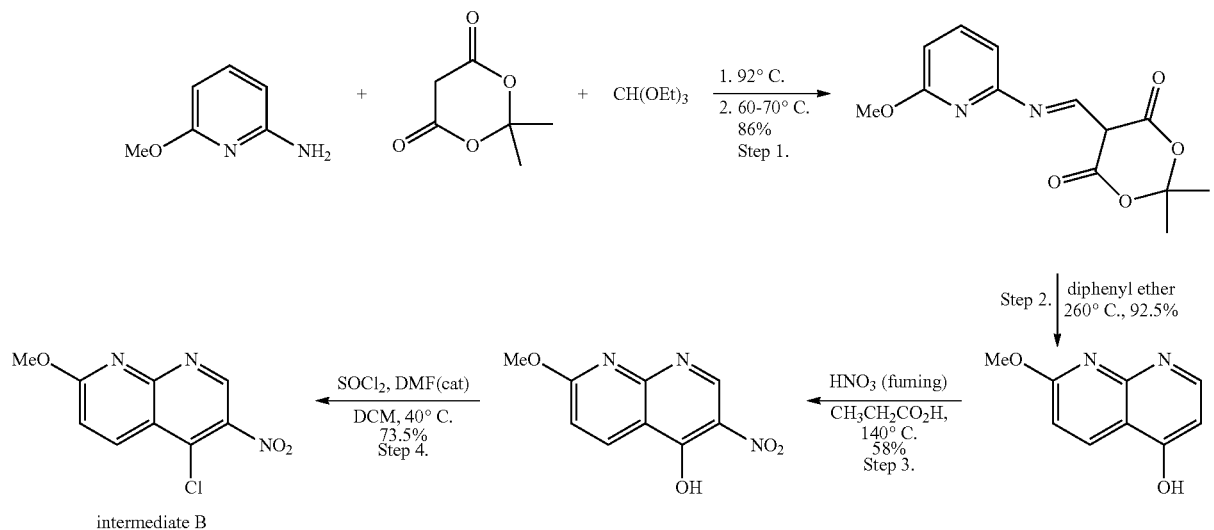

Step 1. A mixture of Meldrum's acid (13.36 g, 92.6 mmol) and triethyl orthoformate (35.8 g, 3.0 eq) was heated at 92° C. for 90 min before addition of 6-methoxypyridin-2-amine (10 g, 80.6 mmol) portionwise at 70° C. over 5 min. Then the reaction mixture was stirred for 20 min, cooled and filtered to give 5-(((6-methoxypyridin-2-yl)imino)methyl)-2,2-dimethyl-1,3-dioxane-4,6-dione as a grey solid (19.27 g, 75%).

Step 2. The above solid (19.2 g, 69 mmol) was added to heated diphenyl ether (30 mL) at 260° C. portionwise then the resulted mixture was stirred at 260° C. for 40 min before being cooled to rt. Hexane (100 mL) was added and the solid was filtered, washed with hexane and dried (11.25 g, 93%).

Step 3. The above solid (1.0 g, 5.7 mmol) in CH$_3$CH$_2$CO$_2$H (35 mL) was treated with fuming HNO$_3$ (0.59 mL) dropwise and then stirred for 2 h. The resulted solid was filtered, washed and dried (725 mg, 58%).

Step 4. The above solid (725 mg, 3.3 mmol) in DCM (20 mL) was treated with SOCl$_2$ (0.60 mL) followed with 2 drops of DMF. After 6 h, the reaction mixture was concentrated and purified by combiflash (DCM/EtOAc) to give a white solid (578 mg, 74%).

Example 28

4-((7-methoxy-1H-imidazo[4,5-c][1,8]naphthyridin-1-yl)methyl)benzenesulfonamide (39)

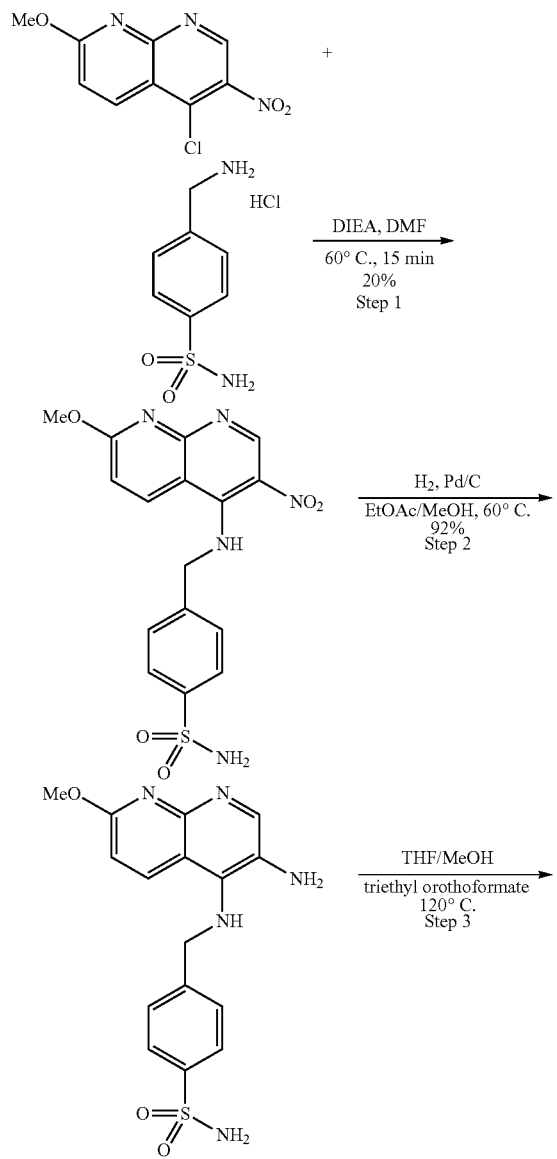

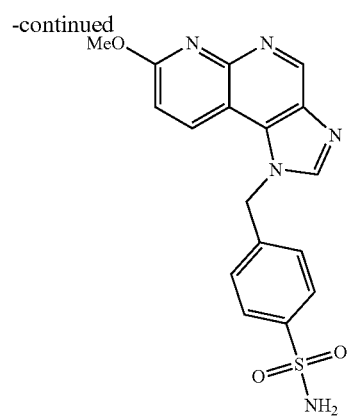

Step 1. A mixture of intermediate B (90 mg, 0.38 mmol), 4-(aminomethyl)benzenesulfonamide HCl salt (100 mg, 1.2 eq), hunig's base (0.33 mL, 5.0 eq) and MeCN (4 mL) was heated to 80° C. for 4 h. After cool to rt, the reaction mixture was concentrated and treated with water (5 mL). The resulted solid was filtered, wash with water and dried (107 mg, 73%). LCMS [M+H]$^+$=390.

Step 2. The above solid (107 mg, 0.28 mmol) in MeOH (5 mL) and EtOAc (5 mL) was heated to 65° C. and then Pd/C (10%, 10 mg) was added. The reaction mixture was stirred under H$_2$ balloon overnight. After cool to rt, the reaction mixture was filtered, concentrated and purified by combiflash (DCM/MeOH) to give a yellow solid (49 mg, 49%). LCMS [M+H]$^+$=360.

Step 3. The above solid (49 mg, 0.17 mmol) was added to a mixture of DMF (1.1 mL) and triethyl orthoformate (2.2 mL) and then heated to 120° C. for 8 h. After cool to rt, the reaction mixture was concentrated and purified by combiflash (DCM/MeOH) to give a yellow solid (41 mg, 65%). LCMS [M+H]$^+$=370; $^1$H NMR (500 MHz, DMSO-d6) δ ppm 3.98 (s, 3H) 6.08 (s, 2H) 7.18 (d, J=9.00 Hz, 1H) 7.24 (d, J=8.39 Hz, 2H) 7.28 (s, 2H) 7.69 (d, J=8.39 Hz, 2H) 8.44 (d, J=9.16 Hz, 1H) 8.76 (s, 1H) 9.51 (s, 1H).

Example 29

6-((7-methoxy-1H-imidazo[4,5-c][1,8]naphthyridin-1-yl)methyl)pyridine-3-sulfonamide (40)

6-((7-methoxy-1H-imidazo[4,5-c][1,8]naphthyridin-1-yl)methyl)pyridine-3-sulfonamide was prepared in the similar manner as Compound 39 from intermediate B and 6-(aminomethyl)pyridine-3-sulfonamide HCl salt. LCMS [M+H]$^+$=371; $^1$H NMR (500 MHz, DMSO-d6) δ ppm 4.02-4.09 (m, 3H) 6.27 (s, 2H) 7.26 (m, J=9.16 Hz, 1H) 7.59 (s, 2H) 7.64 (d, J=8.24 Hz, 1H) 8.20 (dd, J=8.32, 2.36 Hz, 1H) 8.58 (m, J=9.00 Hz, 1H) 8.75 (d, J=2.14 Hz, 1H) 8.81 (s, 1H) 9.57 (s, 1H).

Example 30

5-((7-methoxy-1H-imidazo[4,5-c][1,8]naphthyridin-1-yl)methyl)pyridine-2-sulfonamide (41)

5-((7-methoxy-1H-imidazo[4,5-c][1,8]naphthyridin-1-yl)methyl)pyridine-2-sulfonamide was prepared in the similar manner as Compound 39 from intermediate B and 5-(aminomethyl)pyridine-2-sulfonamide HCl salt. LCMS [M+H]$^+$=371; $^1$H NMR (500 MHz, DMSO-d6) δ ppm 3.99 (s, 4H) 6.15 (s, 2H) 7.21 (d, J=9.16 Hz, 1H) 7.40 (s, 2H) 7.60 (dd, J=8.16, 2.21 Hz, 1H) 7.76 (d, J=8.09 Hz, 1H) 8.54 (d, J=9.16 Hz, 1H) 8.61 (d, J=1.83 Hz, 1H) 8.77 (s, 1H) 9.52 (s, 1H).

Example 31

4-((8,9-dimethoxypyrazolo[1,5-c]quinazolin-1-yl)methyl)benzenesulfonamide (42)

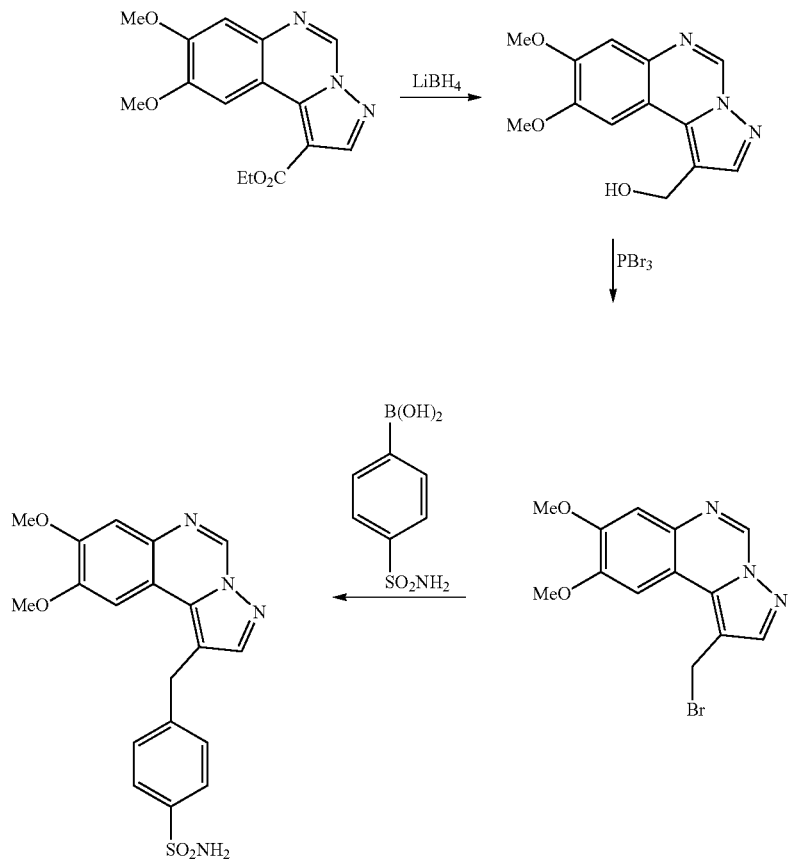

Ethyl 8,9-dimethoxypyrazolo[1,5-c]quinazoline-1-carboxylate (prepared according to a known procedure by Feng, H., RSC Adv., 2016, 6, 95774) is converted to the corresponding alcohol by reducing reagents such as LiBH$_4$. Bromo analog is prepared by treatment of the alcohol with PBr$_3$. Coupling with (4-sulfamoylphenyl)boronic acid under palladium catalyst provides 4-((8,9-dimethoxypyrazolo[1,5-c]quinazolin-1-yl)methyl)benzenesulfonamide (42).

Example 32

(R)-6-(1-(7-methoxy-1H-imidazo[4,5-c][1,8]naphthyridin-1-yl)ethyl)pyridine-3-sulfonamide (43)

(R)-6-(1-(7-methoxy-1H-imidazo[4,5-c][1,8]naphthyridin-1-yl)ethyl)pyridine-3-sulfonamide was prepared in the similar manner as Compound 39 from intermediate B and (R)-6-(1-(-aminoethyl)pyridine-3-sulfonamide HCl salt. LCMS [M+H]$^+$=385; $^1$H NMR (600 MHz, DMSO-d6) S ppm: 2.08 (d, J=6.97 Hz, 3H) 3.99 (s, 4H) 6.67 (q, J=6.91 Hz, 1H) 7.24 (d, J=9.17 Hz, 1H) 7.51 (s, 2H) 7.68 (d, J=8.25 Hz, 1H) 8.13 (dd, J=8.25, 2.38 Hz, 1H) 8.68 (br d, J=8.80 Hz, 1H) 8.74 (d, J=2.38 Hz, 1H) 9.02 (s, 1H) 9.55 (s, 1H).

Example 33

4-((7,8-dimethoxy-2),2λ$^2$,10λ$^4$-[1,2,4]triazolo[4,3-a]quinoxalin-1-yl)methyl)benzenesulfonamide (44)

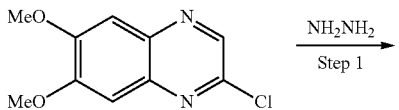

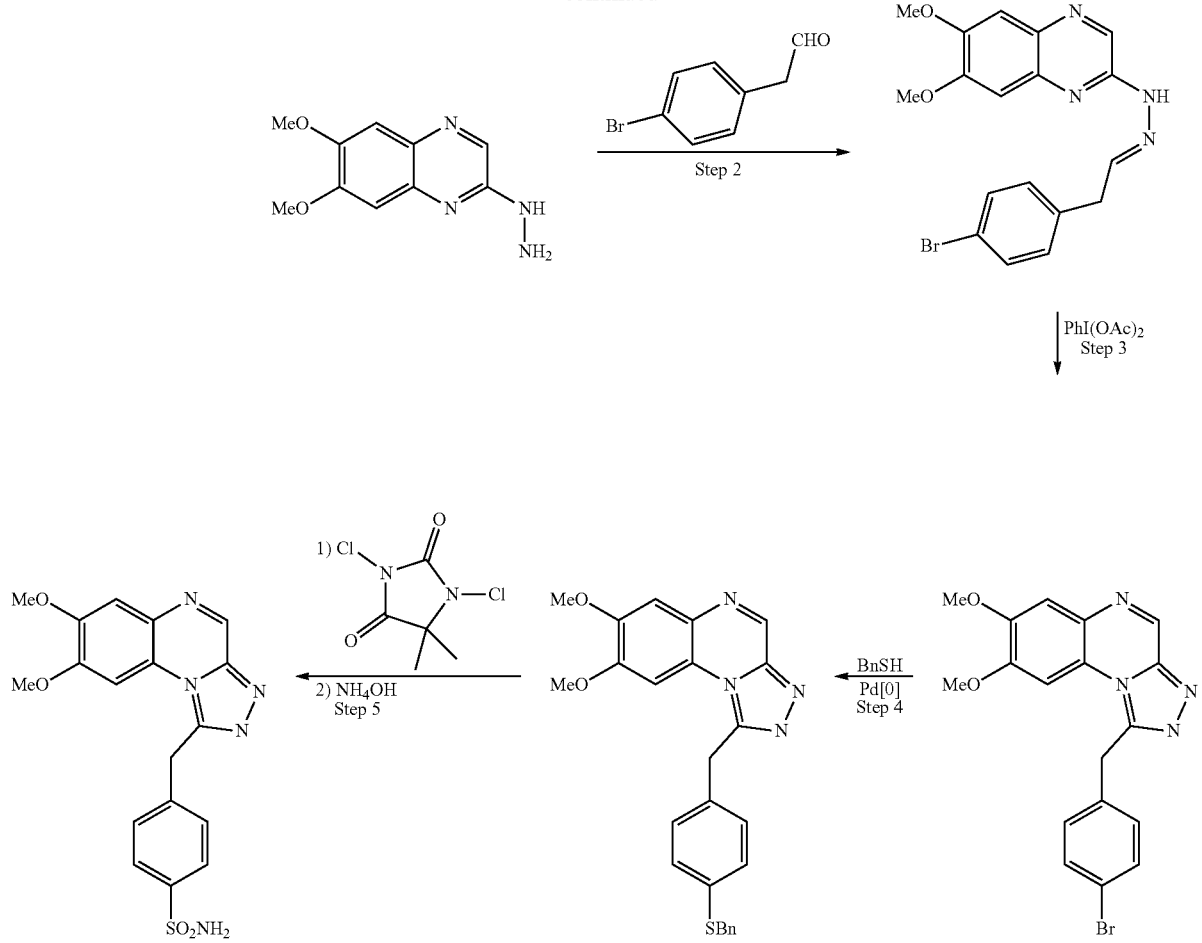

Step 1. 2-chloro-6,7-dimethoxyquinoxaline (0.28 g, 1.24 mmol, 1 eq) was dissolved in reagent alcohol (6.2 mL, 0.2 M) followed by the addition of hydrazine monohydrate (6.2 mL, 0.2 M). The mixture was heated to 80° C. for 2 hrs. Upon completion, the mixture was cooled to room temperature then added to water. The resulting precipitate was filtered and dried (206 mg, 75%).

Step 2. 2-hydrazineyl-6,7-dimethoxyquinoxaline (50 mg, 0.22 mmol, 1 eq) and 2-(4-bromophenyl)acetaldehyde (53 mg, 0.264 mmol, 1.2 eq) were dissolved in reagent alcohol (2.2 mL, 0.1 M). The mixture was heated to reflux for 1 hr. Upon completion, the mixture was cooled to room temperature then added to water. The resulting precipitate was filtered and dried (88 mg, 99%).

Step 3. 2-(2-(2-(4-bromophenyl)ethylidene)hydrazineyl)-6,7-dimethoxyquinoxaline (88 mg, 0.22 mmol, 1 eq) was dissolved in DCM (4.4 mL, 0.05 M) followed by the addition of iodobenzene diacetate (78 mg, 0.24 mmol, 1.1 eq). The mixture was stirred at room temperature for 3 hrs. Upon completion, the mixture was concentrated in vacuo. The resulting oil was triturated with hexanes then used without further purification.

Step 4. 1-(4-bromobenzyl)-7,8-dimethoxy-2λ$^2$, 10λ$^4$-[1,2,4]triazolo[4,3-a]quinoxaline (0.22 mmol, 1 eq), Pd(dba)$_2$ (13 mg, 0.022 mmol, 0.1 eq), and XantPhos (13 mg, 0.022 mmol, 0.1 eq) were dissolved in dioxane followed by the addition of DIEA (153 µL, 0.44 mmol, 2 eq). The mixture was purged with nitrogen for 1 min followed by the addition of benzyl mercaptan (28 µL, 0.24 mmol, 1.1 eq). The mixture was heated to 100° C. for 4 hrs. Upon completion, the mixture was cooled to room temperature and added to water. The aqueous layer was extracted with EtOAc (3×2 mL). The combined organic layers was dried and concentrated in vacuo. The crude was purified through FCC yielding the product (97 mg, 99%).

Step 5. 1-(4-(benzylthio)benzyl)-7,8-dimethoxy-2λ$^2$, 10λ$^4$-[1,2,4]triazolo[4,3-a]quinoxaline (97 mg, 0.22 mmol, 1 eq) was dissolved in MeCN (2.27 mL, 0.1 M) followed by the addition of AcOH (86 µL, 2.57 M) and water (56 µL, 3.9 M). The mixture was cooled to 0° C. followed by the addition of 1,3-dichloro-5,5-dimethylhydantoin (52 mg, 0.264 mmol, 1.2 eq). The mixture was stirred at 0° C. Upon completion, the mixture was diluted with EtOAc and basified with sat. NaHCO$_3$. The aqueous layer was extracted with EtOAc (2×2 mL). The combined organic layers was cooled to 0° C. followed by the addition of NH$_4$OH (2 mL). The mixture was stirred at 0° C. for 1 hr. Upon completion, the mixture was acidified with 2 N HCl to pH 2. Layers separated and the aqueous extracted with EtOAc. The combined organic layers was dried and concentrated in vacuo. The crude was triturated with Et$_2$O to yield the product 44 (18 mg, 20%). LCMS [M+H]$^+$=400; $^1$H NMR (600 MHz, DMSO-d6) δ ppm 3.70 (s, 3H) 3.90 (s, 3H) 5.17 (s, 2H) 7.32 (d, J=7.15 Hz, 3H) 7.39 (d, J=8.44 Hz, 2H) 7.59 (s, 1H) 7.76-7.79(m, 2H) 9.25 (s, 1H).

Example 34

4-((7-methoxy-2λ²,10λ⁴-imidazo[3,4-a]quinoxalin-1-yl)methyl)benzenesulfonamide (45)

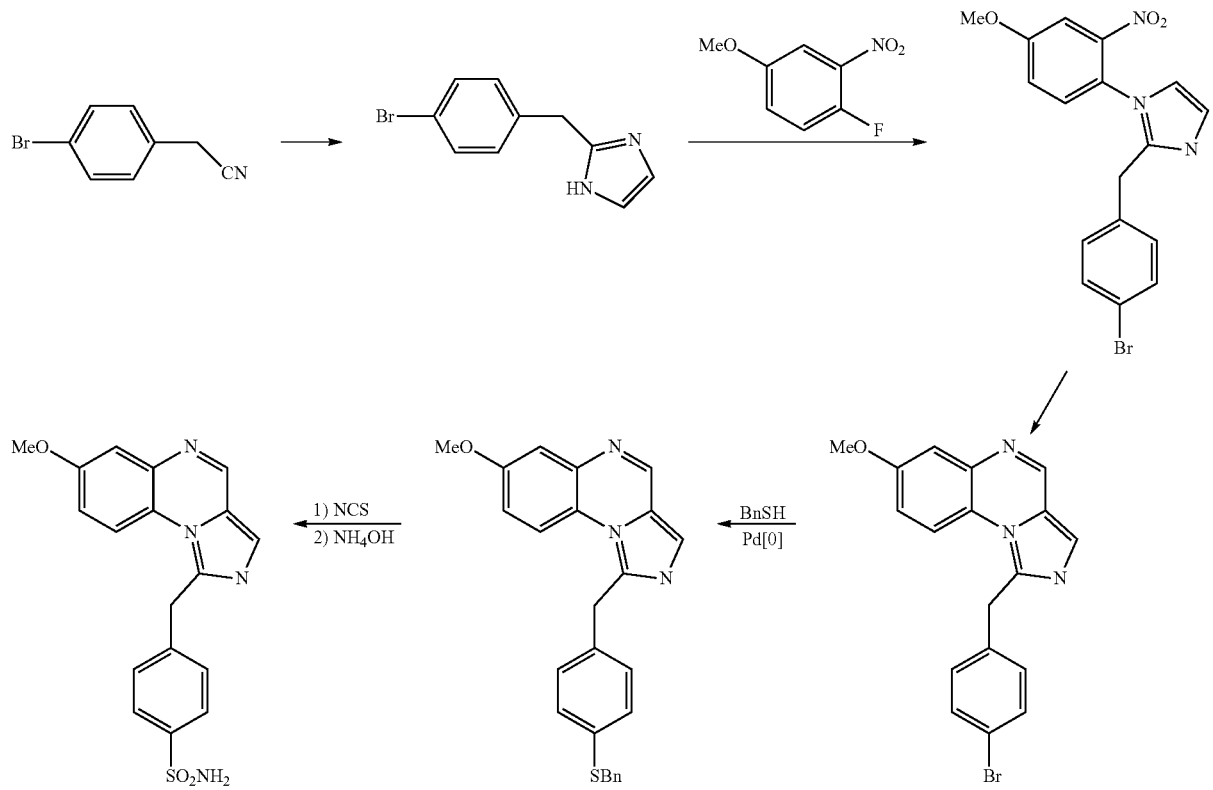

2-(4-Bromophenyl)acetonitrile is converted to 2-(4-bromobenzyl)-1H-imidazole by the treatment of ethylenediamine. This material is reacted with 1-fluoro-4-methoxy-2-nitrobenzene and then the resulted product is cyclized to give 1-(4-bromobenzyl)-7-methoxy-2λ²,10λ⁴-imidazo[3,4-a]quinoxaline. A similar transformation as 44 is used to convert bromo to sulfonamide.

Example 35

4-((7-methoxy-1H-imidazo[4,5-c][1,8]naphthyridin-1-yl)methyl)phenyl Sulfamide (46)

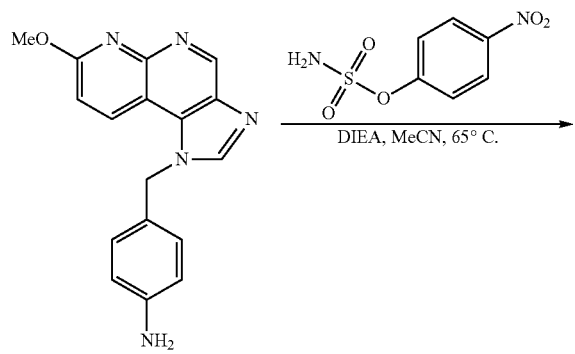

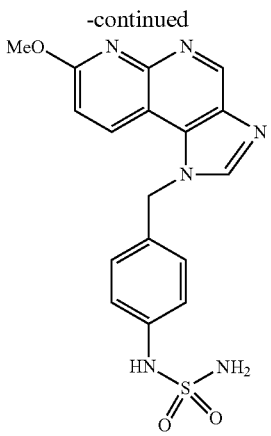

4-((7-methoxy-1H-imidazo[4,5-c][1,8]naphthyridin-1-yl)methyl)aniline was prepared in the similar manner as Compound 39 from intermediate B and 4-(aminomethyl)aniline HCl salt. 4-((7-methoxy-1H-imidazo[4,5-c][1,8]naphthyridin-1-yl)methyl)aniline (41 mg, 0.13 mmol) was dissolved in MeCN (2 mL) and then treated with 4-nitrophenyl sulfamate (44 mg, 1.5 eq) followed with hunig's base (0.046 mL, 2.0 eq). After overnight at rt, the reaction mixture was worked up and purified by reverse HPLC (MeCN/H₂O/0.1% TFA) to give a white solid (1.5 mg). LCMS [M+H]⁺=385.

Example 36

4-((7-methoxy-2-(trifluoromethyl)-1H-imidazo[4,5-c][1,8]naphthyridin-1-yl)methyl)benzenesulfonamide (47)

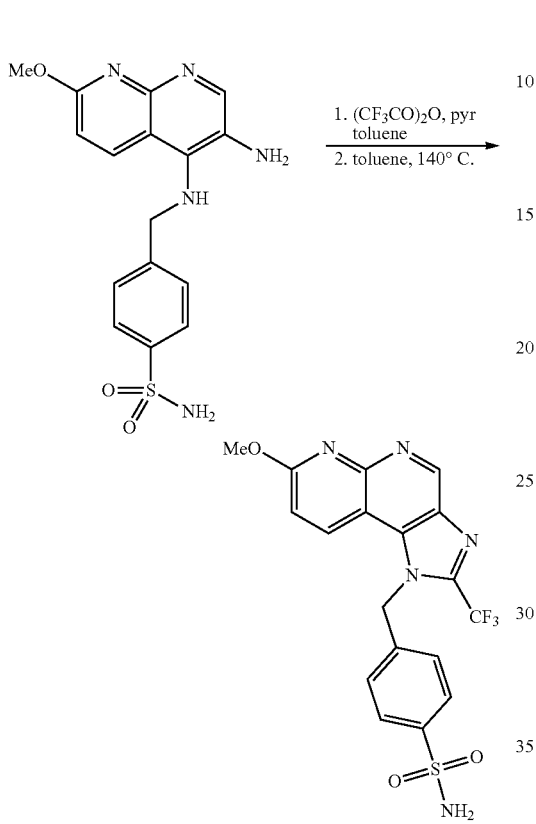

4-(((3-amino-7-methoxy-1,8-naphthyridin-4-yl)amino)methyl)benzenesulfonamide (18 mg, 0.05 mmol) in tol (1 mL) and pyridine (1 mL) was treated with trifluoroacetic anhydride (0.0081 mL, 1.15 eq) and then heated to 140° C. overnight. The reaction mixture was concentrated and purified by reverse HPLC (MeCN/H$_2$O/0.1% TFA) to give a white solid (5.5 mg). LCMS [M+H]$^+$=438; $^1$H NMR (500 MHz, DMSO-d6) δ ppm 3.99-4.05 (m, 3H) 4.46 (d, J=5.80 Hz, 1H) 6.18 (s, 2H) 7.13 (d, J=9.00 Hz, 1H) 7.27 (d, J=8.39 Hz, 2H) 7.32-7.36 (m, 3H) 7.76 (d, J=8.39 Hz, 2H) 8.36 (d, J=9.16 Hz, 1H) 9.50 (s, 1H).

Example 37

4-((7-methoxy-2-methyl-1H-imidazo[4,5-c][1,8]naphthyridin-1-yl)methyl)benzene-sulfonamide (48)

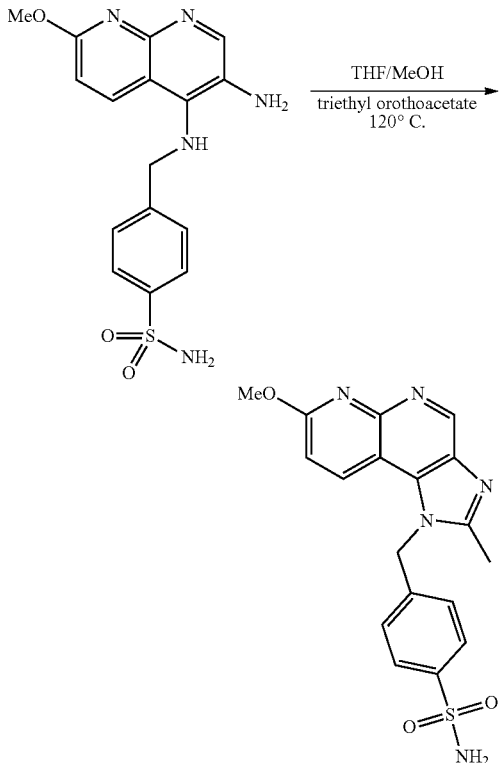

4-((7-methoxy-2-methyl-1H-imidazo[4,5-c][1,8]naphthyridin-1-yl)methyl)benzene-sulfonamide was prepared in the similar manner as Compound 39 from 4-(((3-amino-7-methoxy-1,8-naphthyridin-4-yl)amino)methyl)benzene-sulfonamide and triethyl orthoacetate. LCMS [M+H]$^+$=384; $^1$H NMR (500 MHz, DMSO-d6) δ ppm 2.66-2.72 (m, 3H) 4.06 (s, 3H) 6.10 (s, 2H) 7.26 (br d, J=8.24 Hz, 3H) 7.36 (s, 2H) 7.77 (br d, J=7.42 Hz, 2H) 8.55 (br d, J=8.70 Hz, 1H) 9.50 (br s, 1H).

Example 38

4-((7-methoxy-1H-imidazo[4,5-c][1,5]naphthyridin-1-yl)methyl)benzenesulfonamide (49)

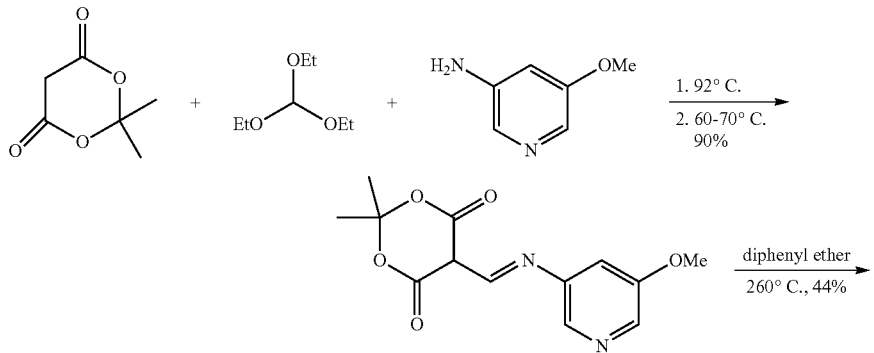

141

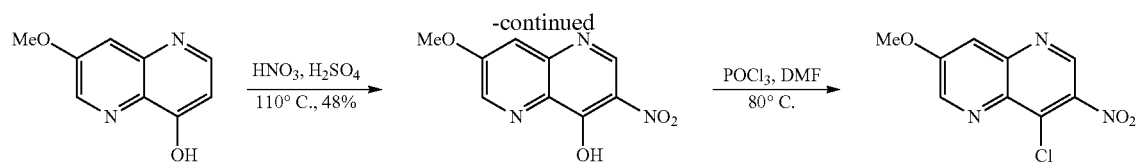

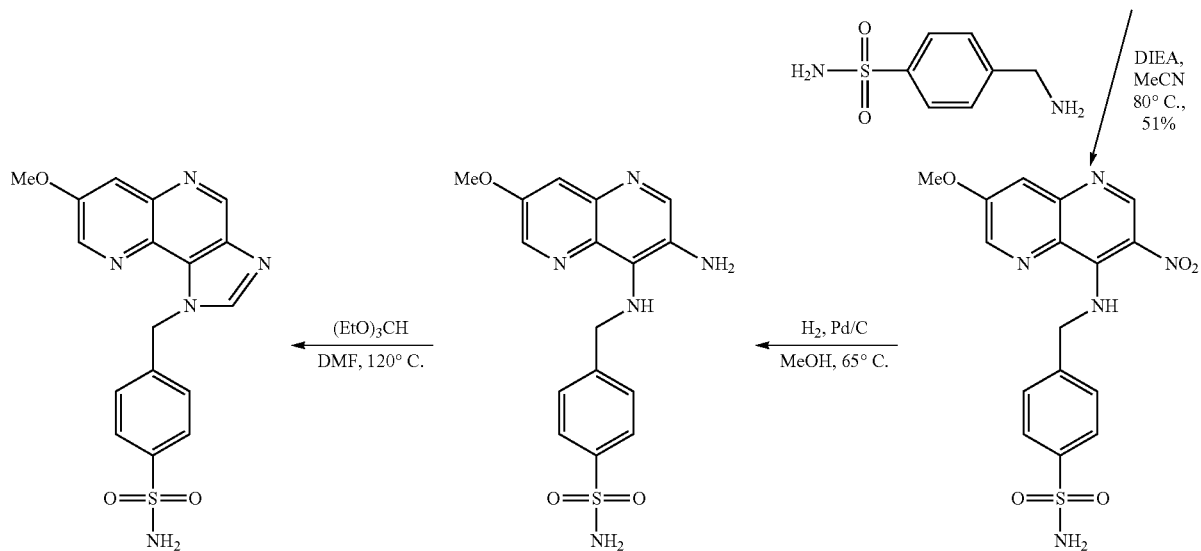

4-chloro-7-methoxy-3-nitro-1,5-naphthyridine was prepared in the similar manner as Intermediate B from 5-methoxypyridin-3-amine; 4-((7-methoxy-1H-imidazo[4,5-c][1,5]naphthyridin-1-yl)methyl)benzenesulfonamide (49) was then prepared in the similar manner as Compound 39 from 4-chloro-7-methoxy-3-nitro-1,5-naphthyridine and 4-(aminomethyl)benzenesulfonamide. LCMS [M+H]⁺=371; ¹H NMR (600 MHz, DMSO-d6) δ ppm 3.97-4.00 (m, 3H) 6.19 (s, 2H) 7.28 (s, 2H) 7.49 (m, J=8.25 Hz, 2H) 7.74 (m, J=8.25 Hz, 2H) 7.97 (d, J=2.75 Hz, 1H) 8.65 (s, 1H) 8.75 (d, J=2.75 Hz, 1H) 9.29 (s, 1H).

Example 39

4-((7-methoxy-1H-imidazo[4,5-c][1,6]naphthyridin-1-yl)methyl)benzenesulfonamide (50)

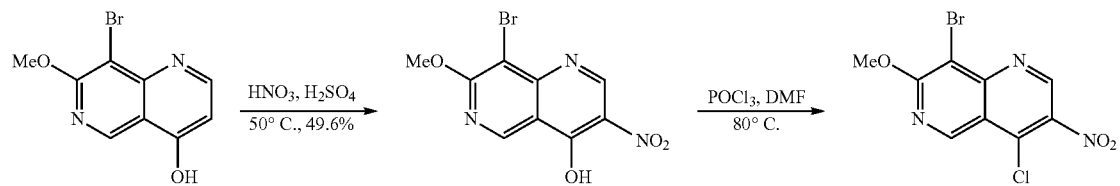

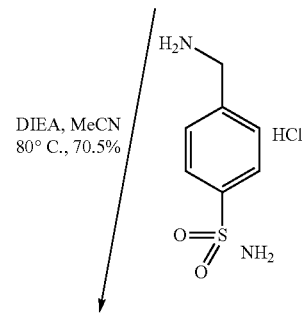

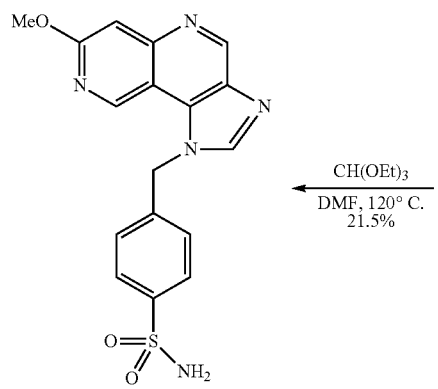
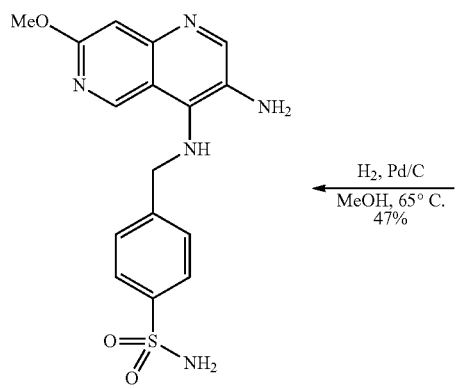

4-((7-methoxy-1H-imidazo[4,5-c][1,6]naphthyridin-1-yl)methyl)benzenesulfonamide was prepared in the similar manner as Compound 39 from a known compound 8-bromo-7-methoxy-1,6-naphthyridin-4-ol (Morgentin, Remy et al, Tetrahedron, 2008, 64, 2772-2782). LCMS [M+H]$^+$=371; $^1$H NMR (500 MHz, DMSO-d6) δ ppm 3.94 (s, 3H) 6.16 (s, 2H) 7.30-7.37 (m, 5H) 7.79 (d, J=8.39 Hz, 2H) 8.66 (s, 1H) 9.10-9.17 (m, 1H) 9.43 (s, 1H).

Example 40

4-(7,8-dimethoxy-[1,2,4]triazolo[4,3-a]quinoxalin-1-yl)benzyl sulfamide (51)

Step 1. 2-hydrazineyl-6,7-dimethoxyquinoxaline (50 mg, 0.22 mmol, 1 eq) and tert-butyl (4-formylbenzyl)carbamate (57 mg, 0.24 mmol, 1.1 eq) were dissolved in reagent alcohol (2.2 mL, 0.1 M). The mixture was heated to reflux for 1 hr. Upon completion, the mixture was cooled to room temperature then added to water. The resulting precipitate was filtered and dried (96 mg, 99%).

Step 2. tert-Butyl-(4-((2-(6,7-dimethoxyquinoxalin-2-yl)hydrazineylidene)methyl)-benzyl)-carbamate (96 mg, 0.22 mmol, 1 eq) was dissolved in DCM (4.4 mL, 0.05 M) followed by the addition of iodobenzene diacetate (78 mg, 0.24 mmol, 1.1 eq). The mixture was stirred at room temperature for 3 hrs. Upon completion, the mixture was concentrated in vacuo. The resulting oil was triturated with hexanes then used without further purification.

Step 3. tert-Butyl (4-(7,8-dimethoxy-[1,2,4]triazolo[4,3-a]quinoxalin-1-yl)benzyl)carbamate (96 mg, 0.22 mmol, 1 eq) dissolved in DCM (0.55 mL, 0.4 M) then cooled to 0° C. TFA (0.55 mL, 0.4 M) was added to the mixture. The mixture was warmed to room temperature and stirred for 1 hr. Upon completion, the mixture was concentrated in vacuo. The crude was dissolved in DCM/DMF (1:1, 8 mL)

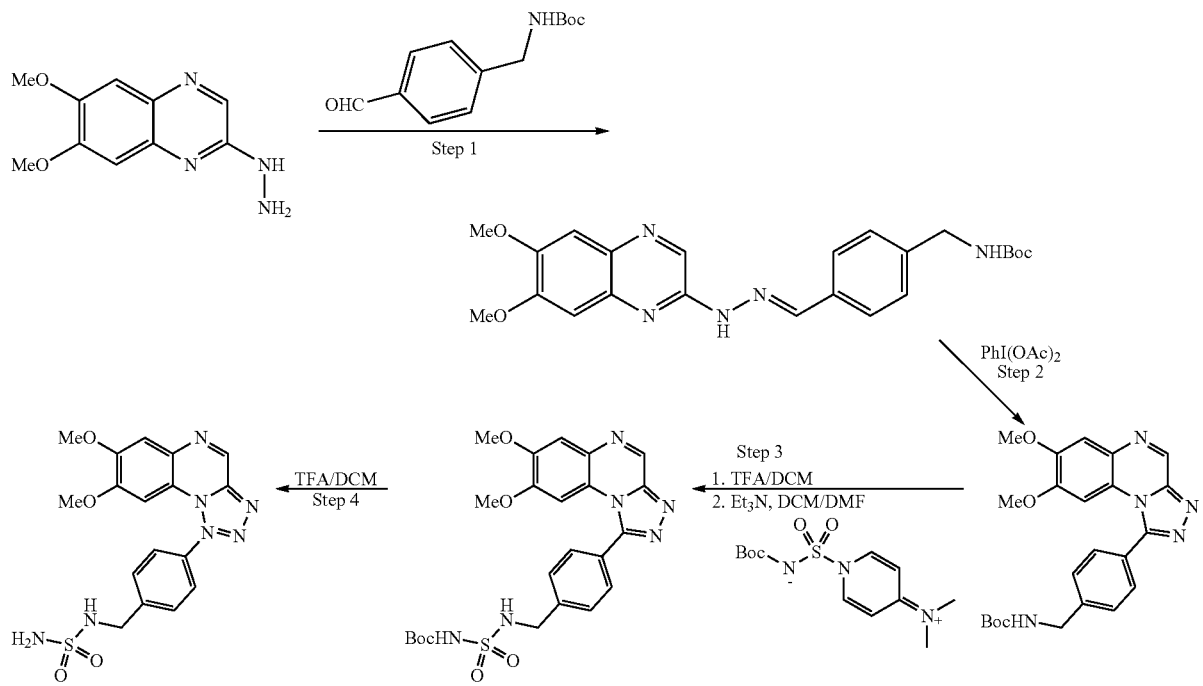

followed by the addition of Et₃N (276 μL, 1.98 mmol, 9 eq) and sulfamoylating reagent (73 mg, 0.242 mmol, 1.1 eq). The mixture was heated to 60° C. for 1 hr. Upon completion, the mixture was concentrated in vacuo. The crude was pushed through a silica plug then used without further purification.

Step 4. tert-butyl (N-(4-(7,8-dimethoxy-[1,2,4]triazolo[4,3-a]quinoxalin-1-yl)benzyl)sulfamoyl)-carbamate (0.22 mmol, 1 eq) was dissolved in DCM (1 mL) then cooled to 0° C. TFA (1 mL) was added to the mixture. The mixture was warmed to room temperature and stirred for 0.5 hr. Upon completion, the mixture was concentrated in vacuo. The crude was purified through FCC yielding the product (11 mg, 10%). LCMS [M+H]⁺=415; ¹H NMR (600 MHz, DMSO-d6) δ ppm 3.38-3.40 (m, 3H) 3.91 (s, 3H) 4.25 (d, J=6.24 Hz, 2H) 6.71 (s, 2H) 6.86 (s, 1H) 7.28 (br t, J=6.42 Hz, 1H) 7.61 (s, 1H) 7.68 (m, J=8.07 Hz, 2H) 7.77 (m, J=8.07 Hz, 2H) 9.31 (s, 1H).

Example 41

3-((7-methoxy-1H-imidazo[4,5-c][1,8]naphthyridin-1-yl)methyl)azetidine-1-sulfonamide (52)

3-((7-methoxy-1H-imidazo[4,5-c][1,8]naphthyridin-1-yl)methyl)azetidine-1-sulfonamide was prepared in the similar manner as Compound 39 from intermediate B and 3-(aminomethyl)azetidine-1-sulfonamide. LCMS [M+H]⁺=349; ¹H NMR (600 MHz, DMSO-d6) δ ppm 3.08-3.17 (m, 2H) 3.59 (br dd, J=8.34, 5.59 Hz, 8H) 3.78-3.84 (m, 3H) 4.12 (s, 3H) 4.97 (d, J=7.34 Hz, 2H) 6.90 (s, 2H) 7.43 (d, J=8.99 Hz, 1H) 8.83 (s, 1H) 8.95 (d, J=9.17 Hz, 1H) 9.60 (s, 1H).

Example 42

7-(7-methoxy-1H-imidazo[4,5-c][1,8]naphthyridin-1-yl)-3,4-dihydroisoquinoline-2(1H)-sulfonamide (53)

7-(7-methoxy-1H-imidazo[4,5-c][1,8]naphthyridin-1-yl)-3,4-dihydroisoquinoline-2(1H)-sulfonamide was prepared in the similar manner as Compound 39 from intermediate B and 7-amino-3,4-dihydroisoquinoline-2(1H)-sulfonamide. LCMS [M+H]⁺=411; ¹H NMR (600 MHz, DMSO-d6) δ ppm 3.10 (br s, 2H) 4.06 (s, 3H) 4.31 (br s, 2H) 7.01 (s, 2H) 7.19 (d, J=8.99 Hz, 1H) 7.51-7.56 (m, 1H) 7.56-7.59 (m, 1H) 7.65 (s, 1H) 7.78 (d, J=9.17 Hz, 1H) 8.72 (s, 1H) 9.58 (s, 1H).

Example 43

(R)-4-(1-(7-methoxy-1H-imidazo[4,5-c][1,8]naphthyridin-1-yl)ethyl)benzenesulfonamide (54)

(R)-4-(1-(7-methoxy-1H-imidazo[4,5-c][1,8]naphthyridin-1-yl)ethyl)benzenesulfonamide was prepared in the similar manner as Compound 39 from intermediate B and (R)-4-(1-aminoethyl)benzenesulfonamide. LCMS [M+H]⁺=384; ¹H NMR (600 MHz, DMSO-d6) δ ppm 2.12 (d, J=6.97 Hz, 3H) 4.05 (s, 3H) 6.64 (q, J=6.91 Hz, 1H) 7.28 (d, J=9.17 Hz, 1H) 7.34 (s, 2H) 7.40 (d, J=8.44 Hz, 2H) 7.75-7.79 (m, 2H) 8.65 (d, J=9.17 Hz, 1H) 9.07 (s, 1H) 9.62 (s, 1H).

Example 44

(4-((7-methoxy-1H-imidazo[4,5-c][1,8]naphthyridin-1-yl)methyl)phenyl)boronic Acid (55)

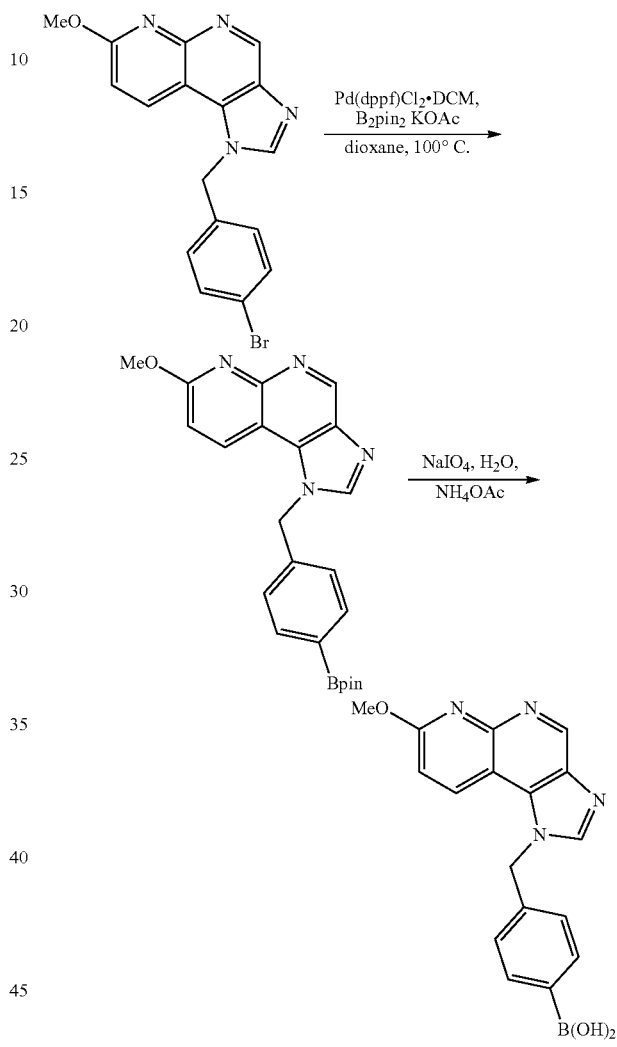

1-(4-bromobenzyl)-7-methoxy-1H-imidazo[4,5-c][1,8]naphthyridine was prepared in the similar manner as Compound 39 from intermediate B and 4-bromobenzylamine. 1-(4-bromobenzyl)-7-methoxy-1H-imidazo[4,5-c][1,8]naphthyridine(10 mg, 0.027 mmol) in a mixture of dioxane/DMF (0.5/0.5 mL) was treated with bis(pinacolato)diboron (10 mg, 1.5 eq), Pd(dppf)₂Cl₂ (2.2 mg, 10%) and KOAc (8 mg, 3.0 eq) and the reaction mixture was purged with N₂ for 2 min and then heated to 100° C. for 2 h. After cool to rt, the reaction mixture was treated with NaIO₄ (17 mg, 3.0 eq), NH₄OAc (6 mg, 3.0 eq) and water (1 mL) for 1 h. Work up and the residue was purified by reverse phase HPLC (MeCN/H₂O/0.1% TFA) to give a white solid as (4-((7-methoxy-1H-imidazo[4,5-c][1,8]naphthyridin-1-yl)methyl)phenyl)boronic acid. LCMS [M+H]⁺=335.

Example 45

4-(8,9-dimethoxypyrazolo[1,5-c]quinazoline-1-carbonyl)piperazine-1-sulfonamide (58)

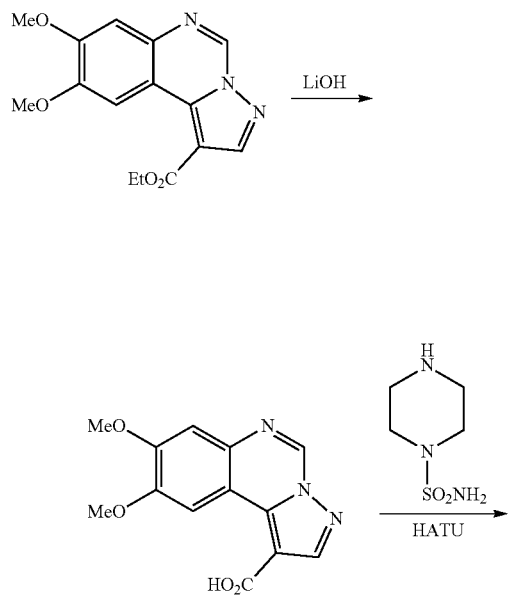

Ethyl 8,9-dimethoxypyrazolo[1,5-c]quinazoline-1-carboxylate (prepared according to a known procedure by Feng, H., RSC Adv., 2016, 6, 95774) is converted to the corresponding acid by saponification with LiOH solution in THF. Coupling with piperazine-1-sulfonamide with HATU provides 4-(8,9-dimethoxypyrazolo[1,5-c]quinazoline-1-carbonyl)piperazine-1-sulfonamide (58).

Example 46

4-(7-methoxy-1H-imidazo[4,5-c][1,6]naphthyridin-1-yl)benzyl sulfamide (59)

4-(7-methoxy-1H-imidazo[4,5-c][1,6]naphthyridin-1-yl) benzyl sulfamide (59) is made in a similar manner as the preparation of compound 43.

Example 47

Synthesis of intermediates

4-bromo-2-(trifluoromethyl)benzenesulfonamide

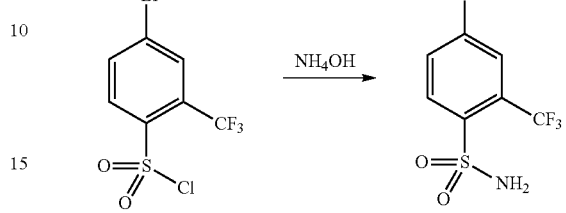

4-bromo-2-(trifluoromethyl)benzenesulfonyl chloride (2.5 g, 7.73 mmol, 1 eq) was dissolved in THF (40 mL, 0.2 M) and added dropwise to a stirring solution of NH$_4$OH at −20° C. keeping the internal temperature below −10° C. during addition. After addition, the reaction mixture was stirred at −10° C. for additional 10 min. Upon completion, the mixture was poured into 2 M HCl (250 mL) and EtOAc (100 mL) at 0° C. Layer separated and the aqueous layer extracted with EtOAc (2×100 mL). The combined organic layers dried over Na$_2$SO$_4$ and concentrated yielding the product (2.3 g, 98%).

The following intermediates were made in the same manner as 4-bromo-2 (trifluoromethyl)-benzenesulfonamide:
4-Bromo-2,3-difluorobenzenesulfonamide
4-Bromo-3,5-difluorobenzenesulfonamide
4-Bromo-2-(trifluoromethoxy)benzenesulfonamide
4-Bromo-3-(trifluoromethyl)benzenesulfonamide

4-(aminomethyl)-2,6-difluorobenzenesulfonamide HCl

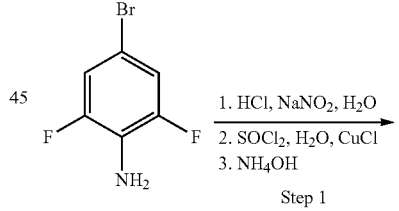

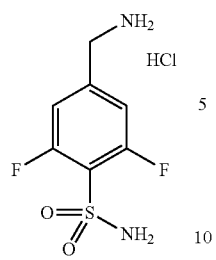

Step 1. To a flask containing water (45 mL, 2.3 M) at 0° C., thionyl chloride (7.5 mL, 103.2 mmol, 4.3 eq) was added dropwise. The resulting mixture was stirred at 22° C. for 18 hr. 4-Bromo-2,6-difluoroaniline (5 g, 24 mmol, 1 eq) at 0° C. was added conc HCl (24 mL, 1 M) and the resulting mixture was heated to 50° C. for 1 hr then cooled to −5° C. (internal temperature). A solution of NaNO$_2$ (1.77 g, 25.7 mmol, 1.07 eq) dissolved in water (7 mL) was added to the reaction mixture. During addition, the internal temperature was kept below 0° C. After addition the mixture was stirred for additional 10 min at −5° C. The aqueous thionyl chloride mixture was cooled to −5° C. (internal temperature) and CuCl (24 mg, 0.24 mmol, 0.01 eq) was added. The freshly formed diazonium mixture was added slowly to the aqueous thionyl chloride mixture while keeping the internal temperature below 0° C. After addition, the mixture was stirred at −5° C. for additional 20 min. The resulting precipitate was filtered and dissolved in THF (100 mL). The sulfonyl chloride in THF was added slowly to a stirring mixture of NH$_4$OH (82 mL) at −10° C. (internal temperature). During the addition, the internal temperature was kept below −5° C. After the addition, the mixture was poured into 2 M HCl (600 mL). At pH 2, the aqueous layer was extracted with EtOAc (3×100 mL). The combined organic layer was dried over Na$_2$SO$_4$ and concentrated yielding the product (5.34 g, 82%).

Step 2. 4-bromo-2,6-difluorobenzenesulfonamide (2 g, 7.35 mmol, 1 eq), Zn(CN)$_2$ (518 mg, 4.41 mmol, 0.6 eq), and Pd(PPh$_3$)$_4$ (424 mg, 0.37 mmol, 0.05 eq) were suspended in DMF (37 mL, 0.2 M). The mixture was purged with nitrogen for 1 min and heated to 100° C. for 5 hr. Upon completion, the mixture was cooled to 22° C. and poured into water. The resulting ligand precipitate was filtered. The filtrate was acidified to pH 2 with 2 M HCl and extracted with EtOAc (3×100 mL). The combined organic layer dried over Na$_2$SO$_4$ and concentrated yielding the product (1.4 g, 88%)Step 3. 4-cyano-2,6-difluorobenzenesulfonamide (844 mg, 3.87 mmol, 1 eq) was dissolved in MeOH (39 mL, 0.1 M) then added to a flask containing 10% Pd/C (844 mg) under nitrogen atmosphere. Conc HCl (355 µL, 4.3 mmol, 1.1 eq) was added and the mixture purged with hydrogen (3 cycles). The resulting mixture was stirred at 22° C. for 1 hr. Upon completion, the mixture was filtered over a pad of celite. The filtrate was concentrated. The residual was triturated with EtOAc several times yielding the product (903 mg, 90%). LCMS [M+H]$^+$=223.

The following intermediates were made in the same manner as 4-(aminomethyl)-2,6-difluorobenzenesulfonamide HCl:
4-(Aminomethyl)-2,5-difluorobenzenesulfonamide HCl
4-(Aminomethyl)-2,3-difluorobenzenesulfonamide HCl
4-(Aminomethyl)-3,5-difluorobenzenesulfonamide HCl
4-(Aminomethyl)-2-(trifluoromethyl)benzenesulfonamide HCl
4-(Aminomethyl)-2-(trifluoromethoxy)benzenesulfonamide HCl
4-(Aminomethyl)-3-(trifluoromethyl)benzenesulfonamide HCl (4-bromo-2,6-difluorophenyl)methanamine

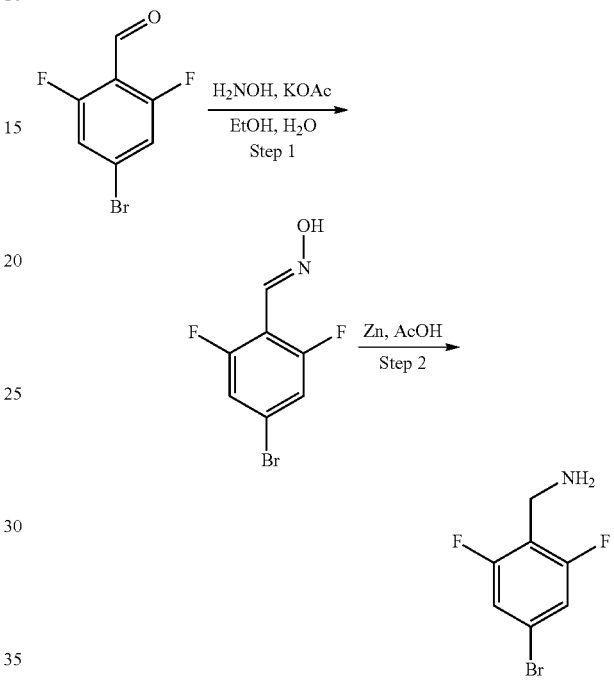

Step 1. To a mixture of 4-bromo-2,6-difluoro-benzaldehyde (2.5 g, 11.31 mmol, 1 eq) in ethanol (40 mL) was added hydroxylamine hydrochloride (1.10 g, 15.84 mmol, 1.40 eq) and potassium acetate (1.30 g, 13.24 mmol, 1.17 eq) in one portion at 22° C. for 1 h. Upon completion, water (40 mL) was added into the reaction mixture at 0° C. and stirred for 1 hr. The resulting precipitate filtered and washed by cold 1:1 EtOH/Water yielding the product (2.5 g, 94%).

Step 2. (E)-4-bromo-2,6-difluoro-benzaldehyde oxime (2.5 g, 10.59 mmol, 1 eq) was dissolved in AcOH (60 mL). Zn (5.54 g, 84.74 mmol, 8 eq) was added in one portion at 65° C. The mixture was stirred at 65° C. for 2 hr. Upon completion, the reaction mixture was filtered and the filtrate was concentrated. The residual was dissolved in water (50 ml) and washed with diethyl ether (3×50 mL). The combined organic layers was back extracted with water (2×50 mL, with AcOH 2 drops), the two aqueous layers were combined, neutralized by NaHCO$_3$. The basic aqueous layer extracted EtOAc (3×50 mL). The EtOAc layers combined and dried over Na$_2$SO$_4$. After concentration, the product was obtained without further purification (1.46 g, 62%). LCMS [M+H]$^+$=222.

Step 3. Product was prepared following the procedure for the (4-bromo-2,6-difluorophenyl)-methanamine. LCMS [M+H]$^+$=240.

(R)-6-(1-Aminoethyl)pyridine-3-sulfonamide HCl

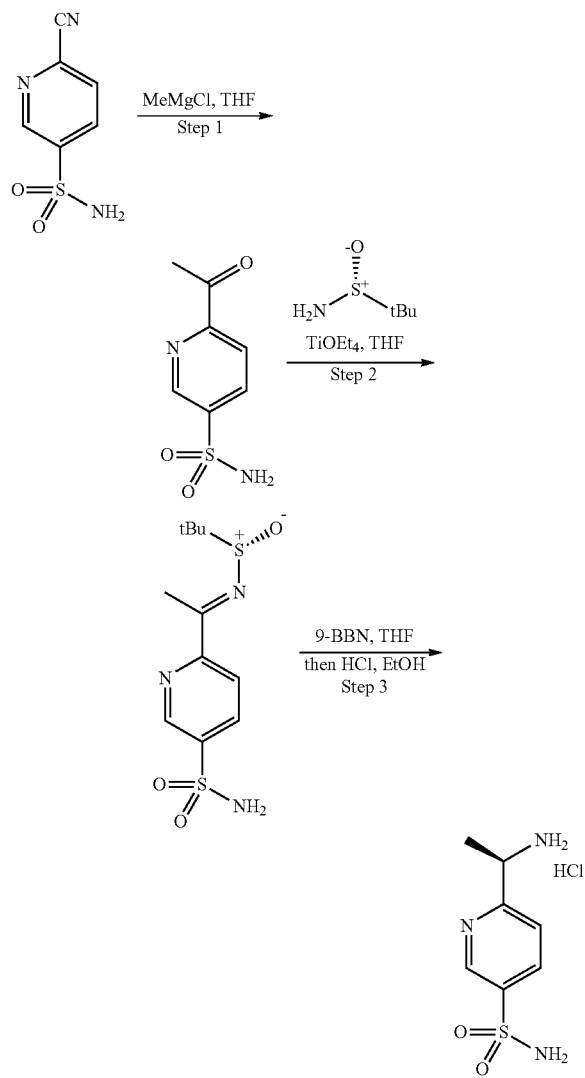

Step 1. 6-cyanopyridine-3-sulfonamide (1.4 g, 7.65 mmol, 1 eq) dissolved in THF (60 mL) then cooled to 0° C. MeMgCl (3.0 M, 7.6 mL, 22.95 mmol, 3 eq) was added to the reaction mixture. After addition, the mixture was stirred at 22° C. for 2 hr. Upon completion, the mixture was quenched with sat. NH₄Cl. Layer separated and the aqueous extracted with EtOAc (2×50 mL). The combined organic layers dried over Na₂SO₄ and concentrated. The crude was purified by FCC yielding the product (1.14 g, 76%).

Step 2. 6-acetylpyridine-3-sulfonamide (1.14 g, 5.69 mmol, 1 eq) dissolved in THF (14 mL, 0.4M) followed by the addition of (R)-2-Methylpropane-2-sulfinamide (828 mg, 6.83 mmol, 1.2 eq). Ti(OEt)₄ (1.72 mL, 11.38 mmol, 2 eq) was added to the mixture and the mixture was heated to reflux for 18 hr. Upon completion, the mixture was cooled to 0° C. and quenched with water. EtOAc was added and the layers separated. The aqueous layer was extracted with EtOAc (2×50 mL). The combined organic layers dried over Na₂SO₄ and concentrated. The crude was purified by FCC using DCM/THF gradient yielding the product (0.97 g, 56%).

Step 3. (E)-6-(1-((tert-butylsulfinyl)imino)ethyl)pyridine-3-sulfonamide (0.97 g, 3.2 mmol, 1 eq) was dissolved in THF (11 mL, 0.3 M) then cooled to 0° C. 9-BBN (0.5 M, 8.3 mL, 4.2 mmol, 1.3 eq) was added to the mixture. The mixture was stirred at 0° C. for 2 hr. Upon completion, the mixture was quenched with MeOH (11 mL) and HCl in EtOH (1.25M, 11 mL) was added. The mixture was stirred at 0° C. for additional 30 min then concentrated. The resulting residual was triturated with EtOAc several times yielding the product (613 mg, 81%). LCMS [M+H]⁺=202.

Compounds 60-69 and 129 were prepared from the amine intermediates in a similar manner as the preparation of compound 39.

Example 48

(R)-6-(1-(7-Methoxy-1H-imidazo[4,5-c][1,8]naphthyridin-1-yl)ethyl)pyridine-3-sulfonamide (60) was prepared in 16 mg. LCMS [M+H]⁺=385; ¹H NMR (600 MHz, DMSO-d6) δ ppm 2.08 (d, J=6.97 Hz, 3H) 3.99 (s, 4H) 6.67 (q, J=6.91 Hz, 1H) 7.24 (d, J=9.17 Hz, 1H) 7.51 (s, 2H) 7.68 (d, J=8.25 Hz, 1H) 8.13 (dd, J=8.25, 2.38 Hz, 1H) 8.68 (br d, J=8.80 Hz, 1H) 8.74 (d, J=2.38 Hz, 1H) 9.02 (s, 1H) 9.55 (s, 1H).

Example 49

2-Fluoro-4-((7-methoxy-1H-imidazo[4,5-c][1,8]naphthyridin-1-yl)methyl)benzene-sulfonamide (61) was prepared in 15 mg. LCMS [M+H]⁺=388.

Example 50

3-Fluoro-4-((7-methoxy-1H-imidazo[4,5-c][1,8]naphthyridin-1-yl)methyl)benzene-sulfonamide (62) was prepared in 24.2 mg. LCMS [M+H]⁺=388.

Example 51

2-Cyano-6-((7-methoxy-1H-imidazo[4,5-c][1,8]naphthyridin-1-yl)methyl)pyridine-3-sulfonamide (63) was prepared in 0.5 mg. LCMS [M+H]⁺=396; ¹H NMR (600 MHz, DMSO-d6) δ ppm 1.08 (s, 6H) 2.02 (s, 1H) 3.98 (s, 3H) 6.22 (s, 2H) 7.16 (br d, J=9.17 Hz, 1H) 7.60-7.75 (m, 1H) 8.44 (d, J=8.07 Hz, 1H) 8.54 (br d, J=8.99 Hz, 2H) 8.73 (br s, 1H) 9.04 (br s, 1H) 9.39-9.51 (m, 1H).

Example 52

2-Methoxy-4-((7-methoxy-1H-imidazo[4,5-c][1,8]naphthyridin-1-yl)methyl)benzene-sulfonamide (64) was prepared in 4.1 mg. LCMS [M+H]⁺=400; ¹H NMR (600 MHz, DMSO-d6) δ ppm 3.93 (s, 3H) 5.68 (s, 1H) 6.19 (s, 2H) 7.17 (dd, J=3.30, 1.65 Hz, 1H) 7.28 (s, 2H) 7.45 (d, J=8.99 Hz, 1H) 7.52 (d, J=8.62 Hz, 2H) 7.68-7.74 (m, 2H) 7.97 (dd, J=3.30, 2.20 Hz, 1H) 8.94 (d, J=8.99 Hz, 1H) 9.93 (s, 1H) 13.70 (br s, 1H).

Example 53

4-((7-Methoxy-1H-imidazo[4,5-c][1,8]naphthyridin-1-yl)methyl)-2-(trifluoromethyl)benzenesulfonamide (65) was prepared in 7.6 mg. LCMS [M+H]⁺=438; ¹H NMR (600 MHz, DMSO-d6) δ ppm 4.06 (s, 3H) 6.23 (s, 2H) 7.25 (d, J=9.17 Hz, 1H) 7.39 (d, J=8.44 Hz, 1H) 7.70 (s, 2H) 7.94 (s, 1H) 8.03 (d, J=8.25 Hz, 1H) 8.56 (d, J=9.17 Hz, 1H) 8.81 (s, 1H) 9.58 (s, 1H).

Example 54

4-((7-Methoxy-1H-imidazo[4,5-c][1,8]naphthyridin-1-yl)methyl)-2-(trifluoromethoxy)-benzene-sulfonamide (66) was prepared in 3.7 mg. LCMS [M+H]$^+$=454.

Example 55

4-((7-Methoxy-1H-imidazo[4,5-c][1,8]naphthyridin-1-yl)methyl)-3-(trifluoromethyl)-benzenesulfonamide (67) was prepared in 3.1 mg. LCMS [M+H]$^+$=438.

Example 56

3-Bromo-4-((7-methoxy-1H-imidazo[4,5-c][1,8]naphthyridin-1-yl)methyl)benzene-sulfonamide (68) was prepared in 214 mg. LCMS [M+H]$^+$=449; $^1$H NMR (300 MHz, DMSO-d6) δ ppm 4.03 (s, 3H) 6.08 (s, 2H) 6.61-6.68 (m, 1H) 7.15-7.24 (m, 1H) 7.48 (s, 2H) 7.56-7.60 (m, 1H) 8.15 (s, 1H) 8.18 (d, J=8.79 Hz, 1H) 8.64 (s, 1H) 9.47-9.54 (m, 1H).

Example 57

3-Cyano-4-((7-methoxy-1H-imidazo[4,5-c][1,8]naphthyridin-1-yl)methyl)benzene-sulfonamide (69) was prepared in 6.7 mg. LCMS [M+H]$^+$=395; $^1$H NMR (300 MHz, DMSO-d6) δ ppm 4.05 (s, 3H) 6.36 (s, 2H) 6.90 (d, J=8.21 Hz, 1H) 7.20 (d, J=9.38 Hz, 1H) 7.58 (s, 2H) 7.85 (dd, J=8.21, 2.34 Hz, 1H) 8.32 (d, J=1.76 Hz, 1H) 8.44 (d, J=8.79 Hz, 1H) 8.71 (s, 1H) 9.58 (s, 1H).

Example 58

3,5-difluoro-4-((7-methoxy-1H-imidazo[4,5-c][1,8]naphthyridin-1-yl)methyl)benzenesulfonamide (129) was prepared in 29.4 mg. LCMS [M+H]$^+$=406; $^1$H NMR (400 MHz, DMSO-d6) δ ppm 4.04 (s, 3H) 6.16 (s, 2H) 7.34 (d, J=9.00 Hz, 1H) 7.52 (s, 1H) 7.54 (s, 1H) 7.65 (s, 2H) 8.64 (s, 1H) 8.83 (d, J=9.00 Hz, 1H) 9.47 (s, 1H).

Compounds 70-73 and 130 were prepared from the amine intermediates in a similar manner as the preparation of compound 39, using triethyl orthoacetate in the place of triethyl orthoformate in the last step.

Example 59

2,5-Difluoro-4-((7-methoxy-2-methyl-1H-imidazo[4,5-c][1,8]naphthyridin-1-yl)methyl)benzenesulfonamide (70) was prepared in 3.7 mg. LCMS [M+H]$^+$=420.

Example 60

2-Fluoro-4-((7-methoxy-2-methyl-1H-imidazo[4,5-c][1,8]naphthyridin-1-yl)methyl)benzenesulfon-amide (71) was prepared in 2.3 mg. LCMS [M+H]$^+$=402; $^1$H NMR (300 MHz, DMSO-d6) δ ppm 2.69 (s, 3H) 4.06 (s, 3H) 6.09 (s, 2H) 6.98 (d, J=7.62 Hz, 1H) 7.17-7.34 (m, 2H) 7.64-7.76 (m, 3H) 8.54 (d, J=9.38 Hz, 1H) 9.54 (s, 1H).

Example 61

6-((7-Methoxy-2-methyl-1H-imidazo[4,5-c][1,8]naphthyridin-1-yl)methyl)pyridine-3-sulfonamide (72) was prepared in 3.4 mg. LCMS [M+H]$^+$=385; $^1$H NMR (300 MHz, DMSO-d6) δ ppm 2.69 (s, 3H) 4.04 (s, 3H) 6.15-6.21 (m, 2H) 7.16-7.30 (m, 1H) 7.55 (s, 2H) 7.70 (d, J=8.79 Hz, 1H) 8.17-8.24 (m, 1H) 8.57-8.67 (m, 1H) 8.71-8.74 (m, 1H) 9.40-9.42 (m, 1H).

Example 62

5-((7-Methoxy-2-methyl-1H-imidazo[4,5-c][1,8]naphthyridin-1-yl)methyl)pyridine-2-sulfonamide (73) was prepared in 6 mg. LCMS [M+H]$^+$=385.

Example 63

3,5-difluoro-4-((7-methoxy-2-methyl-1H-imidazo[4,5-c][1,8]naphthyridin-1-yl)methyl)benzenesulfonamide (130) was prepared in 14 mg. LCMS [M+H]$^+$=420.

Example 64

6-((2-Cyclopropyl-7-methoxy-1H-imidazo[4,5-c][1,8]naphthyridin-1-yl)methyl)pyridine-3-sulfon-amide (74)

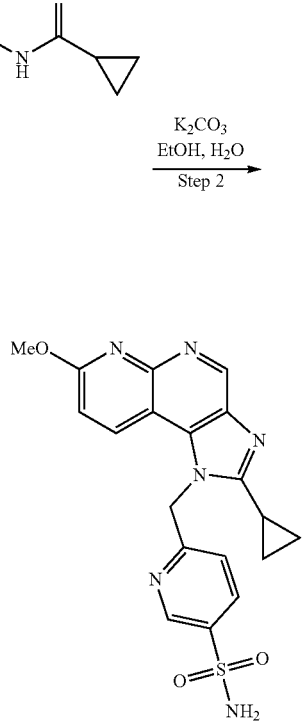

Step 1. To a mixture of cyclopropanecarboxylic acid (6.21 mg, 72.14 μmol, 5.70 μL, 1.3 eq) in DMF (0.3 mL) was added HATU (27.43 mg, 72.14 umol, 1.3 eq) and DIEA (27.97 mg, 216.43 umol, 37.70 μL, 3.9 eq) in one portion at 22° C. The mixture was stirred at 22° C. for 1 hr. 6-(((3-amino-7-methoxy-1,8-naphthyridin-4-yl)amino)methyl)pyridine-3-sulfonamide (20 mg, 55.50 μmol, 1 eq) was then added into reaction mixture and then stirred at 22° C. for 18 hr. Upon completion, water was added into reaction mixture and extracted by EtOAc. The organic layer was dried over Na$_2$SO$_4$ and concentrated. The crude product was used in the next step without further purification.

Step 2. 6-((2-cyclopropyl-7-methoxy-1H-imidazo[4,5-c][1,8]naphthyridin-1-yl)methyl)pyridine-3-sulfonamide in EtOH/Water=4:1 (1 mL) was added K$_2$CO$_3$ (23.01 mg, 166.49 μmol, 3 eq) at 22° C. The reaction was stirred at 65° C. for 18 hr. Upon completion, the mixture was concentrated. The crude was purified by Prep HPLC using water/MeCN (0.1% TFA) gradient yielding the product (2.5 mg, 9%). LCMS [M+H]$^+$=411.

Example 65

6-((7-methoxy-2-(tetrahydro-2H-pyran-4-yl)-1H-imidazo[4,5-c][1,8]naphthyridin-1-yl)methyl)pyridine-3-sulfonamide (75) was prepared in 1.0 mg in a similar manner as the preparation of compound 74. LCMS [M+H]$^+$=455.

Example 66

N-((2-fluoro-4-((7-methoxy-2-methyl-1H-imidazo[4,5-c][1,8]naphthyridin-1-yl)methyl)-phenyl)sulfonyl)acetamide (76) was isolated as a byproduct in the last step of preparation of compound 71. LCMS [M+H]$^+$=444; $^1$H NMR (300 MHz, DMSO-d6) δ ppm 1.92 (s, 3H) 2.70 (s, 3H) 4.08 (s, 3H) 6.10-6.17 (m, 2H) 7.10 (d, J=8.21 Hz, 1H) 7.25 (d, J=11.14 Hz, 1H) 7.33 (d, J=8.79 Hz, 1H) 7.83 (t, J=7.91 Hz, 1H) 8.55-8.61 (m, 1H) 9.59-9.62 (m, 1H).

Example 67

N-((6-((7-methoxy-2-methyl-1H-imidazo[4,5-c][1,8]naphthyridin-1-yl)methyl)pyridin-3-yl)-sulfonyl)acetamide (77) was isolated as a byproduct in the last step of preparation of compound 72. LCMS [M+H]$^+$=427; $^1$H NMR (300 MHz, DMSO-d6) δ ppm 1.89 (s, 3H) 2.71 (s, 3H) 4.07 (s, 3H) 6.25 (s, 2H) 7.27 (br d, J=4.10 Hz, 1H) 7.85 (s, 1H) 8.30-8.40 (m, 1H) 8.69 (d, J=9.38 Hz, 1H) 8.77 (d, J=2.34 Hz, 1H) 9.53 (s, 1H).

Example 68

4-((2,7-Dimethoxy-1H-imidazo[4,5-c][1,8]naphthyridin-1-yl)methyl)-2-fluorobenzenesulfonamide (78) was prepared in 9.7 mg using tetraethyl orthocarbonate in the last step following a similar manner as the preparation of compound 39. LCMS [M+H]$^+$=418; $^1$H NMR (300 MHz, DMSO-d6) δ ppm 4.06 (s, 3H) 4.27 (s, 3H) 5.88 (s, 2H) 7.11 (d, J=8.21 Hz, 1H) 7.30-7.35 (m, 1H) 7.64 (s, 2H) 7.71 (br t, J=7.62 Hz, 2H) 8.50 (d, J=8.79 Hz, 1H) 9.39 (s, 1H).

Example 69

2-Fluoro-4-((7-methoxy-2-(methoxymethyl)-1H-imidazo[4,5-c][1,8]naphthyridin-1-yl)methyl)-benzenesulfonamide (79)

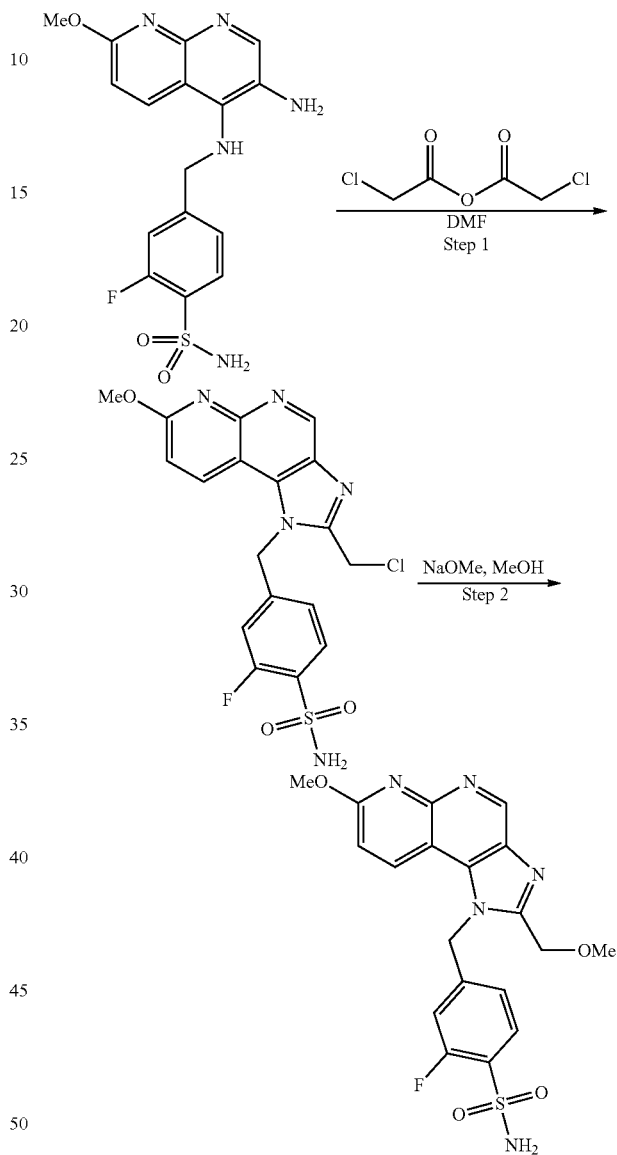

Step 1. 4-(((3-amino-7-methoxy-1,8-naphthyridin-4-yl)amino)methyl)-2-fluorobenzenesulfonamide (70 mg, 0.185 mmol, 1 eq) was dissolved in DMF (1.85 mL, 0.1 M) followed by the addition of chloroacetic anhydride (35 mg, 0.204 mmol, 1.1 eq). The mixture was stirred at 22° C. for 4 days. Upon completion, the mixture was partitioned between water and EtOAc. Layer was separated and the aqueous layer was extracted with EtOAc (3×3 mL). The combined organic layer was dried over Na$_2$SO$_4$ and concentrated yielding 4-((2-(Chloromethyl)-7-methoxy-1H-imidazo[4,5-c][1,8]naphthyridin-1-yl)methyl)-2-fluorobenzenesulfonamide (47.4 mg, 59%) without further purification.

Step 2. 4-((2-(Chloromethyl)-7-methoxy-1H-imidazo[4,5-c][1,8]naphthyridin-1-yl)methyl)-2-fluorobenzenesulfonamide (17 mg, 0.039 mmol, 1 eq) was dissolved in MeOH (0.4 mL, 0.1 M) followed by the addition of 25 wt % NaOMe (286 μL). The mixture was stirred at 22° C. for 1 hr. Upon completion. The mixture was quenched with sat. NH₄Cl and concentrated. The crude was purified by Prep HPLC using water/MeCN (0.1% TFA) gradient yielding the product (10 mg, 59%). LCMS [M+H]⁺=432; ¹H NMR (300 MHz, DMSO-d6) δ ppm 4.03 (s, 3H) 4.84 (s, 2H) 6.09 (s, 2H) 6.88-6.99 (m, 1H) 7.15-7.23 (m, 2H) 7.61 (s, 2H) 7.67 (t, J=7.62 Hz, 1H) 8.34-8.45 (m, 1H) 9.47-9.56 (m, 1H).

Example 70

2-Fluoro-4-((7-methoxy-2-(morpholinomethyl)-1H-imidazo[4,5-c][1,8]naphthyridin-1-yl)methyl)-benzenesulfonamide (80)

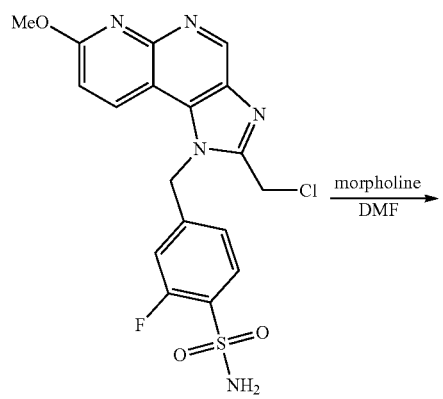

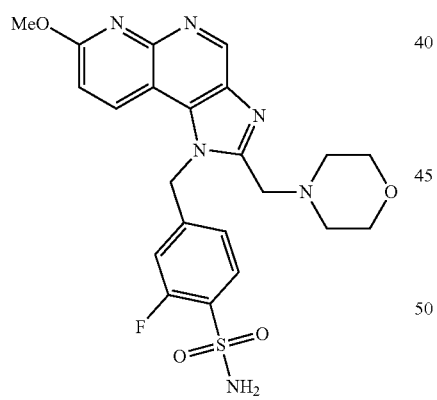

4-((2-(Chloromethyl)-7-methoxy-1H-imidazo[4,5-c][1,8] naphthyridin-1-yl)methyl)-2-fluorobenzenesulfonamide (10 mg, 0.023 mmol, 1 eq) was dissolved in DMF (0.46 mL, 0.05 M) followed by the addition of morpholine (10 μL, 0.115 mmol, 5 eq). The mixture was stirred at 22° C. for 1 hr. Upon completion, the mixture was purified by Prep HPLC using water/MeCN (0.1% TFA) gradient yielding the product (4 mg). LCMS [M+H]⁺=487; ¹H NMR (300 MHz, DMSO-d6) δ ppm 2.58-2.74 (m, 4H) 3.78 (br s, 2H) 4.04 (s, 3H) 4.13-4.24 (m, 2H) 6.14 (s, 2H) 6.92 (s, 1H) 7.13-7.21 (m, 1H) 7.24 (d, J=8.79 Hz, 1H) 7.65 (s, 2H) 7.68-7.71 (m, 1H) 8.43 (d, J=9.38 Hz, 1H) 9.53 (s, 1H).

Example 71

2-Fluoro-4-((7-methoxy-2-((methylsulfonyl)methyl)-1H-imidazo[4,5-c][1,8]naphthyridin-1-yl)-methyl) benzenesulfonamide (81)

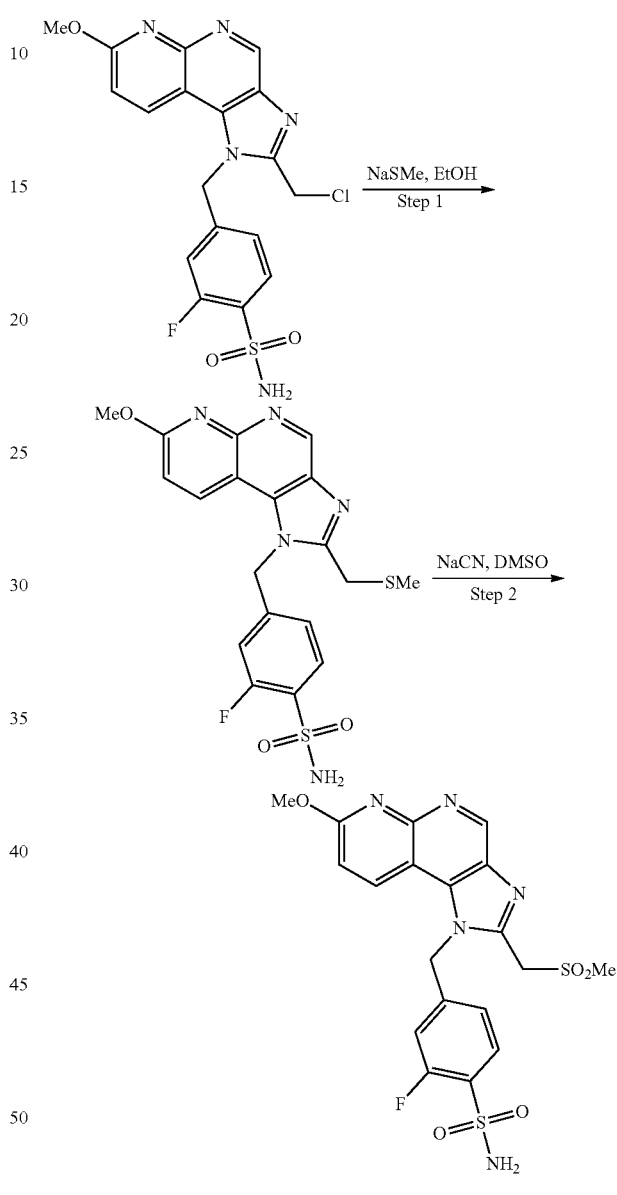

Step 1. 4-((2-(Chloromethyl)-7-methoxy-1H-imidazo[4,5-c][1,8]naphthyridin-1-yl)methyl)-2-fluorobenzenesulfonamide (17.7 mg, 0.041 mmol, 1 eq) was dissolved in EtOH (0.82 mL, 0.05 M) followed by the addition of NaSMe (9 mg, 0.123 mmol, 3 eq). The mixture stirred at 22° C. for 3 hr. Upon completion, the mixture was concentrated yielding the product. The crude product was used in the next step without further purification.

Step 2. 2-Fluoro-4-((7-methoxy-2-((methylthio)methyl)-1H-imidazo[4,5-c][1,8]naphthyridin-1-yl)methyl)benzene-sulfonamide was dissolved in THF (0.18 mL) then added to a solution of oxone (11 mg, 0.018 mmol, 1 eq) in water (0.18 mL). The mixture was stirred at 22° C. for 3 hr. Upon completion, the mixture was purified by Prep HPLC using water/MeCN (0.1% TFA) gradient yielding the product (5.3 mg, 31%). LCMS [M+H]$^+$=480; $^1$H NMR (300 MHz, DMSO-d6) δ ppm 3.26 (s, 3H) 4.02 (s, 3H) 5.26 (s, 2H) 6.21 (s, 2H) 6.93 (d, J=7.86 Hz, 1H) 7.10 (d, J=11.14 Hz, 1H) 7.18 (d, J=8.79 Hz, 1H) 7.61 (s, 2H) 7.67 (t, J=7.91 Hz, 1H) 8.37 (d, J=9.38 Hz, 1H) 9.53 (s, 1H).

Example 72

4-((2-(Cyanomethyl)-7-methoxy-1H-imidazo[4,5-c][1,8]naphthyridin-1-yl)methyl)-2-fluorobenzenesulfonamide (82)

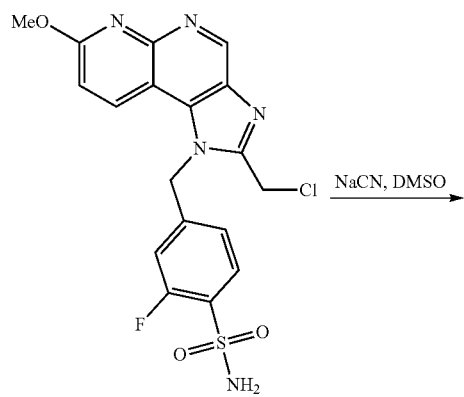

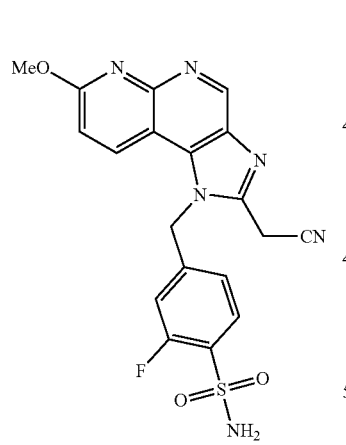

4-((2-(Chloromethyl)-7-methoxy-1H-imidazo[4,5-c][1,8]naphthyridin-1-yl)methyl)-2-fluorobenzenesulfonamide (11.3 mg, 0.026 mmol, 1 eq) was dissolved in DMSO (0.26 mL, 0.1 M) followed by the addition of NaCN (2.5 mg, 0.052 mmol, 2 eq). The mixture was heated to 80° C. for 10 min. Upon completion, the mixture was purified by Prep HPLC using water/MeCN (0.1% TFA) gradient yielding the product (2.6 mg, 24%). LCMS [M+H]$^+$=427.

Example 73

Methyl 2-(1-(3-fluoro-4-sulfamoylbenzyl)-7-methoxy-1H-imidazo[4,5-c][1,8]naphthyridin-2-yl)-acetate (83)

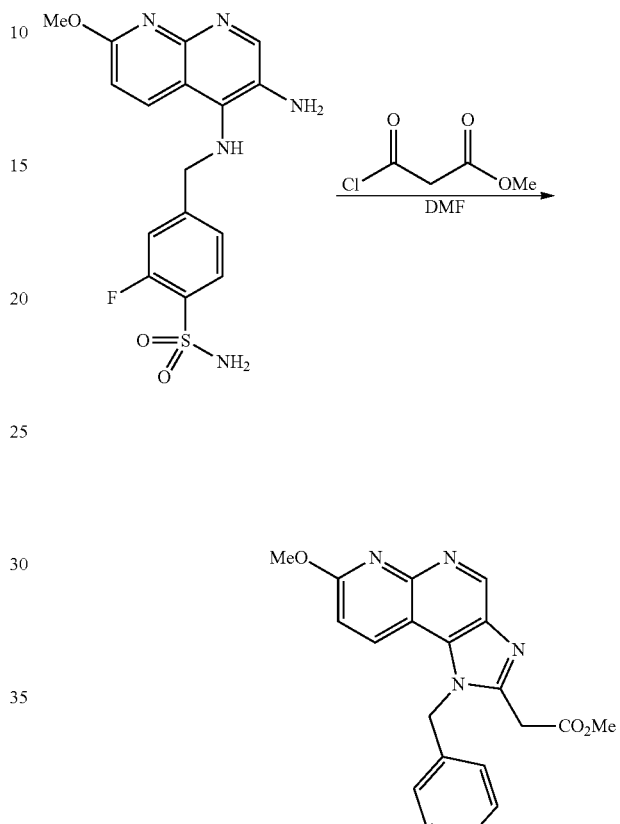

4-(((3-amino-7-methoxy-1,8-naphthyridin-4-yl)amino)methyl)-2-fluorobenzenesulfonamide (80 mg, 0.212 mmol, 1 eq) was dissolved in DMF (4.24 mL, 0.05 M) followed by the addition of Et$_3$N (35 μL, 0.254 mmol, 1.2 eq). The mixture was cooled to 0° C. and methyl malonyl chloride (24 μL, 0.223 mmol, 1.05 eq) was added. The mixture stirred at 0° C. for 1 hr then heated to 100° C. for 3 hr. Upon completion, the mixture was partitioned between water and EtOAc. The layers separated and the aqueous extracted with EtOAc (3×5 mL). The combined organic layers dried over Na$_2$SO$_4$ and concentrated. The crude was purified by FCC using DCM/THF yielding the product (26 mg, 27%). LCMS [M+H]$^+$=460.

Example 74

2-(1-(3-Fluoro-4-sulfamoylbenzyl)-7-methoxy-1H-imidazo[4,5-c][1,8]naphthyridin-2-yl)acetamide (84)

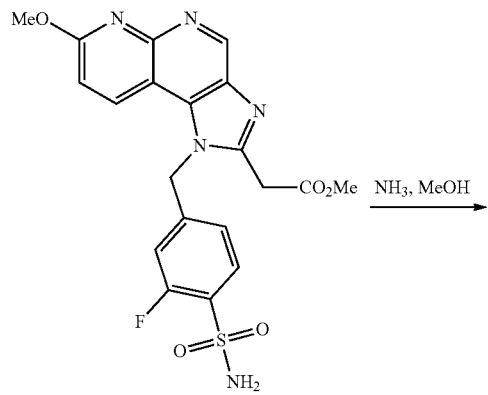

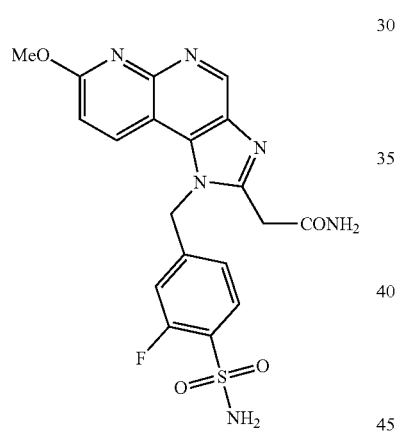

Methyl 2-(1-(3-fluoro-4-sulfamoylbenzyl)-7-methoxy-1H-imidazo[4,5-c][1,8]naphthyridin-2-yl)acetate (10 mg, 0.022 mmol, 1 eq) was dissolved in 2 N ammonia in MeOH (0.21 mL) The mixture was heated to 65° C. for 2 hr. Additional 2 N ammonia in MeOH (0.42 mL) was added and heated to 65° C. for 3 hr. Upon completion, the mixture was concentrated. The crude was purified by Prep HPLC using water/MeCN (0.1% TFA) gradient yielding the product (3.8 mg, 39%). LCMS [M+H]$^+$=445; $^1$H NMR (300 MHz, DMSO-d6) δ ppm 4.03 (s, 3H) 6.11 (s, 2H) 7.01 (s, 1H) 7.11-7.18 (m, 1H) 7.18-7.24 (m, 2H) 7.60 (s, 2H) 7.65-7.70 (m, 1H) 7.75 (br s, 1H) 8.38-8.43 (m, 1H) 9.48 (s, 1H).

Example 75

4-((2-(Azetidin-3-yl)-7-methoxy-1H-imidazo[4,5-c][1,8]naphthyridin-1-yl)methyl)-2-fluorobenzenesulfonamide (85)

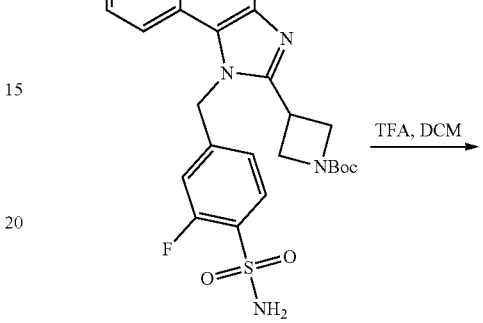

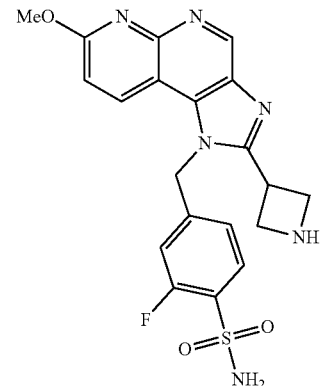

tert-butyl 3-(1-((3-fluoro-4-sulfamoyl-phenyl)methyl)-7-methoxy-imidazo[4,5-c][1,8]naphthyridin-2-yl)azetidine-1-carboxylate obtained from following the procedure for the synthesis of compound 74 (43 mg, 79.25 μmol, 1 eq) dissolved in DCM (1 mL) then cooled to 0° C. followed by the addition of TFA (308.00 mg, 2.70 mmol, 0.2 mL, 34.08 eq). The cooling bath removed and the mixture stirred at 22° C. for 1 hr. Upon completion, the mixture was concentrated yielding the product TFA salt (44 mg, 99%). LCMS [M+H]$^+$=443; $^1$H NMR (300 MHz, DMSO-d6) δ ppm 4.02 (s, 3H) 4.29-4.43 (m, 4H) 4.45-4.57 (m, 1H) 5.95 (s, 2H) 6.95 (d, J=8.21 Hz, 1H) 7.15-7.22 (m, 2H) 7.64 (s, 2H) 7.70 (t, J=7.91 Hz, 1H) 8.42 (d, J=8.79 Hz, 1H) 8.98-9.15 (m, 1H) 9.51 (s, 1H).

Example 76

2-Fluoro-4-((7-methoxy-2-(1-(methylsulfonyl)azetidin-3-yl)-1H-imidazo[4,5-c][1,8]naphthyridin-1-yl)methyl)benzenesulfonamide (86)

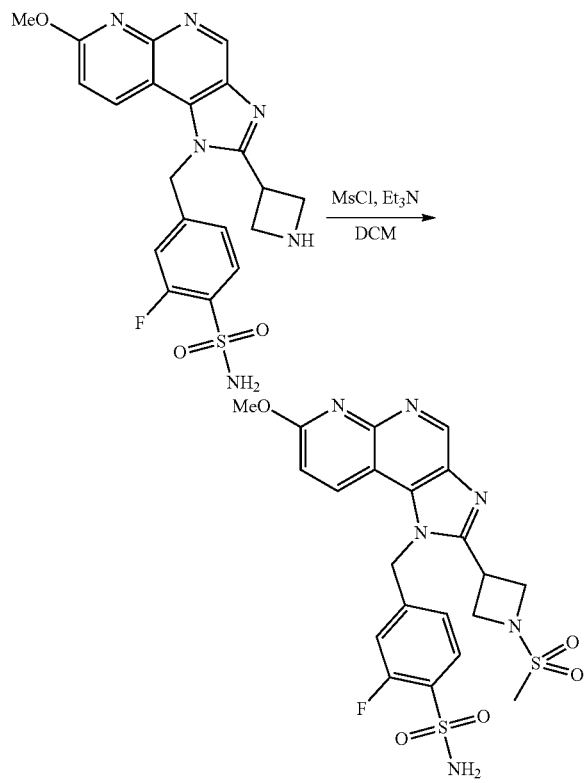

4-[[2-(azetidin-3-yl)-7-methoxy-imidazo[4,5-c][1,8]naphthyridin-1-yl]methyl]-2-fluoro-benzenesulfonamide (19.1 mg, 34.32 µmol, 1 eq, TFA) dissolved in DMF (0.34 mL) then cooled to 0° C. Et₃N (2 M, 17.16 µL, 1 eq) added to the mixture followed by MsCl (2 M, 17.16 µL, 1 eq). The mixture stirred at 0° C. for 0.5 hr. Mixture warmed to 22° C. and stirred for 1.5 hr. Cooled to 0° C., Additional Et₃N (2 M, 17.16 µL, 1 eq) and MsCl (2 M, 17.16 µL, 1 eq) were added and stirred at 0° C. for 30 min. The mixture was stirred to 22° C. over 18 hours. Upon completion, the mixture was concentrated. The crude was purified by Prep HPLC using water/MeCN (0.1% TFA) gradient yielding the product (1.7 mg, 10%). LCMS [M+H]⁺=521.

Example 77

Synthesis of Intermediate 4-chloro-7-methoxy-2-methyl-3-nitro-1,8-naphthyridine

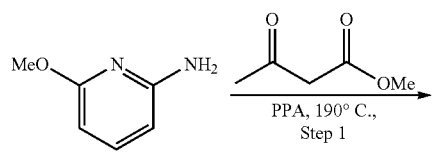

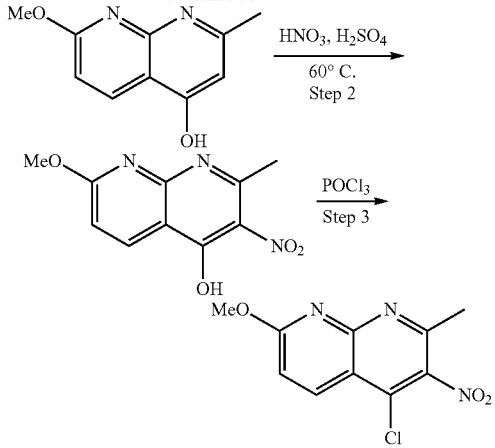

Step 1. 6-methoxy-2-amino-pyridine (5 g, 40.3 mmol, 1 eq) and methyl acetoacetate (43 mL, 400.3 mmol, 10 eq) was added PPA (13 g). The mixture was heated to 190° C. for 3 hr. Upon completion, the mixture cooled to 22° C. diluted with water then washed with EtOAc (2×50 mL) to remove excess ethyl acetoacetate. The aqueous layer added EtOAc (100 mL) and with stirring pH adjusted to 8 with 2 M NaOH. The resulting ppt was filtered and dried yielding the product (2.7 g, 35%).

Step 2. 7-methoxy-2-methyl-1,8-naphthyridin-4-ol (1 g, 5.26 mmol, 1 eq) dissolved in sulfuric acid (50 mL) then cooled to 0° C. Fuming nitric acid (3.70 g, 58.72 mmol, 2.5 mL, 11.17 eq) was added slowly dropwise to the mixture at 0° C. The mixture was stirred at 0° C. for 0.5 hr. The cooling bath removed and the mixture stirred at 22° C. for 18 hr. The mixture heated to 60° C. for 5 hr. Upon completion, the mixture cooled to 22° C. then poured into stirring ice water. The resulting ppt was filtered and dried yielding the product (432 mg, 34%).

Step 3. 7-methoxy-2-methyl-3-nitro-1,8-naphthyridin-4-ol (423 mg, 1.80 mmol, 1 eq) suspended in POCl₃ (5.94 g, 38.74 mmol, 3.6 mL, 21.54 eq) and heated to 80° C. for 1.5 hr. Upon completion, the mixture was concentrated and dissolved in DCM. The organic layer was washed with sat. NaHCO₃(3×10 mL). The organic layer was dried over Na₂SO₄ and concentrated yielding the product (447 mg, 98%).

Compounds 87 and 88 were made in a similar manner as the preparation of compound 39 from intermediate 4-chloro-7-methoxy-2-methyl-3-nitro-1,8-naphthyridine. Example 78

6-((7-Methoxy-4-methyl-1H-imidazo[4,5-c][1,8]naphthyridin-1-yl)methyl)pyridine-3-sulfonamide (87) was prepared in 11.9 mg. LCMS [M+H]⁺=385; ¹H NMR (300 MHz, DMSO-d6) δ ppm 2.86 (s, 3H) 3.94 (s, 3H) 6.14 (s, 2H) 6.94 (d, J=8.79 Hz, 1H) 7.43 (d, J=8.21 Hz, 1H) 7.48-7.60 (m, 2H) 8.10-8.15 (m, 1H) 8.31 (d, J=8.79 Hz, 1H) 8.50 (s, 1H) 8.79 (d, J=2.34 Hz, 1H).

Example 79

2-fluoro-4-((7-methoxy-4-methyl-1H-imidazo[4,5-c][1,8]naphthyridin-1-yl)methyl)benzenesulfonamide (88) was prepared in 7 mg. LCMS [M+H]⁺=370; ¹H NMR (500 MHz, DMSO-d6) δ ppm 3.94 (s, 3H) 6.16 (s, 2H) 7.30-7.37 (m, 5H) 7.79 (d, J=8.39 Hz, 2H) 8.66 (s, 1H) 9.10-9.17 (m, 1H).

Compounds 89 and 90 were made in a similar manner as the preparation of compound 39 using triethyl orthoacetate from intermediate 4-chloro-7-methoxy-2-methyl-3-nitro-1,8-naphthyridine.

Example 80

6-((7-Methoxy-2,4-dimethyl-1H-imidazo[4,5-c][1,8]naphthyridin-1-yl)methyl)pyridine-3-sulfonamide (89) was prepared in 1.4 mg. LCMS [M+H]$^+$=399; $^1$H NMR (300 MHz, DMSO-d6) δ ppm 2.69 (s, 3H) 4.06 (s, 3H) 6.19 (s, 2H) 7.17-7.29 (m, 1H) 7.57 (s, 2H) 7.68-7.78 (m, 1H) 8.17-8.26 (m, 1H) 8.58-8.67 (m, 1H) 8.70 (d, J=2.34 Hz, 1H).

Example 81

2,5-Difluoro-4-((7-methoxy-2,4-dimethyl-1H-imidazo[4,5-c][1,8]naphthyridin-1-yl)methyl)-benzenesulfonamide (90) was prepared in 12.1 mg. LCMS [M+H]$^+$=434; $^1$H NMR (300 MHz, DMSO-d6) δ ppm 2.68 (s, 3H) 3.04 (s, 3H) 4.08 (s, 3H) 6.08 (s, 2H) 6.85-6.95 (m, 1H) 7.28 (d, J=8.79 Hz, 1H) 7.66 (dd, J=9.08, 5.57 Hz, 1H) 7.80 (s, 2H) 8.56 (d, J=8.79 Hz, 1H).

Example 82

2-((7-Methoxy-2,4-dimethyl-1H-imidazo[4,5-c][1,8]naphthyridin-1-yl)methyl)pyrimidine-5-sulfonamide (91a) and 2-((6-cloro-7-Methoxy-2,4-dimethyl-1H-imidazo[4,5-c][1,8]naphthyridin-1-yl)methyl)pyrimidine-5-sulfonamide (91b)

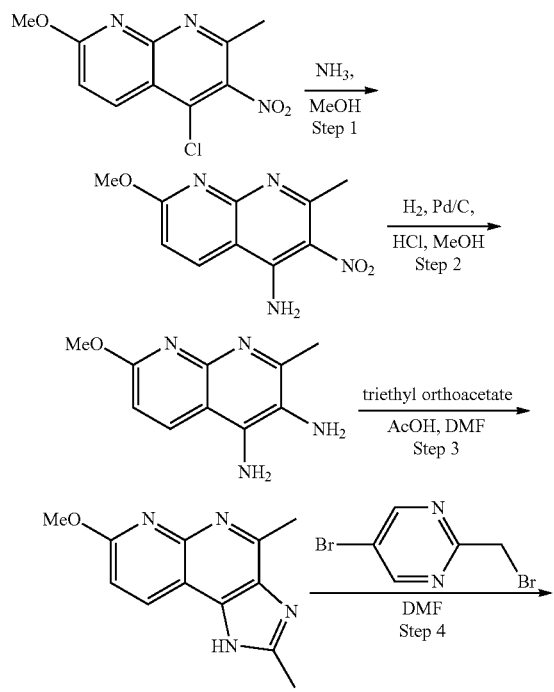

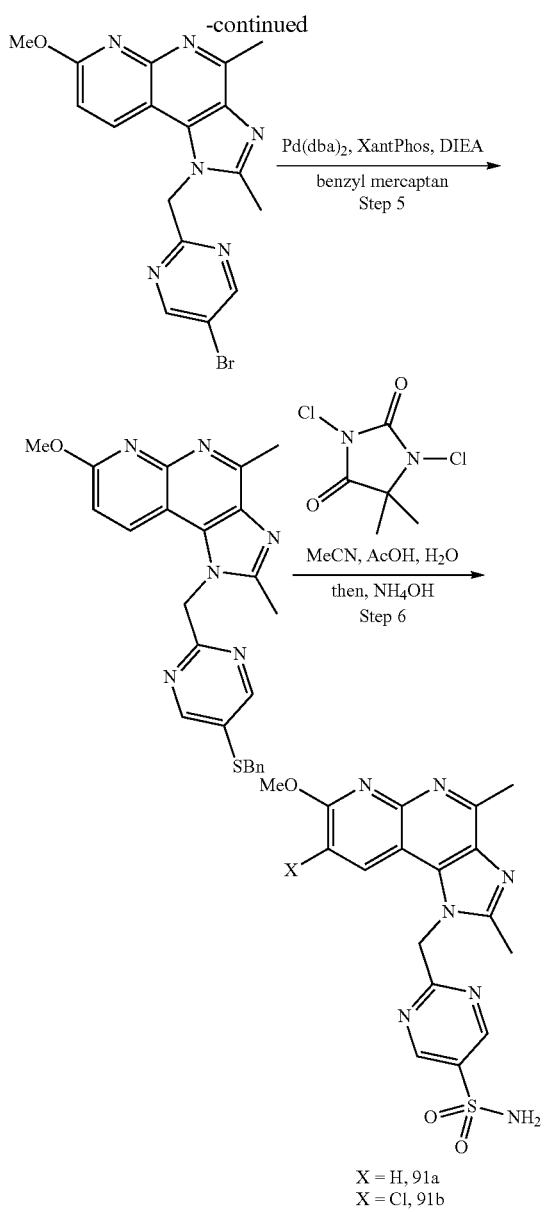

Step 1. 4-chloro-7-methoxy-2-methyl-3-nitro-1,8-naphthyridine (200 mg, 788.51 μmol, 1 eq) dissolved in NH$_3$ in MeOH (2 M, 8 mL, 20.29 eq) and stirred at 22° C. for 3 days. Upon completion, mixture concentrated and the resulting precipitate triturated with water. The resulting precipitate filtered and dried yielding the product (184 mg, 99%).

Step 2. 7-methoxy-2-methyl-3-nitro-1,8-naphthyridin-4-amine (184 mg, 785.62 μmol, 1 eq) suspended in MeOH (8 mL) followed by the addition of 10% palladium on carbon (184 mg, 172.84 μmol, 0.22 eq) and HCl (12 M, 65.47 μL, 1 eq). The mixture purged with hydrogen (3 cycles) and stirred under hydrogen balloon at 22° C. for 3 hr. Upon completion, mixture filtered through a pad of celite. The cake was washed with MeOH/Et$_3$N (90%/10%) and the filtrate concentrated yielding the product (160 mg, 99%).

Step 3. 7-methoxy-2-methyl-1,8-naphthyridine-3,4-diamine (157 mg, 768.75 μmol, 1 eq) dissolved in DMF (8 mL) followed by the addition of triethyl orthoacetate (3.47 g, 21.41 mmol, 3.92 mL, 27.85 eq) and acetic acid (55.40 mg, 922.50 μmol, 52.76 μL, 1.2 eq). Vial sealed and heated to 80° C. for 8 hr. Upon completion, the mixture was concentrated. The resulting residual triturated with sat. NaHCO$_3$ and the brown precipitate filtered. The aqueous layer was allowed to sit at 22° C. for 2 hr and light yellow solid began to form. The light yellow precipitate was filtered and dried yielding the product (48 mg, 27%).

Step 4. 7-methoxy-2,4-dimethyl-1H-imidazo[4,5-c][1,8] naphthyridine (44 mg, 192.77 µmol 1 eq) and 5-bromo-2-(bromomethyl)pyrimidine (58.27 mg, 231.33 µmol, 1.2 eq) were dissolved in DMF (1 mL). The vial sealed and heated to 50° C. for 4 hr. Additional 5-bromo-2-(bromomethyl) pyrimidine (58.27 mg, 231.33 umol, 1.2 eq) was added and heated to 50° C. for 2 hr. Additional 5-bromo-2-(bromomethyl)pyrimidine (58.27 mg, 231.33 µmol, 1.2 eq) was added and stirred at 50° C. for 2 hr. Upon completion, the mixture added 3 drops of TFA. The mixture was purified by Biotage C18 Duo 12 g column using water/MeCN (0.1% TFA) gradient. The product fractions combined and basified with sat. NaHCO$_3$. The aqueous layer extracted with EtOAc (3×5 mL). The combined organic layer dried over Na$_2$SO$_4$ and concentrated yielding the product (33 mg, 43%).

Step 5. 1-((5-bromopyrimidin-2-yl)methyl)-7-methoxy-2,4-dimethyl-imidazo[4,5-c][1,8]naphthyridine (33 mg, 82.66 µmol, 1 eq), Pd(dba)$_2$ (4.75 mg, 8.27 µmol, 0.1 eq), Xantphos (4.78 mg, 8.27 µmol, 0.1 eq), and DIEA (32.05 mg, 247.97 µmol, 43.19 µL, 3 eq) were dissolved in dioxane (0.8 mL). The mixture purged with nitrogen for 20 sec and sealed. Heated to 80° C. for 30 sec then cooled to 22° C. Benzyl mercaptan (11.29 mg, 90.92 µmol, 10.65 µL, 1.1 eq) added to the mixture and mixture purged with nitrogen for 20 sec. The vial sealed and heated to 80° C. for 1 hr. Upon completion, the mixture was diluted with water and extracted with EtOAc (3×5 mL). The combined organic layer dried over Na$_2$SO$_4$ and concentrated. The crude was purified through FCC using Biotage Sfar 5 g silica column using DCM/MeOH (100%/0% to 80%/20%) gradient yielding the product (21.3 mg, 58%).

Step 6. 1-((5-benzylsulfanylpyrimidin-2-yl)methyl)-7-methoxy-2,4-dimethyl-imidazo[4,5-c][1,8]naphthyridine (21.3 mg, 48.13 µmol, 1 eq) dissolved in MeCN (0.5 mL) followed by the addition of H$_2$O (12.14 mg, 673.85 µmol, 12.14 µL, 14 eq) and AcOH (20.23 mg, 336.92 µmol, 19.27 µL, 7 eq) then cooled to 0° C. 1,3-dichloro-5,5-dimethyl-imidazolidine-2,4-dione (13.28 mg, 67.38 µmol, 1.4 eq) was added and stirred at 0° C. for 1 hr. Additional 1,3-dichloro-5,5-dimethyl-imidazolidine-2,4-dione (13.28 mg, 67.38 µmol, 1.4 eq) added and stirred at 0° C. for 10 min. The mixture was added to NH$_4$OH (0.5 mL) at 0° C. and stirred for 10 min. The resulting mixture pH was adjusted to 8 using 2 M HCl. The mixture was concentrated. The crude was purified through Prep HPLC using water/MeCN (0.1% TFA) gradient yielding 91a (3.3 mg, 13%). LCMS [M+H]$^+$=400; 91b, LCMS [M+H]$^+$=434; $^1$H NMR (400 MHz, DMSO-d6) δ ppm 2.78 (s, 3H) 3.39 (br s, 3H) 3.70 (s, 3H) 5.77 (s, 2H) 6.59 (br s, 2H) 7.53 (d, J=9.00 Hz, 1H) 7.78 (s, 2H).

Compounds 92-93 were prepared in a similar manner as the preparation of compound 94.

Example 83

4-((2-((Dimethylamino)methyl)-7-methoxy-4-methyl-1H-imidazo[4,5-c][1,8]naphthyridin-1-yl)methyl)-2,5-difluorobenzenesulfonamide (92) was prepared in 23.1 mg. LCMS [M+H]$^+$=477; $^1$H NMR (300 MHz, DMSO-d6) δ ppm 2.93 (br s, 6H) 3.03-3.05 (m, 3H) 4.04 (s, 3H) 4.81 (br s, 2H) 6.10 (s, 2H) 6.85 (dd, J=9.67, 5.57 Hz, 1H) 7.20 (d, J=9.38 Hz, 1H) 7.67 (dd, J=9.38, 5.86 Hz, 1H) 7.82 (s, 2H) 8.39 (d, J=9.38 Hz, 1H).

Example 84

2,5-Difluoro-4-((7-methoxy-2-(2-methoxyethyl)-4-methyl-1H-imidazo[4,5-c][1,8]naphthyridin-1-yl)methyl) benzenesulfonamide (93) was prepared in 18.8 mg. LCMS [M+H]$^+$=478; $^1$H NMR (300 MHz, DMSO-d6) δ ppm 3.06 (s, 3H) 3.14 (s, 3H) 3.76-3.80 (m, 2H) 4.08 (s, 3H) 6.13 (s, 2H) 6.72-6.84 (m, 1H) 7.28 (d, J=9.38 Hz, 1H) 7.62-7.72 (m, 1H) 7.80 (s, 2H) 8.51 (d, J=8.79 Hz, 1H).

Example 85

2,5-Difluoro-4-((2-(hydroxymethyl)-7-methoxy-4-methyl-1H-imidazo[4,5-c][1,8]naphthyridin-1-yl) methyl)benzenesulfonamide (94)

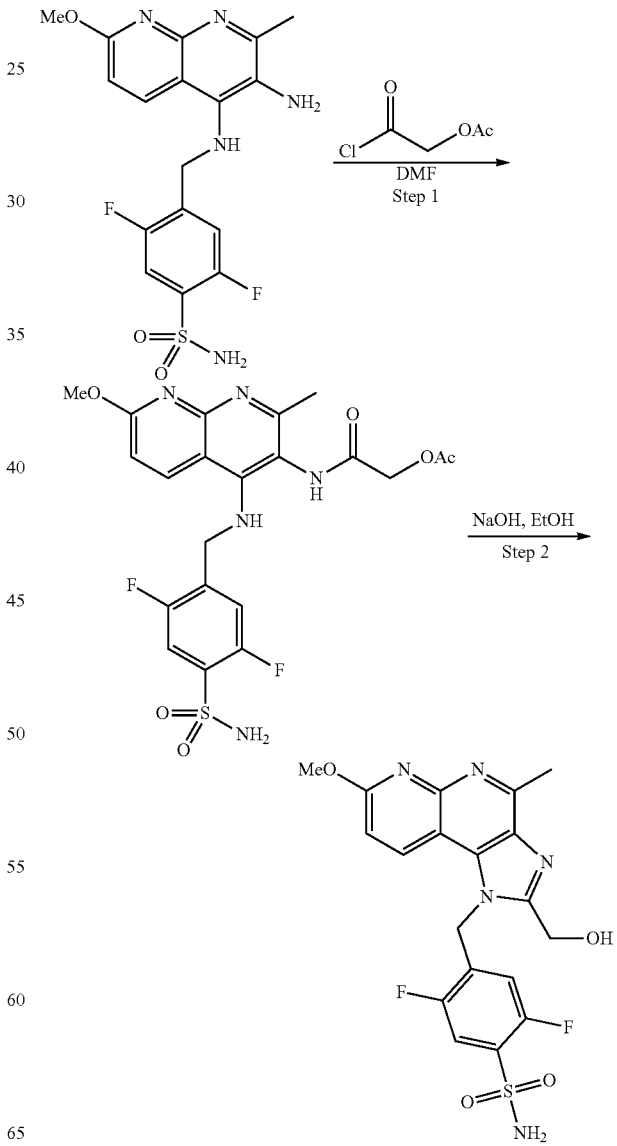

Step 1. 4-[[(3-amino-7-methoxy-2-methyl-1,8-naphthyridin-4-yl)amino]methyl]-2,5-difluoro-benzenesulfonamide (25 mg, 61.06 μcool, 1 eq) dissolved in DMF (0.6 mL) then cooled to 0° C. followed by the addition of (2-chloro-2-oxo-ethyl) acetate (8.34 mg, 61.06 μmol, 6.56 μL, 1 eq). Mixture stirred at 0° C. for 1 hr. Upon completion, mixture quenched with water at 0° C. and sat. NaHCO$_3$ added. The aqueous layer extracted with EtOAc (3×2 mL). The combined organic layer dried over Na$_2$SO$_4$ and concentrated yielding the product. The crude product was used in the next step without further purification.

Step 2. (2-((4-((2,5-difluoro-4-sulfamoyl-phenyl)methyl-amino)-7-methoxy-2-methyl-1,8-naphthyridin-3-yl)amino)-2-oxo-ethyl) acetate (31 mg, 60.85 μmol, 1 eq) dissolved in EtOH (1.2 mL) followed by the addition of NaOH (2 M, 45.63 μL, 1.5 eq). Vial sealed and heated to 60° C. for 1.5 hr. Upon completion, the mixture cooled to 22° C. and neutralized with 2 M HCl (46 μL). The mixture concentrated. The crude was purified by Prep HPLC using water/MeCN (0.1% TFA) gradient yielding the product (19.5 mg, 57%). LCMS [M+H]$^+$=450; $^1$H NMR (300 MHz, DMSO-d6) δ ppm 3.06-3.07 (m, 3H) 4.08 (s, 3H) 4.88 (s, 2H) 6.16 (s, 2H) 6.69 (dd, J=9.96, 5.86 Hz, 1H) 7.28 (d, J=8.79 Hz, 1H) 7.66 (dd, J=9.08, 5.57 Hz, 1H) 7.79 (s, 2H) 8.44 (d, J=9.38 Hz, 1H).

The following compounds were prepared according to the synthesis of compound 38.

Example 86

2,3-Difluoro-4-((7-methoxy-2-oxo-2,3-dihydro-1H-imidazo[4,5-c][1,8]naphthyridin-1-yl)methyl)-benzenesulfonamide (95) was prepared in 16.1 mg. LCMS [M+H]$^+$=422.

Example 87

5-((7-Methoxy-2-oxo-2,3-dihydro-1H-imidazo[4,5-c][1,8]naphthyridin-1-yl)methyl)pyridine-2-sulfonamide (96) was prepared in 0.8 mg. LCMS [M+H]$^+$=387. $^1$H NMR (400 MHz, DMSO-d6) δ ppm 3.93 (s, 3H) 5.54 (s, 2H) 6.99 (d, J=9.00 Hz, 1H) 7.11-7.21 (m, 2H) 7.60 (dd, J=9.39, 5.48 Hz, 1H) 7.78 (s, 2H) 8.19 (d, J=9.00 Hz, 1H) 8.63 (s, 1H) 11.72 (s, 1H).

Example 88

2-Fluoro-4-((7-methoxy-2-oxo-2,3-dihydro-1H-imidazo[4,5-c][1,8]naphthyridin-1-yl)methyl)-benzenesulfonamide (98) was prepared in 34.5 mg. LCMS [M+H]$^+$=404. $^1$H NMR (400 MHz, DMSO-d6) δ ppm 3.88-3.94 (m, 3H) 5.54 (s, 2H) 6.95 (d, J=9.00 Hz, 1H) 7.08 (dd, J=8.02, 1.37 Hz, 1H) 7.34 (d, J=11.04 Hz, 1H) 7.61 (s, 2H) 7.68 (t, J=8.02 Hz, 1H) 8.14 (d, J=9.39 Hz, 1H) 8.63 (s, 1H) 11.73 (br s, 1H).

Example 89

6-((7-Methoxy-2-oxo-2,3-dihydro-1H-imidazo[4,5-c][1,8]naphthyridin-1-yl)methyl)pyridine-3-sulfonamide (99) was prepared in 26 mg. LCMS [M+H]$^+$=387. $^1$H NMR (400 MHz, DMSO-d6) δ ppm 3.95 (s, 3H) 5.69 (s, 2H) 7.02 (d, J=9.39 Hz, 1H) 7.55 (s, 2H) 7.62 (d, J=8.22 Hz, 1H) 8.14 (dd, J=8.41, 2.15 Hz, 1H) 8.32 (d, J=9.00 Hz, 1H) 8.67 (s, 1H) 8.74 (d, J=2.35 Hz, 1H) 11.95 (br s, 1H).

Example 90

2,6-Difluoro-4-((7-methoxy-2-oxo-2,3-dihydro-1H-imidazo[4,5-c][1,8]naphthyridin-1-yl)methyl)-benzenesulfonamide (100) was prepared in 37.3 mg. LCMS [M+H]$^+$=422; $^1$H NMR (400 MHz, DMSO-d6) δ ppm 3.92 (s, 3H) 5.51 (s, 2H) 6.99 (d, J=9.00 Hz, 1H) 7.16-7.21 (m, 2H) 7.95 (s, 2H) 8.13 (d, J=9.00 Hz, 1H) 8.64 (s, 1H).

Example 91

(R)-4-(1-(7-Methoxy-2-oxo-2,3-dihydro-1H-imidazo[4,5-c][1,8]naphthyridin-1-yl)ethyl)benzene-sulfonamide (101) was prepared in 58 mg. LCMS [M+H]$^+$=400; $^1$H NMR (400 MHz, CHLOROFORM-d) δ ppm 1.84-1.87 (m, 3H) 3.87-3.88 (m, 3H) 6.19-6.25 (m, 1H) 6.56-6.69 (m, 1H) 7.07-7.15 (m, 1H) 7.16-7.23 (m, 1H) 7.43-7.45 (m, 2H) 7.74-7.77 (m, 2H) 8.43-8.51 (m, 1H).

Example 92

3-((7-Methoxy-2-oxo-2,3-dihydro-1H-imidazo[4,5-c][1,8]naphthyridin-1-yl)methyl)cyclobutyl sulfamate (97)

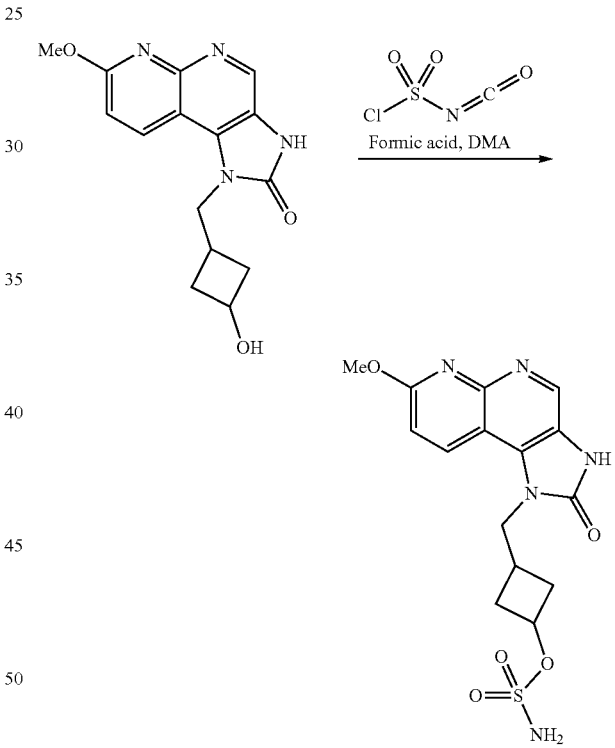

Formic acid (4.90 mg, 106.56 μmol, 4.02 μL, 2 eq) was added into chlorosulfonyl isocyanate (15.08 mg, 106.56 μmol, 9.25 μL, 2 eq) dropwise at 0° C. The resulting mixture was stirred for 18 hr to generate sulfamoyl chloride. To a mixture of 1-((3-hydroxycyclobutyl)methyl)-7-methoxy-1,3-dihydro-2H-imidazo[4,5-c][1,8]-naphthyridin-2-one (16 mg, 0.053 mmol, 1 eq, obtained from following the preparation of compound 38) in DMA (0.5 mL) was added sulfamoyl chloride dropwise at 0° C. The reaction mixture was slowly warmed to 22° C. and stirred for 3 hr. Upon completion, the solution was subjected to Prep HPLC using water/MeCN (0.1% TFA) yielding the product (1.9 mg, 9%). LCMS [M+H]$^+$=380.

Example 93

3-Fluoro-4-((7-methoxy-2-oxo-2,3-dihydro-1H-imidazo[4,5-c][1,8]naphthyridin-1-yl)methyl)-benzenesulfonamide (102) was prepared in 32.7 mg. LCMS [M+H]+=404.

Example 94

3,5-Difluoro-4-((7-methoxy-2-oxo-2,3-dihydro-1H-imidazo[4,5-c][1,8]naphthyridin-1-yl)methyl)benzenesulfonamide (103) was prepared in 8.4 mg. LCMS [M+H]+=422; $^1$H NMR (400 MHz, DMSO-d6) δ ppm 3.93 (s, 3H) 5.58 (s, 2H) 6.99 (d, J=9.00 Hz, 1H) 7.43 (d, J=6.95 Hz, 2H) 8.54-8.57 (m, 2H).

Example 95

2,3,5-Trifluoro-4-((7-methoxy-2-oxo-2,3-dihydro-1H-imidazo[4,5-c][1,8]naphthyridin-1-yl)methyl)-benzenesulfonamide (112) was prepared in 21.9 mg. LCMS [M+H]+=440; $^1$H NMR (300 MHz, DMSO-d6) δ ppm 4.06 (s, 3H) 5.70 (s, 2H) 7.23-7.31 (m, 1H) 7.39-7.50 (m, 1H) 8.01 (s, 2H) 8.67-8.77 (m, 1H) 8.82-8.87 (m, 1H).

Example 96

3,5-Difluoro-4-((7-methoxy-4-methyl-2-oxo-2,3-dihydro-1H-imidazo[4,5-c][1,8]naphthyridin-1-yl)methyl)benzenesulfonamide (113) was prepared in 12.4 mg. LCMS [M+H]+=436; $^1$H NMR (300 MHz, DMSO-d6) δ ppm 2.61 (s, 3H) 3.91-3.98 (m, 3H) 5.56-5.68 (m, 2H) 6.92-7.08 (m, 1H) 7.43-7.56 (m, 2H) 7.56-7.64 (m, 2H) 8.47-8.62 (m, 1H).

Example 97

Sodium acetyl((3,5-difluoro-4-((7-methoxy-2-oxo-2,3-dihydro-1H-imidazo[4,5-c][1,8]naphthyridin-1-yl)methyl)phenyl)sulfonyl)amide (104)

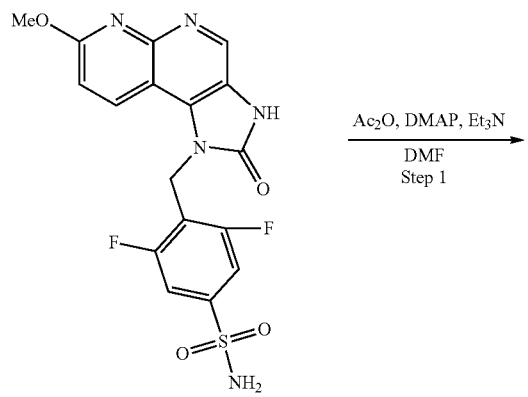

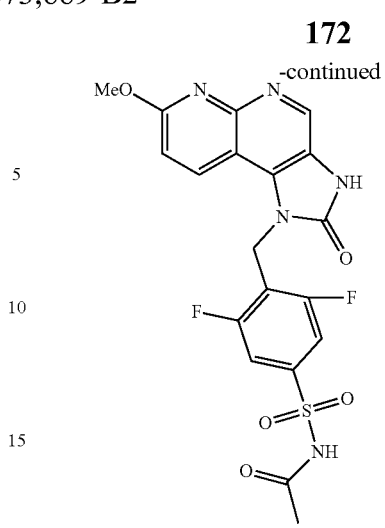

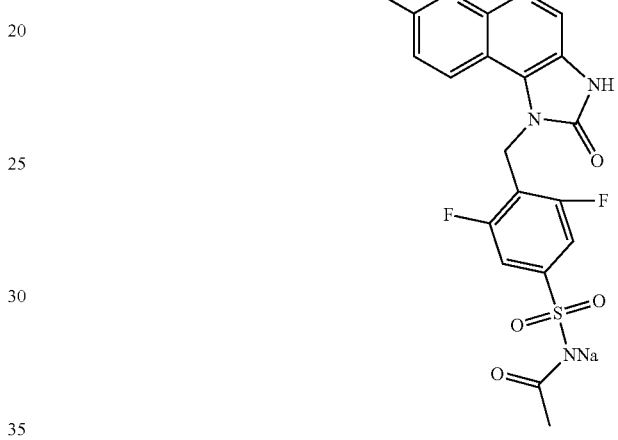

Step 1. 3,5-difluoro-4-((7-methoxy-2-oxo-3H-imidazo[4,5-c][1,8]naphthyridin-1-yl)methyl)benzenesulfonamide (50 mg, 118.66 μmol, 1 eq) dissolved in DMF (0.6 mL) followed by the addition of Et$_3$N (30.02 mg, 296.65 μmol, 41.29 μL, 2.5 eq), DMAP (1.45 mg, 11.87 μmol, 0.1 eq), and acetic anhydride (30.28 mg, 296.65 μmol, 27.78 μL, 2.5 eq). The mixture stirred at 22° C. for 1 hr. The mixture was concentrated and dissolved in MeOH. 2 M NaOH (5 eq) was added and stirred for 5 min. The pH of the mixture adjusted to 4 using 2 M HCl. The resulting precipitate was filtered. The crude was purified through Prep HPLC using water/MeCN (0.1% TFA) gradient. The product fractions combined and pH adjusted to 4 then extracted with EtOH/CHCl$_3$ (3:1). The combined organic layers concentrated yielding the product (31 mg, 56%).

Step 2. N-(3,5-difluoro-4-((7-methoxy-2-oxo-3H-imidazo[4,5-c][1,8]naphthyridin-1-yl)methyl)phenyl)sulfonylacetamide (30 mg, 64.74 μmol, 1 eq) suspended in MeOH (1 mL) followed by the addition of NaOH (0.2 M, 323.68 μL, 1 eq). The mixture became homogenous and stirred at 22° C. for 5 min. Upon completion, the mixture was concentrated yielding the product (30.6 mg, 97%). LCMS [M+H]+=464; LCMS [M+H]+=422; $^1$H NMR (300 MHz, DMSO-d6) δ ppm 1.62-1.67 (m, 3H) 3.96 (s, 3H) 5.56 (s, 2H) 6.97-7.09 (m, 1H) 7.32 (d, J=8.21 Hz, 2H) 8.56-8.62 (m, 2H) 11.51-11.62 (m, 1H).

Example 98

Sodium ((3,5-difluoro-4-((7-methoxy-2-oxo-2,3-dihydro-1H-imidazo[4,5-c][1,8]naphthyridin-1-yl)methyl)phenyl)

sulfonyl)(propionyl)amide (105) was prepared in 16.6 mg following the procedure for the synthesis of compound 104. LCMS [M+H]⁺=478; ¹H NMR (300 MHz, DMSO-d6) δ ppm 0.80 (t, J=7.62 Hz, 3H) 1.88 (q, J=7.62 Hz, 2H) 3.95 (s, 3H) 5.54 (s, 2H) 6.95-7.07 (m, 1H) 7.28 (d, J=8.21 Hz, 2H) 8.53-8.60 (m, 2H).

Example 99

Sodium butyryl((3,5-difluoro-4-((7-methoxy-2-oxo-2,3-dihydro-1H-imidazo[4,5-c][1,8]naph-thyridin-1-yl)methyl)phenyl)sulfonyl)amide (106) was prepared in 25.6 mg following the procedure for the synthesis of compound 104. LCMS [M+H]⁺=492; ¹H NMR (300 MHz, DMSO-d6) δ ppm 0.70 (t, J=7.33 Hz, 3H) 1.25-1.39 (m, 2H) 1.81-1.87 (m, 2H) 3.94 (s, 3H) 5.53 (s, 2H) 6.92-7.02 (m, 1H) 7.25-7.30 (m, 2H) 8.49-8.56 (m, 2H).

Example 100

3,5-Difluoro-4-((7-methoxy-2-oxo-2,3-dihydro-1H-imidazo[4,5-c][1,8]naphthyridin-1-yl)methyl)-N-methylbenzenesulfonamide (107) was prepared in 2 mg following the preparation of compound 38. LCMS [M+H]⁺=436; ¹H NMR (300 MHz, DMSO-d6) δ ppm 2.76 (s, 3H) 3.75-3.81 (m, 3H) 6.48-6.58 (m, 2H) 7.43-7.50 (m, 1H) 7.72-7.81 (m, 2H) 8.77-8.86 (m, 1H) 9.02-9.09 (m, 2H).

Example 101

3,5-difluoro-4-((7-methoxy-2-oxo-2,3-dihydro-1H-imidazo[4,5-c][1,8]naphthyridin-1-yl)methyl)benzoic Acid (108)

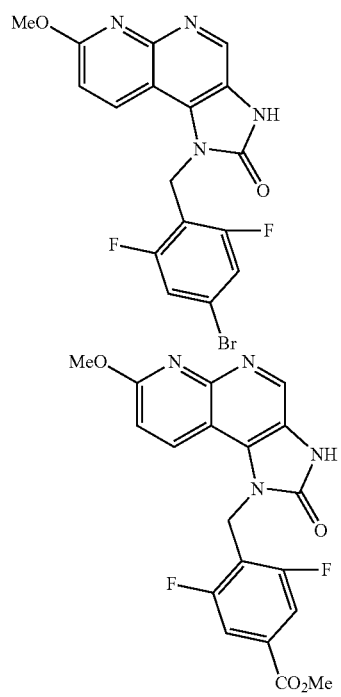

-continued

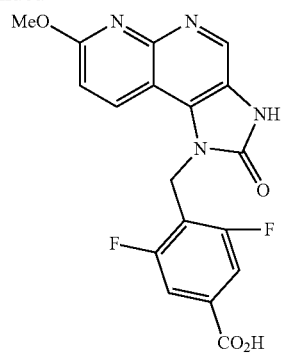

Step 1. To a mixture of 1-(4-bromo-2,6-difluorobenzyl)-7-methoxy-1,3-dihydro-2H-imidazo[4,5-c][1,8]naphthyridin-2-one (84 mg, 198 µmol, 1 eq) in MeOH (1 mL) was added Et₃N (60.23 mg, 595.23 µmol, 82.85 µL, 3 eq), and Pd(dppf)Cl₂ (14.52 mg, 19.84 µmol, 0.1 eq) in one portion at 22° C. The mixture was degassed by CO balloon and stirred at 65° C. for 1 hour. Upon completion, the mixture was concentrated. The crude was purified through FCC using Biotage C18 Duo 12 g column using water/MeCN (0.1% TFA) gradient yielding the product (62 mg, 78%). LCMS [M+H]⁺=401.

Step 2. To a mixture of methyl 3,5-difluoro-4-((7-methoxy-2-oxo-2,3-dihydro-1H-imidazo[4,5-c][1,8]naphthyridin-1-yl)methyl)benzoate (62 mg, 155 µmol, 1 eq) in THF/MeOH (2 mL) was added LiOH (1 M, 1.62 mL, 10 eq) in one portion at 22° C. The mixture was stirred at 55° C. for 1 hour. Upon completion, the mixture was concentrated. The crude was purified through FCC using Biotage C18 Duo 12 g column using water/MeCN (0.1% TFA) gradient yielding the compound 108 (2.4 mg, 4%). LCMS [M+H]⁺=387. ¹H NMR (300 MHz, DMSO-d6) δ ppm 4.04 (s, 3H) 5.69 (s, 2H) 7.24 (d, J=9.38 Hz, 1H) 7.51-7.58 (m, 2H) 8.71 (s, 1H) 8.77 (d, J=9.38 Hz, 1H) 12.15 (br s, 1H).

Example 102

3,5-Difluoro-4-((7-methoxy-2-oxo-2,3-dihydro-1H-imidazo[4,5-c][1,8]naphthyridin-1-yl)methyl)-benzamide (109)

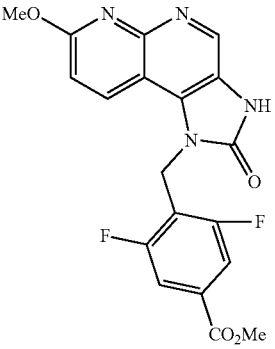 NH₃ in MeOH →

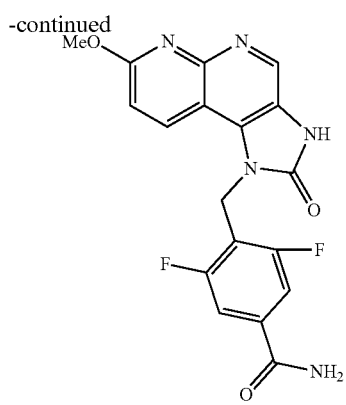

Methyl 3,5-difluoro-4-((7-methoxy-2-oxo-3H-imidazo[4,5-c][1,8]naphthyridin-1-yl)methyl)benzoate (50 mg, 124.90 μmol, 1 eq) dissolved in NH₃ in MeOH (2 M, 2.50 mL, 40 eq). Vial sealed and heated to 65° C. for 2 hr. Additional NH₃ in MeOH (2 M, 2.50 mL, 40 eq) was added and heated to 65° C. for 18 hr. Upon completion, the mixture was concentrated. The resulting precipitate was triturated with sat. NaHCO₃. The precipitate was filtered. The crude was purified through Prep HPLC using water/MeCN (0.1% TFA) gradient yielding the compound 109 (9.3 mg, 15%). LCMS [M+H]⁺=386; ¹H NMR (300 MHz, DMSO-d6) δ ppm 4.05 (s, 3H) 5.68 (s, 2H) 7.27 (d, J=9.38 Hz, 1H) 7.54 (d, J=8.79 Hz, 2H) 7.63 (br s, 1H) 8.07 (br s, 1H) 8.72 (s, 1H) 8.80 (d, J=9.38 Hz, 1H) 12.23 (br s, 1H).

Example 103

3,5-Difluoro-N-hydroxy-4-((7-methoxy-2-oxo-2,3-dihydro-1H-imidazo[4,5-c][1,8]naphthyridin-1-yl)methyl)benzamide (110)

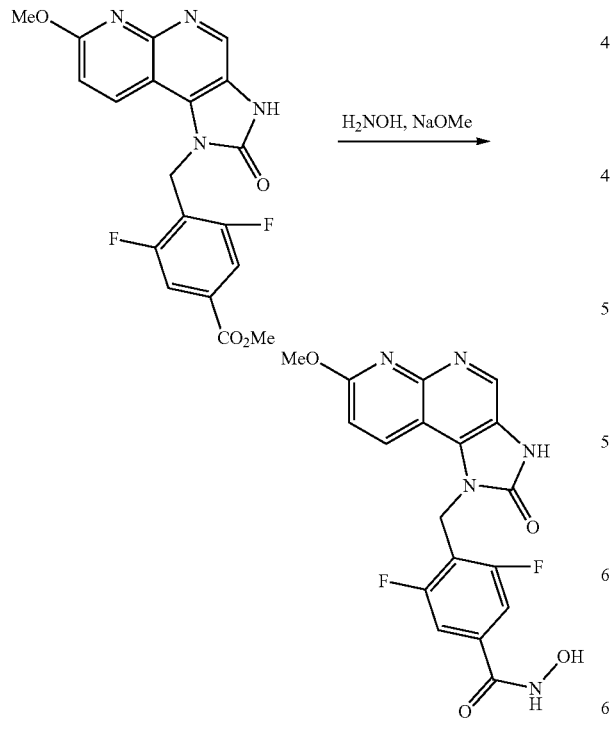

Methyl 3,5-difluoro-4-((7-methoxy-2-oxo-3H-imidazo[4,5-c][1,8]naphthyridin-1-yl)methyl)benzoate (50 mg, 124.90 μmol, 1 eq) dissolved in MeOH (2.5 mL) followed by the addition of hydroxylamine hydrochloride (86.79 mg, 1.25 mmol, 10 eq). The mixture was sonicated until hydroxylamine dissolved then cooled to 0° C. NaOMe (4.4 M, 369.01 μL, 13 eq) was added to the mixture in one portion. The mixture was allowed to stir at 22° for 2 hr. Upon completion, the mixture was stored at −20° C. for 18 hr. The mixture was filtered over a pad of celite and the filtrate concentrated. The crude was triturated with sat. NaHCO₃ and the resulting precipitate was filtered. The crude was purified through Prep HPLC using water/MeCN (0.1% TFA) gradient yielding compound 110 (29.4 mg, 46%). LCMS [M+H]⁺=402; ¹H NMR (300 MHz, DMSO-d6) δ ppm 4.04 (s, 3H) 5.66 (s, 2H) 7.22-7.26 (m, 1H) 7.43 (d, J=8.79 Hz, 2H) 8.71 (s, 1H) 8.77 (br d, J=8.79 Hz, 1H) 11.24-11.50 (m, 1H) 12.02-12.28 (m, 1H). LCMS [M+H]⁺=387.

Example 104

(3,5-difluoro-4-((7-methoxy-2-oxo-2,3-dihydro-1H-imidazo[4,5-c][1,8]naphthyridin-1-yl)methyl)phenyl)boronic Acid (111)

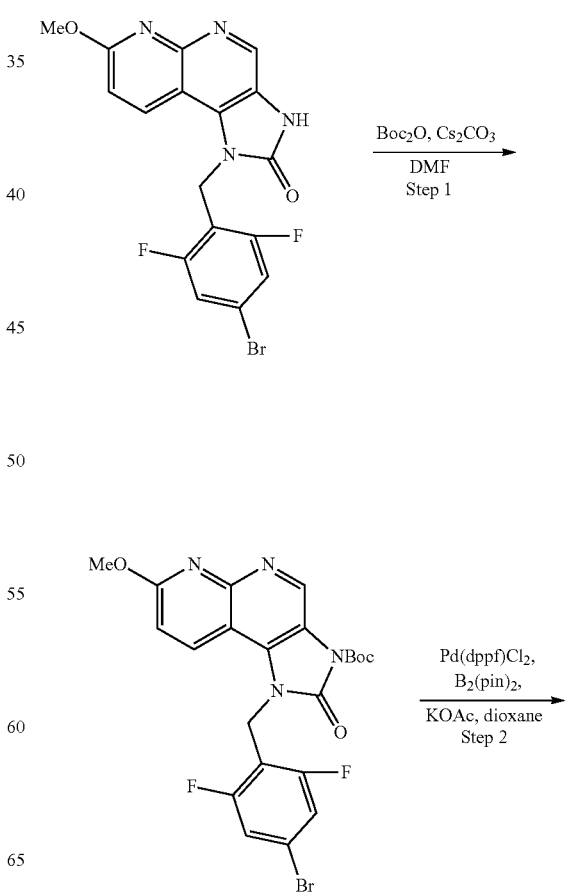

-continued

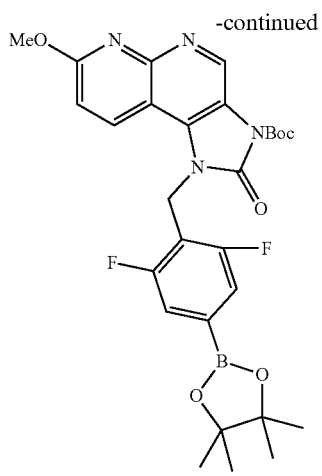

1. NaIO₄, acetone
2. TFA
Step 3

263.91 µmol, 14.62 µL, 3 eq) and NH₄OAc (20.34 mg, 263.91 µmol, 3 eq). The mixture stirred at 22° C. for 4 hr. Upon completion, the mixture was filtered through a pad of celite and concentrated. The residual was suspended in 1:1 DCM:TFA (2 mL) and stirred at 22° C. for 10 min. The mixture was concentrated. The crude was purified through Prep HPLC using water/MeCN (0.1% TFA) gradient yielding the compound 111 (23.6 mg, 54%). LCMS [M+H]⁺=387; ¹H NMR (300 MHz, DMSO-d6) δ ppm 4.04 (s, 3H) 5.65 (s, 2H) 7.25 (d, J=8.79 Hz, 1H) 7.35 (d, J=8.79 Hz, 2H) 8.41 (br s, 1H) 8.71-8.76 (m, 2H) 12.21 (br s, 1H).

Example 105

3,5-Difluoro-4-((7-methoxy-3-methyl-2-oxo-2,3-dihydro-1H-imidazo[4,5-c][1,8]naphthyridin-1-yl)methyl)benzenesulfonamide (114)

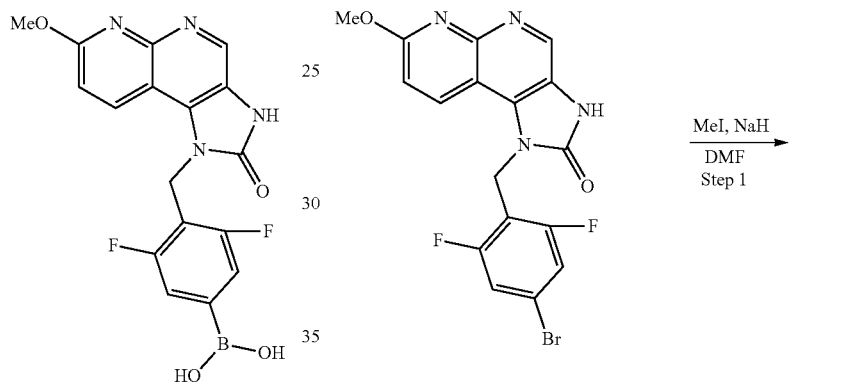

MeI, NaH
DMF
Step 1

Step 1. 1-((4-bromo-2,6-difluoro-phenyl)methyl)-7-methoxy-3H-imidazo[4,5-c][1,8]naphthyridin-2-one (400 mg, 949.68 µmol, 1 eq) dissolved in DMF (2.5 mL) followed by the addition of Boc₂O (298.46 mg, 1.37 mmol, 314.17 µL, 1.44 eq) and Cs₂CO₃ (464.13 mg, 1.42 mmol, 1.5 eq). The mixture stirred at 22° C. for 2 hr. Upon completion, the mixture was added to water and the resulting precipitate was filtered and dried yielding the product (463 mg, 94%).

Step 2. tert-butyl 1-((4-bromo-2,6-difluoro-phenyl)methyl)-7-methoxy-2-oxo-imidazo[4,5-c][1,8]naphthyridine-3-carboxylate (260 mg, 498.74 µmol, 1 eq), 4,4,5,5-tetramethyl-2-(4,4,5,5-tetramethyl-1,3,2-dioxaborolan-2-yl)-1,3,2-dioxaborolane (151.98 mg, 598.49 µmol, 1.2 eq), KOAc (146.84 mg, 1.50 mmol, 3 eq), and Pd(dppf)Cl₂ DCM complex (40.73 mg, 49.87 µmol, 0.1 eq) were suspended in dioxane (2.5 mL). The mixture purged with nitrogen for 30 sec and sealed. The mixture heated to 80° C. for 2 hr. Upon completion, the mixture cooled to 22° C. and diluted with water. The mixture was extracted with EtOAc (3×5 mL). The combined organic layer dried over Na₂SO₄ and concentrated. The crude was purified through FCC using Biotage Sfar 5 g silica column using DCM/MeOH (100%/0% to 80%/20%) gradient yielding the product (198 mg, 70%).

Step 3. tert-butyl 1-((2,6-difluoro-4-(4,4,5,5-tetramethyl-1,3,2-dioxaborolan-2-yl)phenyl)methyl)-7-methoxy-2-oxo-imidazo[4,5-c][1,8]naphthyridine-3-carboxylate (50 mg, 87.97 µmol, 1 eq) dissolved in acetone (1.35 mL) and H₂O (0.9 mL) followed by the addition of NaIO₄ (56.45 mg,

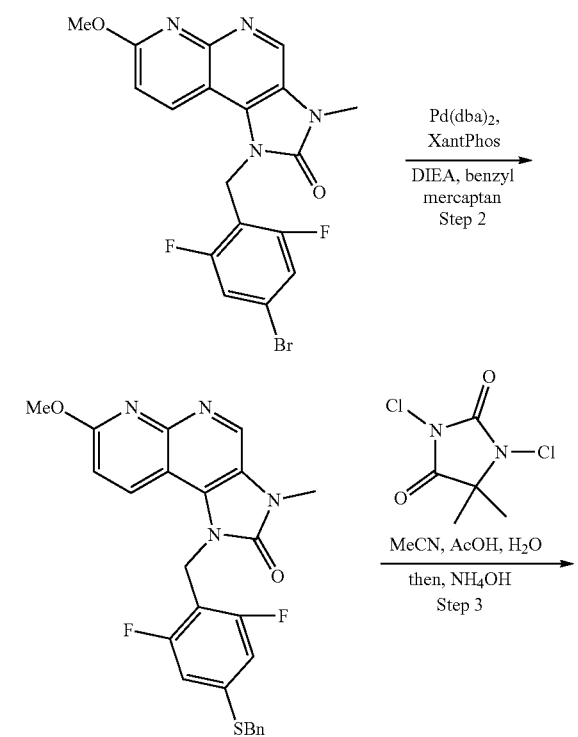

Pd(dba)₂, XantPhos
DIEA, benzyl mercaptan
Step 2

MeCN, AcOH, H₂O
then, NH₄OH
Step 3

-continued

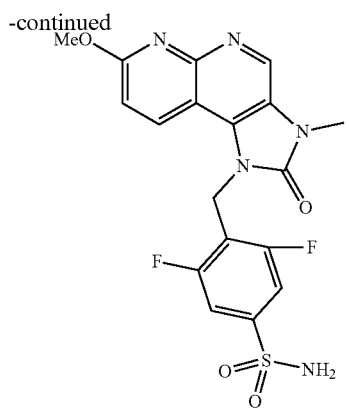

Step 1. To a mixture of 1-((4-bromo-2,6-difluoro-phenyl)methyl)-7-methoxy-3H-imidazo[4,5-c][1,8]naphthyridin-2-one (110 mg, 261.16 μmol, 1 eq) in DMF (2.5 mL) was added MeI (44.48 mg, 313.39 μmol, 19.51 μL, 1.2 eq), and NaH (12.54 mg, 313.39 μmol, 60% purity, 1.2 eq) in one portion at 0° C. The mixture was stirred at 0° C. for 1 hr. Upon completion, water (10 mL) was added into reaction mixture. The aqueous layer was extracted by EtOH/CHCl$_3$=1:3. The organic layer was dried over Na$_2$SO$_4$, and concentrated. The crude was purified by Biotage Sfar 10 g silica column using DCM/EtOAc yielding the product (28 mg, 25%).

Step 2. To a mixture of 1-((4-bromo-2,6-difluoro-phenyl)methyl)-7-methoxy-3-methyl-imidazo[4,5-c][1,8]naphthyridin-2-one (70 mg, 160.84 μmol, 1 eq) in DMF (2 mL) was added DIEA (74.83 mg, 579.02 μmol, 100.85 μL, 3.6 eq), XantPhos (9.31 mg, 16.08 μmol, 0.1 eq), and Pd(dba)$_2$ (9.25 mg, 16.08 μmol, 0.1 eq) in one portion at 22° C. under N$_2$. The mixture was stirred at 80° C. for 10 min. Benzyl mercaptan (23.97 mg, 193.01 μmol, 22.61 μL, 1.2 eq) was added into reaction and then heated to 80° C. for 2 hr. Upon completion, the mixture was concentrated. The crude was purified by Biotage Sfar 5 g silica column using DCM/MeOH yielding the product (60 mg, 78%).

Step 3. To a mixture of 1-((4-benzylsulfanyl-2,6-difluoro-phenyl)methyl)-7-methoxy-3-methyl-imidazo[4,5-c][1,8]naphthyridin-2-one (30 mg, 62.69 μmol, 1 eq) in THF (2 mL) and MeCN (1 mL) was added AcOH (26.35 mg, 438.86 μmol, 25.10 μL, 7 eq), and H$_2$O (15.82 mg, 877.72 μmol, 15.82 μL, 14 eq) in one portion at 0° C. 1,3-Dichloro-5,5-dimethylhydantoin (17.29 mg, 87.77 μmol, 1.4 eq) was then added into reaction mixture at 0° C. The mixture was stirred at 0° C. for 2 hr. NH$_4$OH (659.15 mg, 18.81 mmol, 724.34 μL, 300 eq) was cooled down to 0° C. The reaction mixture was added into NH$_4$OH (659.15 mg, 18.81 mmol, 724.34 μL, 300 eq) dropwise and stirred at 0° C. for 1 hr. Upon completion, the mixture was acidified to pH=1 and concentrated. The crude was purified by Biotage C18 Duo 12 g column using water/MeCN (0.1% TFA) yielding the product (28.6 mg, 83%). LCMS [M+H]$^+$=436; $^1$H NMR (300 MHz, DMSO-d6) δ ppm 3.51 (br s, 3H) 4.08 (s, 3H) 5.72 (s, 2H) 7.31 (d, J=9.38 Hz, 1H) 7.45-7.54 (m, 2H) 7.63 (s, 2H) 8.93 (d, J=9.38 Hz, 1H) 9.05 (s, 1H).

The following compounds were prepared according to the preparation of compound 114.

Example 106

3,5-Difluoro-4-((3-(2-hydroxyethyl)-7-methoxy-2-oxo-2,3-dihydro-1H-imidazo[4,5-c][1,8]naph-thyridin-1-yl)methyl)benzenesulfonamide (115) was prepared in 9.9 mg following the procedure for the synthesis of compound 114. LCMS [M+H]$^+$=466.

Example 107

3,5-Difluoro-4-((7-methoxy-2-oxo-3-(2,2,2-trifluoro-ethyl)-2,3-dihydro-1H-imidazo[4,5-c][1,8]naph-thyridin-1-yl)methyl)benzenesulfonamide (131) was prepared in 29.5 mg following the procedure for the synthesis of compound 114. LCMS [M+H]$^+$=504; $^1$H NMR (400 MHz, DMSO-d6) δ ppm 3.99 (s, 3H) 5.00 (d, J=9.00 Hz, 2H) 5.71 (s, 2H) 7.17-7.20 (m, 1H) 7.46 (d, J=7.43 Hz, 2H) 7.61 (s, 2H) 8.74 (d, J=9.00 Hz, 1H) 9.04 (s, 1H).

Example 108

3,5-Difluoro-4-((7-methoxy-3-(2-methoxyethyl)-2-oxo-2,3-dihydro-1H-imidazo[4,5-c][1,8]naph-thyridin-1-yl)methyl)benzenesulfonamide (132) was prepared in 30 mg following the procedure for the synthesis of compound 114. LCMS [M+H]$^+$=480; $^1$H NMR (400 MHz, CHLOROFORM-d) δ ppm 3.21-3.22 (m, 3H) 3.63-3.67 (m, 2H) 4.02-4.10 (m, 3H) 4.18-4.24 (m, 2H) 5.69-5.77 (m, 2H) 7.23-7.33 (m, 1H) 7.46-7.53 (m, 2H) 7.61-7.68 (m, 2H) 8.82-8.90 (m, 1H) 8.99-9.05 (m, 1H).

Example 109

3,5-Difluoro-4-((3-(3-hydroxypropyl)-7-methoxy-2-oxo-2,3-dihydro-1H-imidazo[4,5-c][1,8]naph-thyridin-1-yl)methyl)benzenesulfonamide (133) was prepared in 29.5 mg following the procedure for the synthesis of compound 114. LCMS [M+H]$^+$=480; $^1$H NMR (400 MHz, DMSO-d6) δ ppm 1.82 (t, J=6.85 Hz, 2H) 3.41-3.42 (m, 2H) 4.02-4.07 (m, 5H) 5.69-5.73 (m, 2H) 7.20-7.28 (m, 1H) 7.47 (d, J=7.43 Hz, 2H) 7.62 (s, 2H) 8.76-8.85 (m, 1H) 9.01 (s, 1H).

Example 110

3,5-difluoro-4-((7-methoxy-3-(oxetan-3-yl)-2-oxo-2,3-dihydro-1H-imidazo[4,5-c][1,8]naphthyridin-1-yl)methyl)benzenesulfonamide (139) was prepared in 6.6 mg following the procedure for the synthesis of compound 114. LCMS [M+H]$^+$=478.

Example 111

4-((7-Methoxy-1H-pyrazolo[4,3-c][1,8]naphthyridin-1-yl)methyl)benzenesulfonamide (116)

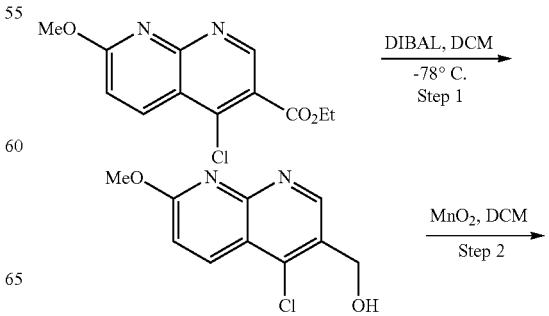

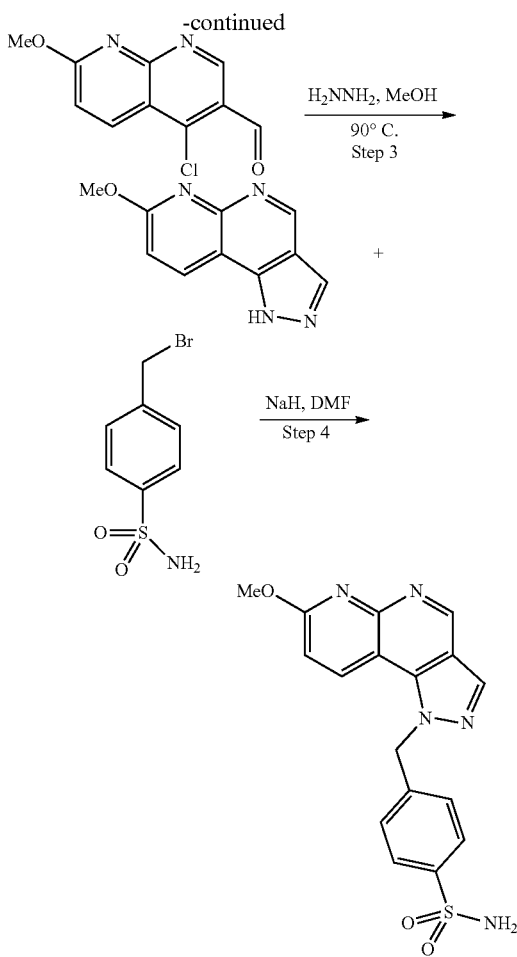

1.2 eq) and 4-(bromomethyl)benzenesulfonamide (30 mg, 0.12 mmol, 1.2 eq). The mixture was stirred at 22° C. for 3 hr then at 40° C. for 1 hr. The mixture was purified through Prep HPLC using water/MeCN (0.1% TFA) yielding the product (7.3 mg, 20%). LCMS [M+H]$^+$=370; $^1$H NMR (300 MHz, DMSO-d6) δ ppm 3.98 (s, 3H) 6.26 (s, 2H) 7.34 (s, 2H) 7.61 (d, J=8.79 Hz, 3H) 7.75-7.79 (m, 3H) 7.99-8.11 (m, 1H) 8.90 (d, J=8.79 Hz, 1H) 10.29 (s, 1H).

Example 112

2-Fluoro-4-((7-methoxy-1H-pyrazolo[4,3-c][1,8]naph-thyridin-1-yl)methyl)benzenesulfonamide (122a) and 2-fluoro-4-((7-methoxy-2H-pyrazolo[4,3-c][1,8]naphthyri-din-2-yl)methyl)benzenesulfonamide (122b): The two products were prepared in 66 mg and 10 mg respectively with 35% yield following the procedure for the synthesis of 4-((7-Methoxy-1H-pyrazolo[4,3-c][1,8]naphthyridin-1-yl)methyl)benzenesulfonamide. 122a: LCMS [M+H]$^+$=388; $^1$H NMR (300 MHz, DMSO-d6) δ ppm 4.06 (s, 3H) 5.93 (s, 2H) 7.29 (br d, J=8.79 Hz, 1H) 7.33 (br d, J=8.21 Hz, 1H) 7.43 (br d, J=11.14 Hz, 1H) 7.65 (s, 2H) 7.77-7.83 (m, 1H) 8.74 (d, J=8.79 Hz, 1H) 9.33 (s, 1H) 9.70 (s, 1H); 122b: LCMS [M+H]$^+$=388; $^1$H NMR (300 MHz, DMSO-d6) δ ppm 3.95 (s, 3H) 6.25 (s, 2H) 7.58 (d, J=8.79 Hz, 1H) 7.75 (t, J=7.91 Hz, 1H) 7.84-7.93 (m, 1H) 7.93-7.98 (m, 2H) 8.07-8.13 (m, 1H) 8.67-8.72 (m, 1H) 8.91 (d, J=8.79 Hz, 1H) 10.26 (s, 1H).

Example 113

6-((7-Methoxy-1H-pyrazolo[4,3-c][1,8]naphthyridin-1-yl)methyl)pyridine-3-sulfonamide (135a) and 6-((7-methoxy-2H-pyrazolo[4,3-c][1,8]naphthyridin-2-yl)methyl)pyridine-3-sulfonamide (135b): Products were prepared in 4.8 mg and 2.6 mg respectively following the procedure for the synthesis of 4-((7-Methoxy-1H-pyrazolo[4,3-c][1,8]naphthyridin-1-yl)methyl)benzenesulfonamide. 135a: LCMS [M+H]$^+$=371; 135b: LCMS [M+H]$^+$=371.

Step 1. Ethyl 4-chloro-7-methoxy-1,8-naphthyridine-3-carboxylate (276 mg, 1.03 mmol, 1 eq) was dissolved in DCM (10 mL, 0.1 M) then cooled to −78° C. 1 M DIBAL in cyclohexane (2.4 mL, 2.4 mmol, 2.4 eq) was added to the mixture. Upon completion, the mixture was warmed to 0° C. and quenched with sat. NH$_4$Cl. The aqueous layer was extracted with EtOAc (3×20 mL). The combined organic layer was dried over Na$_2$SO$_4$ and concentrated. The product was used in the next step without further purification.

Step 2. (4-Chloro-7-methoxy-1,8-naphthyridin-3-yl)methanol from the previous step was dissolved in DCM (10 mL) followed by the addition of MnO$_2$ (870 mg, 10 mmol, 10 eq). The mixture was stirred at 22° C. for 2 hr. Upon completion, the mixture was filtered over a pad of celite and the filtrate concentrated yielding the product (132 mg, 59% over 2 steps).

Step 3. 4-Chloro-7-methoxy-1,8-naphthyridine-3-carbaldehyde (122 mg, 0.55 mmol, 1 eq) was dissolved in MeOH (11 mL, 0.05 M) followed by the addition of hydrazine monohydrate (32 μL, 0.66 mmol, 1.2 eq). The vial was sealed and heated to 90° C. for 24 hr. Upon completion, the mixture was cooled to 22° C. and concentrated. The crude was dissolved in EtOAc and washed with sat. NaHCO$_3$. The aqueous layer was back extracted with EtOAc (2×20 mL). The combined organic layer was dried over Na$_2$SO$_4$ and concentrated yielding the product (100 mg, 91%).

Step 4. 7-Methoxy-1H-pyrazolo[4,3-c][1,8]naphthyridine (20 mg, 0.1 mmol, 1 eq) was dissolved in DMF (1 mL, 0.1 M) followed by the addition of 60% NaH (5 mg, 0.12 mmol, Example 114

4-((7-Methoxy-1H-pyrrolo[3,2-c][1,8]naphthyridin-1-yl)methyl)benzenesulfonamide (117)

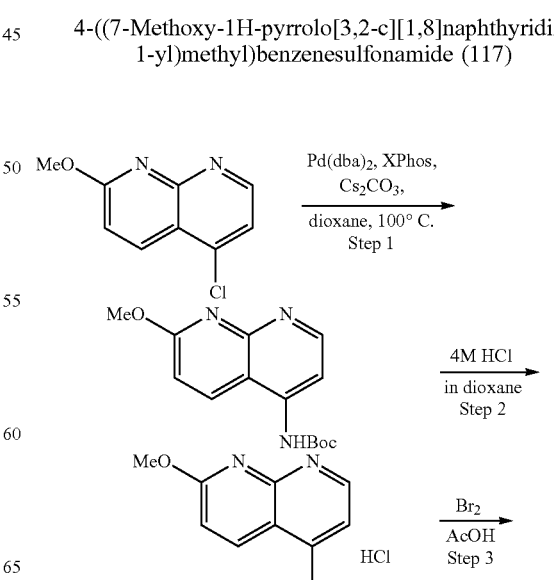

183

-continued

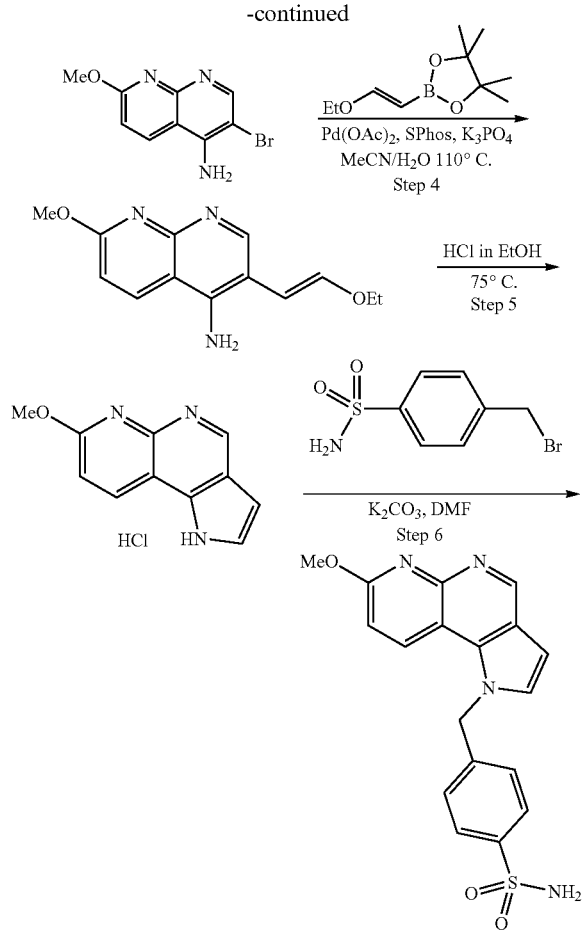

were dissolved in 4:1 MeCN/H$_2$O (10 mL, 0.18 M). The mixture was purged with nitrogen for 1 min then heated to 110° C. Upon completion, the mixture was cooled to 22° C. and poured into sat. NH$_4$Cl. The aqueous layer was extracted with EtOAc (3×30 mL). The combined organic layer dried over Na$_2$SO$_4$ and concentrated. The crude was purified through FCC using DCM/MeOH yielding the product (280 mg, 64%).

Step 5. (E)-3-(2-Ethoxyvinyl)-7-methoxy-1,8-naph-thyridin-4-amine (280 mg, 1.14 mmol, 1 eq) was dissolved in 1.25 M HCl in EtOH (14 mL). The mixture was heated to 75° C. Upon completion, the mixture was cooled to 22° C. and concentrated yielding the product (259 mg, 97%).

Step 6. 7-Methoxy-1H-pyrrolo[3,2-c][1,8]naphthyridine HCl (50 mg, 0.212 mmol, 1 eq) was dissolved in DMF (3 mL) followed by the addition of 4-(bromomethyl)benzenesulfonamide (64 mg, 0.255 mmol, 1.2 eq) and K$_2$CO$_3$ (88 mg, 0.64 mmol, 3 eq). The mixture was heated to 60° C. Upon completion, the mixture was cooled to 22° C. and concentrated. The crude was purified through Prep HPLC using water/MeCN (0.1% TFA) yielding the product (22.7 mg, 22%). LCMS [M+H]$^+$=369; $^1$H NMR (600 MHz, DMSO-d6) δ ppm 3.99 (s, 3H) 6.08 (s, 2H) 6.93-6.97 (m, 1H) 7.21 (br d, J=9.35 Hz, 2H) 7.59 (s, 2H) 7.65 (t, J=7.89 Hz, 1H) 8.43 (d, J=9.17 Hz, 1H) 8.75 (s, 1H) 9.52 (s, 1H).

Example 115

2-fluoro-4-((7-methoxy-1H-pyrazolo[4,3-c]cinnolin-1-yl)methyl)benzenesulfonamide (118)

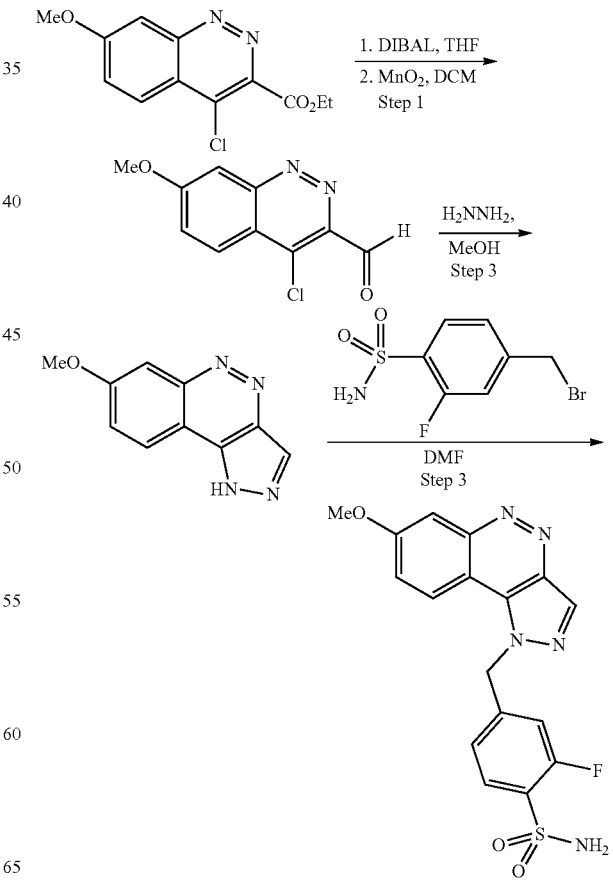

Step 1. 5-chloro-2-methoxy-1,8-naphthyridine (527 mg, 2.7 mmol, 1 eq), tert-butyl carbamate (380 mg, 3.25 mmol, 1.2 eq), Pd(dba)$_2$ (78 mg, 0.135 mmol, 0.05 eq), XPhos (129 mg, 0.27 mmol, 0.1 eq), and Cs$_2$CO$_3$ (1.76 g, 5.4 mmol. 2 eq) were suspended in dioxane (14 mL, 0.2 M). The mixture was purged with nitrogen for 1 min then heated to 100° C. for 5 hr under nitrogen atmosphere. Upon completion, the mixture was cooled to 22° C. and poured into water. The resulting precipitate was filtered and dried. The crude product was used in the next step without further purification.

Step 2. (7-methoxy-1,8-naphthyridin-4-yl)carbamate from previous step was suspending in DCM (5.4 mL, 0.5M) then cooled to 0° C. followed by the addition of 4 M HCl in dioxane (2.7 mL). The mixture was stirred at 22° C. until all starting material was consumed. Upon completion, the mixture was concentrated yielding the product. The product was used in the next step without further purification.

Step 3. 7-Methoxy-1,8-naphthyridin-4-amine HCl was dissolved in AcOH (14 mL, 0.2 M) then cooled to 0° C. Bromine (153 μL, 2.97 mmol, 1.1 eq) was added to the mixture. The mixture was stirred at 22° C. until no more starting material was observed on LCMS. Upon completion, the mixture was poured into water. The resulting precipitate was filtered and dried yielding the product (459 mg, 67% over 3 steps).

Step 4. 3-Bromo-7-methoxy-1,8-naphthyridin-4-amine (455 mg, 1.79 mmol, 1 eq), (E)-2-(2-ethoxyvinyl)-4,4,5,5-tetramethyl-1,3,2-dioxaborolane (709 mg, 3.58 mmol, 2 eq), Pd(OAc)$_2$ (12 mg, 0.05 mmol, 0.03 eq), SPhos (55 mg, 0.133, 0.075 eq), and K$_3$PO$_4$ (760 mg, 3.58 mmol, 2 eq)

Step 1. To a mixture of ethyl 4-chloro-7-methoxy-cinnoline-3-carboxylate (300 mg, 1.12 mmol, 1 eq) in THF (10 mL) was added DIBAL (1 M, 3.37 mL, 3 eq) dropwise at −78° C. The mixture was stirred at −78° C. for 3 hours. Upon completion, sat. NaHCO₃, potassium sodium tartrate, EtOAc were added into reaction mixture at −78° C. and stirred at 22° C. for 18 hr. The aqueous layer was extracted by EtOAc (3×20 mL). The organic layer was combined and dried over Na₂SO₄ and concentrated. The crude residual was dissolved in DCM (10 mL). MnO₂ (978.03 mg, 11.25 mmol, 10 eq) was added into reaction mixture at 22° C. The reaction was stirred at 22° C. for 3 hours. Upon completion, the reaction was filtered through a pad of celite and concentrated. The crude was purified by FCC yielding the product (156 mg, 63%).

Step 2. To a mixture of 4-chloro-7-methoxy-cinnoline-3-carbaldehyde (156 mg, 700.72 μmol, 1 eq) in MeOH (15 mL) was added hydrazine (40.42 mg, 1.26 mmol, 45.63 μL, 1.8 eq) in one portion at 22° C. The mixture was stirred at 65° C. for 18 hr. Upon completion, the mixture was concentrated. The crude was purified by FCC yielding the product (87 mg, 62%).

Step 3. To a mixture of 7-methoxy-1H-pyrazolo[4,3-c]cinnoline (35 mg, 174.83 μmol, 1 eq) in DMF (1 mL) was added NaH (8.39 mg, 209.79 μmol, 60% purity, 1.2 eq) in one portion at 22° C. The mixture was stirred at 22° C. for 5 mins. 4-(bromomethyl)-2-fluoro-benzenesulfonamide (56.25 μg, 0.21 μmol, 1.20e-3 eq) was added into reaction mixture, and stirred for 2 hours. Upon completion, the reaction was quenched by 1N HCl (2 mL). Solid crashed out from solution. The precipitate filtered. The filtrate was purified by Prep HPLC using water/MeCN (0.1% TFA) gradient yielding the product (3.8 mg, 5.6%). LCMS [M+H]⁺=388; ¹H NMR (300 MHz, DMSO-d6) δ ppm 3.96 (s, 3H) 6.25 (s, 2H) 7.41-7.53 (m, 2H) 7.58 (br d, J=7.62 Hz, 1H) 7.63 (s, 2H) 7.75 (br t, J=7.91 Hz, 1H) 7.93 (br s, 1H) 8.91 (d, J=8.79 Hz, 1H) 10.25 (s, 1H).

Example 116

6-((7-Methoxy-1H-[1,2,3]triazolo[4,5-c][1,8]naphthyridin-1-yl)methyl)pyridine-3-sulfonamide (119)

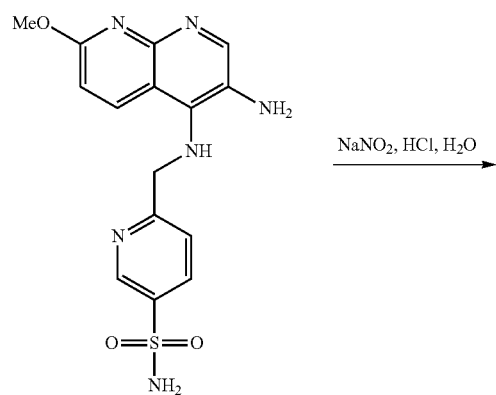

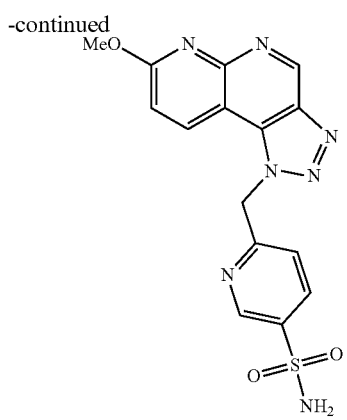

NaNO₂ (4.82 mg, 69.92 μmol, 1.2 eq) was dissolved in water (0.1 mL). To a mixture of 6-(((3-amino-7-methoxy-1,8-naphthyridin-4-yl)amino)methyl)pyridine-3-sulfonamide (21 mg, 58.27 μmol, 1 eq) in HCl (2 M, 291.35 μL, 10 eq) was added NaNO₂ (4.82 mg, 69.92 μmol, 1.2 eq) solution in one portion at 0° C. The mixture was stirred at 0° C. for 30 min. Upon completion, the solution was subjected to Prep HPLC using water/MeCN (0.1% TFA) yielding the product (6.2 mg, 29%). LCMS [M+H]⁺=372; ¹H NMR (300 MHz, DMSO-d6) δ ppm 4.02 (s, 3H) 6.60 (s, 2H) 7.19 (d, J=8.79 Hz, 1H) 7.53 (s, 2H) 7.64 (d, J=8.21 Hz, 1H) 8.19 (dd, J=8.21, 2.34 Hz, 1H) 8.61 (d, J=8.79 Hz, 1H) 8.71 (d, J=2.34 Hz, 1H) 9.66 (s, 1H).

Example 117

2-Fluoro-4-((7-methoxy-1H-[1,2,3]triazolo[4,5-c][1,8]naphthyridin-1-yl)methyl)benzenesulfonamide (120) was prepared in 3.9 mg following the synthesis of compound 119. LCMS [M+H]⁺=389; 1H NMR (400 MHz, DMSO-d6) δ ppm 4.00 (s, 3H) 6.46 (s, 2H) 6.97 (dd, J=8.22, 1.57 Hz, 1H) 7.22 (d, J=8.61 Hz, 1H) 7.32 (d, J=10.62 Hz, 1H) 7.64 (s, 2H) 7.68 (t, J=8.02 Hz, 1H) 8.58 (d, J=9.00 Hz, 1H) 9.67 (s, 1H).

Example 118

6-((7-Methoxy-4-methyl-1H-[1,2,3]triazolo[4,5-c][1,8]naphthyridin-1-yl)methyl)pyridine-3-sulfonamide (136) was prepared in 3.2 mg following the synthesis of compound 119. LCMS [M+H]⁺=386; ¹H NMR (300 MHz, DMSO-d6) δ ppm 3.00 (s, 3H) 4.00 (s, 3H) 6.57 (s, 2H) 7.09 (d, J=8.79 Hz, 1H) 7.53 (s, 2H) 7.61 (d, J=8.21 Hz, 1H) 8.18 (d, J=8.21 Hz, 1H) 8.50-8.56 (m, 1H) 8.71-8.75 (m, 1H).

Example 119

(2-fluoro-4-((7-methoxy-2-oxo-2,3-dihydro-1H-imidazo[4,5-c][1,8]naphthyridin-1-yl)methyl)phenyl)phosphonic Acid (121)

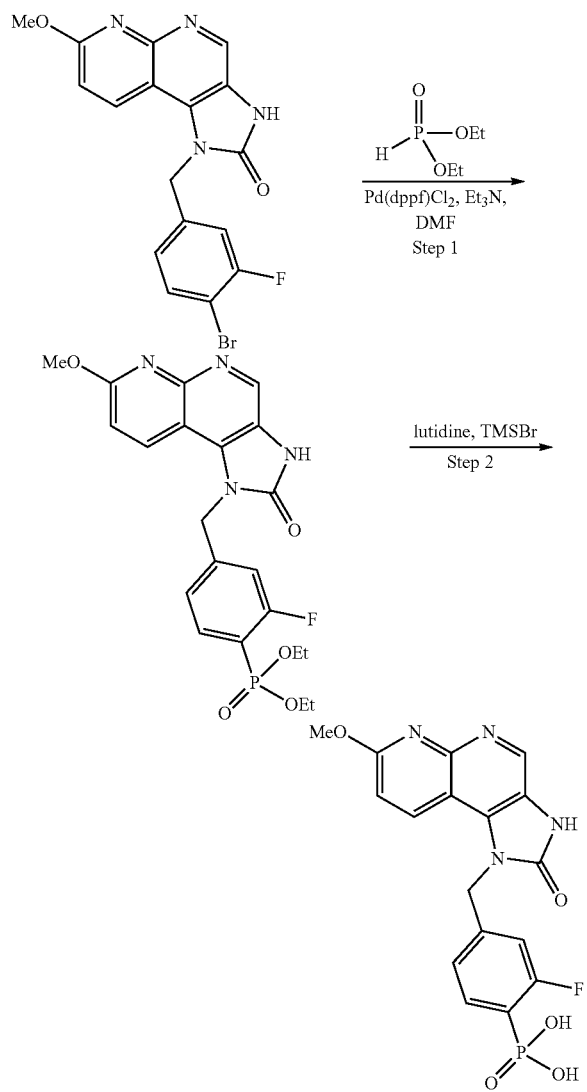

Step 1. To a mixture of 1-ethoxyphosphonoyloxyethane (82.20 mg, 595.23 umol, 76.82 μL, 6 eq) and 1-((4-bromo-3-fluoro-phenyl)methyl)-7-methoxy-3H-imidazo[4,5-c][1,8]naphthyridin-2-one (40 mg, 99.21 μmol, 1 eq) in DMF (1.2 mL) was added Et₃N (30.12 mg, 297.62 μmol, 41.42 μL, 3 eq) and Pd(dppf)Cl₂ (7.26 mg, 9.92 μmol, 0.1 eq) in one portion at 22° C. under N₂. The mixture was stirred at 80° C. for 3 hour. Upon completion, the mixture was concentrated. The crude was purified by Biotage Sfar 5 g silica column using DCM/MeOH yielding the product (44 mg, 96%).

Step 2. To a mixture of 1-((4-diethoxyphosphoryl-3-fluoro-phenyl)methyl)-7-methoxy-3H-imidazo[4,5-c][1,8]naphthyridin-2-one (96 mg, 208.52 μmol, 1 eq) in DCM (10 mL) was added 2,6-lutidine (379.82 mg, 3.54 mmol, 412.85 μL, 17 eq) in one portion at 22° C. The mixture was cooled to 0° C., TMSBr (1.60 g, 10.43 mmol, 1.35 mL, 50 eq) was added into reaction mixture dropwise. The reaction mixture was then stirred at 22° C. for 5 hr. Upon completion, MeOH (20 mL) was added into reaction mixture and stirred for 30 min. The mixture was concentrated and the crude was purified by Prep HPLC using water/MeCN (0.1% TFA) gradient yielding the product (30 mg, 36%). LCMS [M+H]⁺=405; ¹H NMR (400 MHz, DMSO-d6) δ ppm 3.92 (s, 3H) 5.51 (s, 2H) 6.93-7.04 (m, 2H) 7.08-7.18 (m, 1H) 7.51-7.63 (m, 1H) 8.12-8.21 (m, 1H) 8.61-8.68 (m, 1H).

Compounds 124-127 were prepared according to the preparation of compound 121.

Example 120

(3,5-Difluoro-4-((7-methoxy-2-oxo-2,3-dihydro-1H-imidazo[4,5-c][1,8]naphthyridin-1-yl)methyl)-phenyl)phosphonic acid (124) was prepared in 9.1 mg following the procedure for the synthesis of compound 121. LCMS [M+H]⁺=423.

Example 121

(2,5-difluoro-4-((7-methoxy-2-methyl-1H-imidazo[4,5-c][1,8]naphthyridin-1-yl)methyl)phenyl)phosphonic acid (125): LCMS [M+H]⁺=421.

Example 122

(6-((7-methoxy-2,4-dimethyl-1H-imidazo[4,5-c][1,8]naphthyridin-1-yl)methyl)pyridin-3-yl)phosphonic acid (126): LCMS [M+H]⁺=400.

Example 123

Methyl hydrogen (2-fluoro-4-((7-methoxy-2-oxo-2,3-dihydro-1H-imidazo[4,5-c][1,8]naphthyridin-1-yl)methyl)phenyl)phosphonate (127) was prepared in 8.1 mg following the procedure for the synthesis of compound 121. LCMS [M+H]⁺=419.

Example 124

3-Fluoro-4-((7-methoxy-2-oxo-2,3-dihydro-1H-imidazo[4,5-c]cinnolin-1-yl)methyl)benzenesulfon-amide (123) was prepared in 14.6 mg following the preparation of compound 38. LCMS [M+H]⁺=404; ¹H NMR (300 MHz, DMSO-d6) δ ppm 3.95-3.97 (m, 3H) 5.62 (s, 2H) 7.37 (d, J=1.76 Hz, 1H) 7.40 (d, J=2.34 Hz, 1H) 7.49 (s, 2H) 7.51 (br d, J=1.76 Hz, 2H) 7.67 (dd, J=9.96, 1.76 Hz, 1H) 7.96 (d, J=9.38 Hz, 1H).

Example 125

4-((7-Methoxy-2-oxo-2,3-dihydro-1H-imidazo[4,5-c]cinnolin-1-yl)methyl)benzene-sulfonamide (128)

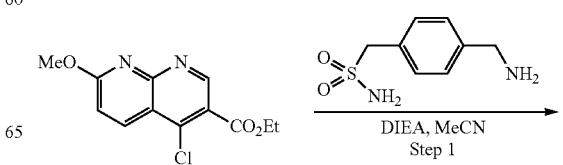

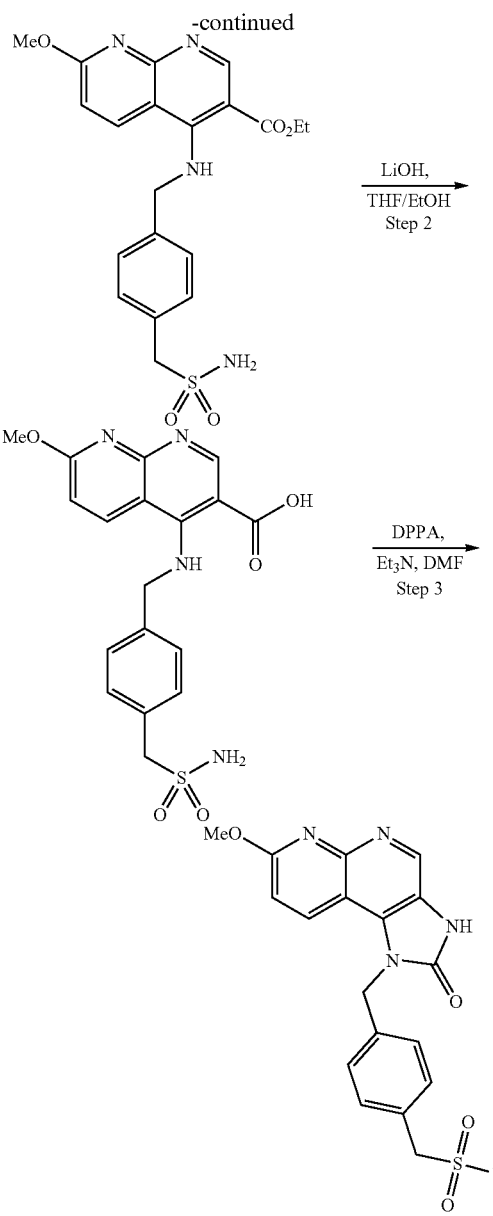

and filtered. The filtrate was concentrated yielding the crude product. The product was used in the next step without further purification.

Step 3. To a mixture of this crude product in DMF (3 mL) was added DPPA (171.84 mg, 624.42 µmol, 135.31 µL, 2.4 eq), Et₃N (263.27 mg, 2.60 mmol, 362.13 µL, 10 eq) in one portion at 22° C. The mixture was stirred at 80° C. for 3 hr. Upon completion, the mixture was concentrated. The crude was purified by DCM/MeOH yielding the product (17 mg, 16%). LCMS [M+H]⁺=400; ¹H NMR (400 MHz, DMSO-d6) δ ppm 4.01 (s, 3H) 4.19 (s, 2H) 5.56 (s, 2H) 6.79 (s, 2H) 7.17 (d, J=9.00 Hz, 1H) 7.22-7.25 (m, 2H) 7.27-7.30 (m, 2H) 8.40 (d, J=9.00 Hz, 1H) 8.76 (s, 1H) 12.16-12.50 (m, 1H).

Example 126

3-chloro-5-fluoro-4-((7-methoxy-2-oxo-2,3-dihydro-1H-imidazo[4,5-c][1,8]naphthyridin-1-yl)methyl)benzenesulfonamide (134) was prepared in 16.8 mg following the preparation of compound 38. LCMS [M+H]⁺=438.

Example 127

4-((7-Methoxy-2-oxo-2,3-dihydro-1H-imidazo[4,5-c]cinnolin-1-yl)methyl)benzene-sulfonamide (137) was prepared in 11 mg from ethyl 4-hydroxy-7-methoxycinnoline-3-carboxylate following the preparation of compound 38. LCMS [M+H]⁺=386; ¹H NMR (300 MHz, DMSO-d6) δ ppm 3.93-3.96 (m, 3H) 5.62 (s, 2H) 7.32 (s, 2H) 7.36 (dd, J=9.67, 2.64 Hz, 1H) 7.45 (d, J=2.34 Hz, 1H) 7.50 (d, J=8.21 Hz, 2H) 7.75 (d, J=8.21 Hz, 2H) 7.91 (d, J=9.38 Hz, 1H).

Example 128

3,5-difluoro-4-(7-methoxy-2-oxo-2,3-dihydro-1H-imidazo[4,5-c][1,8]naphthyridin-1-yl)methyl)benzenesulfamide (138)

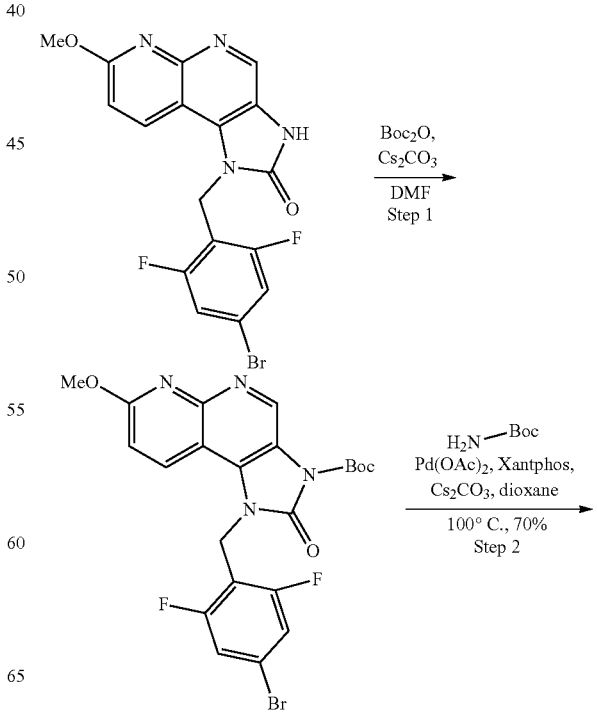

Step 1. To a mixture of ethyl 4-chloro-7-methoxy-1,8-naphthyridine-3-carboxylate (77 mg, 288.74 µmol, 1 eq) and (4-(aminomethyl)phenyl)methanesulfonamide (109.36 mg, 461.98 µmol, 1.6 eq, HCl) in MeCN (5 mL) was added DIEA (373.16 mg, 2.89 mmol, 502.91 µL, 10 eq) in one portion at 22° C. The mixture was stirred at 65° C. for 1 hour. Upon completion, the mixture was concentrated. The resulting residual was triturated with EtOAc yielding the product (112 mg, 90%).

Step 2. To a mixture of ethyl 7-methoxy-4-[[4-(sulfamoylmethyl)phenyl]methylamino]-1,8-naphthyridine-3-carboxylate (112 mg, 260.18 µmol, 1 eq) in EtOH/THF (2.6 mL) was added LiOH (1 M, 2.60 mL, 10 eq) in one portion at 22° C. The mixture was stirred at 50° C. for 1 hour. Upon completion, the organic solvent was removed under vacuum and then acidify to pH=4. The aqueous layer was extracted by EtOH/CHCl₃=1:3. Both water and organic layer contain product. All the solvents were combined and then concentrated. The resulting white solid was extracted with EtOH

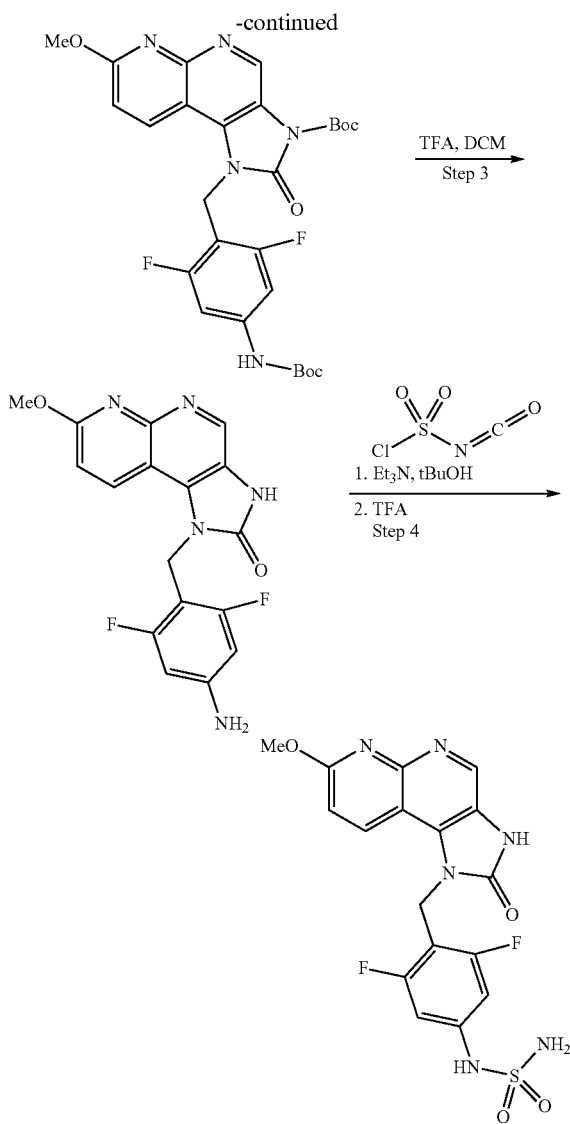

Step 1. 1-((4-bromo-2,6-difluoro-phenyl)methyl)-7-methoxy-3H-imidazo[4,5-c][1,8]naphthyridin-2-one (400 mg, 949.68 µmol, 1 eq) dissolved in DMF (2.5 mL) followed by the addition of Boc$_2$O (298.46 mg, 1.37 mmol, 314.17 µL, 1.44 eq) and Cs$_2$CO$_3$ (464.13 mg, 1.42 mmol, 1.5 eq). The mixture stirred at 22° C. for 2 hr. Upon completion, the mixture was added to water and the resulting precipitate was filtered and dried yielding the product (463 mg, 94%).

Step 2. tert-butyl 1-((4-bromo-2,6-difluoro-phenyl) methyl)-7-methoxy-2-oxo-imidazo[4,5-c][1,8]naphthyridine-3-carboxylate (60 mg, 115.09 µmol, 1 eq), Pd(OAc)$_2$ (1.29 mg, 5.75 µmol, 0.05 eq), Xantphos (3.33 mg, 5.75 µmol, 0.05 eq), Cs$_2$CO$_3$ (112.50 mg, 345.28 µmol, 3 eq), and tert-butyl carbamate (26.97 mg, 230.19 µmol, 2 eq) were dissolved in dioxane (0.8 mL). The mixture purged with nitrogen for 30 sec and sealed. The mixture heated to 100° C. for 1 hr. Upon completion, the mixture cooled to 22° C. and diluted with water. The resulting precipitate was filtered and dried yielding the product (55.5 mg, 60%).

Step 3. tert-butyl 1-((4-(tert-butoxycarbonylamino)-2,6-difluoro-phenyl)methyl)-7-methoxy-2-oxo-imidazo[4,5-c][1,8]naphthyridine-3-carboxylate (108 mg, 193.71 µmol, 1 eq) dissolved in DCM (0.5 mL) followed by the addition of TFA (770.00 mg, 6.75 mmol, 0.5 mL, 34.86 eq). The mixture stirred at 22° C. for 1.5 hr. Upon completion, the mixture was concentrated then dissolved in DCM. The crude was free based using sat. NaHCO$_3$ and extracted with EtOAc (3×10 mL). The combined organic dried over Na$_2$SO$_4$ and concentrated. The crude was purified by Biotage C18 Duo 12 g column using water/MeCN (0.1% TFA) gradient yielding the product (24 mg, 35%).

Step 4. 1-((4-amino-2,6-difluoro-phenyl)methyl)-7-methoxy-3H-imidazo[4,5-c][1,8]naphthyridin-2-one (24 mg, 67.17 µmol, 1 eq) dissolved in DMA (0.7 mL) followed by the addition of sulfamoyl chloride (77.61 mg, 671.68 µmol, 10 eq). The mixture stirred at 22° C. for 2 hr. Et$_3$N (135.93 mg, 1.34 mmol, 186.98 µL, 20 eq) added and stirred at 22° C. for 18 hr. Upon completion, the mixture was purified by Prep HPLC using water/MeCN (0.1% TFA) gradient yielding the product (28.1 mg, 76%). LCMS [M+H]$^+$=437.

Biological Examples

Example B1: ENPP1 Activity Assay Using p-Nitrophenyl-5'-TMP as a Substrate

ENPP1 is a transmembrane glycoprotein that hydrolyzes nucleotides and nucleotide derivatives with the formation of nucleotide-5'-monophosphates. ENPP1 hydrolyzes artificial phosphoric acid ester thymidine 5'monophosphate p-nitrophenyl ester (TMP-pNP) to nucleotide-5'-monophosphate and p-nitrophenol, which is a chromogenic product. The amount of p-nitrophenol product formed is measured using its absorbance at 405 nm, which is directly proportional to enzyme activity.

For determination of IC$_{50}$ values, 8 point of different concentrations of each inhibitor were prepared with the final assay concentrations starting at 1000 nM with 50 mM Tris buffer (pH 9.5) containing 250 mM NaCl. Load into a well with 20 ng of human soluble ENPP1 in 50 µL and incubate at room temperature with 25 µL inhibitor solution (4× Final Concentration) for 30 mins. Then, add 25 µL 2 mM TMP solution (2× Final Concentration) into the well, Incubate at RT for 1 hour. The amounts of released p-nitrophenolate were measured by reading OD value at 405 nm.

The percent inhibition at each compound is calculated as follows: % inhibition=(OD$_{MAX}$–OD$_{COMPOUND}$)/(OD$_{MAX}$–OD$_{MIN}$)*100. (MAX: absence of ENPP1 inhibitors control, MIN: blank control.)

The IC$_{50}$ values for percent inhibition versus compound concentration were determined by fitting the inhibition curves using a four-parameter variable slope model in GraphPad Prism® 8. The IC$_{50}$ values determined were listed in Table 2.

Example B2: ENPP1 Activity Assay Using p-Nitrophenyl-5'-AMP as a Substrate

In some instances, an inhibitor of ENPP-1 is able to selectively blocking the hydrolysis of 2'3'-cGAMP while only minimally inhibiting the hydrolysis of ATP. Therefore, the ATP analog p-Nitrophenyl 5'-Adenosine Monophosphate (AMP-pNP) has been demonstrated to accurately reflect hydrolysis of native ATP by different classes of ENPP1 inhibitors. AMP-pNP can be used as substrate of ENPP-1. Its hydrolysis products were nucleotide-5'-monophosphate and p-nitrophcnol, which is also a chromogenic product. The amount of p-nitrophenol product formed is measured using its absorbance at 405 nm, which is directly proportional to enzyme activity.

For determination of $IC_{50}$ values, 12 point of different concentrations of each inhibitor were prepared with the final assay concentrations starting at 9000 nM, 3× series dilution with 50 mM Tris buffer (pH 9.5) containing 250 mM NaCl. Load into a well with 35 ng of human soluble ENPP1 in 50 µL and incubate at room temperature with 25 µL inhibitor solution (4× Final Concentration) for 30 mins prior adding 25 µL 3 mM AMP solution (2× Final Concentration) into the well, Incubate at RT for 1 hour. The amounts of released p-nitrophenolate were measured by reading OD value at 405 nm.

The percent inhibition at each compound is calculated as follows: % inhibition=$(OD_{MAX}-OD_{COMPOUND})/(OD_{MAX}-OD_{MIN})*100$. (MAX: absence of ENPP1 inhibitors control, MIN: blank control.)

The $IC_{50}$ values for percent inhibition versus compound concentration are determined by fitting the inhibition curves using a four-parameter variable slope model in GraphPad Prism® 8. The $IC_{50}$ values determined are listed in Table 2.

TABLE 2

| Compound ID | TMP-pNP ($IC_{50}$, nM) | AMP-pNP ($IC_{50}$, nM) |
| --- | --- | --- |
| PF-QS1* | 10 | 37 |
| MV0000658** | 6.2 | 237 |
| 1 | 1.7 | 5.9 |
| 2 | 10 | — |
| 8 | 0.30 | — |
| 10 | 1.1 | 27 |
| 11a | 0.88 | 2.5 |
| 11b | 196 | — |
| 12 | 1.2 | 3.9 |
| 13 | 4.3 | 33 |
| 17 | — | — |
| 32 | 7.7 | — |
| 35 | 0.37 | 35 |
| 36 | 3.1 | 36 |
| 37 | 165 | — |
| 38 | 0.31 | 0.75 |
| 39 | 0.25 | 0.42 |
| 40 | 0.15 | 0.23 |
| 41 | 0.21 | 0.9 |
| 44 | 65 | — |
| 46 | 5.2 | — |
| 47 | 1.0 | — |
| 48 | 0.29 | 0.44 |
| 49 | 1.9 | 4.8 |
| 50 | 28 | — |
| 51 | 884 | — |
| 52 | 0.54 | 2.2 |
| 54 | 0.53 | 1.8 |
| 60 | 0.31 | 1.51 |
| 61 | 0.53 | 1.9 |
| 62 | 0.1 | 1.5 |
| 64 | 2.8 | 8.9 |
| 65 | 3.0 | 8.7 |
| 66 | 3.0 | 13 |
| 67 | 2.3 | 8.6 |
| 68 | 0.49 | 1.7 |
| 69 | 0.67 | 2.1 |
| 70 | 0.64 | 1.2 |
| 71 | 1.0 | 2.9 |
| 72 | 0.58 | 1.2 |
| 73 | 0.36 | 0.96 |
| 74 | 0.09 | 0.12 |
| 75 | 0.24 | 0.68 |
| 76 | 13 | 26 |
| 77 | 8.6 | 15 |
| 78 | 1.7 | 7.2 |
| 79 | 2.1 | 9.2 |
| 80 | 1.8 | 6.4 |
| 81 | 6.9 | 23 |
| 82 | 0.8 | 2.4 |
| 83 | 3.2 | 7.7 |
| 84 | 3.5 | 8.4 |
| 85 | 2.0 | 5.2 |
| 86 | 0.81 | 3.2 |
| 87 | 1.3 | 4.0 |
| 88 | 4.0 | 12 |
| 89 | 0.52 | 2.1 |
| 90 | 2.4 | 7.7 |
| 91a | 83 | 323 |
| 91b | 62 | 199 |
| 92 | 9.3 | 29 |
| 93 | 3.7 | 13 |
| 94 | 3.4 | 8.8 |
| 95 | 1.4 | 4.6 |
| 96 | 1.7 | 5.4 |
| 97 | 0.56 | 1.1 |
| 98 | 0.60 | 3.0 |
| 99 | 0.27 | 0.79 |
| 100 | 8.8 | — |
| 101 | 0.67 | 1.1 |
| 102 | 0.51 | 0.74 |
| 103 | 0.090 | 0.06 |
| 104 | 8.9 | 11 |
| 105 | 21 | 19 |
| 107 | 43 | 79 |
| 108 | 16 | 66 |
| 110 | 0.60 | 2.6 |
| 111 | 7.4 | 21 |
| 112 | 0.30 | 0.99 |
| 113 | 1.1 | 5.0 |
| 114 | 0.27 | 0.23 |
| 115 | 0.11 | 0.32 |
| 116 | 0.38 | 1.8 |
| 117 | 8.1 | 34 |
| 118 | 2.9 | 8.2 |
| 119 | 0.70 | 1.1 |
| 120 | 1.78 | 4.4 |
| 121 | 9.4 | 31 |
| 122a | 1.6 | 4.3 |
| 123 | 0.61 | 2.4 |
| 124 | 19 | 56 |
| 125 | 7.2 | 21 |
| 129 | 0.10 | 0.19 |
| 130 | 0.16 | 0.16 |
| 131 | 0.040 | 0.19 |
| 132 | 0.33 | 0.74 |
| 135a | 0.66 | 1.4 |
| 136 | 7.4 | 21 |
| 137 | 1.1 | 2.4 |
| 138 | 38 | 141 |

*PF-QS1 is compound 1 in Bioorganic & Medicinal Chemistry Letters 19 (2009) 3339-3343, Snahel D. Patel et al;
**MV0000658 is a representative compound in WO2019/046778 A1, Gallatin, W. M et al.

Example B3: Quantitation of 2'3'-cGAMP Hydrolysis

The hydrolysis products of 5'-GMP and 5'-AMP were generated when ENPP-1 use 2'3'-cGAMP as substrate. In some instances, ENPP1 activity with 2'3'-cGAMP substrate is measured using the AMP-Glo™ Assay kit (Promega Corporation) to quantitate the production of 5'-AMP. The AMP-Glo™ Assay Kit contains two reagents that are added sequentially. Reagent I converts the 5'-AMP produced in the reaction to 5'ADP. Reagent II converts the 5'-ADP to 5'ATP and reacts the 5'-ATP with the luciferase/luciferin pair to produce the luminescence signal.

The ENPP1 assay with 2'3'-cGAMP substrate is conducted in 50 mM Tris buffer (pH 9.5) containing 250 mM NaCl. 12 point of different concentrations of each inhibitor were prepared with the final assay concentrations starting at 9000 nM, 3× series dilution. Duplicate wells are run at each inhibitor concentration. The final assay volume is 18 μL per well in 384 white assay plate containing 9 μL inhibitor solution, 4.5 μL human recombinant ENPP-1 protein (20 ng/well) and 4.5 μL 2',3'-cGAMP with final concentration of 20 μM. The assay is initiated by the addition of substrate and incubate at room temperature for 2 hours prior to taking 5 μL out to mix with 5 μL Reagent I to stop the reaction. 10 μL of Reagent II is then added and the wells are again incubated for another 60 minutes at room temperature. The luminescence signal is then measured using a plate reader with luminometer.

The percent inhibition at each compound is calculated as follows: % inhibition=$(RLU_{MAX}-RLU_{COMPOUND})/(RLU_{MAX}-RLU_{MIN})*100$. (MAX: absence of ENPP1 inhibitors control, MIN: blank control.)

Example B4: Cellular Enzymatic Assay of ENPP-1 Inhibitors Using TMP-pNP as Substrate ENPP-1 were mainly expressed on the surface of cell membrane where it hydrolytes 2'3'-cGAMP to generate 5'-GMP and 5'-AMP. ENPP-1 also has the ability to hydrolyzes artificial phosphoric acid ester TMP-pNP to nucleotide-5'-monophosphate and p-nitrophcnol there, which is a chromogenic product. Therefore, in cultured MDA-MB-231, HEK293 and/or Saos-2 cells, TMP-pNP was used as substrate to reflect the enzymatic activity of ENPP1. The amount of p-nitrophenol product formed in the culture medium is measured using its absorbance at 405 nm, which is directly proportional to activity of ENPP1. The lower OD value at 405, the higher potency of ENPP-1 inhibitor.

8 point of different concentrations of each inhibitor were prepared with the final assay concentrations starting at 20 μM. 3× series dilution by DMEM medium without FBS was applied. Prior to adding inhibitors, 75000 cells per well were incubated at 37° C., 5% $CO_2$ in DMEM for 24 hours. After removing the supernatant medium, 50 μL inhibitor solution was added into each well with cultured cells and incubate at 37° C., 5% $CO_2$ for 60 minutes. Then, 4 mM (2× Final Concentration) TMP-pNP solution was mixed with inhibitor in each well for 5 hours before reading OD value at 405 nm using a plate reader.

The $IC_{50}$ values for percent inhibition versus compound concentration are determined by fitting the inhibition curves using a four-parameter variable slope model in GraphPad Prism® 8.

TABLE 3-1

| Compound ID | MDA-MB-231 | |
|---|---|---|
| | Relative $IC_{50}$ (μM) | % Inhibition (at 20 μM) |
| PF-QS1 | 1.8 | 50 |
| Mv0000658 | — | 57 |
| 1 | 2.9 | 50 |
| 12 | 0.55 | 79 |
| 11a | 0.60 | 79 |
| 35 | 1.5 | 73 |
| 36 | 1.5 | 66 |
| 39 | 0.40 | 82 |
| 40 | 0.065 | 85 |
| 41 | 0.31 | 81 |
| 46 | 1.6 | 75 |
| 47 | 3.4 | 72 |
| 48 | 0.55 | 80 |
| 49 | 6.0 | 67 |
| 50 | — | — |
| 52 | 1.3 | 79 |
| 54 | 0.9 | 82 |

TABLE 3-1-continued

| Compound ID | MDA-MB-231 | |
|---|---|---|
| | Relative $IC_{50}$ (μM) | % Inhibition (at 20 μM) |
| 60 | 0.49 | 83 |
| 61 | 0.78 | 80 |
| 62 | 0.045 | 89 |
| 64 | 4.7 | 68 |
| 65 | 1.6 | 75 |
| 66 | 3.4 | 71 |
| 67 | 1.3 | 80 |
| 68 | 0.61 | 86 |
| 69 | 0.51 | 79 |
| 70 | 0.29 | 85 |
| 71 | 1.1 | 76 |
| 72 | 0.34 | 81 |
| 73 | 0.27 | 81 |
| 74 | 0.085 | 81 |
| 75 | 0.31 | 81 |
| 76 | 6.9 | 51 |
| 77 | 4.8 | 65 |
| 79 | 1.9 | 74 |
| 80 | 1.8 | 75 |
| 81 | 4.9 | 63 |
| 82 | 0.56 | 82 |
| 83 | 1.2 | 83 |
| 84 | 2.5 | 76 |
| 85 | 0.90 | 79 |
| 86 | 0.62 | 80 |
| 87 | 0.36 | 85 |
| 88 | 2.2 | 81 |
| 89 | 0.41 | 78 |
| 90 | 0.98 | 74 |
| 91a | >6.7 | 53 |
| 92 | 4.1 | 68 |
| 93 | 2.2 | 74 |
| 94 | 2.7 | 74 |
| 95 | 1.4 | 75 |
| 96 | 11 | 57 |
| 97 | 0.81 | 78 |
| 98 | 3.8 | 62 |
| 99 | 0.60 | 77 |
| 101 | 2.4 | 76 |
| 102 | 0.43 | 86 |
| 103 | 0.034 | 87 |
| 104 | 3.4 | 72 |
| 105 | >6.7 | 67 |
| 106 | >6.7 | 57 |
| 108 | 5.7 | 64 |
| 109 | >20 | 11 |
| 110 | 0.15 | 86 |
| 111 | 0.00031 | 80 |
| 112 | 0.07 | 80 |
| 113 | 0.25 | 72 |
| 114 | 0.08 | 77 |
| 115 | 0.056 | 78 |
| 116 | 1.8 | 68 |
| 117 | 16 | 16 |
| 118 | 2.0 | 70 |
| 119 | 0.12 | 83 |
| 120 | 1.1 | 79 |
| 121 | 0.0082 | 91 |
| 122a | 1.7 | 74 |
| 123 | 1.8 | 66 |
| 124 | 0.0096 | 86 |
| 125 | 0.0027 | 82 |
| 126 | 0.48 | 80 |
| 127 | 0.081 | 78 |
| 128 | 20 | 82 |
| 131 | 0.08 | 88 |
| 132 | — | 87 |
| 135a | 0.08 | 88 |
| 136 | 0.00031 | 80 |
| 137 | 1.8 | 59 |

TABLE 3-2

| Compound ID | HEK 293 Relative IC$_{50}$ (μM) | % Inhibition (at 20 μM) |
|---|---|---|
| PF-QS1 | — | 41 |
| Mv0000658 | — | 29 |
| 1 | — | 19 |
| 11a | 2.1 | 84 |
| 12 | 2.3 | 85 |
| 35 | 3.4 | 51 |
| 36 | 5.0 | 57 |
| 39 | 0.73 | 94 |
| 40 | 0.13 | 96 |
| 41 | 0.66 | 96 |
| 46 | 2.4 | 85 |
| 47 | 5.0 | 77 |
| 48 | 0.67 | 95 |
| 49 | 10 | 67 |

TABLE 3-3

| Compound ID | Saos-2 Relative IC$_{50}$ (μM) | % Inhibition (@20 μM) |
|---|---|---|
| PF-QS1 | — | 50 |
| Mv0000658 | — | 52 |
| 1 | — | 32 |
| 11a | 1.2 | 87 |
| 12 | 1.0 | 87 |
| 35 | 5.6 | 76 |
| 36 | 2.0 | 48 |

Example B5: ENPP1 Inhibitors Screening on cGAMP Activated THP-1 Cells

THP-1 cells from bulk cultures were counted and suspended in RPMI 1640, 20% FBS, 2.5 mM L-alanyl-L-glutamine at a concentration of 5.5×10$^6$ cells/mL. The THP-1 cells were subsequently seeded into 96 well round bottom plates 180 μL/well (1×10$^6$ cells per well), incubated for 1 hour at 37° C., 5% CO$_2$.

Test compounds were screened in triplicate on THP-1 cells at a final concentration of 10 μM. A working solutions at 0.2 mM. Each well contains 180 μL of THP-1 cell suspension, 10 μL (30 μM, 40 μM or 50 μM) 2'3'-cGAMP (InvivoGen, catalog #tlrl-nacga23) solution (600 μM, 800 μM or 1000 μM) and 10 μL test compound working solution. Incubate for 1 hour.

Vehicle control wells contain 2'3'-cGAMP at concentrations of 30 1M and 50 μM without any test compound. Positive control, 2'3'-cGAMP or 2',3'-cGAM(PS)$_2$ (Rp/Sp) (InvivoGen, cat #tlrl-nacga2srs) at 40 μM and 80 μM (final concentration).

The final assay volume were 200 μL/well contains: 1) THP-1 cells=180 μL, 2) test compounds=10 μL, 3) 2'3'-cGAMP or 2'3'-cGAM(PS)$_2$ (Rp/Sp) or vehicle control=10 μL.

After incubation for 24 hours at 37° C., 5% CO$_2$, the supernatants were harvested at 200×g for 10 minutes. Cell culture supernatants were then transferred to a clean plate and stored at −80° C. until ready to analyze for IFN-β levels. The IFN-β levels in cell culture supernatants were determined by ELISA kits (PBL Assay Science, catalog #41410) according to the manufacturer's instructions.

Figure 1B:
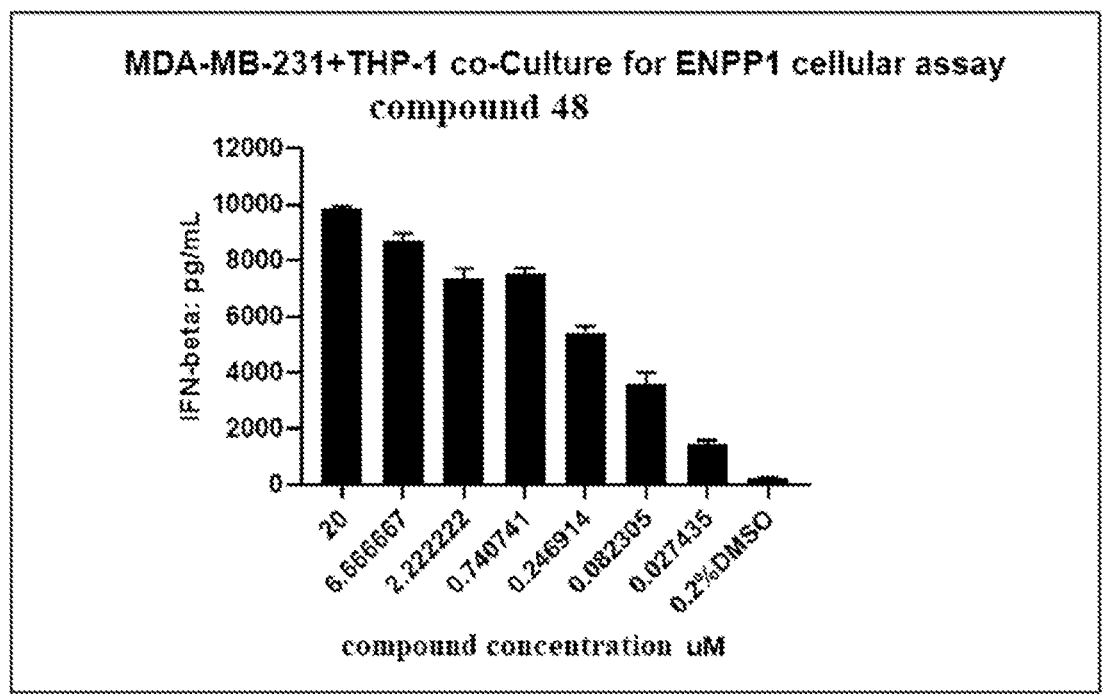
Figure 1C:
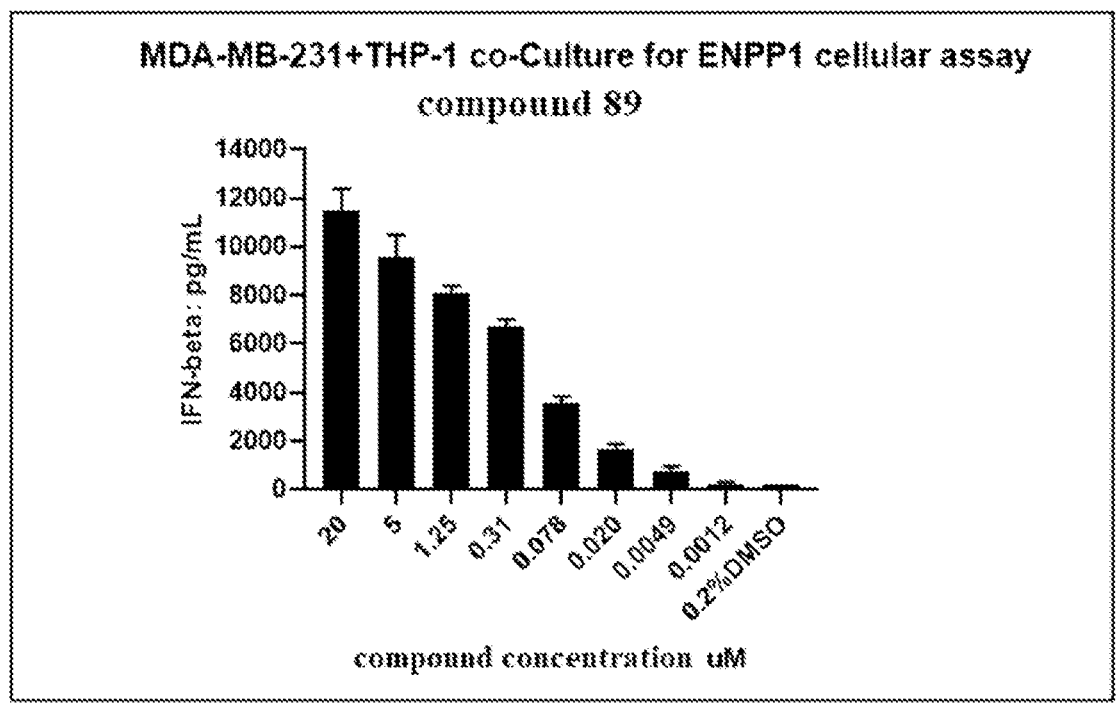
Figure 1D:
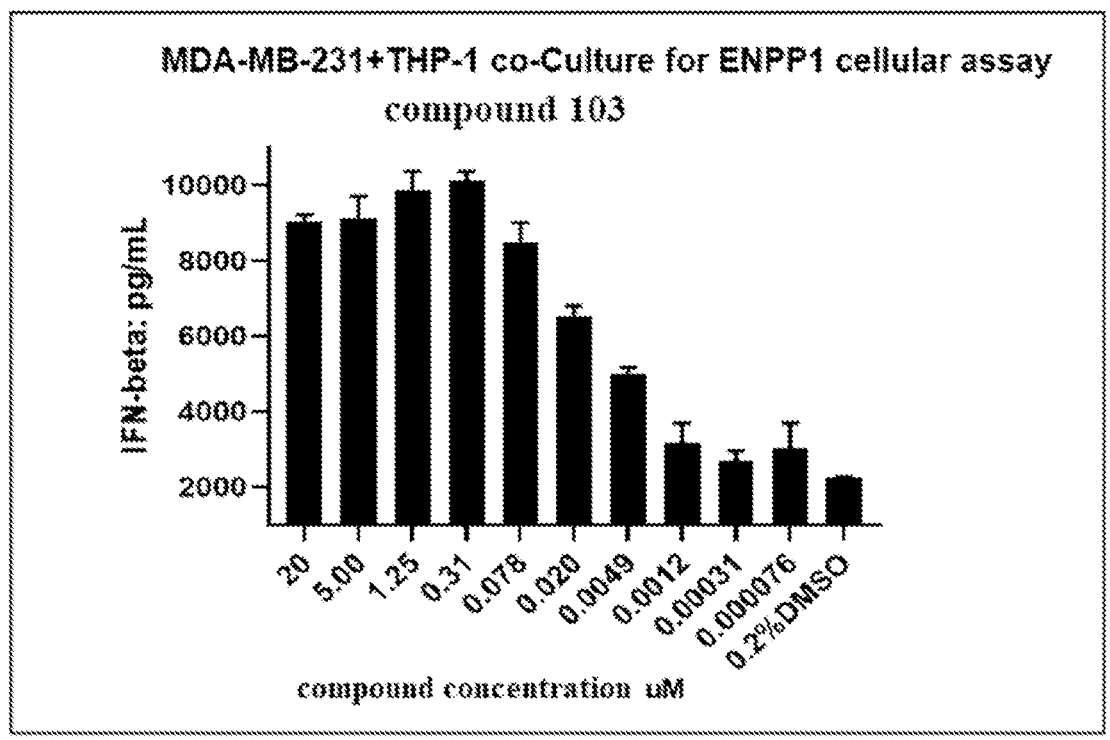
Figure 1E:
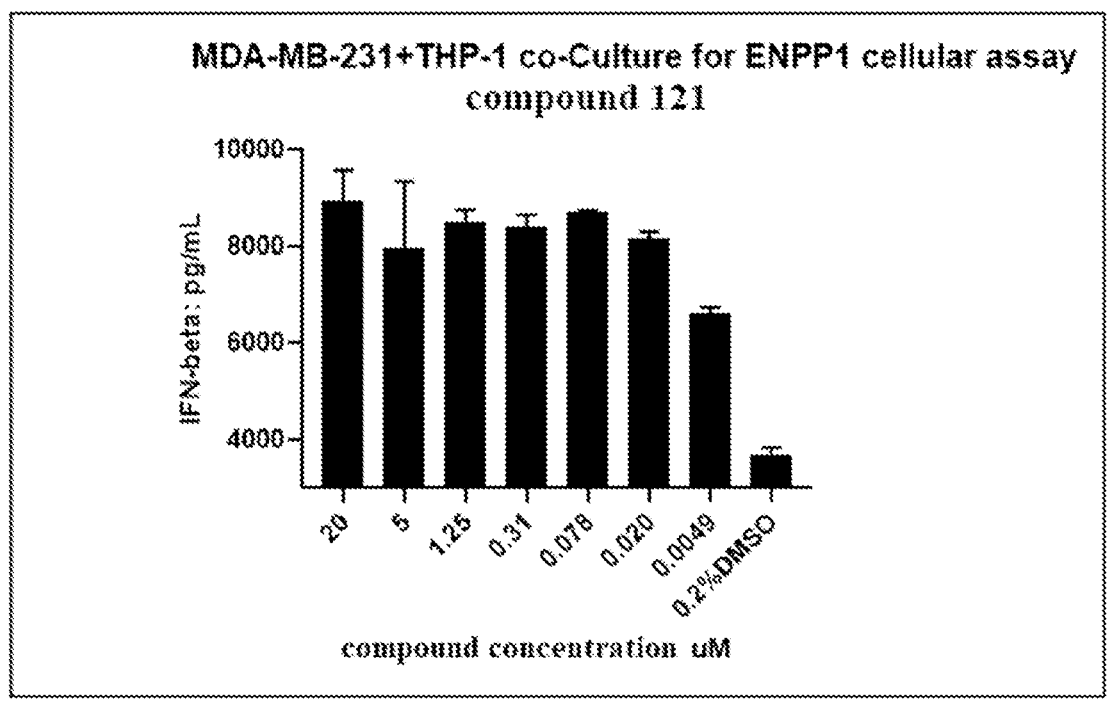

The % increase measured for IFN-β in cells treated by the test compounds 12, 48, 89, 103 and 121 relative to that of untreated cells were tested (as shown in FIGS. 1A-1E). The test compounds potently increased the IFN-β levels at very low concentrations.

Example B6: Liver Microsome Stability

Liver microsome assay was used to evaluate the metabolic stability of I-VI. The test article at the concentration of 104 was incubated with 0.5 mg/mL liver microsome in the presence of NADPH and UDPGA as the co-factors for 0, 15, 30, 45 and 60 minutes. The incubation was carried out at 37° C. with 5% CO$_2$ and saturating humidity. Disappearance of the test article was monitored by LC/MS/MS. the disappearance half-life ($t_{1/2}$), intrinsic clearance and hepatic extraction ratio were determined.

TABLE 4

Stability of selected compounds in liver microsomes

| Compound | Half-life $t_{1/2}$ (min) | Intrinsic clearance Cl'$_{int}$ (μL/min/mg protein) | Hepatic extraction ratio Re |
|---|---|---|---|
| Mouse liver microsome | | | |
| 1 | ∞ | 0 | 0 |
| 12 | 237 | 5.9 | 0.20 |
| 11a | 11 | 131 | 0.85 |
| 35 | ∞ | 0 | 0 |
| 36 | 49 | 28 | 0.55 |
| Human liver microsome | | | |
| 10 | ∞ | 0 | 0 |
| 12 | 496 | 2.8 | 0.14 |
| 35 | ∞ | 0 | 0 |

Example B6: Pharmacokinetics in Mice

A dosing solution of test sample was prepared at 1.0 mg/mL in 5% DMSO/40% PEG400/55% water and administered to male CD-1 mice (4-6 weeks old, 20-30 grams, 3 animals each group) via intravenous (IV) bolus at 1 mg/kg and by oral gavage (PO) at 5 mg/kg. Blood samples (~0.03 mL each time point) were collected via the jugular vein into tubes containing sodium heparin as the anticoagulant at 0.033, 0.083, 0.25, 0.5, 1, 2, 4, 8 and 24 hours post dose for IV administration and 0.083, 0.25, 0.5, 1, 2, 4, 8 and 24 hours post dose for PO administration. The blood samples were then centrifuged for 5 minutes in a centrifuge refrigerated at 4° C. The resultant plasma samples were analyzed using LC/MS/MS to determine concentrations of test sample. Non-compartmental model with WinNonlin (Phoenix™, version 8.0) software was used to calculate pharmacokinetic (PK) parameters. The PK results are listed in Table 5. In comparison with the quinoline analog of compound 12, most of naphthyridine analogs showed significant improvement in terms of clearance, AUC, half-life and oral bioavailability.

TABLE 5

Pharmacokinetic parameters in male CD-1 mice (1 mg/kg, iv)

| Compounds | $T_{1/2}$ (h) | Cl (ml/min/kg) | AUC (h*ng/mL) | Vdss (L/kg) | % F |
|---|---|---|---|---|---|
| 12 | 0.25 | 180 | 93 | 2.9 | 0% |
| 38 | 1.9 | 45 | 370 | 3.3 | NT |
| 39 | 0.33 | 115 | 115 | 3.1 | NT |
| 40 | 2.7 | 70 | 241 | 7.3 | NT |

TABLE 5-continued

Pharmacokinetic parameters in male CD-1 mice (1 mg/kg, iv)

| Compounds | $T_{1/2}$ (h) | Cl (ml/min/kg) | AUC (h*ng/mL) | Vdss (L/kg) | % F |
|---|---|---|---|---|---|
| 41 | 1.2 | 74 | 227 | 4.0 | NT |
| 48 | 0.33 | 70 | 239 | 1.7 | NT |
| 52 | 0.35 | 103 | 179 | 1.1 | NT |
| 60 | 2.5 | 78 | 215 | 11 | NT |
| 61 | 1.4 | 62 | 271 | 4.5 | NT |
| 62 | 4.9 | 105 | 163 | 39 | NT |
| 65 | 0.72 | 92 | 185 | 3.1 | NT |
| 70 | 2.6 | 26 | 668 | 4.3 | NT |
| 71 | 0.74 | 60 | 288 | 2.8 | NT |
| 72 | 1.4 | 56 | 303 | 2.9 | NT |
| 73 | 0.60 | 63 | 267 | 1.6 | NT |
| 74 | 1.4 | 123 | 138 | 14 | NT |
| 80 | 0.13 | 107 | 158 | 1.0 | NT |
| 82 | 0.86 | 66 | 253 | 2.2 | NT |
| 89 | 0.54 | 26 | 656 | 0.80 | NT |
| 102 | 5.1 | 26 | 657 | 5.2 | 8.4% |
| 114 | 3.9 | 37 | 454 | 12 | 33% |
| 119 | 1.4 | 56 | 301 | 4.5 | NT |
| 120 | 2.0 | 65 | 260 | 8.9 | NT |
| 122a | 0.33 | 100 | 170 | 2.0 | NT |
| 137 | 1.2 | 39 | 429 | 1.6 | NT |

*NT: not tested

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

The invention claimed is:

1. A compound of Formula (A):

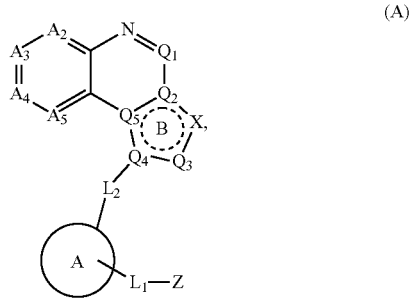

(A)

or a pharmaceutically acceptable salt, stereoisomer, or tautomer thereof,
wherein:

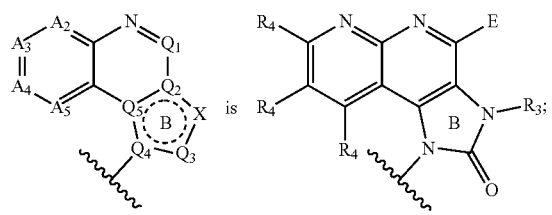

Ring A is phenyl, wherein the phenyl is optionally substituted with one or more substituents independently selected from the group consisting of halogen, CN, $C_1$-$C_3$ alkyl, $C_1$-$C_3$ haloalkyl, $NH_2$, OH, $OC_1$-$C_4$ alkyl, and $OC_1$-$C_4$ haloalkyl;

$L_1$ is a bond;
$L_2$ is —$CR_1R_2$—;
$R_1$ is H;
$R_2$ is H;
E is H, D, halogen, CN, $NO_2$, $C_1$-$C_6$ alkyl, $C_2$-$C_6$ alkenyl, $C_2$-$C_6$ alkynyl, C(O)$R_3$, C(O)$NR_3R_3'$, C(O)OR$_3$, OR$_3$, =O, S(O)$_2R_3$, S(O)$_2NR_3R_3'$, $C_3$-$C_8$ cycloalkyl, or 3- to 8-membered heterocyclyl, wherein the $C_1$-$C_6$ alkyl, $C_2$-$C_6$ alkenyl, $C_2$-$C_6$ alkynyl, $C_3$-$C_8$ cycloalkyl, or 3- to 8-membered heterocyclyl is optionally substituted with one or more substituents independently selected from the group consisting of halogen, CN, $C_1$-$C_3$ alkyl, $C_1$-$C_3$ haloalkyl, C(O)$NH_2$, C(O)O$C_1$-$C_4$ alkyl, $NH_2$, N($C_1$-$C_6$ alkyl)$_2$, OH, $OC_1$-$C_3$ alkyl, $OC_1$-$C_3$ haloalkyl, S(O)$_2C_1$-$C_6$ alkyl, 3- to 8-membered heterocyclyl, and phenyl;
each $R_3$ is independently H, $C_1$-$C_6$ alkyl, $C_3$-$C_6$ cycloalkyl, or 3- to 8-membered heterocyclyl, wherein each $C_1$-$C_6$ alkyl is optionally and independently substituted with one or more substituents independently selected from the group consisting of halogen, CN, $NH_2$, OH, $OC_1$-$C_4$ alkyl, $OC_1$-$C_3$ haloalkyl, and phenyl, and further wherein each $C_3$-$C_6$ cycloalkyl is optionally and independently substituted with one or more substituents independently selected from the group consisting of halogen, CN, $C_1$-$C_3$ alkyl, $C_1$-$C_3$ haloalkyl, $NH_2$, OH, $OC_1$-$C_4$ alkyl, $OC_1$-$C_3$ haloalkyl, and phenyl;
each $R_3'$ is independently H, $C_1$-$C_6$ alkyl, $C_3$-$C_6$ cycloalkyl, or 3- to 8-membered heterocyclyl, wherein each $C_1$-$C_6$ alkyl is optionally and independently substituted with one or more substituents independently selected from the group consisting of halogen, CN, $NH_2$, OH, $OC_1$-$C_4$ alkyl, $OC_1$-$C_3$ haloalkyl, and phenyl, and further wherein each $C_3$-$C_6$ cycloalkyl is optionally and independently substituted with one or more substituents independently selected from the group consisting of halogen, CN, $C_1$-$C_3$ alkyl, $C_1$-$C_3$ haloalkyl, $NH_2$, OH, $OC_1$-$C_4$ alkyl, $OC_1$-$C_3$ haloalkyl, and phenyl;
each $R_4$ is independently H, D, halogen, CN, $NO_2$, $C_1$-$C_6$ alkyl, $C_2$-$C_6$ alkenyl, $C_2$-$C_6$ alkynyl, C(O)$R_3$, C(O)$NR_3R_3'$, C(O)OR$_3$, $NR_3R_3'$, OR$_3$, S(O)$_2R_3$, S(O)$_2NR_3R_3'$, $C_3$-$C_8$ cycloalkyl, or 3- to 8-membered heterocyclyl, wherein each $C_1$-$C_6$ alkyl, $C_2$-$C_6$ alkenyl, and $C_2$-$C_6$ alkynyl is optionally and independently substituted with one or more substituents independently selected from the group consisting of halogen, CN, $NH_2$, OH, $OC_1$-$C_4$ alkyl, $OC_1$-$C_3$ haloalkyl, and phenyl, and further wherein each $C_3$-$C_8$ cycloalkyl and 3- to 8-membered heterocyclyl is optionally and independently substituted with one or more substituents independently selected from the group consisting of halogen, CN, $C_1$-$C_3$ alkyl, $C_1$-$C_3$ haloalkyl, $NH_2$, OH, $OC_1$-$C_4$ alkyl, $OC_1$-$C_3$ haloalkyl, and phenyl;
Z is B(OH)$_2$, C(O)NHR$_5$, C(O)NHOR$_5$, C(O)OH, P(O)(OR$_5$)$_2$, S(O)$_2R_5$, or S(O)$_2NHR_5$; and each $R_5$ is independently H, $C_1$-$C_6$ alkyl, $C_2$-$C_6$ alkenyl, $C_2$-$C_6$ alkynyl, C(O)$C_1$-$C_6$ alkyl, $C_3$-$C_8$ cycloalkyl, or 3- to 8-membered heterocyclyl, wherein each $C_1$-$C_6$ alkyl, $C_2$-$C_6$ alkenyl, and $C_2$-$C_6$ alkynyl is optionally and independently substituted with one or more substituents independently selected from the group consisting of halogen, CN, $NH_2$, OH, $OC_1$-$C_4$ alkyl, $OC_1$-$C_3$ haloalkyl, and phenyl, and further wherein each $C_3$-$C_8$ cycloalkyl and 3- to 8-membered heterocyclyl is optionally and independently substituted with one or more substituents independently selected from the group consisting of halogen, CN, $C_1$-$C_3$ alkyl, $C_1$-$C_3$ haloalkyl, $NH_2$, OH, $OC_1$-$C_4$ alkyl, $OC_R$—$C_3$ haloalkyl, and phenyl.

2. The compound of claim 1, or a pharmaceutically acceptable salt, stereoisomer, or tautomer thereof, wherein Ring A is phenyl, wherein the phenyl is substituted with one or more independently selected halogen substituents.

3. The compound of claim 1, or a pharmaceutically acceptable salt, stereoisomer, or tautomer thereof, wherein E is H, D, halogen, CN, or $CH_3$.

4. The compound of claim 3, or a pharmaceutically acceptable salt, stereoisomer, or tautomer thereof, wherein E is H.

5. The compound of claim 1, or a pharmaceutically acceptable salt, stereoisomer, or tautomer thereof, wherein each $R_3$ is independently H.

6. The compound of claim 1, or a pharmaceutically acceptable salt, stereoisomer, or tautomer thereof, wherein each $R_4$ is independently H, D, halogen, CN, $C_1$-$C_6$ alkyl, or $OR_3$, wherein each $C_1$-$C_6$ alkyl is optionally and independently substituted with one or more independently selected halogen substituents.

7. The compound of claim 6, or a pharmaceutically acceptable salt, stereoisomer, or tautomer thereof, wherein each $R_4$ is independently H, D, halogen, CN, $C_1$-$C_6$ alkyl, or $OCH_3$.

8. The compound of claim 1, or a pharmaceutically acceptable salt, stereoisomer, or tautomer thereof, wherein Z is $P(O)(OR_5)_2$.

9. The compound of claim 1, or a pharmaceutically acceptable salt, stereoisomer, or tautomer thereof, wherein each $R_5$ is independently H.

10. The compound of claim 1, or a pharmaceutically acceptable salt, stereoisomer, or tautomer thereof, wherein:
    each $R_4$ is independently H, D, F, Cl, Br, CN, $CF_3$, or $OCH_3$; and
    Z is $S(O)_2NH_2$.

11. The compound of claim 1, wherein the compound is:

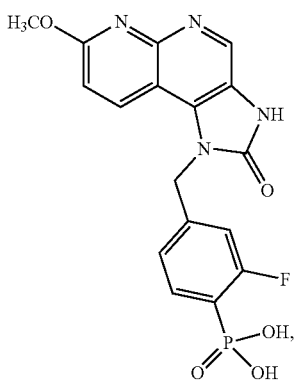

or a pharmaceutically acceptable salt or tautomer thereof.

12. The compound of claim 1, wherein the compound is:

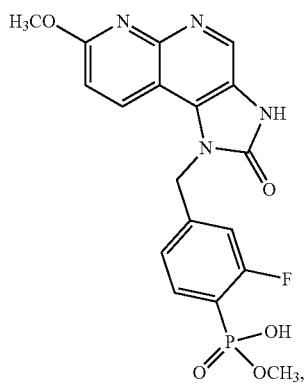

or a pharmaceutically acceptable salt or tautomer thereof.

13. The compound of claim 1, wherein the compound is:

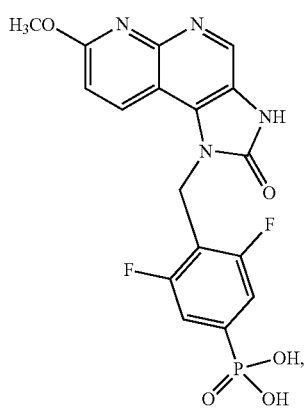

or a pharmaceutically acceptable salt or tautomer thereof.

14. The compound of claim 1, wherein the compound is selected from the group consisting of:

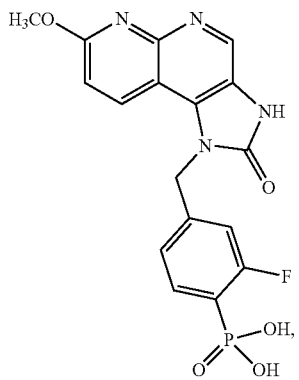 [SMILES: COc1ccc2c(ncc3[nH]c(=O)n(Cc4ccc(P(=O)(O)O)c(F)c4)c32)n1]

203
-continued
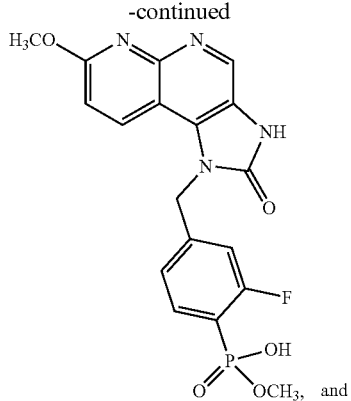
and
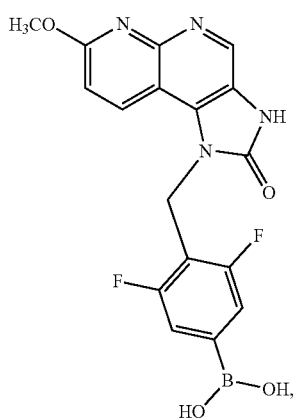
or a pharmaceutically acceptable salt or tautomer thereof.
15. The compound of claim 1, wherein the compound is selected from the group consisting of:
204
-continued
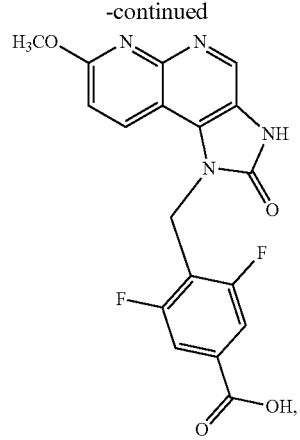
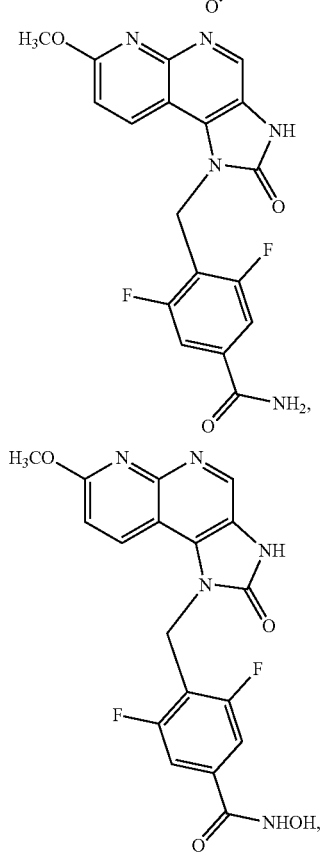
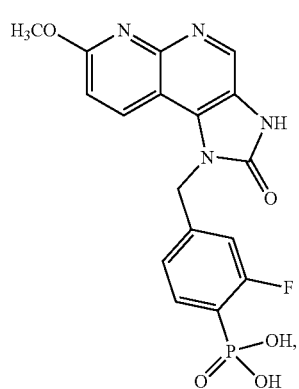

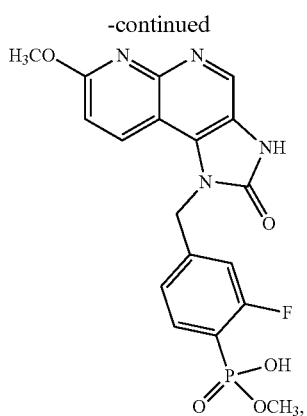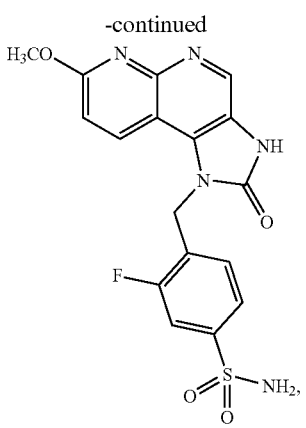

207
-continued
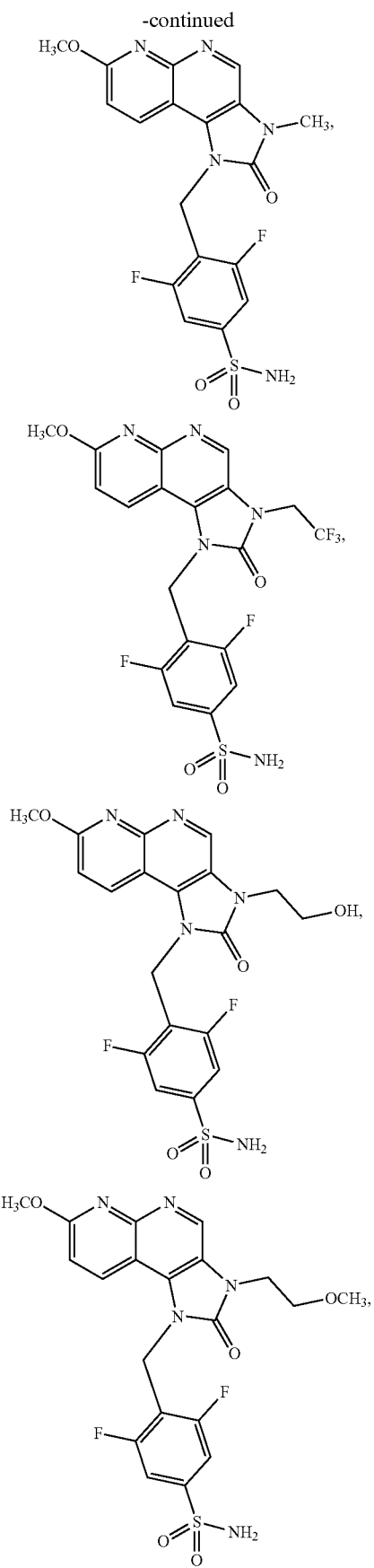
208
-continued
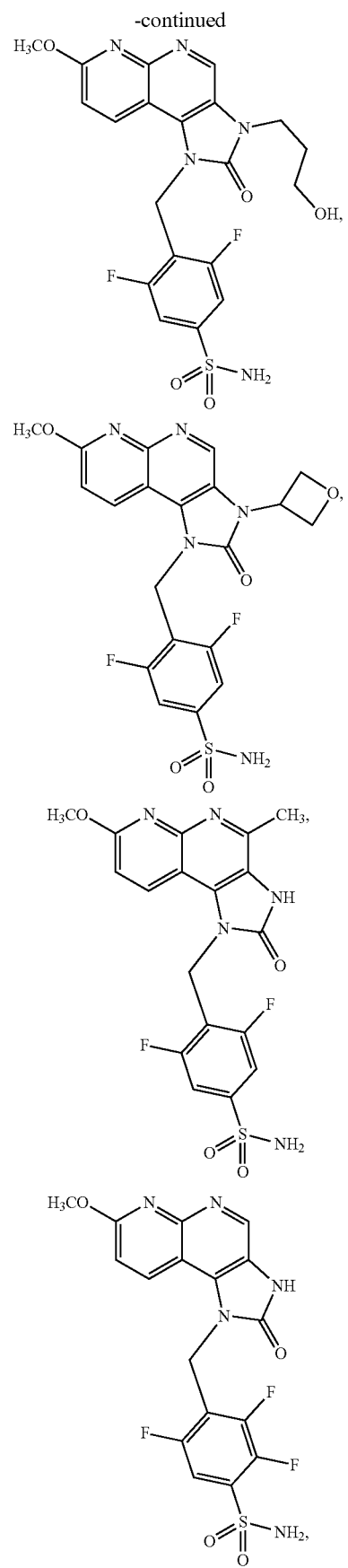

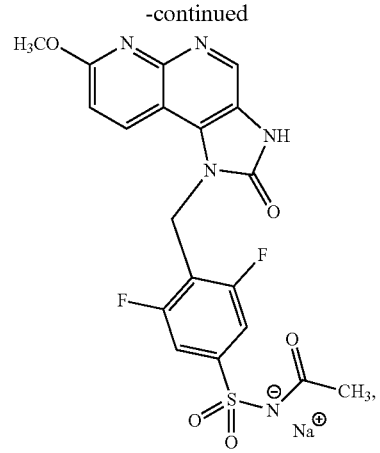
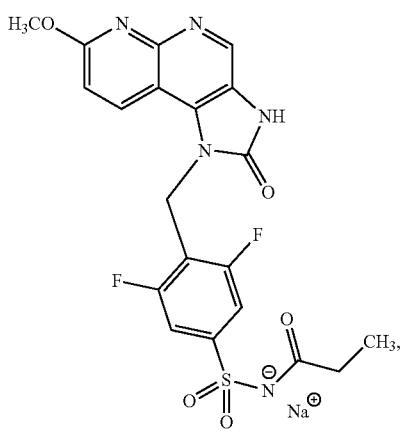
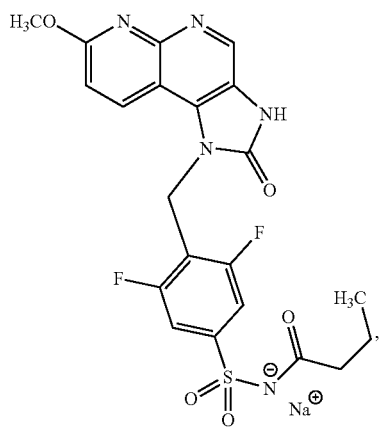
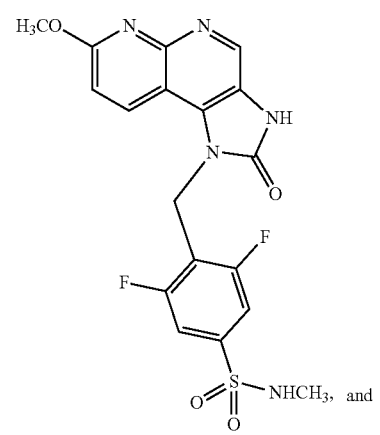
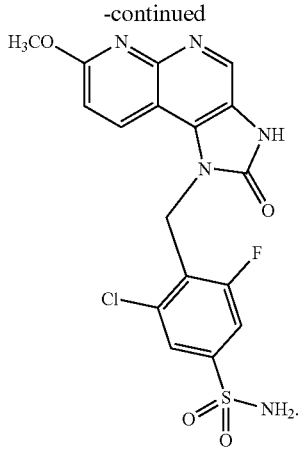
16. The compound of claim 1, wherein the compound is selected from the group consisting of:
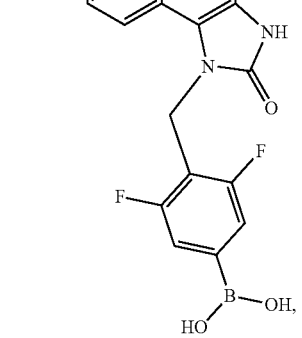
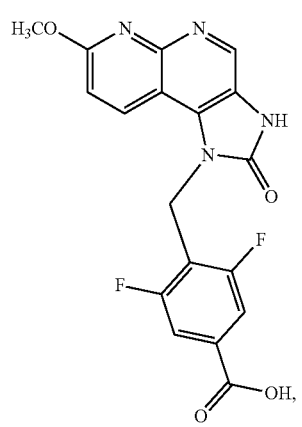

211
-continued
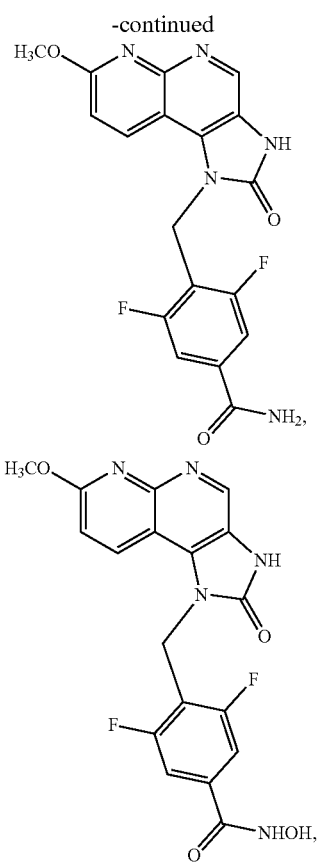
212
-continued
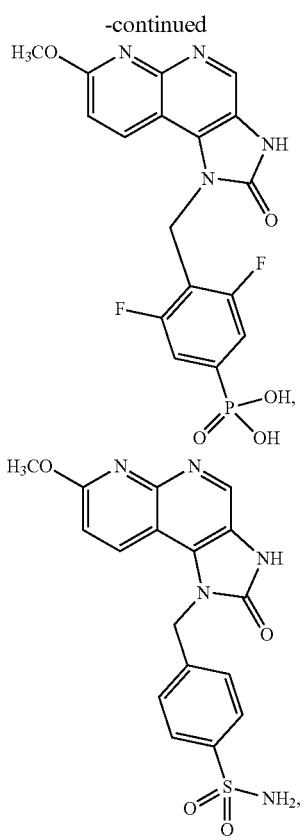
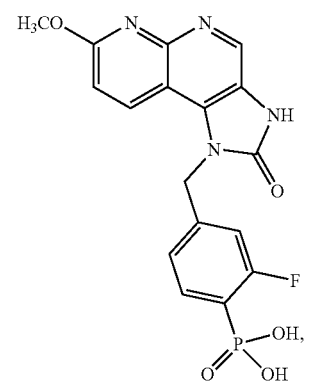
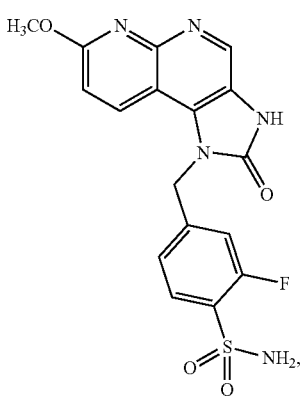
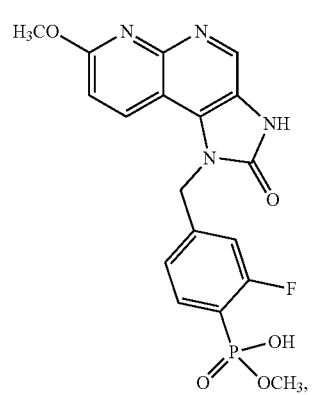 [SMILES: COc1ccc2c(ncc3[nH]c(=O)n(Cc4ccc(P(=O)(O)OC)c(F)c4)c32)n1]

213
-continued
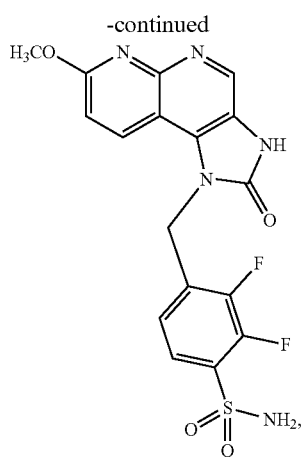
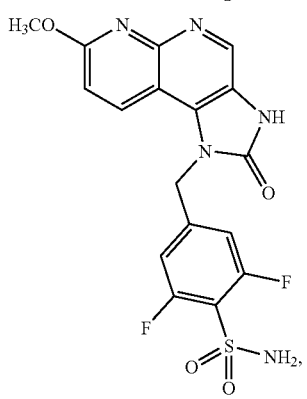
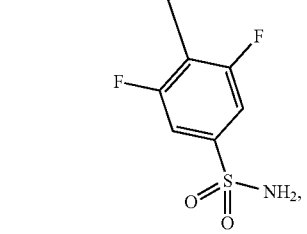
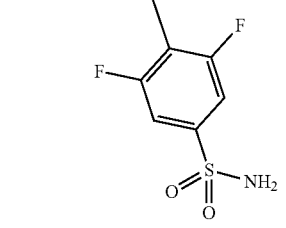
214
-continued
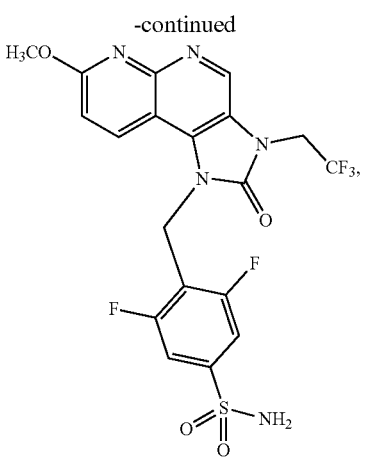
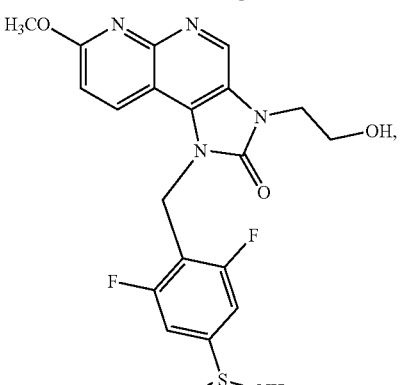
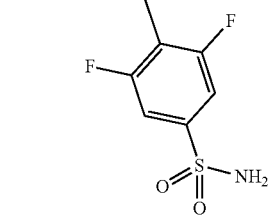
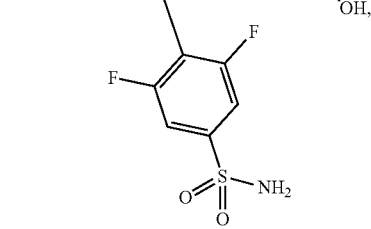

215
-continued
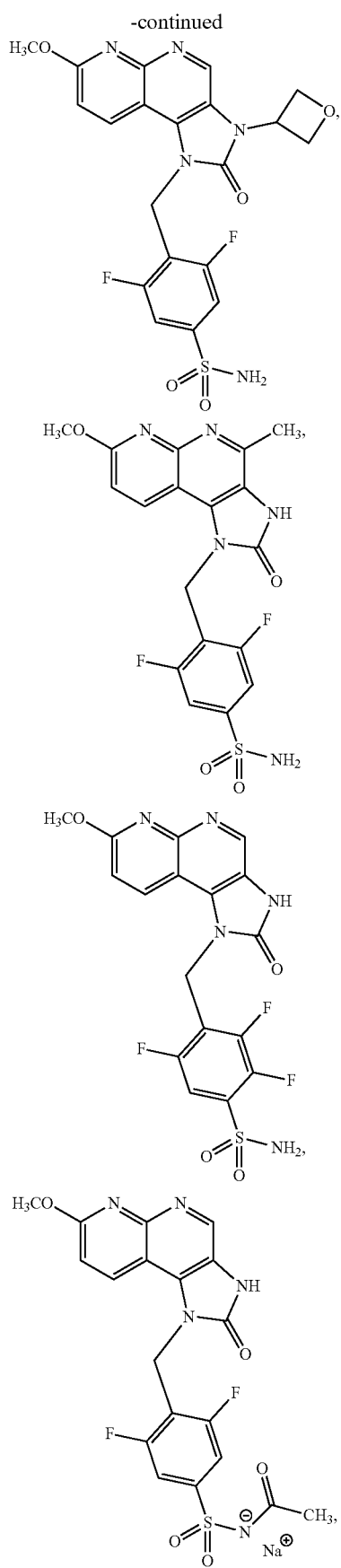
216
-continued
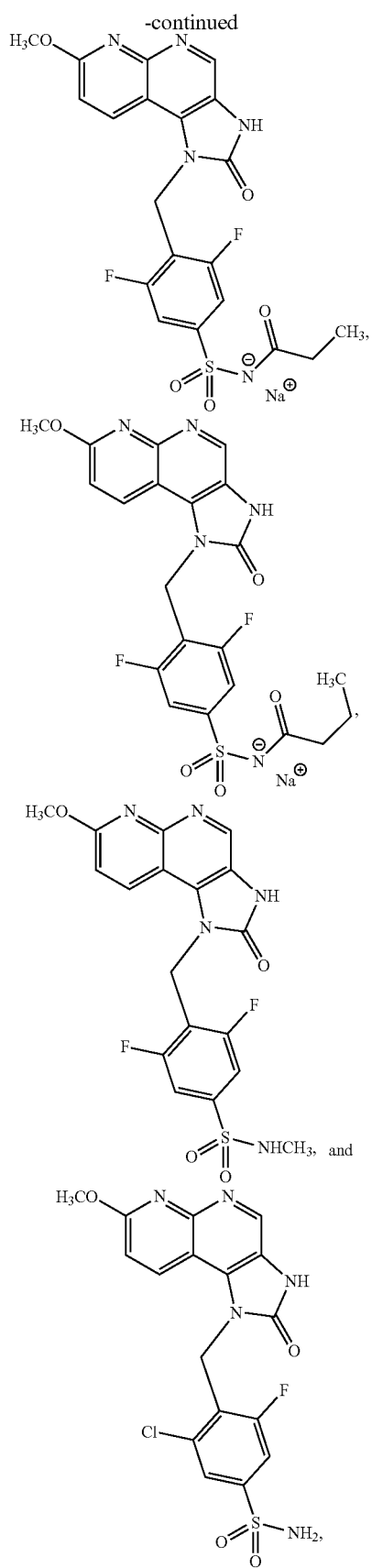
or a pharmaceutically acceptable salt or tautomer thereof.

17. A pharmaceutical composition comprising one or more pharmaceutically acceptable carriers and a compound of claim 1, or a pharmaceutically acceptable salt, stereoisomer, or tautomer thereof.

\* \* \* \* \*